United States Patent
Tokunaga et al.

(10) Patent No.: US 6,759,429 B2
(45) Date of Patent: Jul. 6, 2004

(54) PYRROLE DERIVATIVES

(75) Inventors: Teruhisa Tokunaga, Toyonaka (JP); William Ewan Hume, Nishinomiya (JP); Makoto Kitoh, Osaka (JP); Ryu Nagata, Nishinomiya (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 10/352,067

(22) Filed: Jan. 28, 2003

(65) Prior Publication Data

US 2003/0181496 A1 Sep. 25, 2003

Related U.S. Application Data

(63) Continuation-in-part of application No. PCT/JP01/06495, filed on Jul. 27, 2001.

(30) Foreign Application Priority Data

Jul. 28, 2000 (JP) ......................................... 2000-229423

(51) Int. Cl.$^7$ ................. A61K 30/4015; C07D 207/325
(52) U.S. Cl. ........................................ 514/423; 548/539
(58) Field of Search ........................... 548/539; 514/423

(56) References Cited

U.S. PATENT DOCUMENTS 6,407,102 B1 6/2002 Mahboobi et al.

FOREIGN PATENT DOCUMENTS

| JP | 8-333249 A | 12/1996 |
|----|-----------|---------|
| JP | 2001-89412 A | 4/2001 |
| WO | WO92/22537 | 12/1992 |
| WO | WO97/36876 | 10/1997 |
| WO | WO99/57117 | 11/1999 |
| WO | WO00/20371 | 4/2000 |

OTHER PUBLICATIONS

Massa et al., Il Farmaco, vol. 49, No. 1, pp. 51–55, (1994).

*Primary Examiner*—Joseph K. McKane
*Assistant Examiner*—Kamal Saeed
(74) *Attorney, Agent, or Firm*—Birch, Stewart, Kolasch & Birch, LLP

(57) ABSTRACT

Pyrrole derivatives represented by the following formula:

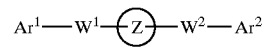

wherein Ring Z is an optionally substituted pyrrole ring, etc.; $W^2$ is —CO—, —SO$_2$—, an optionally substituted C$_1$–C$_4$ alkylene, etc.; Ar$^2$ is an optionally substituted aryl, etc.; $W^1$ and Ar$^1$ mean the following (1) and (2): (1) $W^1$ is an optionally substituted C$_1$–C$_4$ alkylene, etc.; Ar$^1$ is an optionally substituted bicyclic heteroaryl having 1 to 4 nitrogen atoms as ring-forming atoms: (2) $W^1$ is an optionally substituted C$_2$–C$_5$ alkylene, an optionally substituted C$_2$–C$_5$ alkenylene, etc.; and Ar$^1$ is an aryl or monocyclic heteroaryl, which are substituted by carboxyl, an alkoxycarbonyl, etc. at the ortho- or meta-position thereof with respect to the binding position of $W^1$, or a pharmaceutically acceptable salt thereof. These compounds are useful as medicaments such as a fibrosis inhibitor for organs or tissues.

9 Claims, No Drawings

PYRROLE DERIVATIVES

The application is a Continuation-In-Part application of PCT International application No. PCT/JP01/06495 filed on Jul. 27, 2001, which designated the United States and on which priority is claimed under 35 U.S.C. § 120, the entire contents of which are hereby incorporated by reference. This application also claims right of priority under 35 U.S.C. § 119 based on Application Ser. No. 2000-229423 filed in Japan on Jul. 28, 2000, the entire contents of which are hereby incorporated by reference.

TECHNICAL FIELD

The present invention relates to pyrrole derivatives exhibiting TGF-β inhibitory activity and being useful as fibrosis inhibitors for organs or tissues, a prodrug thereof, and pharmaceutically acceptable salts thereof.

BACKGROUND ART

Fibrosis of organs or tissues is induced by excessive accumulation of extracellular matrix within the organ, as repair or defenses, when said organ is invaded or damaged by some causes. The extracellular matrix is a substance surrounding the cells of tissues, and representative ones thereof are, for example, fibrinoproteins such as collagen, elastin, etc., complex carbohydrates such as proteoglycan, etc., glycoproteins such as fibronectin, laminin, etc. When the degree of the degeneration of organs, etc. by invasion or injury is not serious, then the organs, etc. can return to normality without any scarring of repair. However, when the degree of the degeneration of organs, etc. by invasion or injury is serious or the degeneration of organs persists, then the fibrosis of scarring of repair will further damage the original function of said organ, etc. And, further fibrosis is induced by said damage. Then, it falls into a vicious cycle thereof. Eventually, there will be caused a deficiency of organs, and at worst, the patient will die.

TGF-β (Transforming Growth Factor-β) plays an important role in the accumulation of extracellular matrix. When TGF-β is administered to normal animals, there occurred many fibrotic events at various organs of said animals (International Review of Experimental Pathology, 34B: 43–67, 1993). In addition, it was reported that the fibrosis of tissues was observed in transgenic mice which highly express TGF-β (Proc. Natl. Acad. Sci. USA, 92:2572–2576, 1995; Laboratory Investigation, 74:991–1003, 1995).

TGF-β participates in the fibrosis of tissues in the following manner:

(1) Acting on cells, the extracellular matrix such as fibronectin (Journal of Biological Chemistry, 262:6443–6446, 1987), collagen (Proc. Natl. Acad. Sci. USA, 85:1105–1108, 1988), proteoglycan (Journal of Biological Chemistry, 263:3039–3045, 1988), etc. is potently produced;

(2) Decreasing the expression of an enzyme for degrading extracellular matrix (Journal of Biological Chemistry, 263:16999–17005, 1988) and potently promoting the expression of inhibitors of the extracelluar matrix degrading enzyme (Cancer Research, 49:2533–2553, 1989), by which the degradation of extracellular matrix is inhibited:

(3) Proliferating cells producing extracellular matrix (American Journal of Physiology, 264:F199–F205, 1993).

Thus, the inhibition of TGF-β is a useful means for inhibiting the accumulation of extracellular matrix. In fact, it is reported that the fibrosis is alleviated by administering antiserum of TGF-β to animal models for fibrosis (Nature, 346:371–374, 1990).

DISCLOSURE OF INVENTION

An object of the present invention is to provide a compound being useful as fibrosis inhibitors for organs or tissues. In order to solve the above problems, the present inventors have intensively studied, and found that pyrrole derivatives inhibit the fibrosis of organs or tissues, and have accomplished the present invention.

The present invention is as follows:

[1] A pyrrole derivative of the formula:

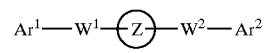

wherein Ring Z is an optionally substituted pyrrole ring, an optionally substituted indole ring, an optionally substituted thiophene ring, an optionally substituted pyrazole ring, an optionally substituted benzene ring, an optionally substituted imidazole ring, or an optionally substituted isothiazole ring;

$W^2$ is —CO—, —SO$_2$—, —CONR—, an optionally substituted $C_1$–$C_4$ alkylene or an optionally substituted $C_2$–$C_4$ alkenylene, and R is hydrogen or an alkyl;

$Ar^2$ is an optionally substituted aryl or an optionally substituted heteroaryl;

$W^1$ and $Ar^1$ mean the following (1) or (2):

(1) $W^1$ is an optionally substituted $C_1$–$C_4$ alkylene or an optionally substituted $C_2$–$C_4$ alkenylene; $Ar^1$ is an optionally substituted bicyclic heteroaryl having 1 to 4 nitrogen atoms as ring-forming atoms:

(2) $W^1$ is an optionally substituted $C_2$–$C_5$ alkylene, an optionally substituted $C_2$–$C_5$ alkenylene, an optionally substituted $C_2$–$C_5$ alkynylene, or —Y—$W^3$—, Y is an oxygen atom or a cycloalkanediyl, and $W^3$ is an optionally substituted $C_1$–$C_5$ alkylene, an optionally substituted $C_2$–$C_5$ alkenylene, or an optionally substituted $C_2$–$C_5$ alkynylene; and $Ar^1$ is an aryl or monocyclic heteroaryl, which is substituted at the ortho- or meta-position thereof with respect to the binding position of $W^1$ by a group selected from carboxyl, an alkoxycarbonyl, a carbamoyl having optionally alkyl-substituent(s), a cyclic aminocarbonyl, an alkyl-sulfonylcarbamoyl, an arylsulfonylcarbamoyl, an alkylsulfonyl, a sulfamoyl having optionally alkyl-substituent(s), a cyclic aminosulfonyl, tetrazolyl, cyano, an alkoxy and an alkylsulfonylamino, and said aryl or monocyclic heteroaryl being optionally further substituted, or a prodrug thereof, or a pharmaceutically acceptable salt thereof.

[2] The pyrrole derivative according to the above [1], wherein the divalent group including Ring Z may be any one of the following divalent groups (any direction of bonds is included), or a prodrug thereof, or a pharmaceutically acceptable salt thereof.

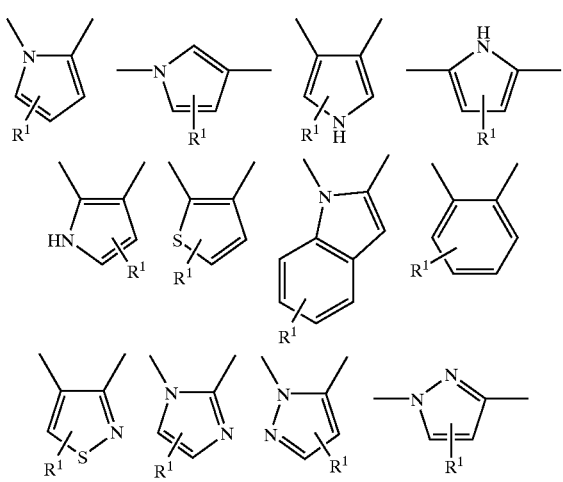

wherein the number of $R^1$ is one or more, and each is independently hydrogen, a halogen or an optionally substituted alkyl.

[3] The pyrrole derivative according to the above [1] or [2], wherein Ring Z is an optionally substituted pyrrole ring, an optionally substituted indole ring or an optionally substituted thiophene ring, or a prodrug, or a pharmaceutically acceptable salt thereof.

[4] The pyrrole derivative according to the above [1], which is a compound of the formula:

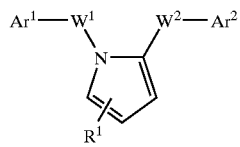

wherein $W^1$, $W^2$, $Ar^1$, $Ar^2$ and $R^1$ are as defined above, or a prodrug thereof, or a pharmaceutically acceptable salt thereof.

[5] The pyrrole derivative according to any one of the above [1] to [4], wherein $W^2$ is —CO—, —SO$_2$—, —CONR—, methylene, or hydroxymethylene, or a prodrug thereof, or a pharmaceutically acceptable salt thereof.

[6] The pyrrole derivative according to any one of the above [1] to [5], wherein $Ar^2$ is a substituted phenyl, or a prodrug thereof, or a pharmaceutically acceptable salt thereof.

[7] The pyrrole derivative according to any one of the above [1] to [6], wherein $W^1$ is an optionally substituted $C_2$–$C_5$ alkylene, an optionally substituted $C_2$–$C_5$ alkenylene, or an optionally substituted $C_2$–$C_5$ alkynylene; and $Ar^1$ is an aryl, which is substituted at the ortho-position thereof with respect to the binding position of $W^1$ by a group selected from carboxyl, an alkoxycarbonyl, a carbamoyl having optionally alkyl-substituent(s), a cyclic aminocarbonyl, an alkylsulfonylcarbamoyl, an arylsulfonylcarbamoyl, an alkylsulfonyl, a sulfamoyl having optionally alkyl-substituent(s), a cyclic aminosulfonyl, tetrazolyl, cyano, an alkoxy and an alkylsulfonylamino, and said aryl being optionally further substituted, or a prodrug thereof, or a pharmaceutically acceptable salt thereof.

[8] The pyrrole derivative according to any one of the above [1] to [6], wherein $W^1$ is an optionally substituted trans-$C_3$–$C_4$ alkenylene; and $Ar^1$ is an aryl, which is substituted at the ortho-position thereof with respect to the binding position of $W^1$ by a group selected from carboxyl, an alkoxycarbonyl, a carbamoyl having optionally alkyl-substituent(s), a cyclic aminocarbonyl, an alkylsulfonylcarbamoyl, an arylsulfonylcarbamoyl, tetrazolyl, cyano, an alkoxy and an alkylsulfonylamino, and said aryl being optionally further substituted by a halogen, cyano, an optionally substituted alkoxy or an optionally substituted alkyl, or a prodrug thereof, or a pharmaceutically acceptable salt thereof.

[9] The compound according to the above [1], which is a compound of the formula:

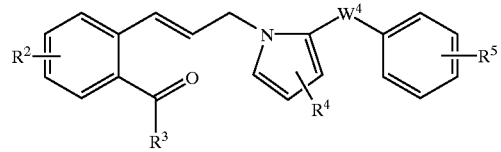

wherein $W^4$ is —CO—, —CONR— or methylene, R is as defined above;

$R^2$ is a halogen, cyano, an optionally substituted alkoxy or an optionally substituted alkyl;

$R^3$ is hydroxyl, an alkoxy, an amino having optionally alkyl-substituent(s), a cyclic amino or an alkylsulfonylamino;

$R^4$ is hydrogen, a halogen or an alkyl;

$R^5$ is an optionally substituted alkoxy or an optionally substituted alkyl, or a prodrug thereof, or a pharmaceutically acceptable salt thereof.

[10] The compound according to the above [9], wherein $W^4$ is —CO—; $R^2$ is a halogen, cyano, an alkoxy being optionally substituted by a halogen or an alkoxy, or an alkyl being optionally substituted by a halogen or an alkoxy; $R^4$ is hydrogen or an alkyl; $R^5$ is an alkoxy being optionally substituted by a halogen, an alkoxy or morpholino, or an alkyl being optionally substituted by a halogen, an alkoxy or morpholino, or a prodrug thereof, or a pharmaceutically acceptable salt thereof.

[11] The compound according to the above [9] or [10], which is a compound of the formula:

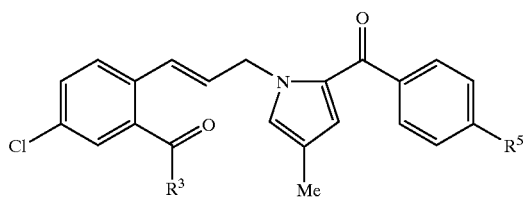

wherein $R^3$ and $R^5$ are as defined above, or a prodrug thereof, or a pharmaceutically acceptable salt thereof.

[12] A pyrrole derivative of the formula:

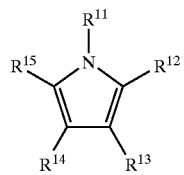

wherein $R^{14}$ and $R^{15}$ are independently hydrogen or an optionally substituted alkyl;

$R^{11}$, $R^{12}$ and $R^{13}$ are as follows:

(1) $R^{11}$ is —$W^{11}$—$Ar^3$ or —$W^{12}$—Het, one of $R^{12}$ and $R^{13}$ is —$W^{13}$—A, and the other is hydrogen or an optionally substituted alkyl, $W^{11}$ is an optionally substituted $C_2$–$C_5$ alkylene or an optionally substituted $C_2$–$C_5$ alkenylene, $W^{12}$ is an optionally substituted $C_1$–$C_4$ alkylene, $W^{13}$ is —CO—, an optionally substituted $C_1$–$C_6$ alkylene, or an optionally substituted $C_2$–$C_5$ alkenylene; or (2) $R^{11}$ is —$W^{21}$—A, one of $R^{12}$ and $R^{13}$ is —$W^{22}$—$Ar^3$ or —$W^{23}$—Het, and the other is hydrogen or an optionally substituted alkyl, $W^{21}$ is an optionally substituted $C_1$–$C_6$ alkylene, an optionally substituted $C_2$–$C_5$ alkenylene, or —$SO_2$—, $W^{22}$ is an optionally substituted $C_2$–$C_5$ alkylene, or an optionally substituted $C_2$–$C_5$ alkenylene, $W^{23}$ is —CO— or an optionally substituted $C_1$–$C_4$ alkylene, $Ar^3$ is an aryl being substituted by —$COR^{16}$, —$SO_2R^{17}$ or tetrazolyl, and said aryl being optionally further substituted by hydroxy, an optionally substituted $C_1$–$C_4$ alkyl, an optionally substituted $C_2$–$C_4$ alkenyl, an optionally substituted $C_2$–$C_4$ alkynyl, an optionally substituted $C_1$–$C_4$ alkoxy, a halogen, cyano, a carbamoyl having optionally alkyl-substituent(s), or a cyclic aminocarbonyl;

Het is an optionally substituted monocyclic or bicyclic heteroaryl having 1 to 4 nitrogen atoms as ring-forming atoms;

A is an optionally substituted aryl, or an optionally substituted monocyclic or bicyclic heteroaryl;

$R^{16}$ is hydroxyl, an alkoxy, an amino having optionally alkyl-substituent(s), a cyclic amino, or an alkylsulfonylamino;

$R^{17}$ is an alkyl, an amino having optionally alkyl-substituent(s), or a cyclic amino;

or a pharmaceutically acceptable salt thereof.

[13] The pyrrole derivative according to the above [12], wherein $R^{11}$, $R^{12}$ and $R^{13}$ mean as follows:

$R^{11}$ is —$W^{11}$—$Ar^3$ or —$W^{12}$—Het;

one of $R^{12}$ and $R^{13}$ is —$W^{13}$—A, and the other is hydrogen or an optionally substituted $C_1$–$C_4$ alkyl;

$W^{11}$ is an optionally substituted $C_2$–$C_5$ alkenylene;

$W^{12}$ is an optionally substituted $C_1$–$C_4$ alkylene;

$W^{13}$ is —CO—, an optionally substituted $C_1$–$C_6$ alkylene, or an optionally substituted $C_2$–$C_5$ alkenylene;

$Ar^3$ is an aryl being substituted at the ortho-position thereof with respect to the binding position of $W^{11}$ by a group selected from —$COR^{16}$, —$SO_2R^{17}$ and tetrazolyl, and said aryl being optionally further substituted by a group selected from hydroxy, an optionally substituted $C_1$–$C_4$ alkyl, an optionally substituted $C_2$–$C_4$ alkenyl, an optionally substituted $C_2$–$C_4$ alkynyl, an optionally substituted $C_1$–$C_4$ alkoxy, a halogen, cyano, a carbamoyl having optionally $C_1$–$C_4$ alkyl-substituent(s), and a cyclic aminocarbonyl;

Het is an optionally substituted 3-quinolyl, an optionally substituted 3-naphthyridinyl or an optionally substituted 2-quinoxalyl;

A is an optionally substituted aryl, or an optionally substituted monocyclic or bicyclic heteroaryl;

$R^{16}$ is hydroxy, a $C_1$–$C_4$ alkoxy, an amino having optionally $C_1$–$C_4$ alkyl-substituent(s), a cyclic amino, or a $C_1$–$C_4$ alkylsulfonylamino;

$R^{17}$ is a $C_1$–$C_4$ alkyl, an amino having optionally $C_1$–$C_4$ alkyl-substituent(s), or a cyclic amino.

[14] A medicament containing the pyrrole derivative according to any one of the above [1] to [13], or a prodrug thereof, or a pharmaceutically acceptable salt thereof.

[15] The medicament according to the above [14], which is a TGF-β inhibitor.

[16] The medicament according to the above [14], which is a fibrosis inhibitor.

The number of the substituents on the "substituted pyrrole ring", "substituted indole ring", "substituted thiophene ring", "substituted pyrazole ring", "substituted benzene ring", "substituted imidazole ring" and "substituted isothiazole ring" is 1 or more, for example, 2 or 3, and the substituents include the same groups for $R^1$ except for hydrogen, i.e., a halogen or an optionally substituted alkyl.

The "alkyl" includes, for example, a straight chain or branched chain $C_1$–$C_6$ alkyl group, such as methyl, ethyl, 2-propyl, 2-methyl-1-propyl, butyl, 2-butyl, t-butyl, pentyl, 3-methyl-2-butyl, 2-methyl-2-butyl, hexyl, etc., and preferably a straight chain or branched chain $C_1$–$C_4$ alkyl.

The substituent of the "substituted alkyl for $R^2$ and $R^5$" includes, for example, hydroxy, an alkanoyloxy, a halogen, cyano, an alkanoyl, an alkoxy, an alkoxycarbonyl, carboxy, an amino having optionally alkyl-substituent(s), an amino having optionally alkoxyalkyl-substituent(s), a cyclic amino, a monocyclic heteroaryl, a carbamoyl having optionally alkyl-substituent(s), a cyclic aminocarbonyl, a sulfamoyl having optionally alkyl-substituent(s), a cyclic aminosulfonyl, azide, etc. The number of the substituents may be one or more, for example, 2 or 3, and the substituents are the same or different. The preferable substituents of the substituted alkyl for $R^2$ are a halogen, an alkoxy, etc. The preferable substituents of the substituted alkyl for $R^5$ are a halogen, an alkoxy, morpholino, hydroxy, etc.

The substituent of the "substituted alkyl for $R^1$, $R^{12}$, $R^{13}$, $R^{14}$ and $R^{15}$" includes, for example, a halogen, an alkoxy, hydroxy, oxo, etc., and the number of the substituents are one or more, for example, 2 or 3, and the substituents may be the same or different.

The "alkoxy" includes, for example, a straight chain or branched chain $C_1$–$C_6$ alkoxy, such as methoxy, ethoxy, propyloxy, 2-propyloxy, 2-methyl-2-propyloxy, butoxy, pentyloxy, hexyloxy, etc. and preferably a straight chain or branched chain $C_1$–$C_4$ alkoxy.

The substituent of the "substituted alkoxy for $R^2$ and $R^5$" is, for example, hydroxy, an alkanoyloxy, a halogen, cyano, an alkanoyl, an alkoxy, an alkoxycarbonyl, carboxy, an amino having optionally alkyl-substituent(s), an amino having optionally alkoxyalkyl-substituent(s), a cyclic amino, a monocyclic heteroaryl, a carbamoyl having optionally alkyl-substituent(s), a cyclic aminocarbonyl, a sulfamoyl having optionally alkyl-substituent(s), a cyclic aminosulfonyl, azide, etc. The number of the substituents may be one or more, for example, 2 or 3, and the substituents may be the same or different. The preferable substituents of the substituted alkoxy for $R^2$ are a halogen, an alkoxy, etc. The preferable substituents of the substituted alkoxy for $R^5$ are a halogen, an alkoxy, morpholino, hydroxy, etc., and especially preferable substituted alkoxy is 2-morpholinoethoxy, etc.

The "alkanoyl" includes, for example, a straight chain or branched chain $C_1$–$C_6$ alkanoyl, such as formyl, acetyl, propanoyl, butanoyl, isobutanoyl, pentanoyl, hexanoyl, etc., and preferably a straight chain or branched chain $C_2$–$C_5$ alkanoyl.

The "alkenyl" includes, for example, a straight chain or branched chain $C_2$–$C_6$ alkenyl, such as vinyl, allyl, isopropenyl, 2-butenyl, 3-butenyl, 2-pentenyl, 3-hexenyl, etc., and preferably a straight chain or branched chain $C_2$–$C_4$ alkenyl.

The "alkenyloxy" includes, for example, a straight chain or branched chain $C_3$–$C_6$ alkenyloxy, such as allyloxy, 3-butenyloxy, 2-butenyloxy, etc., and preferably a straight chain or branched chain $C_3$–$C_4$ alkenyloxy.

The "alkynyl" includes, for example, a straight chain or branched chain $C_2$–$C_6$ alkynyl, such as ethynyl, 2-propynyl, 1-propynyl, 3-butynyl, 2-butynyl, 2-pentynyl, 3-hexynyl, etc., and preferably a straight chain or branched chain $C_2$–$C_4$ alkynyl.

The "alkynyloxy" includes, for example, a straight chain or branched chain $C_3$–$C_6$ alkynyloxy, such as allyloxy, 3-butynyloxy, 2-butynyloxy, 3-pentynyloxy, etc., and preferably a straight chain or branched chain $C_3$–$C_4$ alkynyloxy.

The "alkylene" includes, for example, a straight chain alkylene having carbon atoms in a number, within the scope of each, alkylene, such as methylene, ethylene, trimethylene, tetramethylene, pentamethylene, hexamethylene, etc.

Preferable examples of the "$C_1$–$C_4$ alkylene for $W^2$" are methylene and ethylene, and especially preferable one is methylene.

Preferable examples of the "$C_1$–$C_4$ alkylene for $W^1$ when $Ar^1$ is an optionally substituted bicyclic heteroaryl having 1 to 4 nitrogen atoms as ring-forming atoms" are methylene, etc.

Preferable examples of the "$C_2$–$C_5$ alkylene for $W^1$, when $Ar^1$ is an aryl or monocyclic heteroaryl, which is substituted at the ortho- or meta-position thereof with respect to the binding position of $W^1$ by a group selected from carboxyl, an alkoxycarbonyl, a carbamoyl having optionally alkyl-substituent(s), a cyclic aminocarbonyl, an alkyl-sulfonylcarbamoyl, an arylsulfonylcarbamoyl, an alkylsulfonyl, a sulfamoyl having optionally alkyl-substituent(s), a cyclic aminosulfonyl, tetrazolyl, cyano, an alkoxy and an alkylsulfonylamino, and said aryl or monocyclic heteroaryl being optionally further substituted" are trimethylene, tetramethylene, etc.

Preferable examples of "$C_1$–$C_5$ alkylene for $W^3$" are methylene, ethylene, etc.

The substituents of the "substituted alkylene" includes, for example, an alkyl, an alkoxy, hydoxy, an alkanoyloxy, a halogen, etc., and the substituted alkylene has 1 or 2 substituents, which are the same or different.

The "alkenylene" includes, for example, a straight chain alkenylene having carbon atoms in a number within the scope of each alkenylene, such as vinylene, 1-propenylene, 2-propenylene, 1-butenylene, 2-butenylene, 3-butenylene, 1-pentenylene, 2-pentenylene, 3-pentenylene, 4-pentenylene, 2,4-pentadienylene, etc. The configuration at the double bonds may be either cis-configuration or trans-configuration, and preferable configuration is trans-configuration.

Preferable examples of the "$C_2$–$C_5$ alkenylene for $W^1$, when $Ar^1$ is an aryl or monocyclic heteroaryl, which is substituted at the ortho- or meta-position thereof with respect to the binding position of $W^1$ by a group selected from carboxyl, an alkoxycarbonyl, a carbamoyl having optionally alkyl-substituent(s), a cyclic aminocarbonyl, an alkyl-sulfonylcarbamoyl, an arylsulfonylcarbamoyl, an alkylsulfonyl, a sulfamoyl having optionally alkyl-substituent(s), a cyclic aminosulfonyl, tetrazolyl, cyano, an alkoxy and an alkylsulfonylamino, and said aryl or monocyclic heteroaryl being optionally further substituted" are a straight chain trans-$C_3$–$C_4$ alkenylene, and especially preferable example is trans-2-propenylene.

The "$C_2$–$C_5$ alkynylene" includes, for example, a straight chain $C_2$–$C_5$ alkynylene, such as ethynylene, 2-propynylene, 2-butynylene, 3-butynylene, 2-pentynylene, 3-pentynylene, etc.

The substituents of the "substituted alkenylene" and the "substituted alkynylene" are, for example, an alkyl, etc., and these groups have independently 1 or 2 substituents.

The "aryl" includes, for example, a $C_6$–$C_{10}$ aryl, such as phenyl, 1-naphthyl, 2-naphthyl, etc., and preferably one is phenyl.

The "heteroaryl" includes, for example, a monocyclic or bicyclic heteroaryl having 1 to 3 heteroatom selected from a nitrogen, an oxygen and a sulfur, and these heteroatoms are the same or different, such as a monocyclic 5-membered heteroaryl (e.g., thiophene, furan, pyrrole, imidazole, pyrazole, thiazole, oxazole, isothiazole, isoxazole, etc.), a monocyclic 6-membered heteroaryl (e.g., pyridine, pyrimidine, pyrazine, pyridazine, triazine, etc.), a bicyclic heteroaryl (e.g., indole, isoindole, indolidine, indazole, purine, 4-H-quinolidine, quinoline, isoquinoline, phthalazine, naphthyridine, quinoxaline, quinazoline, benzothiazole, benzoxazole, benzisothiazole, benzisoxazole, benzofuran, benzothiophene, etc.), etc.

The "monocyclic heteroaryl" includes monocyclic heteroaryls among heteroaryls.

Preferable examples of the "monocyclic heteroaryl for $Ar^1$" are a monocyclic heteroaryl being weak basic (pKb<7), and more preferable ones are a monocyclic 5-membered heteroaryl containing a sulfur atom or an oxygen atom, and especially preferable ones are thiophene, furan, thiazole, oxazole, isothiazole, isoxazole, etc.

Preferable examples of the "heteroaryl for $Ar^2$" are a heteroaryl being weak basic (pKb<7), and more preferable ones are a monocyclic 5-membered heteroaryl and bicyclic heteroaryl containing a sulfur atom or an oxygen atom, and especially preferable ones are thiophene, furan, thiazole, oxazole, isothiazole, isoxazole, indole, isoindole, benzothiazole, benzoxazole, benzisothiazole, benzisoxazole, benzofuran, benzothiophene, etc.

The "monocyclic or bicyclic heteroaryl having 1 to 4 nitrogen atoms as ring-forming atoms" includes, for example, a monocyclic 5-membered heteroaryl (e.g., pyrrolyl, imidazolyl, 3H-pyrazolyl, tetrazolyl, etc.), a monocyclic 6-membered heteroaryl (e.g., pyridyl, pyrimidyl, pyrazinyl, pyridazinyl, triazinyl, etc.), a bicyclic heteroaryl (e.g., indolyl, isoindolyl, indolidinyl, indazolyl, puryl, 4-H-quinolidinyl, quinolinyl, isoquinolinyl, phthalazinyl, naphthyridyl, quinoxalyl, quinazolyl, etc.), etc. Preferable examples are a bicyclic heteroaryl, and more preferable ones are quinolyl, quinoxalyl, naphthyridyl, etc., and especially preferable ones are 3-quinolyl, 2-quinoxalyl, 3-naphthyridyl, etc.

The substituents of the "substituted aryl", "substituted phenyl", "substituted heteroaryl", "substituted monocyclic or bicyclic heteroaryl", "monocyclic or bicyclic heteroaryl having substituted 1 to 4 nitrogen atoms", "substituted 3-quinolyl", "substituted 3-naphthyridyl" and "substituted 2-quinoxalyl", and the other substituents of the "substituted aryl and substituted monocyclic heteroaryl for $Ar^1$" are exemplified as follows. These groups may have one or more, for example, 2 or 3 substituents, which are the same or different.

Optionally substituted alkyl
(the substituents of this substituted alkyl include, for example, hydroxy, an alkanoyloxy, a halogen, cyano, an alkanoyl, an alkoxy, an alkoxycarbonyl, carboxy, an amino having optionally alkyl-substituent(s), an amino having optionally alkoxyalkyl-substituent(s), a cyclic amino, a monocyclic heteroaryl, a carbamoyl having optionally alkyl-substituent(s), a cyclic aminocarbonyl, a sulfamoyl having optionally alkyl-substituent(s), a cyclic aminosulfonyl, azide, etc. The number of the substituents is 1 or more, for example, 2 or 3, and the substituents are the same or different.)

Optionally substituted alkoxy:
(the substituents of this substituted alkoxy include, for example, hydroxy, an alkanoyloxy, a halogen, cyano, an alkanoyl, an alkoxy, an alkoxycarbonyl, carboxy, an amino having optionally alkyl-substituent(s), an amino having optionally alkoxyalkyl-substituent(s), a cyclic amino, a monocyclic heteroaryl, a carbamoyl having optionally alkyl-substituent(s), a cyclic aminocarbonyl, a sulfamoyl having optionally alkyl-substituent(s), a cyclic aminosulfonyl, azide, etc. The number of the substituents is 1 or more, for example, 2 or 3, and the substituents are the same or different.)

Optionally substituted alkenyl, optionally substituted alkynyl:
(the substituents of these substituted alkenyl and substituted alkynyl include, for example, an alkoxy, an alkoxycarbonyl, an alkanoyl, hydroxy, an alkanoyloxy, a halogen, cyano, a carbamoyl having optionally alkyl-substituent(s), a cyclic aminocarbonyl, carboxy, an amino having optionally alkyl-substituent(s), a cyclic amino, a sulfamoyl having optionally alkyl-substituent(s), a cyclic aminosulfonyl, etc. The number of the substituents is 1 or more, for example, 2 or 3, and the substituents are the same or different.)

An alkenyloxy, hydroxy, an alkanoyl, an alkanoyloxy, a halogen, an alkylsulfonyl, an amino having optionally alkyl-substituent(s), a cyclic amino, a carbamoyl having optionally alkyl-substituent(s), a cyclic aminocarbonyl, a sulfamoyl having optionally alkyl-substituent(s), a cyclic aminosulfone, cyano, methylenedioxy, a heteroaryl, 1,3-dioxan-2-yl, etc.

Preferable examples of the substituents of the "substituted aryl for $Ar^2$ and A", "substituted phenyl for $Ar^{2}$", "substituted heteroaryl for $Ar^{2}$" and "substituted monocyclic or bicyclic heteroaryl for A" are an optionally substituted alkyl, an optionally substituted alkoxy, hydroxy, morpholino, etc. More preferable examples are an optionally substituted alkyl (the substituents of the substituted alkyl is a halogen, an alkoxy, morpholino, hydroxy, etc.), a substituted alkoxy (the substituents of the substituted alkoxy is a halogen, an alkoxy, morpholino, hydroxy, etc.), hydroxy, etc., and especially perferable ones are methyl, methoxy, 2-morpholinoethoxy, hydroxy, etc. When $Ar^2$ and A are a substituted phenyl, then the substitution position of these substituents is preferably para-position with respect to the binding position of $W^{13}$ or $W^{21}$, respectively.

Preferable examples of the substituents of the "substituted monocyclic or bicyclic heteroaryl containing 1 to 4 nitrogen atoms as ring-forming atoms for $Ar^1$ and Het", "substituted 3-quinolyl for Het", "substituted 3-naphthyridyl for Het", and "substituted 2-quinoxalyl for Het", and the other substituents of the "substituted aryl and substituted monocyclic heteroaryl for $Ar^1$ " are a halogen, cyano, an optionally substituted alkyl, an optionally substituted alkoxy, etc. More preferable examples are a halogen, an optionally substituted alkyl (the substituent of the substituted alkyl is a halogen, an alkoxy, etc.), a substituted alkoxy (the substituent of the substituted alkyl is a halogen, an alkoxy, etc.), cyano, etc., and especially preferable examples are a halogen, an alkyl, an alkoxy, cyano, etc., and further most preferable examples are chlorine, methyl, cyano, etc. When $Ar^1$ is a substituted phenyl, the substitution position of these substituents is preferably para-position with respect to the binding position of $W^1$.

The substituents of the "substituted $C_1-C_4$ alkyl, substituted $C_2-C_4$ alkenyl, substituted $C_2-C_4$ alkynyl, and substituted $C_1-C_4$ alkoxy, which are substituents for aryl for $Ar^{3}$" are, for example, an alkoxy, an alkoxycarbonyl, an alkanoyl, hydroxy, an alkanoyloxy, a halogen, cyano, a carbamoyl having optionally alkyl-substituent(s), a cyclic aminocarbonyl, carboxy, an amino having optionally alkyl-substituent(s), a cyclic amino, a sulfamoyl having optionally alkyl-substituent(s), a cyclic aminosulfonyl, etc. The number of the substituents of these groups is 1 or more, for example, 2 or 3, and the substituents are the same or different.

In the aryl or monocyclic heteroaryl for $Ar^1$, the ortho- or meta-position with respect to the binding position of $W^1$ means a position adjacent to the binding position of $W^1$ and further a position adjacent thereto, respectively. For example, the ortho-, meta- and para-positions are indicated below in cases wherein $Ar^1$ is phenyl:

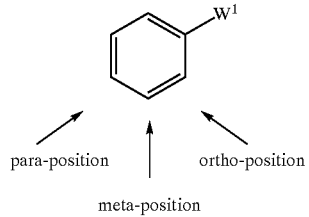

The "halogen" is fluorine, chlorine, bromine, etc.
The "cycloalkanediyl" includes, for example, a $C_3-C_6$ cyclo-alkanediyl, such as 1,2-cyclopropanediyl, 1,2-cyclobutanediyl, 1,2-cyclopentanediyl, 1,2-cyclohexanediyl, 1,3-cyclohexanediyl, 1,4-cyclohexanediyl, etc.

In the "amino having optionally alkyl-substituent(s)", "amino being optionally substituted by an alkoxyalkyl", "carbamoyl having optionally alkyl-substituent(s)", and "sulfamoyl having optionally alkyl-substituent(s)", when these groups are substituted by an alkyl or an alkoxyalkyl, then these groups can be substituted by 1 or 2 alkyls or alkoxyalkyls which are the same or different.

The "cyclic amino" includes a 5- to 7-membered cyclic amino optionally containing an oxygen atom, a sulfur atom or a nitrogen atom as ring-forming atoms, and this cyclic amino may be further substituted by an alkyl, hydroxy, etc., for example, pyrrolidino, piperidino, piperazinyl, 4-methylpiperazinyl, morpholino, thiomorpholino, 4-hydroxypiperidino, etc., and especially preferable cyclic amino is morpholino.

The "prodrug" means a compound, which can be hydrolyzed chemically or biochemically in the living body and converted into the compound of the present invention. For example, when the pyrrole derivative of the present invention has a carboxyl group, then a compound wherein said carboxyl group is converted into a suitable ester group is a prodrug thereof. Preferable examples of the ester are pivaloyloxymethyl ester, acetyloxymethyl ester, cyclohexylacetyloxy-methyl ester, 1-methylcylohexylcarbonyloxymethyl ester, ethyloxycarbonyloxy-1-ethyl ester, cyclohexyloxycarbonyloxy-1-ethyl ester, etc.

The "pharmaceutically acceptable salt" includes, for example, an alkali metal salt such as sodium salt, potassium salt, etc., an alkaline earth metal salt such as calcium salt, magnesium salt, etc., an inorganic metal salt such as zinc salt, a salt with an organic base such as triethylamine, triethanolamine, trihydroxymethylaminomethane, amino acid, etc., when the pyrrole derivatives of the present invention or a pharmaceutically acceptable salt thereof have an acidic group. When the pyrrole derivatives of the present invention or a pharmaceutically acceptable salt thereof have a basic group, the pharmaceutically acceptable salt includes, for example, a salt with an inorganic acid such as hydrochloride, hydrobromide, sulfate, phosphate, nitrate, etc., a salt with an organic acid such as acetate, propionate, succinate, lactate, malate, tartrate, citrate, maleate, fumarate, methanesulfonate, p-toluenesulfonate, benzenesulfonate, ascorbate, etc.

The pyrrole derivatives of the present invention and a pharmaceutically acceptable salt thereof exhibit TGF-β inhibitory activity and are useful as a fibrosis inhibitor for organs or tissues. To be more precise, the present compounds are useful as a medicament for treating the following diseases, which is caused by the fibrosis of organs or tissues.

Kidney diseases: diabetic renal disease, glomerular nephritis, tubulointerstitial nephritis, hereditary renal disease
Respiratory diseases: interstitial pneumonia, chronic obstructive pulmonary disease, asthma
Digestive diseases: cirrhosis hepatis, chronic pancreatitis, scirrhousgastric cancer
Cardiovascular diseases: myocardial fibrosis, restenosis after PTCA, arteriosclerosis
Bone-joint diseases: myelofibrosis, arthrorheumatism
Skin diseases: post-surgical scarring, burn scarring, keloid, hypertrophic scar, atopic dermatitis, scleroderma
Obstetrics diseases: uterus myoma
Urinary diseases: prostatomegaly
Other diseases: Alzheimer's disease, sclerosing peritonitis, diabetic retinopathy, type 1 diabetes mellitus, Post-surgical organ adhesion The pyrrole derivatives of the present invention may be prepared, for example, by the following process.

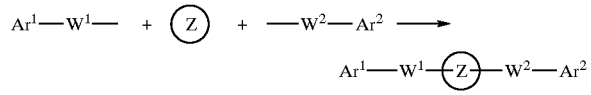

wherein Ring Z, $W^2$, $Ar^2$, $W^1$ and $Ar^1$ are as defined above.

The present pyrrole derivatives can be prepared by binding the groups of $Ar^1$—$W^1$— and $Ar^2$—$W^2$— to Ring Z. The binding reaction of the groups $Ar^1$—$W^1$— and $Ar^2$—$W^2$— with Ring Z is carried out, for example, by the following reactions.

(1) Friedel-Crafts reaction
(2) Reaction of a compound having a multiple bond between carbon and carbon or an organic metal compound with an organic halide in the presence of a palladium catalyst
(3) Nucleophilic substitution to a corresponding organic halide
(4) Reaction of a carbonyl compound with an organic metal compound
(5) Reaction of a carboxylic acid derivative with an organic metal compound
(6) Wittig reaction, Horner-Emmons reaction These reactions are listed just for illustration, and the present derivatives can also be prepared by other processes, based on the knowledge of a skilled person in the organic synthesis. Besides, in this process, firstly the groups for $W^2$ or $W^1$ are bound to Ring Z, and then the groups for $Ar^1$ or $Ar^2$ are bound to the resultant. The method for binding these groups can be the same ones as those for the reaction with Ring Z as mentioned above.

In each reaction as mentioned above, a function group can be protected if necessary. The protecting groups to be employed, and the conditions for protection or deprotection are disclosed in detail in the literature of Greene, et al., (T. W. Greene and P. G. M. Wuts, "Protecting Groups in Organic Synthesis", 1991, JOHN WILEY & SONS, INC.)

Double bond, hydroxy group and carbonyl group, etc. being produced in each reaction as mentioned above are subjected to hydrogenolysis, reduction, oxidization, etc., if necessary. Besides, after each reaction as mentioned above, function groups may be converted into other function groups. The conversion reaction of these function groups is carried out, for example, according to the following articles.

Jikken Kagaku Koza (in Japanese, i.e, Experimental Chemical Lecture), vol. 19–26 (1992, MARUZEN CO., LTD.)

Seimitsu-Yuki-Gosei (in Japanese, i.e., Fine Organic Synthesis) (1993, Nankodo, Co., Ltd.)

Compendium of Organic Synthetic Methods, Vol. 1–9 (John Wiley & Sons)

Comprehensive Organic Synthesis, Vol. 1–9 (1991, Pergamon Press)

Comprehensive Organic Transformations (1989, VCH Publishers)

Survey of Organic Syntheses, Vol. 1–2 (1970, 1977, John Wiley & Sons)

For example, the reduction of the hydroxy group existing at the 1-position of the alkylene bound to Ring Z is carried out by using a combined reducing agent such as sodium borohydride/isopropanol, triethylsilane/trifluoroacetic acid, etc. The reaction solvent is, for example, tetrahydrofuran (THF), dioxane, dichloromethane, chloro-benzene, etc., and the reaction is carried out at a temperature of from about −20° C. to a boiling point of the solvent to be used. The reduction of carbonyl into methylene is carried out, for example, by using a combined reducing agent such as sodium borohydride/isopropanol, hydrazine/potassium hydroxide or sodium hydroxide, zinc amalgam/hydrochloric acid, etc. The reaction solvent is, for example, THF, dioxane, etc., and the reaction is carried out at a temperature of from 0° C. to a boiling point of the solvent to be used.

For example, the oxidization of hydroxy group existing at the 1-positin of the alkylene bound to Ring Z is carried out by using an oxidizing reagent such as manganese dioxide, etc., a composite oxidizing reagent such as 4-methylmorpholine-4-oxide/tetra-n-propylammonium perruthenate, etc. The reaction solvent is, for example, THF, dioxane, dichloromethane, chlorobenzene, chloroform, etc., and the reaction is carried out at a temperature of from about 0° C. to a boiling point of the solvent to be used.

(1) Friedel-Crafts reaction

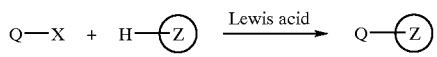

wherein Ring Z is as defined above, Q is an organic group, and X is a chlorine, bromine, etc.

The Friedel-Crafts reaction is carried out, for example, according to J. Org. Chem., 48, 3214–3219 (1983), to introduce Q- on the carbon atom of Ring Z. In this reaction, preferable Q-X is, for example, an alkyl halide, an acid halide, etc. The reaction is carried out in the presence of a Lewis acid such as $AlCl_3$, $BF_3.OEt_2$, $ZnCl_2$, $SnCl_4$, etc., in an inert solvent such as dichloromethane, dichloroethane, etc. and usually at a temperature of from room temperature to a boiling point of the solvent to be used.

When Ring Z is pyrrole ring, indole ring, pyrazole ring or imidazole ring, the Friedel-Crafts reaction is preferably carried out by firstly protecting the nitrogen atom at the 1-position with a phenyl-sulfonyl (or toluylsulfonyl) moiety. When the 1-position is protected with phenylsulfonyl moiety, the reaction is carried out, for example, by reacting with phenylsulfonyl chloride, etc. in the presence of a base such as NaH, etc. When Ring Z is a pyrrole ring protected with phenylsulfonyl, the reaction position can be controlled by the kind of a Lewis acid to be used. For example, by using $AlCl_3$, the 3-position is reacted (J. Org. Chem., 48, 3214–3219 (1983)), and by using $BF_3.OEt_2$, the 2-position is reacted. After the Friedel-Crafts reaction, the phenylsulfonyl is removed by hydrolysis. For example, the phenylsulfonyl is removed by reacting in the presence of a base such as sodium hydroxide, potassium hydroxide, etc. in a mixed solvent of water and methanol, ethanol, etc. at a temperature of from room temperature to a boiling point of the solvent to be use.

(2) Reaction of a compound having a multiple bond between carbon and carbon or an organic metal compound with an organic halide in the presence of a palladium catalyst

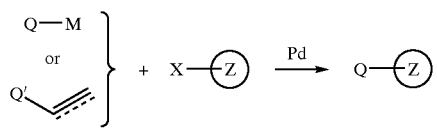

wherein Ring Z, Q and X are as defined above, M is a substituted tin atom, a substituted boron atom, etc., and Q' is a corresponding organic group.

This reaction is carried out, for example, according to the methods disclosed in Synth. Commun., 11, 513 (1981), J. Am. Chem. Soc., 111, 314 (1989), J. Org. Chem., 52, 422 (1987), J. Org. Chem., 37, 2320 (1972), etc. To be more precise, the reaction is carried out by reacting a compound having a multiple bond between carbon and carbon or an organic metal compound with an organic halide in an inert solvent in the presence of a palladium catalyst, a base, etc. The palladium catalyst includes, for example, a palladium (II) catalyst such as $Pd(OAc)_2$, $PdCl_2(PPh_3)_2$, etc., and a palladium (0) catalyst such as $Pd(PPh_3)_4$, $Pd(dba)_2$, etc. The base includes, for example, an inorganic base such as $NaHCO_3$, $K_2CO_3$, etc., an organic base such as $NEt_3$, $iPr_2NEt$, $Et_2NH$, etc., and the reaction can be accelerated by addition of a phosphine ligand such as $PPh_3$, etc., a phase-transfer catalyst such as $BnEt_3NCl$, etc., or an inorganic salt such as CuI, etc. The inert solvent includes, for example, N,N-dimethylformamide (DMF), THF, dioxane, toluene, etc. The reaction temperature is usually in the range of from around room temperature to a boiling point of the solvent to be used.

(3) Nucleophilic substitution to a corresponding organic halide

wherein Ring Z, Q and X are as defined above, M is an alkali metal atom, a magnesium halide, a zinc halide, etc.

This reaction is carried out according to the method disclosed in J. Org. Chem., 26, 3202 (1961). The organic metal compound containing Ring Z can be prepared, for example, by halogen-metal exchange reaction, or by removing hydrogen atom using a base, which is further reacted with Q-X.

When Ring Z is a pyrrole ring, an indole ring, a pyrazole ring or an imidazole ring, the group Q- can be introduced on the nitrogen atom of these rings by reacting in an inert solvent (e.g., THF, ether, DMF, etc.) in the presence of a base (e.g., NaH, KH, potassium t-butoxide, ethyl-magnesium bromide, butyl lithium, lithium 2,2,6,6-tetramethyl-piperidine, etc.). The reaction temperature is in the range of from about 0° C. to about 80° C.

(4) Reaction of a carbonyl compound with an organic metal compound

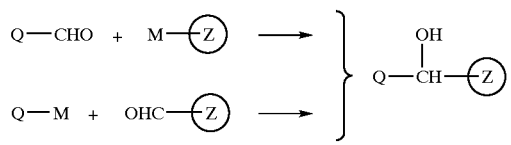

wherein Ring Z, Q and X are as defined above.

This reaction is carried out, for example, by the method disclosed in Tetrahedron, 26, 2239 (1970), J. Org. Chem., 55, 6317 (1990), etc. The organic metal compound in this reaction can be prepared in a similar manner to the preparation of the organic metal compound of the above (3). The organic metal compound thus obtained is reacted, for example, with an aldehyde in an inert solvent (e.g., THF, ether, toluene, etc.). The reaction temperature is in the range of from about −100° C. to room temperature.

(5) Reaction of a carboxylic acid derivative with an organic metal compound

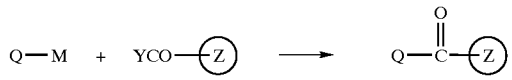

wherein Ring Z, Q and M are as defined above, Y is chlorine, an alkanoyloxy, an alkoxycarbonyloxy, an alkoxy, a dialkylamino, 2-pyridylthio, etc.

This reaction is carried out, for example, by the method disclosed in Org. Lett., 2, 1649 (2000). The organic metal compound in this reaction can be prepared in a similar manner to the preparation of the organic metal compound of the above (3) & (4). The organic metal compound thus obtained is reacted, for example, with a compound having an activated carbonyl group in an inert solvent (e.g., THF, ether, toluene, etc.). The reaction temperature is in the range of from about −100° C. to room temperature.

(6) Wittig reaction, Horner-Emmons reaction

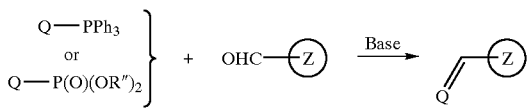

wherein Ring Z and Q are as dfined above, and R" is an alkyl.

This reaction is carried out, for example, by the method disclosed in Tetrahedron, 49, 1343 (1993). To be precise, an organic phosphorus compound (e.g., a phosphonium salt, a phosphoric acid ester, etc.) is treated with a base (e.g., NaH, BuLi, KOtBu, etc.) and reacted with a carbonyl compound in an inert solvent (e.g., THF, ether, dichloro-methane, etc.). The reaction temperature is in the range of from about −100° C. to a boiling point of the solvent to be used.

For example, the following compound 8 is preferably prepared as follows:

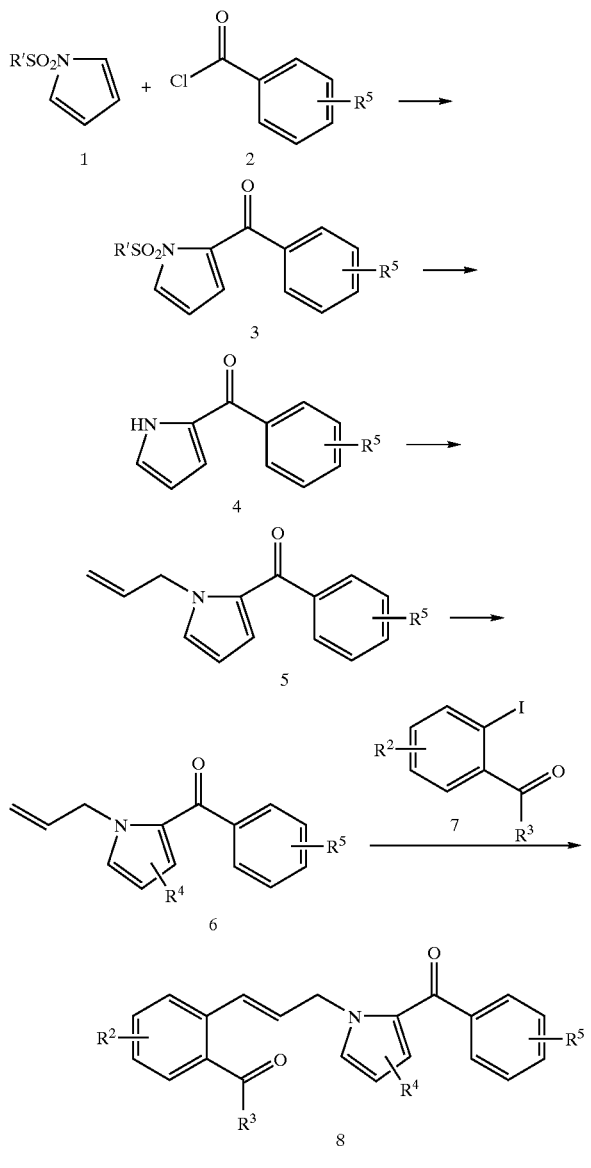

wherein $R^2$, $R^3$, $R^4$ and $R^5$ are as defined above, and R' is phenyl or 4-toluyl.

The compound 3 is prepared by reacting the compound 1 with the compound 2 in the presence of a Lewis acid in an inert solvent, according to J. Org. Chem., 48, 3214–3219 (1983). The 2-position of the pyrrole ring is advantageously preferentially reacted with the compound 2 by using $BF_3 \cdot OEt_2$, $ZnCl_2$, $SnCl_4$ as a Lewis acid. The inert solvent is preferably halogenated hydrocarbons such as dichloromethane, dichloroethane, etc., and the reaction temperature is in the range of from about 0° C. to a boiling point of the solvent to be used, and preferably around room temperature.

The compound 3 is hydrolyzed in the presence of a base to give the compound 4. The base includes NaOH, KOH, etc., and the solvent includes a mixed solvent of dioxane and water, a mixed solvent of methanol and water, etc. The reaction temperature is in the range of from about 50° C. to about 90° C.

The compound 4 is reacted with an allyl halide in an inert solvent in the presence of a base to give the compound 5. The base is preferably KOtBu, etc., and NaH can also be used. The inert solvent includes, for example, THF, DMF, etc., and the reaction temperature is in the range of about 40° C. to about 60° C.

The compound 6 wherein $R^4$ is methyl is prepared by reacting the compound 5 with a Vilsmeier reagent (Org. Synth. Coll. Vol. IV, 831, etc.), followed by subjecting the product to reduction in a halogenated hydrocarbon solvent. The reduction is carried out, for example, by using triethylsilane-trifluoroacetic acid as a reducing agent, etc., and usually at a temperature of from about 0° C. to around room temperature. The compound 6 wherein $R^4$ is an alkyl group other than methyl is prepared by reacting the compound 5 with an alkanoyl halide in the presence of a Lewis acid, followed by reduction of the product. The Lewis acid includes $AlCl_3$, etc., and the reaction is usually carried out at a temperature of from about 0° C. to a boiling point of the solvent to be used.

The compound 8 is prepared by reacting the compound 6 and the compound 7 in the presence of a palladium catalyst and a base in an inert solvent. The palladium catalyst includes a palladium (II) catalyst such as $Pd(OAc)_2$, etc., a palladium (0) catalyst such as $Pd(dba)_2$, etc. The base includes $NaHCO_3$, $K_2CO_3$, triethylamine, etc., and the reaction can be accelerated by addition of a phosphine ligand such as $PPh_3$, etc., a phase-transfer catalyst such as $BnEt_3NCl$, etc. The inert solvent includes DMF, THF, toluene, etc., and the reaction temperature is usually in the range of from room temperature to a boiling point of the solvent to be used.

The present invention also includes hydrates and solvates such as ethanolates of the present pyrrole derivatives, a prodrug thereof, and a pharmaceutically acceptable salt thereof. When the pyrrole derivatives, etc. of the present invention exist in the form of an optical isomer, a stereoisomer, an enatiomer, then the present invention also includes each isomer or a mixture thereof. In order to obtain an optical isomer of the present compound, the present pyrrole derivatives, etc. are converted into a salt with an optically active acid (e.g., mandelic acid, N-benzyloxyalanine, lactic acid, tartaric acid, o-diisopropilidene tartrate, malic acid, camphor sulfonic acid, bromo camphor sulfonic acid, etc.) or an optically active amine (e.g., α-phenethylamine, kinin, quinidine, cinchonidine, cinchonine, strychnine, etc.), and the precipitated crystals are collected by filtration, and further converted into a free compound.

The pyrrole derivative of the present invention, or a prodrug thereof, or a pharmaceutically acceptable salt thereof can be administered either orally or parenterally. The pharmaceutical composition for oral administration includes, for example, tablets, pills, granules, powders, capsules, cachets, liquids, suspensions, emulsions, syrups, etc. The pharmaceutical composition for parenteral administration includes, for example, injections (e.g., intravenous injection, intramuscular injection, etc.), percutaneous formulations (e.g., creams, ointments, lotions, patches, matrixes, etc.), intranasal formulations, rectal formulations (e.g., suppositories, etc.), etc.

These formulations are prepared by a conventional method.

Oral solid preparations such as tablets are prepared, for example, by mixing the present pyrrole derivative, etc., with excipients (e.g., lactose, D-mannitol, sugar, corn starch, cellulose, calcium hydrogen-phosphate, etc.), disintegrants (e.g., calcium carmerose, low substituted hydroxypropyl cellulose, crosscarmerose sodium, sodium carboxy-methyl starch, carboxymethylcellulose sodium, starch sodium glycolate, etc.), binders (e.g., polyvinylpyrrolidone, polyvinyl alcohol, hydroxy-propylcellulose, hydroxypropylmethylcellulose, methyl cellulose, etc.), lubricants (e.g., magnesium stearate, talc, magnesium stearate, etc.), flavors and corrigents, stabilizers, coloring agents, etc., and formulated into tablets, granules, powders, capsules, etc. by a conventional method.

Oral liquid preparations are prepared, for example, by adding the present pyrrole derivative, etc. into water, and further adding thereto a coloring agent, a flavor, a stabilizer, a sweetening agent, a solubilizer, a thickening agent, etc. if necessary. The thickening agent includes, for example, a pharmaceutically acceptable natural or synthesized gum, resin, methyl cellulose, sodium carboxymethyl cellulose, or a conventional suspending agent, etc.

Injections are prepared by dissolving or suspending the present pyrrole derivative, etc. into a pharmaceutically acceptable carrier such as water, a physiological saline, an oil, aqueous glucose solution, etc., and further adding thereto as a coadjuvant a pH adjuster, a buffer, a stabilizer, a solubilizing agent, an emulsifier, etc. if necessary.

The dosage and the frequency of administration of the present pyrrole derivative, etc. may vary according to the diseases, ages, weights of the patients and the administration form, etc., but the present compounds can usually be administered orally in a dose of about 1 to about 500 mg per day, preferably in a dose of about 3 to about 300 mg per day, especially preferably in a dose of about 5 to about 100 mg per day, in adult (body weight: 60 kg), once a day, or divided into several dosage units. When the present compound is administered in an injection preparation, the dosage thereof is in the range of about 0.1 to about 300 mg per day, preferably in the range of about 1 to about 100 mg per day, in an adult (body weight: 60 kg), once a day, or divided into several dosage units, or continuously.

EXAMPLES

The present invention is illustrated by the following Examples, but should not be construed to be limited thereto.

Reference Example 1

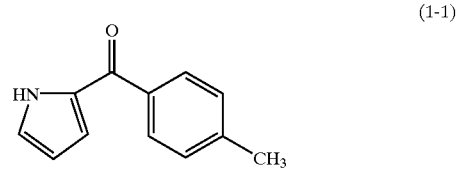

(1-1)

Under nitrogen atmosphere, to a solution of 1-benzenesulfonyl-1H-pyrrole (283.9 g) in methylene chloride (1.0 L) were added p-toluoyl chloride (318 g) and boron trifluodie ether complex (350 g), and the mixture was allowed to stand at room temperature for 7 days. The reaction solution was washed twice with 1N hydrochloric acid (750 mL), washed with 1N aqueous sodium hydroxide solution (750 mL) and a saturated brine (100 mL), dried, and filtered. The filtrate was concentrated to about a half volume thereof under atmospheric pressure, and thereto was added hexane (500 mL). The mixture was further concentrated, and methylene chloride was evaporated off. The resultant was cooled to 10° C., and the precipitated crystals were collected by filtration, washed with hexane and toluene, and dried to give (1-benzenesulfonyl-1H-pyrrol-2-yl) (4-methylphenyl) ketone (315 g, 71%).

$^1$H NMR (CDCl$_3$, 300 MHz) δ 8.12 (d, 2H, J=8.3 Hz), 7.75–7.78 (m, 1H), 7.72 (brd, 2H, J=7.9 Hz), 7.65 (brt, 1H, J=7.9Hz), 7.58 (brt, 2H, J=7.9 Hz), 7.25 (d, 2H, J=8.3 Hz), 6.69–6.72 (m, 1H), 6.35 (dd, 1H, J=3.1 and 0.5 Hz), 2.42 (s, 3H).

(1-2)

The compound (145 g) obtained in Reference Example 1-1 was suspended in methanol (1.0 L), and thereto was added a 5N NaOH (1.1 kg), and the mixture was refluxed for 30 minutes to give a homogenous solution. This solution was gradually cooled to 0° C., and the precipitated crystals were collected by filtration, and dried to give (1H-pyrrol-2-yl)(4-methylphenyl)ketone (80 g, 97%).

$^1$H NMR (CDCl$_3$, 300 MHz) δ 9.52 (brs, 1H), 8.25 (d, 2H, J=8.3 Hz), 7.29 (d, 2H, J=8.3 Hz), 7.12 (brs, 1H), 6.88–6.91 (m, 1H), 6.32–6.36 (m, 1H), 2.44 (s, 3H).

Reference Example 2

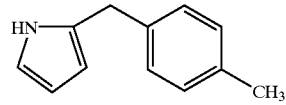

The compound (600 mg) obtained in Reference Example 1-2 and sodium borohydride (492 mg) were refluxed for 3 hours in 2-propanol (15 g). The reaction solution was cooled to room temperature, and thereto was added water (3 mL), and concentrated. The residue was dissolved in ether, washed with water, dried, treated with activated carbon, filtered, and the filtrate was concentrated. The residue was purified by silica gel column chromatography to give the title compound (465 mg, 84%) as a colorless liquid.

$^1$H NMR (CDCl$_3$, 300 MHz) δ 7.42 (brs, 1H), 7.10 (d, 2H, J=8.1 Hz), 7.08 (d, 2H, J=8.1 Hz), 6.63 (brs, 1H), 6.11–6.17 (m, 1H), 5.98 (s, 1H), 3.93 (brs, 2H), 2.32 (s, 3H).

Reference Example 3

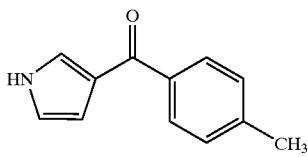
(3-1)

Under nitrogen atmosphere, to a suspension of aluminum chloride (4.62 g) in dichloroethane (50 mL) was added a solution of p-toluoyl chloride (4.91 g) in dichloroethane (5 mL) at room temperature over a period of 10 minutes. After stirring for 30 minutes, to the mixture was added a solution of 1-benzenesulfonyl-1H-pyrrole (6.00 g) in dichloroethane (10 mL) over a period of 10 minutes. The mixture was stirred at room temperature for 2 hours, and the reaction mixture was poured into ice water, and the aqueous layer was extracted twice with methylene chloride. The organic layers were combined, dried, filtered and concentrated. The residue was purified by silica gel column chromatography to give (1-benzenesulfonyl-1H-pyrrol-2-yl)(4-methyl-phenyl) ketone (9.9 g, 100%).

$^1$H NMR (CDCl$_3$, 300 MHz) δ7.89 (brd, 2H, J=7.9 Hz), 7.73 (d, 2H, J=8.0 Hz), 7.65 (brt, 1H, J=7.9 Hz), 7.65 (brs, 1H), 7.34 (brt, 2H, J=7.9 Hz), 7.29 (d, 2H, J=8.0 Hz), 7.22 (dd, 1H, J=2.2 and 2.8 Hz), 6.80 (dd, 1H, J=1.5 and 2.8 Hz), 2.44 (s, 3H).

(3-2)

The compound (6.50 g) obtained in Reference Example 3-1 and 5N aqueous NaOH solution (70 mL) and THF (70 mL) were stirred at 45° C. for 6 hours. The organic layer was concentrated till the solvent was reduced to 5 mL, and then allowed to stand at room temperature for 2 days. The precipitated crystals were collected by filtration to give (1H-pyrrol-3-yl) (4-methylphenyl) ketone (3.1 g, 84%).

$^1$H NMR (CDCl$_3$, 300 MHz) δ 7.76 (d, 2H, J=8.1 Hz), 7.35 (brquint., 1H, J=1.5 Hz), 7.26 (d, 2H, J=8.1 Hz), 6.84 (brq, 1H, J=1.5 Hz), 6.76 (brs, 1H), 2.43 (s, 3H).

Example 1

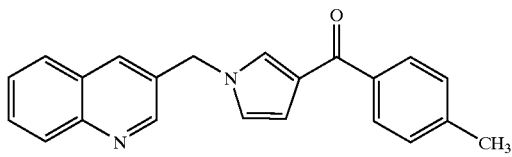

A solution of 3-methylquinoline (275 mg), N-bromosuccinimide (343 mg) and 2,2'-azobis(isobutyronitrile) (31.6 mg) in carbon tetrachloride (8.0 g) was heated under reflux for 2 hours. The mixture was cooled to room temperature, and the insoluble materials were removed by filtration, and thereto was added toluene, and the mixture was concentrated under reduced pressure. To the residue was added toluene (5 mL) to give a solution of 3-bromomethylquinoline in toluene. To a 60% suspension of NaH (70 mg) in THF (2 mL) was added dropwise a solution of the compound (300 mg) obtained in Reference Example 3-2 in THF (3 mL). To the solution was added the solution of 3-bromo-methylquinoline in toluene as mentioned above, and the mixture was stirred at 35° C. for one hour. Water was added to the reaction solution, and the organic layer was separated, dried, filtered and concentrated. The residue was purified by silica gel column chromatography to give the title compound (460 mg, 74%).

$^1$H NMR (CDCl$_3$, 300 MHz) δ 8.77 (d, 1H, J=2.2 Hz), 8.11 (d, 1H, J=8.6 Hz), 7.86 (brs, 1H), 7.71–7.81 (series of m, 2H), 7.75 (d, 2H, J=8.1 Hz), 7.57 (brt, 1H, J=8.0 Hz), 7.34 (brt, 1H, J=1.8 Hz), 7.25 (d, 2H, J=8.1 Hz), 6.75 (brs, 1H), 6.74 (brs, 1H), 5.26 (s, 2H), 3.38 (s, 3H).

Example 2

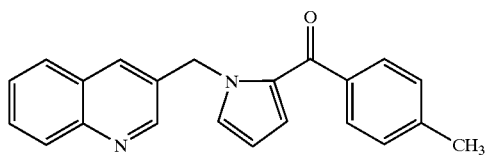

The title compound was obtained from 3-methylquinoline and the compound obtained in Reference Example 1 in a similar manner to Example 1.

$^1$H NMR (CDCl$_3$, 300 MHz) δ 8.81 (d, 1H, J=2.2 Hz), 8.06 (d, 1H, J=8.6 Hz), 7.93 (brs, 1H), 7.74 (brd, 1H, J=8.1 Hz), 7.68 (d, 2H, J=8.1 Hz), 7.66 (brt, 1H, J=8.1 and 1.1 Hz), 7.51 (ddd, 1H, J=8.6, 8.1 and 1.1Hz), 7.23 (d, 2H, J=8.1 Hz), 7.10 (dd, 1H, J=1.7 and 2.6 Hz), 6.82 (dd, 1H, J=1.7 and 4.0 Hz), 6.26 (dd, 1H, J=2.6 and 4.0 Hz), 5.84 (s, 2H), 2.38 (s, 3H).

Example 3

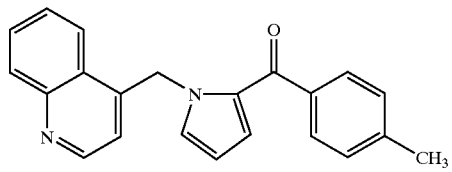

The title compound was obtained from 4-methylquinoline and the compound obtained in Reference Example 1 in a similar manner to Example 1.

$^1$H NMR (CDCl$_3$, 300 MHz) δ 8.78 (d, 1H, J=4.6 Hz), 8.14 (brd, 1H, J=7.7 Hz), 8.04 (brd, 1H, J=8.4 Hz), 7.74 (ddd, 1H, J=8.4, 7.7 and 1.5 Hz), 7.71 (d, 2H, J=8.1 Hz), 7.61 (ddd, 1H, J=8.4, 7.7 and 1.3 Hz), 7.24 (d, 2H, J=8.1 Hz), 7.00 (dd, 1H, J=1.7 and 2.6 Hz), 6.91 (dd, 1H, J=1.7 and 4.0 Hz), 6.33 (dd, 1H, J=2.6 and 4.0 Hz), 6.18 (s, 2H), 2.41 (s, 3H).

Example 4

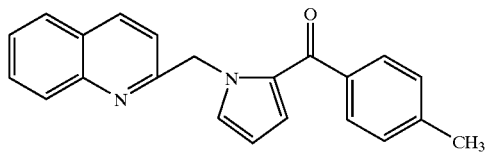

After converting 2-chloromethylquinoline hydrochloride into a free compound, the title compound was obtained from the free compound and the compound obtained in Reference Example 1 in a similar manner to Example 1.

$^1$H NMR (CDCl$_3$, 300 MHz) δ 8.07 (d, 1H, J=8.4 Hz), 8.06 (brd, 1H, J=8.4 Hz), 8.04 (brd, 1H, J=8.4 Hz), 7.74 (d, 2H, J=8.1 Hz), 7.66–7.79 (m, 2H), 7.50 (ddd, 1H, J=8.4, 7.7 and 1.3 Hz), 7.25 (d, 2H, J=8.1 Hz), 7.17 (d, 1H, J=8.4 Hz), 7.15 (dd, 1H, J=1.7 and 2.6 Hz), 6.83 (dd, 1H, J=1.7 and 4.0 Hz), 6.26 (dd, 1H, J=2.6 and 4.0 Hz), 5.94 (s, 2H), 2.42 (s, 3H).

Example 5

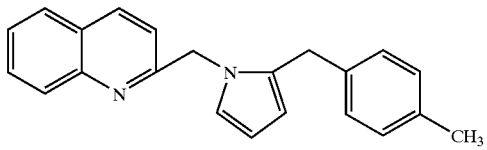

After converting 2-chloromethylquinoline hydrochloride into a free compound, the title compound was obtained from the free compound and the compound obtained in Reference Example 2 in a similar manner to Example 1.

$^1$H NMR (CDCl$_3$, 300 MHz) δ 8.03 (brd, 1H, J=8.4 Hz), 7.96 (d, 1H, J=8.4 Hz), 7.76 (brd, 1H, J=8.4 Hz), 7.72 (ddd, 1H, J=8.4, 7.5 and 1.3 Hz), 7.52 (ddd, 1H, J=8.4, 7.5 and 1.3 Hz), 6.95 (d, 2H, J=8.1 Hz), 6.93 (d, 2H, J=8.1 Hz), 6.74 (dd, 1H, J=1.7 and 2.6 Hz), 6.60 (d, 1H, J=8.4 Hz), 6.20 (dd, 1H, J=1.7 and 4.0 Hz), 6.00 (dd, 1H, J=2.6 and 4.0 Hz), 5.26 (s, 2H), 3.81 (brs, 2H), 2.20 (s, 3H).

Example 6

(6-1)

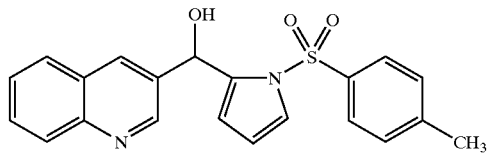

To a suspension of 60% NaH (3.13 g) in THF (20 mL) was added dropwise a solution of pyrrole (5.00 g) in THF (20 mL). The mixture was stirred for 30 minutes, and thereto was added a solution of p-toluene sulfonylchloride (14.2 g) in THF (20 mL), and the mixture was stirred at room temperature for 3 hours. Water was added to the reaction solution, and the organic layer was separated, dried, filtered, and concentrated. The residue was recrystallized from a mixed solvent of methanol and water (each 35 mL), and the resulting crystals were collected by filtration, and dried to give 1-p-toluenesulfonyl-1H-pyrrole (16.3 g, 99%).

$^1$H NMR (CDCl$_3$, 300 MHz) δ 7.73 (dt, 2H, J=8.4 and 2.0 Hz), 7.27 (dt, 2H, J=8.4 and 2.0 Hz), 7.15 (dd, 2H, J=2.2 and 2.4 Hz), 6.28 (dd, 2H, J=2.2 and 2.4 Hz), 2.40 (s, 3H).

(6-2)

A solution of 2,2,6,6-tetramethylpiperidine (1.34 g) in THF (20 mL) was cooled to −70° C. under nitrogen atmosphere, and thereto was added dropwise a 1.5 M n-butyl lithium in hexane (6.40 mL), and the mixture was stirred for 20 minutes. To the solution was added dropwise a solution of the compound (2.0 g) obtained in Example 6-1 in THF (10 mL) over a period of 15 minutes, and the mixture was stirred at −70° C. for one hour to give a solution of the lithiatied compound of Example 6-1. A solution of 3-quinolinecarboxyaldehyde (1.42 g) in THF (10 mL) was cooled to −78° C., and thereto was added dropwise a solution of the lithiatied compound of Example 6-1 via a cannula. The mixture was warmed to room temperature, and thereto was added water. The aqueous layer was extracted twice with ethyl acetate, and the combined organic layer was dried, filtered, and concentrated. The residue was purified by silica gel column chromatography to give (1-p-toluenesulfonyl-1H-pyrrol-2-yl)(3-quinolyl)methanol (1.68 g, 49%) and (1H-pyrrol-2-yl)(3-quinolyl)methanol (150 mg, 7.4%).

(1-p-toluenesulfonyl-1H-pyrrol-2-yl)(3-quinolyl)methanol:

$^1$H NMR (CDCl$_3$, 300 MHz) δ 8.55 (d, 1H, J=2.2 Hz), 8.04 (d, 1H, J=2.2 Hz), 8.02 (brd, 1H, J=8.4 Hz), 7.62–7.72 (m, 2H), 7.52 (brt, 1H, J=7.0 Hz), 7.49 (d, 2H, J=8.4 Hz), 7.37 (dd, 1H, J=3.1 and 1.7 Hz), 7.07 (brd, 2H, J=8.4 Hz), 6.30 (brs, 1H), 6.21 (t, 1H, J=3.5 Hz), 5.94 (brquint., 1H, J=1.7 Hz), 4.25 (brs, 1H), 2.25 (s, 3H).

(1H-pyrrol-2-yl)(3-quinolyl)methanol:

$^1$H NMR (CDCl$_3$, 300 MHz) δ 8.87 (d, 1H, J=2.0 Hz), 8.19 (brs, 1H), 8.08 (brd, 1H, J=8.4 Hz), 7.79 (brd, 1H, J=8.4 Hz), 7.70 (brt, 1H, J=8.4 Hz), 7.55 (brt, 1H, J=8.4 Hz), 6.80 (brd, 1H, J=1.5 Hz), 6.16 (brq, 1H, J=2.8 Hz), 6.11 (brs, 1H), 6.04 (brs, 1H).

Example 7

(7-1)

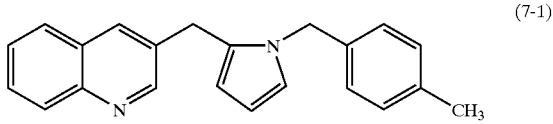

To a solution of (1H-pyrrol-2-yl)(3-quinolyl)methanol (40.0 mg) in 2-propanol (3 mL) was added sodium borohydride (33.9 mg), and the mixture was refluxed for one hour. To the mixture was added water, and the mixture was concentrated. The residue was separated using water and ethyl acetate, and the organic layer was dried, filtered, and concentrated. The residue was purified by silica gel column chromatography to give 2-(3-quinolylmethyl)-1H-pyrrole (30.0 mg, 75%).

$^1$H NMR (CDCl$_3$, 300 MHz) δ 8.68 (d, 1H, J=2.2 Hz), 8.57 (brs, 1H), 8.04 (d, 1H, J=8.4 Hz), 7.86 (brs, 1H), 7.69 (brd, 1H, J=8.1 Hz), 7.63 (ddd, 1H, J=8.4, 7.0 and 1.5 Hz), 7.49 (ddd, 1H, J=8.1, 7.0 and 1.1 Hz), 6.75 (brdd, 1H, J=2.9 and 4.0 Hz), 6.18 (brq, 1H, J=2.9 Hz), 6.04 (brs, 1H), 4.12 (s, 2H).

(7-2)

To a suspension of 60% NaH (5.3 mg) in DMF (1 mL) was added dropwise a solution of the compound of Example 7-1 (25.0 mg) in DMF (1.5 mL) at room temperature under nitrogen atmosphere. The mixture was stirred for 30 minutes, and thereto was added a solution of p-methylbenzyl bromide (26.6 mg) in DMF (1 mL), and the mixture was stirred at room temperature for 30 minutes. Water was added to the reaction solution, and the mixture was extracted with diethyl ether, and the ether layer was dried, filtered, and concentrated. The residue was purified by silica gel column chromatography to give 1-(4-methyl-benzyl)-2-(3-quinolylmethyl)-1H-pyrrole (8.0 mg, 21%).

$^1$H NMR (CDCl$_3$, 300 MHz) δ 8.70 (d, 1H, J=2.2 Hz), 8.06 (brd, 1H, J=8.4 Hz), 7.70 (d, 1H, J=1.7 Hz), 7.66 (d, 1H, J=8.2 Hz), 7.59–7.65 (m, 1H), 7.49 (ddd, 1H, J=8.2, 7.0 and 1.1 Hz), 7.01 (brd, 2H, J=8.4 Hz), 6.81 (brd, 2H, J=8.4 Hz), 6.72 (brt, 1H, J=2.4 Hz), 6.17 (t, 1H, J=3.0 Hz), 5.97 (brs, 1H), 4.92 (s, 2H), 3.99 (s, 2H), 2.23 (s, 3H).

Example 8

(8-1)

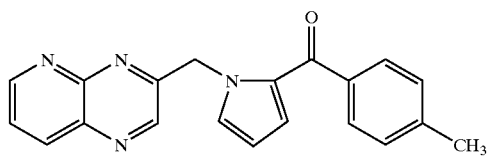

2,3-Diaminopyridine (2.0 g) and a 40% aqueous pyruvic aldehyde solution (3.30 g) were refluxed in ethanol for 20 minutes. The reaction solution was concentrated, and the residue was recrystallized from 2-propanol, collected by filtration, and dried to give 3-methylpyrido[2,3-b]pyrazine (1.61 g, 60%).

$^1$H NMR (CDCl$_3$, 400 MHz) δ 9.15 (dd, 1H, J=4.2 and 1.9 Hz), 8.85 (s, 1H), 8.45 (dd, 1H, J=8.3 and 1.9 Hz), 7.68 (dd, 1H, J=8.3 and 4.2 Hz), 2.88 (s, 3H).

(8-2)

The title compound was obtained from the compound of Example 8-1 and the compound of Reference Example 1 in a similar manner to Example 1.

$^1$H NMR (CDCl$_3$, 400 MHz) δ 9.17 (dd, 1H, J=4.2 and 1.9 Hz), 8.88 (s, 1H), 8.46 (dd, 1H, J=8.3 and 1.9 Hz), 7.72 (dd, 1H, J=8.3 and 4.2 Hz), 7.71 (d, 2H, J=8.0 Hz), 7.27 (dd, 1H, J=2.6 and 1.6 Hz), 7.25 (d, 2H, J=8.0 Hz), 6.87 (dd, 1H, J=4.1 and 1.6 Hz), 6.31 (dd, 1H, J=4.1 and 2.6 Hz), 6.01 (s, 2H), 2.42 (s, 3H).

Example 9

(9-1)

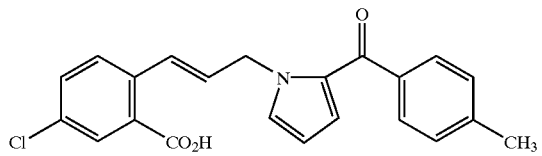

To a solution of methyl 2-bromo-5-chlorobenzoate (6.30 g), tri-o-tolylphosphine (P(o-tol)$_3$) (770 mg), tri-n-butylamine (9.38 g) and acrylic acid (3.64 g) in toluene (20 mL) was added palladium acetate (284 mg) under nitrogen atmosphere, and the mixture was heated at 110° C. for 3 hours. The mixture was washed with 1N HCl, dried, filtered, and concentrated. The residue was purified by silica gel column chromatography, and the fractions containing the desired compound were combined, dissolved in ethyl acetate, and extracted with a saturated aqueous sodium hydrogen carbonate solution. The aqueous layer was acidified with hydrochloric acid, extracted with ethyl acetate, and the organic layer was dried, filtered, and concentrated to give 2-(4-chloro-2-methoxycarbonylphenyl)acrylic acid (4.0 g, 66%).

$^1$H NMR (CDCl$_3$, 400 MHz) δ 8.51 (d, 1H, J=15.9 Hz), 7.98 (d, 1H, J=1.9 Hz), 7.58 (d, 1H, J=8.4 Hz), 7.53 (dd, 1H, J=8.4 and 1.9 Hz), 6.31 (d, 1H, J=15.9 Hz), 3.95 (s, 3H).

(9-2)

To a solution of 2-(4-chloro-2-methoxycarbonylphenyl) acrylic acid (1.40 g) and triethylamine (705 mg) in THF (20 mL) was added dropwise a solution of ethyl chloroformate (694 mg) in THF (10 mL) at 0° C. under nitrogen atmosphere. The mixture was stirred for 30 minutes, and the insoluble materials were removed by filtration to give a solution of a mixed acid anhydride. To a solution of sodium borohydride (212 mg) in THF (10 mL) and (5 mL) was added dropwise 93% of the solution of mixed acid anhydride prepared above at 0° C. under nitrogen atmosphere. To the solution was added sodium borohydride (210 mg). To the reaction solution was added 3N HCl, and the mixture was extracted with diethyl ether. The extract was washed with a saturated aqueous sodium hydrogen carbonate solution, dried, filtered, and concentrated to give 3-(4-chloro-2-methoxycarbonyl-phenyl)propenol (880 mg, 70%, containing a saturate compound in about 15%).

$^1$H NMR (CDCl$_3$, 400 MHz) δ 7.88 (d, 1H, J=2.2 Hz), 7.50 (d, 1H, J=8.5 Hz), 7.44 (dd, 1H, J=8.5 and 2.2 Hz), 7.35 (brd, 1H, J=15.9 Hz), 6.26 (dt, 1H, J=15.9 and 5.6 Hz), 4.36 (brd, 2H, J=5.6 Hz), 3.91 (s, 3H).

(9-3)

To a solution of the compound (870 mg) of Example 9-2 and triphenylphosphine (PPh$_3$) (1.01 g) in methylene chloride (20 mL) was added N-bromosuccinimide (683 mg) at 0° C. in portions. The mixture was stirred for 10 minutes, and the reaction solution was concentrated, and the residue was purified by silica gel column chromatography to give a bromide (942 mg, 85%). To a suspension of 60% NaH (167 mg) in THF (5 mL) was added dropwise a solution of the compound (774 mg) of Reference Example 1 in THF (15 mL). To the solution was slowly added dropwise a solution of the above bromide (930 mg) in THF (20 mL), which was previously heated to 55° C. The mixture was stirred for 2 hours, and thereto was added 3N HCl. The mixture was extracted with diethyl ether, and the extract was dried, filtered, and concentrated. The residue was purified by silica gel column chromatography to give a mixture of a methyl ester of the title compound and the comound of Reference Example 1 (1.4 g, molar ratio; 3:7). This mixture was e dissolved in a mixture of THF (7 mL) and methanol (7 mL), and thereto was added 1N aqueous NaOH solution (7 mL), and the mixture was stirred at 40° C. for 15 minutes under nitrogen atmosphere. The organic solvent was evaporated under reduced pressure, and the residue was washed with ether. The ether layer was extracted twice with 1N aqueous NaOH solution, and the combined aqueous layer was washed with hexane and acidified with hydrochloric acid. The resultant was extracted with ethyl acetate, dried, treated with activated carbon, filtered, and concentrated to give the title compound (320 mg, 60%). To the title compound (596 mg) were added 1N aqueous NaOH solution (1.52 mL) and THF (2 mL), and the mixture was subjected to supersonic treatment. The mixture was concentrated with toluene, and the residue was washed with diethyl ether, and dried to give a sodium salt of the title compound (520 mg, 83%).

$^1$H NMR (DMSO-d$_6$, 400 MHz) δ 7.67 (d, 2H, J=8.1 Hz), 7.46 (brd, 1H, J=16.2 Hz), 7.40 (brd, 1H, J=8.5 Hz), 7.39 (brs, 1H), 7.33 (dd, 1H, J=1.7 and 2.4 Hz), 7.31 (d, 2H, J=8.1 Hz), 7.13 (brdd, 1H, J=8.4 and 2.3 Hz), 6.65 (dd, 1H, J=1.7 and 4.0 Hz), 6.25 (dt, 1H, J=16.2 and 6.4 Hz), 6.20 (dd, 1H, J=2.4 and 4.0 Hz), 5.10 (brd, 1H, J=6.4 Hz), 2.38 (s, 3H).

Example 10

(10-1)

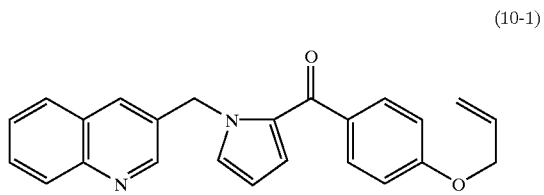

To a mixture of methyl 4-allyloxybenzoate (10.0 g), THF (50 mL) and methanol (50 mL) was added 2N aqueous NaOH solution (50 mL), and the mixture was stirred at 50° C. for 40 minutes. The reaction solution was concentrated to about 50 g, washed with hexane, and acidified with conc. hydrochloric acid. The precipitated crystals were collected by filtration, dissolved in ethyl acetate, dried over magnesium sulfate, and the solvent was evaproated under reduced prssure to give crude crystals of 4-allyloxybenzoic acid (4.68 g, 50%). To the crystals were added dichloroethane (50 mL) and DMF (2 drops), and the mixture was heated to 80° C., and thereto was added dropwise thionyl chloride (4.61 g) over a period of 10 minutes. The mixture was stirred for 30 minutes, and the reaction solution was concentrated to give an oily acid chloride (5.3 g). The compound (3.81 g) of Example 6-1 and the above acid chloride (5.07 g) were dissolved in methylene chloride (50 mL), and thereto was added boron trifluoride diethyl ether complex (4.39 g), and the mixture was allowed to stand at room temperature for 5 days. The reaction solution was washed successively with aqueous hydrochloric acid, water, and aqueous sodium hydroxide solution, dried, filtered, and concentrated. The residue was purified by silica gel chromatography to give a mixture of (1-p-toluenesulfonyl-1H-pyrrol-2-yl) (4-allyloxyphenyl) ketone and 4-allyloxybenzoic acid. This mixture was dissolved in 1N aqueous NaOH solution, and extracted three time with ethyl acetate. The combined oil layer was dried and concentrated to give crude crystals of (1-p-toluenesulfonyl-1H-pyrrol-2-yl) (4-allyloxyphenyl) ketone (5.79 g), which was dissolved in methanol (70 mL), and thereto was added 5N aqueous NaOH solution (70 mL), and the mixture was heated for 1.5 hour. The methanol was evaporated under reduced pressure, and extracted with ethyl acetate, dried, and concentrated. The residue was purified by silica gel column chromatography to give (1H-pyrrol-2-yl) (4-allyloxyphenyl) ketone (2.51 g, 43%).

$^1$H NMR (CDCl$_3$, 400 MHz) δ 9.51(brs, 1H), 7.92 (dt, 2H, J=8.4 and 2.0 Hz), 7.12 (dt, 1H, J=1.3 and 2.7 Hz), 6.99 (dt, 2H, J=8.4 and 2.0 Hz), 6.89 (ddd, 1H, J=3.8, 2.4 and 1.3 Hz), 6.35 (dt, 1H, J=3.8 and 2.7 Hz), 6.08 (ddt, 1H, J=17.3, 10.6 and 5.0 Hz), 5.45 (ddt, 1H, J=17.3, 1.6 and 1.6 Hz), 5.33 (ddt, 1H, J=10.6, 1.6 and 1.6 Hz), 4.63 (ddd, 2H, J=5.0, 1.6 and 1.6 Hz).

(10-2)

The title compound was obtained from 3-methylquinoline and the compound of Example 10-1 in a similar manner to Example 1.

$^1$H NMR (CDCl$_3$, 400 MHz) δ 8.80 (d, 1H, J=2.2 Hz), 8.07 (d, 1H, J=8.4 Hz), 7.92 (d, 1H, J=2.0 Hz), 7.78 (dt, 2H, J=8.4 and 2.0 Hz), 7.76 (brd, 1H, J=8.1 Hz), 7.68 (ddd, 1H, J=8.4, 7.0 and 1.5 Hz), 7.52 (ddd, 1H, J=8.1, 7.0 and 1.1 Hz), 7.09 (dd, 1H, J=1.7 and 2.5 Hz), 6.99 (dt, 2H, J=8.4 and 2.0 Hz), 6.83 (dd, 1H, J=1.7 and 4.0 Hz), 6.28 (dd, 1H, J=2, 5 and 4.0 Hz), 6.06 (ddt, 1H, J=17.3, 10.6 and 5.0 Hz), 5.84 (brs, 2H), 5.43 (ddt, 1H, J=17.3, 1.6 and 1.6 Hz), 5.32 (ddt, 1H, J=10.6, 1.6 and 1.6 Hz), 4.59 (ddd, 2H, J=5.0, 1.6 and 1.6 Hz).

Example 11

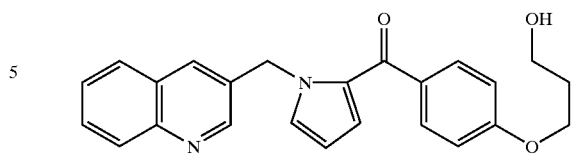

To a solution of 2,3-dimethyl-2-buten (37.8 mg) in THF (1 mL) was added dropwise a solution of borane dimethyl-sulfide complex (31.0 mg) in THF (1.5 mL) at −10° C. over a period of 10 minutes, and the mixture was stirred at the same temperature for 2 hours. To the solution was added a solution of the compound of Example 10 (50.0 mg) in THF (1.5 mL) over a period of 10 minutes, and the mixture was stirred for one hour. To this solution were added a 30% aqueous hydrogen peroxide solution (1 mL) and a 3N aquoues NaOH solution (1 mL), and the mixture was stirred for 30 minutes. The reaction solution was extracted with ethyl acetate, and the organic layer was washed with an aqueous sodium thiosulfate solution, dried, filtered, and concentrated. The residue was purified by silica gel column chromatography to give the compound of Example 11 (24 mg, 46%) and the compound of Example 12 (4.2 mg, 8%).

$^1$H NMR (CDCl$_3$, 400 MHz) δ 8.80 (d, 1H, J=2.2 Hz), 8.07 (d, 1H, J=8.4 Hz), 7.92 (d, 1H, J=2.0 Hz), 7.77 (dt, 2H, J=8.4 and 2.0 Hz), 7.76 (brd, 1H, J=8.1 Hz), 7.67 (ddd, 1H, J=8.4, 7.0 and 1.5 Hz), 7.51 (ddd, 1H, J=8.1, 7.0 and 1.1 Hz), 7.08 (dd, 1H, J=1.7 and 2.5 Hz), 6.91 (dt, 2H, J=8.4 and 2.0 Hz), 6.81 (dd, 1H, J=1.7 and 4.0 Hz), 6.27 (dd, 1H, J=2.5 and 4.0 Hz), 5.82 (brs, 2H), 4.16 (t, 2H, J=6.0 Hz), 3.86 (brt, 2H, J=6.0 Hz), 2.12 (brs, 1H), 2.06 (quint, 2H, J=6.0 Hz).

Example 12

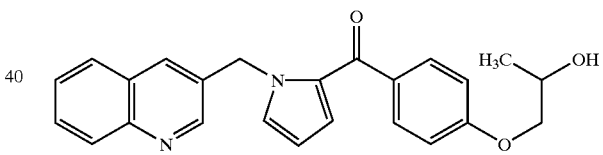

$^1$H NMR (CDCl$_3$, 300 MHz) δ 8.80 (d, 1H, J=2.2 Hz), 8.07 (d, 1H, J=8.4 Hz), 7.93 (d, 1H, J=2.0 Hz), 7.78 (dt, 2H, J=8.4 and 2.0 Hz), 7.76 (brd, 1H, J=8.1 Hz), 7.68 (ddd, 1H, J=8.4, 7.0 and 1.5 Hz), 7.52 (ddd, 1H, J=8.1, 7.0 and 1.1 Hz), 7.10 (dd, 1H, J=1.7 and 2.5 Hz), 6.93 (dt, 2H, J=8.4 and 2.0 Hz), 6.81 (dd, 1H, J=1.7 and 4.0 Hz), 6.28 (dd, 1H, J=2.5 and 4.0 Hz), 5.84 (brs, 2H), 4.23 (brddd, 1H, J=7.7, 6.4 and 3.2 Hz), 3.99 (dd, 1H, J=9.3 and 3.2 Hz), 3.86 (dd, 1H, J=9.3 and 7.7 Hz), 1.30 (d, 3H, J=6.4 Hz).

Example 13

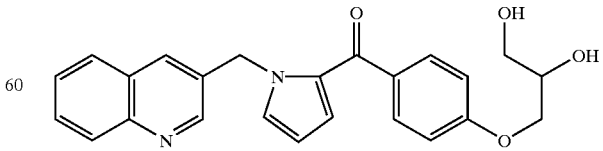

To a solution of the compound (74.0 mg) of Example 10 in (0.5 mL) and acetonitrile (0.5 mL) were added N-methylmorpholine-N-oxide (30.6 mg), osmium tetraoxide microcapsules (purity; 10%, 25.4 mg) and water (0.5 mL), and the mixure was stirred at room temperature for 20 hours. The reaction solution was filtered, and the filtrate was concentrated. The residue was purified by silica gel column chromatography to give the title compound (38.0 mg, 44%).

¹H NMR (CDCl₃, 300 MHz) δ 8.79 (d, 1H, J=2.2 Hz), 8.07 (d, 1H, J=8.4 Hz), 7.92 (d, 1H, J=2.0 Hz), 7.73–7.78 (series of m, 3H), 7.67 (ddd, 1H, J=8.4, 7.0 and 1.5 Hz), 7.51 (ddd, 1H, J=8.1, 7.0 and 1.1 Hz), 7.09 (dd, 1H, J=1.7 and 2.5 Hz), 6.89 (brd, 2H, J=8.4 Hz), 6.80 (dd, 1H, J=1.7 and 4.0 Hz), 6.27 (dd, 1H, J=2.5 and 4.0 Hz), 5.82 (brs, 2H), 4.04–4.16 (m, 3H), 3.84 (dd, 1H, J=11.4 and 3.8 Hz), 3.75 (dd, 1H, J=11.4 and 5.5 Hz).

Example 14

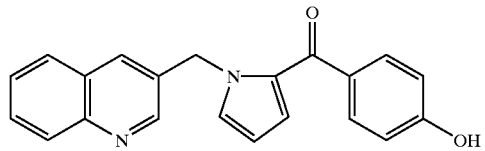

The compound of Example 10 (200 mg) and pyrrolidine (77.2 mg) were dissolved in a mixture of THF (1 mL) and ethanol (3 mL), and thereto was added P(PPh₃)₄ (62.7 mg), and the mixture was stirred at room temperature for 30 minutes. The reaction solution was concentrated, and the residue was purified by silica gel column chromatography to give the title compound (190 mg, 100%).

¹H NMR (CDCl₃, 400 MHz) δ 8.61 (brs, 1H), 8.07 (brd, 1H, J=8.4 Hz), 8.05 (brs, 1H), 7.79 (brd, 1H, J=8.1 Hz), 7.68 (ddd, 1H, J=8.4, 7.0 and 1.5 Hz), 7.66 (dt, 2H, J=8.4 and 2.0 Hz), 7.54 (ddd, 1H, J=8.1, 7.0 and 1.1 Hz), 7.12 (dd, 1H, J=1.7 and 2.5 Hz), 6.81 (dd, 1H, J=1.7 and 4.0 Hz), 6.79 (dt, 2H, J=8.4 and 2.0 Hz), 6.27 (dd, 1H, J=2.5 and 4.0 Hz), 5.86 (brs, 2H).

Example 15

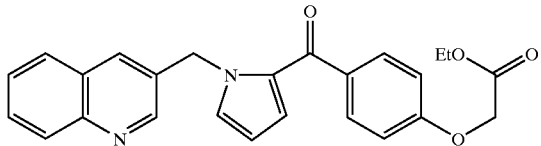

To a suspension of 60% NaH (7.3 mg) in THF (1 mL) was added dropwise a solution of the compound of Example 14 (50.0 mg) in THF (1.5 mL). The mixture was stirred for 30 minutes, and thereto was added a solution of ethyl bromoacetate (29.2 mg) in THF (1 mL), and the mixture was stirred at room temperature for one hour. Water was added to the reaction solution, and the mixture was extracted with ethyl acetate, dried, filtered and concentrated. The residue was purified by silica gel column chromatography to give the title compound (46.4 mg, 74%).

¹H NMR (CDCl₃, 400 MHz) δ8.80 (d, 1H, J=2.2 Hz), 8.07 (d, 1H, J=8.4 Hz), 7.91 (d, 1H, J=2.0 Hz), 7.78 (dt, 2H, J=8.4 and 2.0 Hz), 7.75 (brd, 1H, J=8.1 Hz), 7.68 (ddd, 1H, J=8.4, 7.0 and 1.5 Hz), 7.51 (ddd, 1H, J=8.1, 7.0 and 1.1 Hz), 7.10 (dd, 1H, J=1.7 and 2.5 Hz), 6.92 (dt, 2H, J=8.4 and 2.0 Hz), 6.82 (dd, 1H, J=1.7 and 4.0 Hz), 6.27 (dd, 1H, J=2.5 and 4.0 Hz), 5.83 (brs, 2H), 4.67 (s, 2H), 4.28 (q, 2H, J=7.1 Hz), 1.30 (t, 3H, J=7.1 Hz).

Example 16

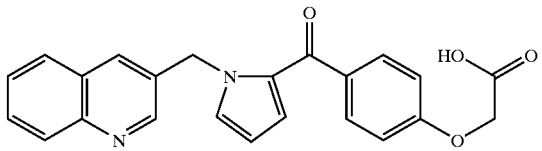

To a mixture of the compound of Example 15 (23.0 mg), THF (1 mL) and methanol (1 mL) was added 1N aqueous NaOH solution (1 mL), and the mixture was stirred at 40° C. for 40 minutes. The reaction solution was concentrated to about 1.0 g, and diluted with water. The mixture was washed with hexane, and acidified with hydrochloric acid. The mixture was extracted with ethyl acetate, dried over magnesium sulfate, and the solvent was evaporated under reduced pressure to give the title compound (19.4 mg, 91%).

¹H NMR (CDCl₃, 400 MHz) δ 8.78 (d, 1H, J=2.2 Hz), 8.12 (d, 1H, J=8.4 Hz), 8.04 (brs, 1H), 7.78 (brd, 1H, J=8.1 Hz), 7.76 (brd, 2H, J=8.4 Hz), 7.68 (ddd, 1H, J=8.4, 7.0 and 1.5 Hz), 7.54 (ddd, 1H, J=8.1, 7.0 and 1.1 Hz), 7.11 (dd, 1H, J=1.7 and 2.5 Hz), 6.93 (brd, 2H, J=8.4 Hz), 6.82 (dd, 1H, J=1.7 and 4.0 Hz), 6.28 (dd, 1H, J=2.5 and 4.0 Hz), 5.81 (brs, 2H), 4.73 (s, 2H).

Example 17

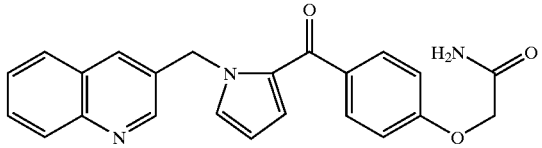

To a suspension of 60% NaH (7.3 mg) in THF (1 mL) was added dropwise a solution of the compound of Example 14 (50.0 mg) in THF (1.5 mL). The mixture was stirred for 30 minutes, and thereto was added 2-bromoacetamide (25.2 mg) in THF (1 mL), and the mixture was stirred at room temperature for one hour. To the reaction solution was added water, and the mixture was extracted twice with ethyl acetate. The organic layer was dried, filtered, and concentrated. The residue was purified by silica gel column chromatography to give the title compound (40.0 mg, 68%).

¹H NMR (CDCl₃, 400 MHz) δ 8.80 (d, 1H, J=2.2 Hz), 8.07 (d, 1H, J=8.4 Hz), 7.92 (d, 1H, J=2.0 Hz), 7.80 (dt, 2H, J=8.4 and 2.0 Hz), 7.76 (brd, 1H, J=8.1 Hz), 7.68 (ddd, 1H, J=8.4, 7.0 and 1.5 Hz), 7.52 (ddd, 1H, J=8.1, 7.0 and 1.1 Hz), 7.12 (dd, 1H, J=1.7 and 2.5 Hz), 6.94 (dt, 2H, J=8.4 and 2.0 Hz), 6.81 (dd, 1H, J=1.7 and 4.0 Hz), 6.55 (brs, 1H), 6.29 (dd, 1H, J=2.5 and 4.0 Hz), 5.92 (brs, 1H), 5.84 (brs, 2H), 4.55 (s, 2H).

Example 18

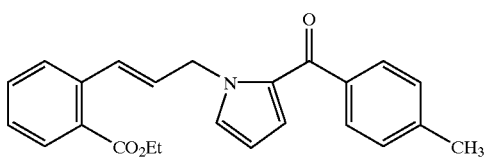

(18-1)

To a solution of ethyl o-bromobenzoate (20.0 g), P(o-tol)$_3$ (2.66 g), triethylamine (17.6 g) and acrylic acid (12.6 g) in toluene (70 mL) was added palladium acetate (980 mg) under nitrogen atmosphere, and the mixture was heated at 110° C. for one hour. The reaction solution was filtered, and extracted with a saturated aqueous sodium hydrogen carbonate solution. The aqueous layer was acidified with hydrochloric acid, extracted with ethyl acetate, dried, filtered, and concentrated to give 3-(2-ethoxycarbonylphenyl)acrylic acid (19.8 g, 103%).

$^1$H NMR (CDCl$_3$, 400 MHz) δ 8.58 (d, 1H, J=15.9 Hz), 7.99 (dd, 1H, J=1.2 and 7.7 Hz), 7.62 (brd, 1H, J=7.7 Hz), 7.56 (dt, 1H, J=1.1 and 7.7 Hz), 7.47 (dt, 1H, J=1.2 and 7.7 Hz), 6.31 (d, 1H, J=15.9 Hz), 4.41 (q, 2H, J=7.2 Hz), 1.42 (t, 3H, J=7.2 Hz).

(18-2)

To a solution of the compound of Example 18-1 (11.7 g) and triethylamine (5.91 g) in THF (150 mL) was added dropwise a solution of ethyl chloroformate (6.34 g) in THF (75 mL) at 0° C. under nitrogen atmosphere. The mixture was stirred for 30 minutes, and the insoluble materials were removed by filtration to give a solution of a mixed acid anhydride. To a solution of sodium borohydride (2.03 g) in THF (10 mL) and water (5 mL) was added dropwise the above solution of the mixed acid anhydride at 0° C. under nitrogen atmosphere. To the solution was added sodium borohydride (2.00 g), and thereto was added 3N HCl, and the mixture was extracted with diethyl ether. The extract was washed with a saturated aqueous sodium hydrogen carbonate solution, dried, filtered, and concentrated to give 3-(2-ethoxycarbonylphenyl)propenol (8.82 g, 81%, containing a saturated compound in about 15%).

$^1$H NMR (CDCl$_3$, 400 MHz) δ 7.89 (dd, 1H, J=1.2 and 7.7 Hz), 7.56 (brd, 1H, J=7.7 Hz), 7.47 (dt, 1H, J=1.1 and 7.7 Hz), 7.38 (brd, 1H, J=15.9 Hz), 7.32 (dt, 1H, J=1.2 and 7.7 Hz), 6.26 (dt, 1H, J=15.9 and 5.6 Hz), 4.36 (brd, 2H, J=5.6 Hz), 4.35 (q, 2H, J=7.2 Hz), 1.39 (t, 3H, J=7.2 Hz).

(18-3)

To a solution of the compound of Example 18-2 (8.87 g) and PPh$_3$ (12.3 g) in methylene chloride (40 mL) was added N-bromosuccinimide (8.37 g) at 0° C. in portions, and the reaction solution was stirred for 10 minutes, and concentrated. The residue was purified by silica gel column chromatography to give a bromide compound (8.40 g, 73%). To a solution of the compound of Reference Example 1 (4.05 g) in THF (40 mL) was added potassium t-butoxide (2.45 g), and the mixture was stirred at 40° C. for one hour. To the solution was added slowly a solution of the above bromide compound (8.40 g) in THF (120 mL), and the mixture was stirred for one hour. Water was added to the reaction solution, and the mixture was extracted with diethyl ether. The extract was dried, filtered, and concentrated. The residue was purified by silica gel column chromatography to give the title compound (6.90 g, 85%).

$^1$H NMR (CDCl$_3$, 400 MHz) δ 7.87 (dd, 1H, J=1.2 and 7.7 Hz), 7.74 (dt, 2H, J=8.4 and 2.0 Hz), 7.54 (brd, 1H, J=7.7 Hz), 7.43 (dt, 1H, J=1.1 and 7.7 Hz), 7.30 (brd, 1H, J=15.7 Hz), 7.29 (dt, 1H, J=1.2 and 7.7 Hz), 7.25 (brd, 2H, J=8.4 Hz), 7.11 (dd, 1H, J=1.7 and 2.5 Hz), 6.76 (dd, 1H, J=1.7 and 4.0 Hz), 6.36 (dt, 1H, J=15.7 and 5.6 Hz), 6.21 (dd, 1H, J=2.5 and 4.0 Hz), 5.23 (dd, 2H, J=6.2 and 1.4 Hz), 4.34 (q, 2H, J=7.2 Hz), 2.43 (s, 3H), 1.37 (t, 3H, J=7.2 Hz).

Example 19

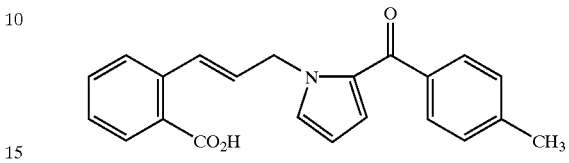

The compound of Example 18 (2.00 g) was dissolved in THF (20 mL) and methanol (20 mL), and thereto was added 1N aqueous NaOH solution (20 mL). The mixture was stirred at 40° C. for one hour under nitrogen atmosphere. The organic solvent was evaporated under reduced pressure, and the residue was washed with ether. The ether layer was extracted with iN aqueous NaOH solution, and the combined aqueous layer was washed with hexane and acidified with hydrochloric acid. The mixture was extracted with ethyl acetate, and the extract was dried, and treated with activated carbon, filtered, and concentrated to give the title compound (1.55 g, 84%).

$^1$H NMR (CDCl$_3$, 400 MHz) δ 8.02 (dd, 1H, J=1.2 and 7.7 Hz), 7.74 (brd, 2H, J=8.4 Hz), 7.57 (brd, 1H, J=7.7 Hz), 7.50 (dt, 1H, J=1.1 and 7.7 Hz), 7.36 (brd, 1H, J=15.7 Hz), 7.34 (dt, 1H, J=1.2 and 7.7 Hz), 7.24 (brd, 2H, J=8.4 Hz), 7.11 (dd, 1H, J=1.7 and 2.5 Hz), 6.78 (dd, 1H, J=1.7 and 4.0 Hz), 6.38 (dt, 1H, J=15.7 and 5.6 Hz), 6.22 (dd, 1H, J=2.5 and 4.0 Hz), 5.25 (dd, 2H, J=6.2 and 1.4 Hz), 2.40 (s, 3H).

Example 20

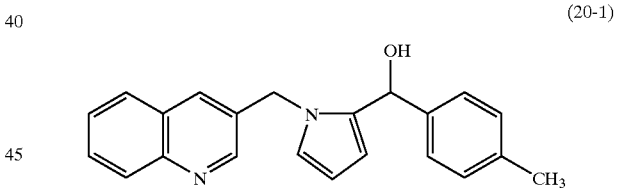

(20-1)

To a solution of 3-methylquinoline (11.0 ml) in carbon tetrachloride (290 ml) were added N-bromosuccinimide (14.7 g) and 2,2'-azobis(isobutyronitrile) (1.13 g) under nitrogen atmosphere, and the mixture was refluxed for 1.5 hour. The reaction solution was cooled to room temperature, and the insoluble materials were removed by filtration, and the solvent was evaporated under reduced pressure to about 80 ml. Toluene was added to the mixture, and further evaporated under reduced pressure to about 80 ml, and this procedure was repeated three time to give a solution of a crude bromo compound in toluene.

A suspension of 60% NaH (3.28 g) in THF (400 ml) was cooled to 0° C. under nitrogen atmosphere, and thereto was added pyrrol-2-carbaldehyde (7.81 g) in portions. To the mixture was added a solution of the above crude bromo compound in toluene, and the mixture was stirred at room temperature for 0.5 hour, and stirred at 40° C. for one hour, and further stirred at 50° C. for 2 hours. The mixture was cooled to room temperature, and poured into water, and extracted with ethyl acetate. The extract was washed with a saturated brine, dried over magnesium sulfate, and the solvent was evaporated under reduced pressure, and the residue was purified by silica gel column (hexane/ethyl acetate=3/1→2/1→1/1) to give 1-(3-quinolylmethyl)-1H-pyrrol-2-carbaldehyde (10.5 g, 54%).

$^1$H NMR (CDCl$_3$, 270 MHz) δ 9.57 (d, 1H, J=1.3 Hz), 8.80 (d, 1H, J=2.3 Hz), 8.08 (d, 1H, J=7.9 Hz), 7.87 (d, 1H, J=2.3 Hz), 7.76 (d, 1H, J=7.9 Hz), 7.70 (dd, 1H, J=7.9 and 7.9 Hz), 7.53 (dd, 1H, J=7.9 and 7.9 Hz), 7.08 (m, 1H), 7.02 (dd, 1H, J=1.7 and 4.0 Hz), 6.33 (dd, 1H, J=2.6 and 4.0 Hz), 5.76 (s, 2H).

(20-2)

Ether (10 ml) was added to magnesium (1.05 g) under nitrogen atmosphere, and thereto was added dropwise a solution of 4-bromo-toluene (5.3 ml) in ether (80 ml) under reflux. The mixture was further refluxed for another hour to give 0.452 N Grignard reagent.

A solution of the compound of Example 20-1 (6.00 g) in THF (130 ml) was cooled to 0° C. under nitrogen atmosphere, and thereto was added dropwise the above 0.452N Grignard reagent (62.5 ml), and the mixture was stirred at the same temperature. One hour thereafter, the 0.452N Grignard reagent (10 ml) was added, and the mixture was further stirred for one hour. The reaction solution was poured into water, and extracted twice with ethyl acetate. The extract was washed three times with a saturated aqueous sodium hydrogen carbonate solution, and washed with a saturated brine, dried over magnesium sulfate, and filtered. The solvent was evaporated under reduced pressure, and the precipitated solid was suspended in ethyl acetate, and collected by filtration to give [1-(3-quinolylmethyl)-1H-pyrrol-2-yl](4-methylphenyl)methanol (6.80 g, 81%).

$^1$H NMR (CDCl$_3$, 270 MHz) δ 8.63 (d, 1H, J=2.3 Hz), 8.06 (d, 1H, J=8.3 Hz), 7.65–7.71 (m, 2H), 7.49–7.54 (m, 2H), 7.20 (d, 2H, J=8.1 Hz), 7.03 (d, 2H, J=8.1 Hz), 6.71 (dd, 1H, J=1.7 and 2.7 Hz), 6.15 (dd, 1H, J=2.7, 3.5 Hz), 5.99 (dd, 1H, J=1.7, 3.5 Hz), 5.81 (d, 1H, J=4.3 Hz), 5.37 (d, 1H, J=16.3 Hz), 5.28 (d, 1H, J=16.3 Hz), 2.36 (d, 1H, J=4.3 Hz), 2.21 (s, 3H).

Example 21

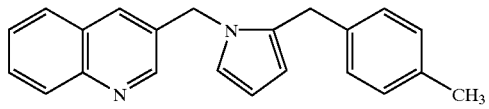

To the compound of Example 20-2 (4.16 g) were added at 0° C. trifluoroacetic acid (32 ml) and triethylsilane (1.70 ml) under nitrogen atmosphere, and the mixture was stirred at room temperature for 20 minutes. The solvent in the reaction solution was evaporated under reduced pressure, and the residue was neutralized with a saturated aqueous sodium hydrogen carbonate solution, and extracted with ethyl acetate. The extract was washed with a saturated aqueous sodium hydrogen carbonate solution, dried over magnesium sulfate, filtered, and the solvent was evaporated under reduced pressure. The residue was purified by silica gel column (hexane/ethyl acetate=5/1→4/1→3/1) to give the title compound (1.35 g, 34%).

$^1$H NMR (CDCl$_3$, 270 MHz) δ 8.60 (d, 1H, J=1.8 Hz), 8.07 (d, 1H, J=7.7 Hz), 7.63–7.71 (m, 2H), 7.51 (dd, 1H, J=7.7 and 7.7 Hz), 7.38 (d, 1H, J=1.8 Hz), 6.96 (s, 4H), 6.68 (dd, 1H, J=1.8 and 2.8 Hz), 6.20 (m, 1H), 6.06 (m, 1H), 5.09 (s, 2H), 3.84 (s, 2H), 2.18 (s, 3H).

Example 22

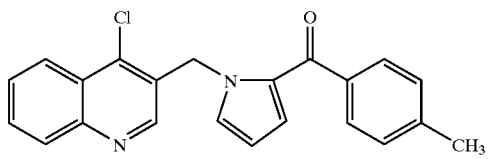

(22-1)

A 2.0N solution of ethylmagnesium chloride in THF (100 ml) was cooled to 0° C. under nitrogen atmosphere, and thereto was added dropwise a solution of 2-cyanoaniline (7.90 g) in THF (65 ml) over a period of 50 minutes. The mixture was stirred at room temperature for 20 minutes, and refluxed for 3 hours. The reaction solution was cooled to 0° C., and thereto was added a 4N aqueous hydrochloric acid solution (80 ml) over a period of 40 minutes, and the mixture was further refluxed for 3 hours. The solvent in the reaction solution was evaporated under reduced pressure, and the resultant was added to a saturated aqueous sodium hydrogen carbonate solution for neutralization. The mixture was extracted three times with ethyl acetate, and the extract was washed with a saturated brine, dried over magnesium sulfate, and filtered. The solvent was evaporated under reduced pressure, and the residue was purified by silica gel column (hexane/ethyl acetate=8/1) to give 1-(2-aminophenyl)-1-propanone (6.78 g, 68%).

$^1$H NMR (CDCl$_3$, 300 MHz) δ 7.75 (dd, 1H, J=1.5, 8.6 Hz), 7.25 (ddd, 1H, J=1.5, 7.7 and 7.7 Hz), 6.62–6.67 (m, 2H), 6.28 (brs, 2H), 2.98 (q, 2H, J=7.3 Hz), 1.21 (t, 3H, J=7.3 Hz).

(22-2)

To a solution of the compound of Example 22-1 (5.12 g) in THF (200 ml) was added triethylamine (5.80 ml) under nitrogen atmosphere, and the mixture was cooled to 0° C. To the mixture was added dropwise acetyl chloride (2.55 ml), and the mixture was stirred for 30 minutes. Acetyl chloride (0.50 ml) was further added thereto, and the mixture was stirred at room temperature for 30 minutes. The reaction solution was poured into water, and extracted three times with ethyl acetate. The extract was washed with a saturated brine, dried over magnesium sulfate, filtered, and the solvent was evaporated under reduced pressure. The residue was purified by silica gel column (hexane/ethyl acetate=5/1→3/1) to give 1-(2-acetylaminophenyl)-1-propanone (5.13 g, 78%).

$^1$H NMR (CDCl$_3$, 300 MHz) δ 11.76 (brs, 1H), 8.74 (d, 1H, J=7.9 Hz), 7.93 (d, 1H, J=7.9 Hz), 7.54 (dd, 1H, J=7.9 and 7.9 Hz), 7.11 (dd, 1H, J=7.9 and 7.9 Hz), 3.08 (q, 2H, J=7.2 Hz), 2.24 (s, 3H), 1.23 (t, 3H, J=7.2 Hz).

(22-3)

A solution of the compound of Example 22-2 (4.20 g) in DMF (21 mL) was cooled to 0° C. under nitrogen atmosphere, and thereto was added dropwise phosphorus oxychloride (16.2 mL). The mixture was stirred at room temperature for 40 minutes, and further stirred at 90° C. for 5 hours. The reaction solution was poured into ice water-aqueous sodium hydrogen carbonate solution for neutralization. The mixture was extracted three times with ethyl acetate, and the extract was washed with a saturated aqueous sodium hydrogen carbonate solution, dried over magnesium sulfate, filtered, and evaporated under reduced pressure. The residue was purified by silica. gel column (hexane/ethyl acetate=3/1) to give 4-chloro-3-methylquinoline (3.58 g, 92%).

$^1$H NMR (CDCl$_3$, 300 MHz) δ 8.75 (s, 1H), 8.24 (d, 1H, J=7.7 Hz), 8.09 (d, 1H, J=7.7 Hz), 7.72 (dd, 1H, J=7.7 and 7.7 Hz), 7.63 (dd, 1H, J=7.7 and 7.7 Hz), 2.58 (s, 3H).

(22-4)

To a solution of the compound of Example 22-3 (500 mg) in carbon tetrachloride (15 mL) were added N-bromosuccinimide (508 mg) and 2,2'-azobis (isobutyronitrile) (30.1 mg) under nitrogen atmosphere, and the mixture was refluxed for one hour. The reaction solution was cooled to room temperature, and the insoluble materials were removed by filtration, and the solvent was evaporated under reduced pressure to about 5 mL. Toluene was added to the resultant, and the mixture was evaporated under reduced pressure to about 5 mL, which was repeated five times to give an about 0.56N solution of a crude bromo compound in toluene.

A solution of the compound of Reference Example 1 (90.1 mg) in THF (2.0 mL) was cooled to 0° C. under nitrogen atmosphere, and thereto was added 60% NaH (21.3 mg) in portions. Then, to the mixture was added the above 0.56 N solution of the crude bromo compound in toluene (1.05 mL), and the mixture was stirred at 50° C. for one hour. The reaction solution was cooled to room temperature, and thereto was added a saturated aqueous sodium hydrogen carbonate solution. The mixture was extracted with ethyl acetate, and the extract was dried over magnesium sulfate, filtered, and the solvent was evaporated under reduced pressure. The residue was purified by silica gel column (hexane/ethyl acetate=8/1→6/1→3/1) to give the title compound (92.1 mg, 43%, 2 steps).

$^1$H NMR (CDCl$_3$, 300 MHz) δ 8.26–8.29 (m, 2H), 8.06 (d, 1H, J=7.9 Hz), 7.63–7.76 (m, 4H), 7.23 (d, 2H, J=7.9 Hz), 7.07 (dd, 1H, J=1.7, 2.6 Hz), 6.86 (dd, 1H, J=1.7 and 4.1 Hz), 6.29 (dd, 1H, J=2.6 and 4.1 Hz), 5.99 (s, 2H), 2.41 (s, 3H).

Example 23

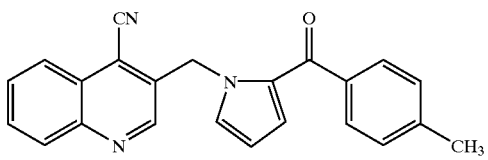

To the compound of Example 22 (47.1 mg) and 60% zinc cyanide (28.4 mg) were added DMF (1.3 mL), bis(dibenzylideneacetone)palladium (0) (32.1 mg), and a 2.47 N solution of tri-t-butylphosphine in toluene (120 μl) under nitrogen atmosphere, and the mixture was stirred at 110° C. for 6 hours. The reaction solution was cooled to room temperature, and thereto was added a saturated aqueous sodium hydrogen carbonate solution. The mixture was extracted with ethyl acetate-toluene, and the extract was washed twice with a saturated aqueous sodium hydrogen carbonate solution, dried over magnesium sulfate, and filtered. The solvent was evaporated under reduced pressure, and the residue was purified by silica gel column (hexane/ethyl acetate=5/1) to the title compound (5.1 mg, 11%).

$^1$H NMR (CDCl$_3$, 300 MHz) δ 8.65 (s, 1H), 8.22 (d, 1H, J=7.9 Hz), 8.15 (d, 1H, J=7.9 Hz), 7.83 (dd, 1H, J=7.9, 7.9 Hz), 7.76 (dd, 1H, J=7.9, 7.9 Hz), 7.69 (d, 2H, J=8.0 Hz), 7.24 (d, 2H, J=8.0 Hz), 7.17 (dd, 1H, J=1.7, 2.6 Hz), 6.89 (dd, 1H, J=1.7, 4.1 Hz), 6.33 (dd, 1H, J=2.6, 4.1 Hz), 6.08 (s, 2H), 2.41 (s, 3H).

Example 24

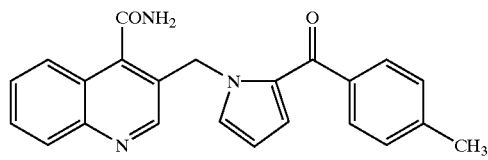

To the compound of Example 23 (4.4 mg) was added t-butanol (1.0 mL) under nitrogen atmosphere, and the mixture was warmed to 50° C. To the mixture was added potassium hydroxide powder (25.0 mg), and the mixture was stirred at 50° C. for 30 minutes. The reaction solution was cooled to room temperature, filtered, and the insoluble materials were removed by filtration. Ethyl acetate was added to the filtrate, and the mixture was filtered again. The solvent was evaporated under reduced pressure, and the residue was purified by silica gel column (hexane/ethyl acetate=1/1→0/1) to give the title compound (6.7 mg, quantitatively).

$^1$H NMR (CDCl$_3$, 300 MHz) δ 8.19 (s, 1H), 8.01–8.04 (m, 2H), 7.81 (brs, 1H), 7.70 (dd, 1H, J=7.2, 7.2 Hz), 7.60 (dd, 1H, J=7.2, 7.2 Hz), 7.54 (d, 2H, J=8.0 Hz), 7.30 (dd, 1H, J=1.7, 2.6 Hz), 7.17 (d, 2H, J=8.0 Hz), 6.92 (dd, 1H, J=1.7, 4.0 Hz), 6.36 (dd, 1H, J=2.6, 4.0 Hz), 6.23 (brs, 1H), 5.84 (brs, 2H), 2.37 (s, 3H).

Example 25

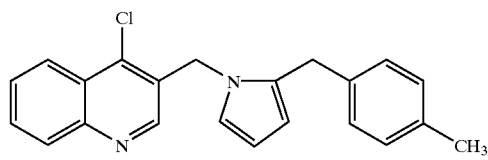

A solution of the compound of Reference Example 2 (80.2 mg) in DMF (2.0 ml) was cooled to 0° C. under nitrogen atmosphere, and thereto was added 60% NaH (22.0 mg), and the mixture was stirred at 50° C. for 30 minutes. The solution (about 0.56 N) of the crude bromo compound obtained from the compound of Example 22-3 in toluene (1.0 mL) was added thereto, and the mixture was stirred at 50° C. for one hour. The reaction solution was cooled to room temperature, and thereto was added a saturated aqueous sodium hydrogen carbonate solution, and the mixture was extracted three times with ethyl acetate-toluene. The extract was washed with a saturated aqueous sodium hydrogen carbonate solution and a saturated brine, dried over magnesium sulfate, filtered, and the solvent was evaporated under reduced pressure. The residue was purified by silica gel column (hexane/ethyl acetate=8/1→6/1) to give the title compound (27.0 mg, 27%, 2 stesp).

$^1$H NMR (CDCl$_3$, 300 MHz) δ 8.20 (d, 1H, J=7.2 Hz), 8.04 (d, 1H, J=7.2 Hz), 7.88 (s, 1H), 7.74 (dd, 1H, J=7.2, 7.2 Hz), 7.64 (dd, 1H, J=7.2, 7.2 Hz), 6.94 (d, 2H, J=7.9 Hz), 6.87 (d, 2H, J=7.9 Hz), 6.69 (dd, 1H, J=1.8, 3.1 Hz), 6.20 (dd, 1H, J=3.1, 3.1 Hz), 6.06 (dd, 1H, J=1.8, 3.1 Hz), 5.21 (s, 2H), 3.86 (s, 2H), 2.06 (s, 3H).

Example 26

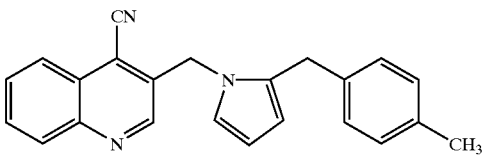

To the compound of Example 25 (37.3 mg) and 60% zinc cyanide (24.0 mg) were added DMF (1.0 mL), bis(dibenzilidenacetone)palladium (0) (52.1 mg) and a 2.47N solution of tri-t-butylphosphine in toluene (150 μL) under nitrogen atmosphere, and the mixture was stirred at 110° C. for 3 hours. The reaction solution was cooled to room temperature, and thereto was added a saturated aqueous sodium hydrogen carbonate solution. The mixture was extracted with ethyl acetate-toluene, and the extract was washed twice with a saturated aqueous sodium hydrogen carbonate solution, dried over magnesium sulfate, filtered, and the solvent was evaporated under reduced pressure. The residue was purified by silica gel column (hexane/ethyl acetate 10/1→7/1) to give the title compound (29.0 mg, 80%).

$^1$H NMR (CDCl$_3$, 300 MHz) δ 8.17 (s, 1H), 8.10 (d, 1H, J=7.4 Hz), 8.07 (d, 1H, J=7.4 Hz), 7.80 (dd, 1H, J=7.4, 7.4 Hz), 7.73 (dd, 1H, J=7.4, 7.4 Hz), 6.87 (d, 2H, J=7.9 Hz), 6.77 (dd, 1H, J=1.8, 3.1 Hz), 6.72 (d, 2H, J=7.9 Hz), 6.25 (dd, 1H, J=3.1, 3.1 Hz), 6.12 (dd, 1H, J=1.8, 3.1 Hz), 5.32 (s, 2H), 3.92 (s, 2H), 1.87 (s, 3H).

Example 27

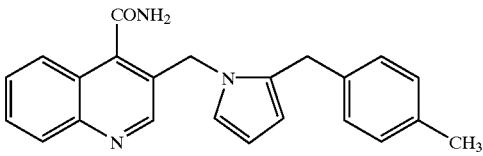

The title compound (22.4 mg, 80%) was obtained from the compound of Example 26 (26.2 mg) in a similar manner to the preparation of the compound of Example 24.

$^1$H NMR (CDCl$_3$, 300 MHz) δ 8.34 (s, 1H), 8.09 (d, 1H, J=7.6 Hz), 7.91 (d, 1H, J=7.6 Hz), 7.74 (dd, 1H, J=7.6, 7.6 Hz), 7.59 (dd, 1H, J=7.6, 7.6 Hz), 6.90–6.96 (m, 4H), 6.58 (dd, 1H, J=2.0, 3.1 Hz), 6.15 (dd, 1H, J=3.1, 3.1 Hz), 6.01 (dd, 1H, J=2.0, 3.1 Hz), 5.90 (brs, 1H), 5.57 (brs, 1H), 5.14 (s, 2H), 3.88 (s, 2H), 2.15 (s, 3H).

Example 28

(28-1)

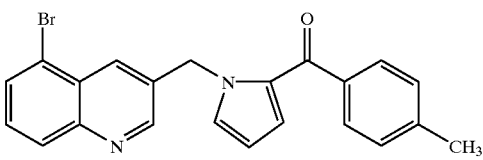

2-Bromo-6-nitrobenzaldehyde was synthesized by the method disclosed in J. Chem. Soc., Perkin Trans. 1, 1996, 1699.

$^1$H NMR (CDCl$_3$, 300 MHz) δ 10.29 (s, 1H), 8.02 (d, 1H, J=7.8 Hz), 7.94 (d, 1H, J=7.8 Hz), 7.54 (dd, 1H, J=7.8, 7.8 Hz).

(28-2)

A solution of triethyl 2-phosphonopropionate (3.60 mL) in THF (50 mL) was cooled to 0° C. under nitrogen atmosphere, and thereto was added potassium t-butoxide (1.88 g). The mixture was stirred at the same temperature for 10 minutes, and thereto was added the compound of Example 28-1 (3.00 g), and the mixture was stirred at 60° C. for 3 hours. To the reaction solution was added a 5% aqueous potassium hydrogen sulfate solution, and the mixture was extracted three times with ethyl acetate. The extract was washed with water and a saturated brine, dried over magnesium sulfate, and filtered. The solvent was evaporated under reduced pressure, and the residue was purified by silica gel column (hexane/ethyl acetate=8/1→6/1) to give ethyl 2-methyl-3-(2-bromo-6-nitrophenyl)acrylate (4.04 g, 99%).

$^1$H NMR (CDCl$_3$, 300 MHz) δ 7.89–7.97 (m, 3×1/2H), 7.83 (dd, 1×1/2H, J=1.2, 7.9 Hz), 7.62 (s, 1×1/2H), 7.38 (dd, 1×1/2H, J=8.4, 8.4 Hz), 7.31 (dd, 1×1/2H, J=7.9, 7.9 Hz), 6.89 (s, 1×1/2H), 4.30 (q, 2×1/2H, J=7.1 Hz), 3.94 (q, 2×1/2H, J=7.2 Hz), 2.14 (s, 3×1/2H), 1.67 (s, 3×1/2H), 1.37 (t, 3×1/2H, J=7.1 Hz), 0.95 (t, 3×1/2H, J=7.2 Hz).

(28-3)

A solution of the compound of Example 28-2 (3.80 g) in toluene (75 ml) was cooled to −78° C. under nitrogen atmosphere, and thereto was added dropwise a 1.01N solution of diisobutyl aluminium hydride in toluene (25.5 mL) over a period of 30 minutes. The mixture was stirred at −78° C. for 2 hours. To the reaction solution were added water and a 1N aqueous hydrochloric acid, and the mixture was extracted twice with ethyl acetate. The extract was washed with a 1N aqueous hydrochloric acid solution, water and a saturated brine, dried over magnesium sulfate, filtered, and the solvent was evaporated under reduced pressure. The residue was purified by silica gel column (hexane/ethyl acetate=3/1) to give 2-methyl-3-(2-bromo-6-nitrophenyl) propenol (2.89 g, 88%).

$^1$H NMR (CDCl$_3$, 300 MHz) δ 7.73–7.86 (m, 2H), 7.30 (dd, 1×1/2H, J=8.1, 8.1 Hz), 7.29 (dd, 1×1/2H, J=8.1, 8.1 Hz), 6.47 (s, 1×1/2H), 6.22 (s, 1×1/2H), 4.21 (s, 2×1/2H), 3.85 (s, 2×1/2H), 2.01 (s, 3×1/2H), 1.48 (s, 3×1/2H).

(28-4)

To a solution of the compound of Example 28-3 (2.72 g) in chloroform (50 mL) was added manganese dioxide (22.3 g) under nitrogen atmosphere, and the mixture was stirred at room temperature. Further, to the mixture was added manganese dioxide (total; 7.29 g), and the mixture was stirred at room temperature for 7 hours. The reaction solution was filtered, and the solvent was evaporated under reduced pressure to give 2-methyl-3-(2-bromo-6-nitrophenyl) propenal (2.53 g, 94%).

$^1$H NMR (CDCl$_3$, 300 MHz) δ 9.74 (s, 1×1/2H), 9.41 (s, 1×1/2H), 7.92–8.06 (m, 2H), 7.43–7.47 (m, 2H), 2.02 (s, 3×1/2H), 1.59 (s, 3×1/2H).

(28-5)

To a 20% aqueous titanium trichloride solution (10.8 g) was added water (10 mL) under nitrogen atmosphere, and the mixture was cooled to 0° C., and thereto was added dropwise a solution of the compound of Example 28-4 (540 mg) in ethanol (20 mL). The mixture was stirred at room temperature for one hours, and heated under reflux for 3 hours. To the reaction solution was added a saturated aqueous sodium hydrogen carbonate solution for neutralization, and the mixture was extracted three times with ethyl acetate. The extract was washed with a saturated aqueous sodium hydrogen carbonate solution and a saturated brine, dried over magnesium sulfate, filtered, and the solvent was evaporated under reduced pressure. The residue was purified by silica gel column (hexane/ethyl acetate=3/1) to give 5-bromo-3-methylquinoline (206 mg, 46%).

¹H NMR (CDCl₃, 300 MHz) δ 8.79 (d, 1H, J=2.2 Hz), 8.30 (d, 1H, J=2.2 Hz), 8.05 (d, 1H, J=8.2 Hz), 7.80 (d, 1H, J=8.2 Hz), 7.50 (dd, 1H, J=8.2, 8.2 Hz), 2.59 (s, 3H).

(28-6)

To a solution of the compound of Example 28-5 (194 mg) in carbon tetrachloride (5.0 mL) were added N-bromosuccinimide (156 mg) and 2,2'-azobis (isobutyronitrile) (16.3 mg) under nitrogen atmosphere, and the mixture was heated under reflux for 2 hours. The reaction solution was cooled to room temperature, and the insoluble materials were removed by filtration. The solvent was evaporated under reduced pressure to about 3 ml. Further, toluene was added thereto, and the mixture was evaporated under reduced pressure to about 3 mL. This procedure was repeated five times to give a solution of a crude bromo compound in toluene.

Under nitrogen atmosphere, a solution of the compound of Reference Example 1 (158 mg) in THF (5.0 mL) was cooled to 0° C., and thereto was added 60% NaH (37.06 mg). Further, thereto was added the solution of the crude bromo compound in toluene, and the mixture was stirred at 50° C. for 2 hours. The reaction solution was cooled to room temperature, and water was added to the mixture, and further extracted twice with ethyl acetate. The extract was washed with water and a saturated brine, dried over magnesium sulfate, filtered, and the solvent was evaporated under reduced pressure. The residue was purified by silica gel column (hexane/ethyl acetate=3/1→1/1) to give the title compound (90.9 mg, 26%).

¹H NMR (CDCl₃, 400 MHz) δ 8.79 (d, 1H, J=2.1 Hz), 8.20 (d, 1H, J=2.1 Hz), 8.04 (d, 1H, J=8.4 Hz), 7.80 (d, 1H, J=7.5 Hz), 7.70 (d, 2H, J=8.0 Hz), 7.53 (dd, 1H, J=7.5, 8.4 Hz), 7.23 (d, 2H, J=8.0 Hz), 7.11 (dd, 1H, J=1.7, 2.5 Hz), 6.86 (dd, 1H, J=1.7, 4.0 Hz), 6.31 (dd, 1H, J=2.5, 4.0 Hz), 5.91 (s, 2H), 2.41 (s, 3H).

Example 29

(29-1)

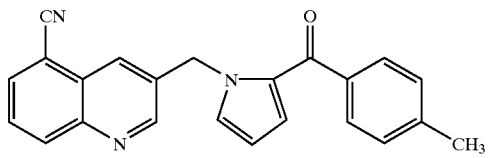

Under nitrogen atmosphere, to the compound of Example 28-5 (269 mg) and 60% zinc cyanide (243 mg) were added DMF (6.0 ml), and P(PPh₃)₄ (620 mg), and the mixture was stirred at 100° C. for 2 hours. The reaction solution was cooled to room temperature, and thereto was added a saturated aqueous sodium hydrogen carbonate solution. The mixture was extracted three times with ethyl acetate-toluene, and the extract was washed twice with a saturated aqueous sodium hydrogen carbonate solution, and then washed with a saturated brine, dried over magnesium sulfate, and filtered. The solvent was evaporated under reduced pressure, and the residue was purified by silica gel column (hexane/ethyl acetate=3/1→2/1) to give 5-cyano-3-methylquinoline (190 mg, 93%).

¹H NMR (CDCl₃, 300 MHz) δ 8.90 (d, 1H, J=2.0 Hz), 8.30–8.33 (m, 2H), 7.96 (d, 1H, J=7.3 Hz), 7.71 (dd, 1H, J=7.3, 7.3 Hz), 2.62 (s, 3H).

(29-2)

In a similar manner to Example 22-4, a solution (about 0.71 N) of a crude bromo compound in toluene was obtained from the compound of Example 29-1, and the title compound (59.9 mg, 32%, 2 steps) was obtained from said solution (about 0.71 N) of the crude bromo compound (750 μl) and the compound of Reference Example 1 (91.7 mg).

¹H NMR (CDCl₃, 300 MHz) δ 8.90 (d, 1H, J=2.2 Hz), 8.32 (d, 1H, J=7.9 Hz), 8.13 (d, 1H, J=2.2 Hz), 7.95 (d, 1H, J=7.9 Hz), 7.69–7.76 (m, 3H), 7.24 (d, 2H, J=7.9 Hz), 7.12 (dd, 1H, J=1.7 and 2.6 Hz), 6.89 (dd, 1H, J=1.7 and 4.0 Hz), 6.34 (dd, 1H, J=2.6 and 4.0 Hz), 5.93 (s, 2H), 2.41 (s, 3H).

Example 30

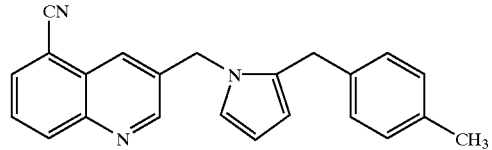

In a similar manner to the preparation of the compound of Example 25, the title compound (5.5 mg, 3.5%, 2 steps) was obtained from a solution (about 0.71 N) of a crude bromo compound in toluene (650 μL) obtained from the compound of Example 29-1 and the compound of Reference Example 2 (66.9 mg).

¹H NMR (CDCl₃, 300 MHz) δ 8.57 (d, 1H, J=2.0 Hz), 8.29 (d, 1H, J=8.6 Hz), 7.94 (d, 1H, J=7.2 Hz), 7.78 (d, 1H, J=2.0 Hz), 7.27 (dd, 1H, J=7.2 and 8.6 Hz), 6.90 (d, 2H, J=8.2 Hz), 6.85 (d, 2H, J=8.2 Hz), 6.72 (dd, 1H, J=1.8 and 3.0 Hz), 6.24 (dd, 1H, J=3.0 and 3.0 Hz), 6.12 (dd, 1H, J=1.8 and 3.0 Hz), 5.15 (s, 2H), 3.87 (s, 2H), 2.03 (s, 3H).

Example 31

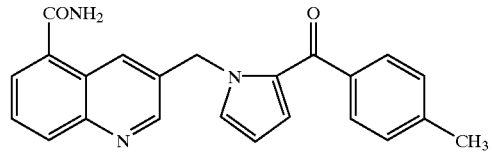

Under nitrogen atmosphere, to the compound of Example 29 (27.5 mg) was added t-butanol (3.0 mL), and the mixture was warmed to 50° C. To the mixture wad added potassium hydroxide powder (140 mg), and the mixture was stirred at 50° C. for 1.5 hour. The reaction solution was cooled to room temperature, and the insoluble materials were removed by filtration. Water was added to the filtrate, and the mixture was extracted with ethyl acetate. The extract was washed with a saturated brine, dried over magnesium sulfate, filtered, and the solvent was evaporated under reduced pressure. The residue was purified by silica gel column (ethyl acetate) to give the title compound (5.0 mg, 17%).

¹H NMR (CDCl₃, 300 MHz) δ 8.79 (d, 1H, J=1.7 Hz), 8.32 (d, 1H, J=7.9 Hz), 8.13 (d, 1H, J=2.2 Hz), 7.95 (d, 1H, J=7.9 Hz), 7.69–7.76 (m, 3H), 7.24 (d, 2H, J=7.9 Hz), 7.12 (dd, 1H, J=1.7, 2.6 Hz), 6.89 (dd, 1H, J=1.7, 4.0 Hz), 6.34 (dd, 1H, J=2.6, 4.0 Hz), 5.93 (s, 2H), 2.41 (s, 3H).

Example 32

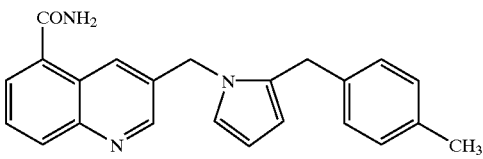

The title compound (5.5 mg, quantitatively) was obtained from the compound of Example 30 (4.8 mg) in a similar manner to Example 24.

$^1$H NMR (CDCl$_3$, 300 MHz) δ 8.52 (d, 1H, J=2.2 Hz), 8.38 (d, 1H, J=2.2 Hz), 8.18 (d, 1H, J=8.4 Hz), 7.79 (d, 1H, J=7.0 Hz), 7.68 (dd, 1H, J=7.0, 8.4 Hz), 6.95 (s, 4H), 6.69 (dd, 1H, J=1.8, 3.1 Hz), 6.18 (dd, 1H, J=3.1, 3.1 Hz), 6.03 (dd, 1H, J=1.8, 3.1 Hz), 5.86 (brs, 2H), 5.10 (s, 2H), 3.85 (s, 2H), 2.17 (s, 3H).

Example 33

(33-1)

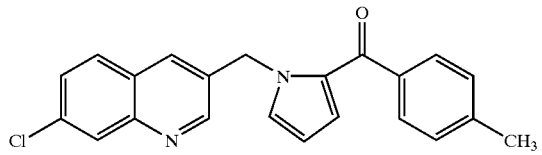

Under nitrogen atmosphere, to a solution of 2-amino-4-chloro-benzaldehyde (467 mg) in ethanol (10 mL) were added propanal (250 μL) and piperidine (50 μl), and the mixture was heated under reflux. Further, to the mixture were added propanal (800 μL) and piperidine (250 μL) in several portions, and the mixture was heated under reflux for total 9 hours. The solvent was evaporated under reduced pressure, and the residue was purified by silica gel column (hexane/ethyl acetate=6/1) to give 7-chloro-3-methylquinoline (401 mg, 75%).

$^1$H NMR (CDCl$_3$, 300 MHz) δ 8.77 (d, 1H, J=2.0 Hz), 8.06 (d, 1H, J=2.1 Hz), 7.90 (d, 1H, J=2.0 Hz), 6.68 (d, 1H, J=8.7 Hz), 7.47 (dd, 1H, J=2.1, 8.7 Hz), 2.51 (s, 3H).

(33-2)

Under nitrogen atmosphere, to a solution of the compound of Example 33-1 (100 mg) in carbon tetrachloride (5.0 mL) were added N-bromosuccinimide (105 mg) and 2,2'-azobis(isobutyronitrile) (11.8 mg), and the mixture was heated under-reflux for 2 hours. The reaction solution was cooled to room temperature, and the insoluble materials were removed by filtration. The solvent was evaporated under reduced pressure to about 1 mL. Then, to the resultant was added toluene, and the mixture was evaporated under reduced pressure to about 1 mL. This procedure was repeated three times to give a solution of a crude bromo compound in toluene.

Under nitrogen atmosphere, the solution of the compound of Reference Example 1 (89.4 mg) in THF (2.0 mL) was cooled to 0° C., and thereto was added 60% NaH (20.6 mg). Further, thereto was added the solution of the crude bromo compound in toluene, and the mixture was stirred at 50° C. for 2 hours. The reaction solution was cooled to room temperature, and thereto was added a saturated aqueous sodium hydrogen carbonate solution. The mixture was extracted with ethyl acetate, dried over magnesium sulfate, filtered, and the solvent was evaporated under reduced pressure. The residue was purified by silica gel column (hexane/ethyl acetate=3/1→2/1) to give the title compound (54.7 mg, 31%).

$^1$H NMR (CDCl$_3$, 400 MHz) δ 8.80 (d, 1H, J=1.7 Hz), 8.07 (d, 1H, J=2.0 Hz), 7.90 (d, 1H, J=1.7 Hz), 7.69 (d, 1H, J=8.7 Hz), 7.67 (d, 2H, J=8.2 Hz), 7.47 (dd, 1H, J=2.0, 8.7 Hz), 7.23 (d, 2H, J=8.2 Hz), 7.11 (dd, 1H, J=1.7, 2.5 Hz), 6.84 (dd, 1H, J=1.7, 4.0 Hz), 6.29 (dd, 1H, J=2.5, 4.0 Hz), 5.83 (s, 2H), 2.41 (s, 3H).

Example 34

(34-1)

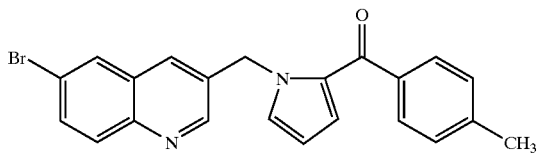

In a similar manner to the preparation of the compound of Example 33-1, 6-bromo-3-methylquinoline (1.04 g, 75%) was obtained from 2-amino-5-bromobenzaldehyde (1.25 g).

$^1$H NMR (CDCl$_3$, 300 MHz) δ 8.77 (d, 1H, J=2.0 Hz), 7.93 (d, 1H, J=9.0 Hz), 7.91 (d, 1H, J=2.2 Hz), 7.83 (d, 1H, J=2.0 Hz), 7.71 (dd, 1H, J=2.2, 9.0 Hz), 2.53 (s, 3H).

(34-2)

Under nitrogen atmosphere, to a solution of the compound of Example 34-1 (150 mg) in monochlorobenzene (5.0 mL) were added N-bromosuccinimide (123 mg) and 2,2'-azobis(isobutyronitrile) (13.1 mg), and the mixture was stirred at 110° C. for 2 hours. The solvent in the reaction solution was evaporated under reduced pressure to about a half volume thereof, and thereto was added toluene-hexane. The insoluble materials were removed by filtration, and the filtrate was evaporated under reduced pressure to about 2 mL to a solution of the crude bromo compound in toluene.

Under nitrogen atmosphere, a solution of the compound of Reference Example 1 (59.4 mg) in THF (1.5 mL) was cooled to 0° C., and thereto was added 60% NaH (15.9 mg). To the mixture was added the solution of the crude bromo compound in toluene, and the mixture was stirred at 50° C. for 4 hours. The reaction solution was cooled to room temperature, and thereto was added water. The mixture was extracted with ethyl acetate, and the extract was dried over magnesium sulfate, filtered, and the solvent was evaporated under reduced pressure. The residue was purified by silica gel column (hexane/ethyl acetate=3/1→2/1) to give the title compound (62.5 mg, 48%).

$^1$H NMR (CDCl$_3$, 300 MHz) δ 8.81 (d, 1H, J=2.2 Hz), 7.93 (d, 1H, J=9.1 Hz), 7.91 (d, 1H, J=2.2 Hz), 7.78 (d, 1H, J=2.2 Hz), 7.73 (dd, 1H, J=2.2, 9.1 Hz), 7.67 (d, 2H, J=8.1 Hz), 7.23 (d, 2H, J=8.1 Hz), 7.10 (dd, 1H, J=1.7, 2.6 Hz), 6.84 (dd, 1H, J=1.7, 4.1 Hz), 6.29 (dd, 1H, J=2.6, 4.1 Hz), 5.84 (s, 2H), 2.41 (s, 3H).

Example 35

(35-1)

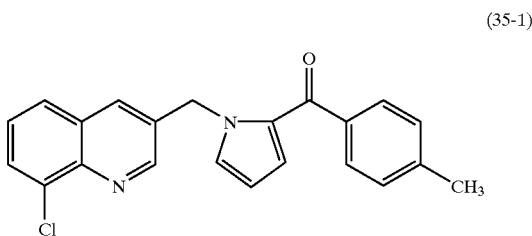

In a similar manner to the preparation of the compound of Example 33-1, 8-chloro-3-methylquinoline (1.09 g, 95%) was obtained from 2-amino-3-chlorobenzaldehyde (1.00 g).

$^1$H NMR (CDCl$_3$, 300 MHz) δ 8.90 (d, 1H, J=2.2 Hz), 7.95 (d, 1H, J=2.2 Hz), 7.77 (dd, 1H, J=1.6, 7.5 Hz), 7.68 (dd, I1H, J=1.6, 7.5 Hz), 7.43 (dd, 1H, J=7.5, 7.5 Hz), 2.55 (s, 3H).

(35-2)

In a similar manner to the preparation of the compound of Example 33, the title compound (92.4 mg, 69%) was obtained from the compound of Example 35-1 (134 mg) and the compound of Reference Example 1 (69.0 mg).

$^1$H NMR (CDCl$_3$, 300 MHz) δ 8.89 (d, 1H, J=2.2 Hz), 7.97 (d, 1H, J=2.2 Hz), 7.80 (dd, 1H, J=1.3, 7.7 Hz), 7.65–7.71 (m, 3H), 7.44 (dd, 1H, J=7.7, 7.7 Hz), 7.22 (d, 2H, J=8.1 Hz), 7.11 (dd, 1H, J=1.7, 2.6 Hz), 6.84 (dd, 1H, J=1.7, 4.0 Hz), 6.29 (dd, 1H, J=2.6, 4.0 Hz), 5.87 (s, 2H), 2.41 (s, 3H).

Example 36

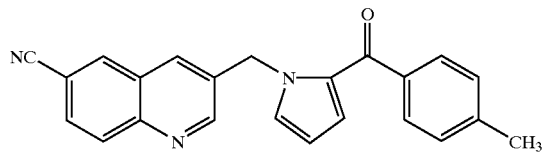

Under nitrogen atmosphere, to the compound of Example 34-2 (50.0 mg) and 60% zinc cyanide (38.6 mg) were added DMF (1.0 mL) and P(PPh$_3$)$_4$ (63.1 mg), and the mixture was stirred at 100° C. for 2 hours. The reaction solution was cooled to room temperature, and thereto was added a saturated aqueous sodium hydrogen carbonate solution. The mixture was extracted three times with ethyl acetate-toluene, and the extract was washed twice with a saturated aqueous sodium hydrogen carbonate solution, dried over magnesium sulfate, and filtered. The solvent was evaporated under reduced pressure, and the residue was purified by silica gel column (hexane/ethyl acetate=3/1→1/1) to give the title compound (37.3 mg, 86%).

$^1$H NMR (CDCl$_3$, 300 MHz) δ 8.94 (d, 1H, J=2.2 Hz), 8.14–8.17 (m, 2H), 7.90 (d, 1H, J=2.2 Hz), 7.81 (dd, 1H, J=1.7, 8.8 Hz), 7.66 (d, 2H, J=7.9 Hz), 7.23 (d, 2H, J=7.9 Hz), 7.13 (dd, 1H, J=1.7, 2.6 Hz), 6.87 (dd, 1H, J=1.7, 4.0 Hz), 6.32 (dd, 1H, J=2.6, 4.0 Hz), 5.86 (s, 2H), 2.41 (s, 3H).

Example 37

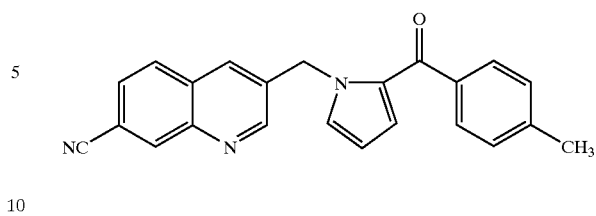

Under nitrogen atmosphere, to the compound of Example 33 (39.5 mg) and 60% zinc cyanide (30.4 mg) were DMF (1.0 mL), bis(dibenzilidenacetone)palladium (0) (32.5 mg) and a 2.47N solution of tri-t-butylphosphine in toluene (100 μL), and the mixture was stirred at 120° C. for 5 hours. The reaction solution was filtered to remove the insoluble materials, and to the filtrate was added a saturated aqueous sodium hydrogen carbonate solution. The mixture was extracted twice with ethyl acetate-toluene, and the extract was washed twice with a saturated aqueous sodium hydrogen carbonate solution, and washed with a saturated brine, dried over magnesium sulfate, and filtered. The solvent was evaporated under reduced pressure, and the residue was purified by silica gel column (hexane/ethyl acetate=3/1→2/1→1/1) to give the title compound (33.8 mg, 88%).

$^1$H NMR (CDCl$_3$, 300 MHz) δ 8.90 (d, 1H, J=2.2 Hz), 8.44 (s, 1H), 7.91 (d, 1H, J=2.2 Hz), 7.85 (d, 1H, J=8.4 Hz), 7.65–7.67 (m, 3H), 7.23 (d, 2H, J=7.9 Hz), 7.13 (dd, 1H, J=1.7, 2.6 Hz), 6.87 (dd, 1H, J=1.7, 4.0 Hz), 6.32 (dd, 1H, J=2.6, 4.0 Hz), 5.86 (s, 2H), 2.41 (s, 3H).

Example 38

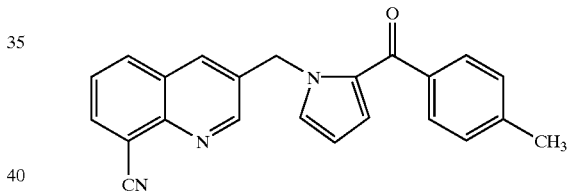

In a similar manner to the preparation of the compound of Example 37, the title compound (32.3 mg, 55%) was obtained from the compound of Example 35 (60.0 mg), while the purification was carried out as follows. That is, after the purification of silica gel column, the product was suspended in ethyl acetate, and the precipitates were collected by filtration, and dried.

$^1$H NMR (CDCl$_3$, 300 MHz) δ 8.93 (d, 1H, J=2.2 Hz), 8.09 (dd, 1H, J=1.2, 7.6 Hz), 8.00–8.03 (m, 2H), 7.66 (d, 2H, J=8.1 Hz), 7.58 (dd, 1H, J=7.6, 7.6 Hz), 7.23 (d, 2H, J=8.1 Hz), 7.14 (dd, 1H, J=1.7, 2.6 Hz), 6.86 (dd, 1H, J=1.7, 4.0 Hz), 6.31 (dd, 1H, J=2.6, 4.0 Hz), 5.87 (s, 2H), 2.41 (s, 3H).

Example 39

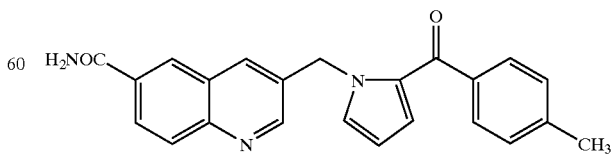

Under nitrogen atmosphere, t-butanol (5.0 mL) was added to the compound of Example 36 (30.0 mg), and the mixture was warmed to 50° C. Potassium hydroxide powder (150 mg) was added thereto, and the mixture was stirred at 50° C. for 1 hour. The reaction solution was cooled to room temperature, and filtered to remove the insoluble materials. The solvent was evaporated under reduced pressure, and the residue was purified by silica gel column (ethyl acetate ethyl acetate/ethanol=20/1) to give the title compound (29.3 mg, 93%).

$^1$H NMR (DMSO-d$_6$, 400 MHz) δ 8.88 (d, 1H, J=2.2 Hz), 8.45 (d, 1H, J=1.9 Hz), 8.16 (brs, 1H), 8.14 (dd, 1H, J=1.9, 8.8 Hz), 8.03 (d, 1H, J=8.8 Hz), 7.98 (d, 1H, J=2.2 Hz), 7.59–7.62 (m, 3H), 7.55 (brs, 1H), 7.28 (d, 2H, J=7.9 Hz), 6.79 (dd, 1H, J=1.7, 4.0 Hz), 6.34 (dd, 1H, J=2.5, 4.0 Hz), 5.86 (s, 2H), 2.36 (s, 3H).

Example 40

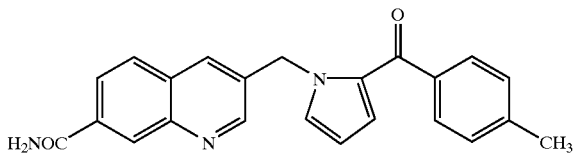

In a similar manner to the preparation of the compound of Example 39, the title compound (15.7 mg, 59%) was obtained from the compound of Example 37 (25.5 mg).

$^1$H NMR (DMSO-d$_6$, 300 MHz) δ 8.85 (d, 1H, J=2.0 Hz), 8.54 (s, 1H), 8.26 (brs, 1H), 7.97–8.03 (m, 3H), 7.58–7.61 (m, 4H), 7.28 (d, 2H, J=7.9 Hz), 6.78 (dd, 1H, J=1.7, 3.9 Hz), 6.34 (dd, 1H, J=2.6, 3.9 Hz), 5.85 (s, 2H), 2.36 (s, 3H).

Example 41

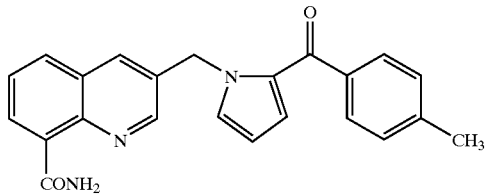

Under nitrogen atmosphere, t-butanol (4.0 mL) and THF (3.0 mL) were added to the compound of Example 38 (24.3 mg), and the mixture was warmed to 50° C. Potassium hydroxide powder (120 mg) was added thereto, and the mixture was stirred at 50° C. for 15 hours. The reaction solution was cooled to room temperature, and filtered to remove the insoluble materials, which was duly washed with THF. The solvent in the filtrate was evaporated under reduced pressure, and the residue was purified by silica gel column (hexane/ethyl acetate=1/1→0/1) to give the title compound (24.2 mg, 95%).

$^1$H NMR (DMSO-d$_6$, 400 MHz) δ 10.04 (brs, 1H), 8.92 (d, 1H, J=2.3 Hz), 8.51 (dd, 1H, J=1.5, 7.5 Hz), 8.13–8.16 (m, 2H), 7.90 (brs, 1H), 7.70 (dd, 1H, J=7.5, 7.5 Hz), 7.59–7.62 (m, 3H), 7.28 (d, 2H, J=7.9 Hz), 6.79 (dd, 1H, J=1.6, 4.0 Hz), 6.34 (dd, 1H, J=2.6, 4.0 Hz), 5.88 (s, 2H), 2.36 (s, 3H).

Example 42

(42-1)

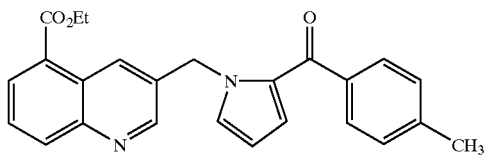

Under nitrogen atmosphere, to a solution of the compound of Example 28-5 (300 mg) in toluene (3.5 mL)-ethanol (3.5 ml) were added triethylamine (400 μl), and dichlorobistriphenylphosphine palladium (158 mg), and the mixture was stirred at 100° C. under carbon monoxide atmosphere. To the mixture were added triethylamine (300 μL), and dichlorobistriphenylphosphine palladium (43.2 mg), and the mixture was stirred for total 10 hours. Water was added to the reaction solution, and the mixture was extracted with ethyl acetate. The extract was dried over magnesium sulfate, filtered, and the solvent was evaporated under reduced pressure, and the residue was purified by silica gel column (hexane/ethyl acetate=3/1) to give 5-ethoxycarbonyl-3-methylquinoline (100 mg, 34%). The starting compound (150 mg, 50%) was recovered as well.

$^1$H NMR (CDCl$_3$, 400 MHz) δ 9.12 (d, 1H, J=2.0 Hz), 8.81 (d, 1H, J=2.0 Hz), 8.24–8.27 (m, 2H), 7.67 (dd, 1H, J=7.4, 8.3 Hz), 4.47 (q, 2H, J=7.1 Hz), 2.57 (s, 3H), 1.47 (t, 3H, J=7.1 Hz).

(42-2)

Under nitrogen atmosphere, to a solution of the compound of Example 42-1 (93.0 mg) in monochlorobenzene (4.0 mL) were added N-bromosuccinimide (79.7 mg) and 2,2'-azobis(isobutyronitrile) (9.6 mg), and the mixture was stirred at 100° C. for 5 hours. The solvent in the reaction solution was evaporated under reduced pressure to about a half volume thereof, and thereto was added toluene-hexane. The insoluble materials were removed by filtration, and the solvent was evaporated under reduced pressure to about 2 ml to give a solution of a crude bromo compound in toluene.

Under nitrogen atmosphere, a solution of the compound of Reference Example 1 (79.3 mg) in THF (2.0 mL) was cooled to 0° C., and thereto was added 60% NaH (17.9 mg). Further, to the mixture was added the solution of crude bromo compound in toluene, and the mixture was stirred at 50° C. for 3 hours. The mixture was cooled to room temperature, and the reaction solution was poured into a 5% aqueous potassium hydrogen sulfate solution, and the mixture was extracted with ethyl acetate. The aqueous layer was neutralized with a saturated aqueous sodium hydrogen carbonate solution, and extracted with ethyl acetate. The organic layers were combined, dried over magnesium sulfate, and filtered. The solvent was evaporated under reduced pressure (hexane/ethyl acetate=3/1→2/1→1/1) to give {1-[(5-ethoxycarbonyl-3-quinolyl)methyl]-1H-pyrrol-2-yl} (4methylphenyl) ketone (50.6 mg, 29%).

$^1$H NMR (CDCl$_3$, 400 MHz) δ 9.10 (d, 1H, J=2.1 Hz), 8.82 (d, 1H, J=2.1 Hz), 8.24–8.28 (m, 2H), 7.70 (dd, 1H, J=7.4, 8.3 Hz), 7.70 (d, 2H, J=8.0 Hz), 7.22 (d, 2H, J=8.0 Hz), 7.11 (dd, 1H, J=1.7, 2.5 Hz), 6.85 (dd, 1H, J=1.7, 4.0 Hz), 6.29 (dd, 1H, J=2.5, 4.0 Hz), 5.90 (s, 2H), 4.43 (q, 2H, J=7.1 Hz), 2.41 (s, 3H), 1.42 (t, 3H, J=7.1 Hz).

Example 43

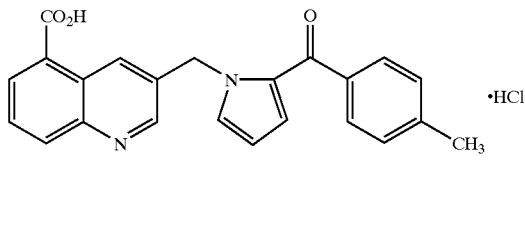

Under nitrogen atmosphere, to the compound of Example 42 (45.0 mg) are added acetic acid (2.0 mL), water (1.0 mL) and conc. hydrochloric acid (1.0 mL), and the mixture was stirred at 100° C. for 4 hours. Toluene was added to the mixture, and the solvent was evaporated under reduced pressure to give the title compound (60.8 mg, quantitatively).

$^1$H NMR (CD$_3$OD, 400 MHz) δ 9.85 (s, 1H), 9.27 (s, 1H), 8.63 (d, 1H, J=7.6 Hz), 8.38 (d, 1H, J=8.4 Hz), 8.17 (dd, 1H, J=7.6, 8.4 Hz), 7.62 (d, 2H, J=8.0 Hz), 7.51 (dd, 1H, J=1.5, 2.6 Hz), 7.26 (d, 2H, J=8.0 Hz), 6.94 (dd, 1H, J=1.5, 4.0 Hz), 6.42 (dd, 1H, J=2.6, 4.0 Hz), 6.00 (s, 2H), 2.39 (s, 3H).

Example 44

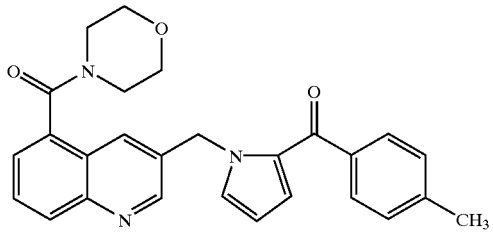

Under nitrogen atmosphere, to a solution of the compound of Example 43 (13.1 mg) in DMF (0.65 mL) were added successively morpholine (10 μL), 1-hydroxybenzotriazole (7.2 mg), 1-(3-dimethyl-aminopropyl)-3-ethylcarbodiimide hydrochloride (12.9 mg), and triethylamine (15 μL), and the mixture was stirred at room temperature for 15 hours. To the reaction solution was added a saturated aqueous sodium hydrogen carbonate solution, and the mixture was extracted with ethyl acetate-toluene. The extract was washed twice with a saturated aqueous sodium hydrogen carbonate solution, and washed with a saturated brine, dried over magnesium sulfate, and filtered. The solvent was evaporated under reduced pressure, and the residue was purified by silica gel column (ethyl acetate) to give the title compound (2.4 mg, 17%).

$^1$H NMR (CDCl$_3$, 400 MHz) δ 8.87 (d, 1H, J=2.1 Hz), 8.12 (d, 1H, J=8.5 Hz), 7.88 (d, 1H, J=2.1 Hz), 7.70 (dd, 1H, J=7.0, 8.5 Hz), 7.67 (d, 2H, J=8.1 Hz), 7.47 (d, 1H, J=7.0 Hz), 7.23 (d, 2H, J=8.1 Hz), 7.13 (dd, 1H, J=1.6, 2.5 Hz), 6.86 (dd, 1H, J=1.6, 4.0 Hz), 6.31 (dd, 1H, J=2.5, 4.0 Hz), 5.83 (m, 2H), 3.68–3.97 (m, 4H), 3.23–3.41 (m, 2H), 2.96–3.11 (m, 2H), 2.40 (s, 3H).

Example 45

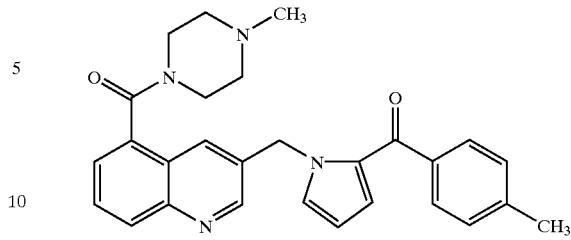

In a similar manner to the preparation of the compound of Example 44, the title compound (10.0 mg, 69%) was obtained from the compound of Example 43 (13.1 mg) and N-methylpiperazine (5.7 mg).

$^1$H NMR (CDCl$_3$, 400 MHz) δ 8.85 (d, 1H, J=2.1 Hz), 8.13 (d, 1H, J=8.4 Hz), 7.92 (brs, 1H), 7.70 (dd, 1H, J=7.1, 8.4 Hz), 7.63 (brd, 2H, J=7.9 Hz), 7.47 (d, 1H, J=7.1 Hz), 7.22 (d, 2H, J=7.9 Hz), 7.13 (brs, 1H), 6.83 (dd, 1H, J=1.5, 4.0 Hz), 6.30 (dd, 1H, J=2.6, 4.0 Hz), 5.82 (m, 2H), 2.23–3.79 (m, 8H), 2.41 (s, 3H), 2.33 (brs, 3H).

Example 46

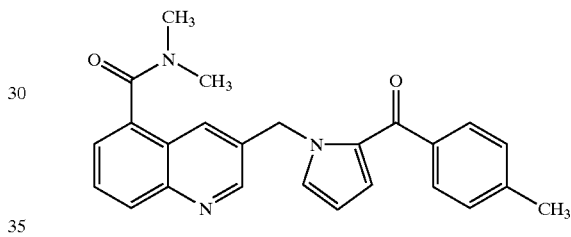

In a similar manner to the preparation of the compound of Example 44, the title compound (11.9 mg, 93%) was obtained from the compound of Example 43 (13.1 mg) and dimethylamine hydrochloride (12.0 mg).

$^1$H NMR (CDCl$_3$, 400 MHz) δ 8.79 (d, 1H, J=2.2 Hz), 8.18 (brd, 1H, J=8.4 Hz), 7.93 (brs, 1H), 7.72 (dd, 1H, J=7.1, 8.4 Hz), 7.66 (d, 2H, J=8.0 Hz), 7.52 (d, 1H, J=7.1 Hz), 7.23 (d, 2H, J=8.0 Hz), 7.09 (dd, 1H, J=1.7, 2.5 Hz), 6.85 (dd, 1H, J=1.7, 4.0 Hz), 6.29 (dd, 1H, J=2.5, 4.0 Hz), 5.84 (s, 2H), 3.18 (s, 3H), 2.69 (s, 3H), 2.41 (s, 3H).

Example 47

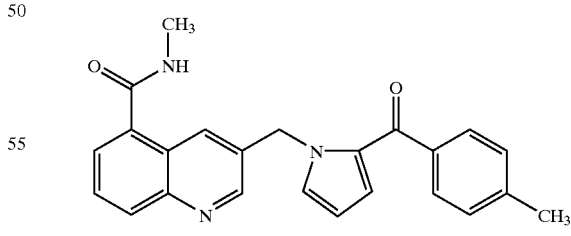

In a similar manner to the preparation of the compound of Example 44, the title compound (4.4 mg, 36%) was obtained from the compound of Example 43 (13.1 mg) and methylamine hydrochloride (37.0 mg).

$^1$H NMR (CDCl$_3$, 400 MHz) δ 8.74 (d, 1H, J=1.9 Hz), 8.59 (d, 1H, J=1.9 Hz), 8.13 (d, 1H, J=8.2 Hz), 7.69 (d, 2H, J=8.0 Hz), 7.60–7.67 (m, 2H), 7.23 (d, 2H, J=8.0 Hz), 7.10

(dd, 1H, J=1.7, 2.5 Hz), 6.84 (dd, 1H, J=1.7, 4.0 Hz), 6.28 (dd, 1H, J=2.5, 4.0 Hz), 6.17 (brs, 2H), 5.84 (s, 2H), 3.06 (d, 3H, J=4.9 Hz), 2.41 (s, 3H).

Example 48

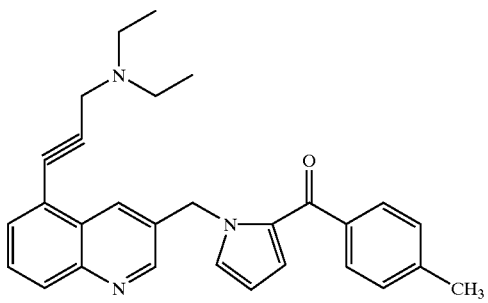

Under nitrogen atmosphere, to a solution of the compound of Example 28 (41.2 mg) and 3-diethylamino-1-propine (30 μL) in triethylamine (0.9 mL) were added dichlorobistriphenylphosphine palladium (14.6 mg) and cupper iodide (2.5 mg), and the mixture was stirred at 70° C. for 2.5 hours. To the mixture was added water, and the mixture was extracted with ethyl acetate. The extract was washed with a saturated aqueous sodium hydrogen carbonate solution, dried over magnesium sulfate, and filtered. The solvent was purified by silica gel column (ethyl acetate→ethyl acetate/ethanol=10/1) and further purified by silica gel column (chloroform/methanol=60/1→40/1) to give the title compound (28.7 mg, 65%).

$^1$H NMR (CDCl$_3$, 400 MHz) δ 8.83 (d, 1H, J=2.1 Hz), 8.31 (d, 1H, J=2.1 Hz), 8.04 (d, 1H, J=8.4 Hz), 7.68 (d, 1H, J=7.2 Hz), 7.68 (d, 2H, J=8.1 Hz), 7.60 (dd, 1H, J=7.2, 8.4 Hz), 7.23 (d, 2H, J=8.1 Hz), 7.10 (dd, 1H, J=1.7, 2.5 Hz), 6.83 (dd, 1H, J=1.7, 4.0 Hz), 6.28 (dd, 1H, J=2.5, 4.0 Hz), 5.89 (s, 2H), 3.79 (s, 2H), 2.66–2.70 (brs, 4H), 2.41(s, 3H), 1.17 (t, 6H, J=7.1 Hz).

Example 49

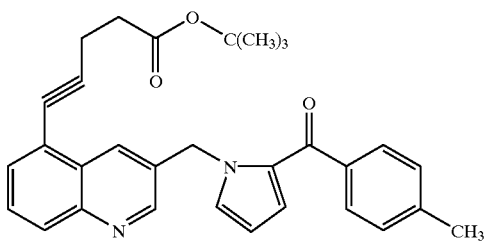

In a similar manner to the preparation of the compound of Example 48, the title compound (23.4 mg, 67%) was obtained from the compound of Example 28 (29.7 mg) and t-butyl 4-pentynate (32.6 mg).

$^1$H NMR (CDCl$_3$, 400 MHz) δ 8.79 (d, 1H, J=2.1 Hz), 8.35 (brs, 1H), 8.05 (brd, 1H, J=7.5 Hz), 7.70 (d, 2H, J=8.0 Hz), 7.58–7.63 (m, 2H), 7.24 (d, 2H, J=8.0 Hz), 7.12 (dd, 1H, J=1.7, 2.5 Hz), 6.85 (dd, 1H, J=1.7, 4.0 Hz), 6.29 (dd, 1H, J=2.5, 4.0 Hz), 5.91 (s, 2H), 2.77 (t, 2H, J=7.4 Hz), 2.59 (t, 2H, J=7.4 Hz), 2.41 (s, 3H), 1.48 (s, 9H).

Example 50

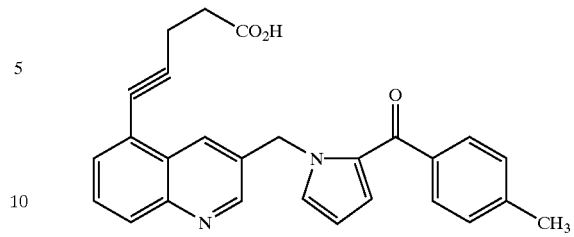

Under nitrogen atmosphere, to the compound of Example 49 (17.4 mg) was added a 4N solution of hydrochloric acid in dioxane (1.0 mL), and the the mixture was stirred at 50° C. for 8 hours. To the reaction solution was added toluene, and the solvent was evaporated under reduced pressure to give the title compound (14.3 mg, 86%).

$^1$H NMR (DMSO-d$_6$, 400 MHz) δ 9.00 (s, 1H), 8.33 (s, 1H), 8.08 (d, 1H, J=8.0 Hz), 7.87 (dd, 1H, J=8.0, 8.0 Hz), 7.60–7.62 (m, 3H), 7.29 (d, 2H, J=7.7 Hz), 6.78 (s, 1H), 6.32 (s, 1H), 5.86 (m, 3H), 2.83 (t, 2H, J=6.5 Hz), 2.40 (t, 2H, J=6.5 Hz), 2.37 (s, 3H).

Example 51

(51-1)

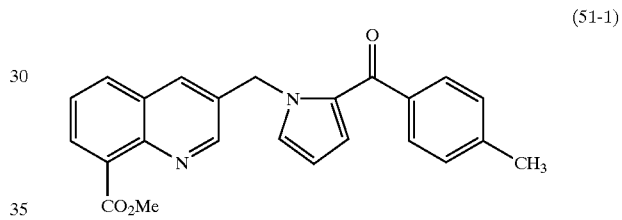

Methyl 2-amino-3-formylbenzoate was obtained according to the methods disclosed in J. Med. Chem., 40, 2040 (1997) and Synth. Commun., 29, 4223 (1999).

$^1$H NMR (CDCl$_3$, 400 MHz) δ 9.88 (s, 1H), 8.41 (brs, 2H), 8.14 (t, 1H, J=7.7 Hz), 7.67 (t, 1H, J=7.7 Hz), 6.70 (t, 1H, J=7.7 Hz), 3.89 (s, 3H).

(51-2)

Under nitrogen atmosphere, to a solution of methyl 2-amino-3-formylbenzoate (3.00 g) in methanol (80 ml) were added propanal (1.50 mL) and piperidine (800 μL), and the mixture was heated under reflux. To the mixture were further added propanal (700 μL) and piperidine (400 μL), and the mixture was further heated under reflux for total 4 hours. The solvent in the reaction solution was evaporated under reduced pressure, and water was added to the residue. The mixture was extracted with ethyl acetate, and the extract was washed twice with water, and washed with a saturated brine, dried over magnesium sulfate, and filtered. The solvent was evaporated under reduced pressure, and the residue was purified twice by silica gel column (hexane/ethyl acetate=3/1→2/1→1/1) and silica gel column (hexane/ethyl acetate=3/1→2/1) to give 3-methyl-8-methoxycarbonylquinoline (2.21 g, 66%).

$^1$H NMR (CDCl$_3$, 400 MHz) δ 8.93 (d, 1H, J=2.1 Hz), 8.00 (dd, 1H, J=1.2, 7.2 Hz), 7.96 (d, 1H, J=2.1 Hz), 7.89 (dd, 1H, J=1.2, 8.2 Hz), 7.54 (dd, 1H, J=7.2, 8.2 Hz), 4.06 (s, 3H), 2.54 (s, 3H).

(51-3)

Under nitrogen atmospher, to a solution of the compound of Example 51-2 (2.11 g) in monochlorobenzene (60 ml)

were added N-bromosuccinimide (1.87 g) and 2,2'-azobis(isobutyronitrile) (144 mg), and the mixture was stirred at 100° C. for 2 hours. The solvent in the reaction solution was evaporated under reduced pressure to about 20 mL, and thereto was added toluene-hexane, and the insoluble materials were removed by filtration to about 20 ml to give a solution of a crude bromo compound.

Under nitrogen atmosphere, the solution of the compound of Reference Example 1 (1.94 g) in THF(30 ml) was cooled to 0° C., and thereto was added 60% NaH (440 mg). Thereto was added the solution of the crude bromo compound, and the mixture was further stirred at 50° C. for 2 hours. The mixture was cooled to room temperature, and poured into a 5% aqueous potassium hydrogen sulfate solution, and the mixture was made weak basic by addition of sodium hydrogen carbonate thereto. The mixture was extracted twice with ethyl acetate, and the extract was washed with water and a saturated brine, and dried over magnesium sulfate, and filtered. The solvent was purified by silica gel column (hexane/ethyl acetate=3/1→2/1→3/2) to give the title compound (1.40 g, 35%). The starting compound (686 mg, 33%) was also recovered.

$^1$H NMR (CDCl$_3$, 400 MHz) δ 8.95 (d, 1H, J=2.0 Hz), 8.02–8.04 (m, 2H), 7.91 (d, 1H, J=7.9 Hz), 7.66 (d, 2H, J=7.8 Hz), 7.55 (dd, 1H, J=7.9, 7.9 Hz), 7.22 (d, 2H, J=7.8 Hz), 7.11 (brs, 1H), 6.82 (dd, 1H, J=1.1, 2.8 Hz), 6.27 (dd, 1H, J=2.8, 3.3 Hz), 5.86 (s, 2H), 4.04 (s, 3H), 2.40 (s, 3H).

Example 52

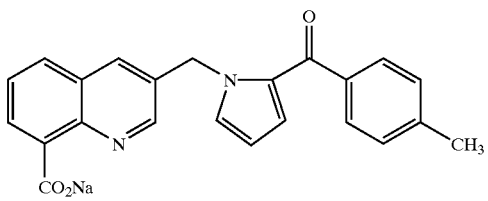

Under nitrogen atmosphere, to the compound of Example 51 (1.74 g) were added successively methanol (4.1 mL), THF (4.1 ml) and 1N aqueous NaOH solution (4.07 mL), and the mixture was stirred at 45° C. for 2 hours. The reaction solution was cooled to room temperature, and the precipitated solid was suspended in ether, and collected by filtration to give the title compound (1.67 g, 94%).

$^1$H NMR (DMSO-d$_6$, 400 MHz) δ 8.71 (d, 1H, J=2.2 Hz), 7.88 (d, 1H, J=2.2 Hz), 7.56–7.63 (m, 4H), 7.38–7.43 (m, 2H), 7.27 (d, 2H, J=7.9 Hz), 6.74 (dd, 1H, J=1.6, 4.0 Hz), 6.30 (dd, 1H, J=2.6, 4.0 Hz), 5.81 (s, 2H), 2.36 (s, 3H).

Example 53

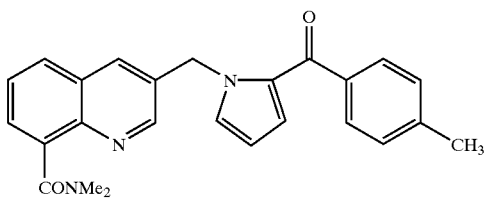

Under nitrogen atmosphere, to a suspension of the compound of Example 52 (30.0 mg) in THF (1.0 mL) was added pivaloyl chloride (10 μL), and the mixture was stirred at room temperature for 3 hours. To the mixture were added diethylamine hydrochloride (12.4 mg) and triethylamine (30 μL), and the mixture was stirred at room temperature. Further, thereto were added diethylamine hydrochloride (16.5 mg) and triethylamine (40 μl), and the mixture was stirred for 4.5 hours. Water was added to the reaction solution, and the mixture was extracted with ethyl acetate. The extract was washed with a saturated aqueous sodium hydrogen carbonate solution and a saturated brine, dried over magnesium sulfate, and filtered. The solvent was evaporated under reduced pressure, and the residue was purified by silica gel column (ethyl acetate/ethanol=1/0→20/1) to give the title compound (21.2 mg, 70%).

$^1$H NMR (CDCl$_3$, 400 MHz) δ 8.82 (d, 1H, J=2.0 Hz), 7.97 (d, 1H, J=2.0 Hz), 7.79 (dd, 1H, J=1.4, 8.1 Hz), 7.67 (d, 2H, J=8.0 Hz), 7.63 (dd, 1H, J=1.4, 7.1 Hz), 7.54 (dd, 1H, J=7.1, 8.1 Hz), 7.23 (d, 2H, J=8.0 Hz), 7.09 (dd, 1H, J=1.6, 2.6 Hz), 6.83 (dd, 1H, J=1.6, 4.0 Hz), 6.27 (dd, 1H, J=2.6, 4.0 Hz), 5.85 (s, 2H), 3.26 (s, 3H), 2.78 (s, 3H), 2.41 (s, 3H).

Example 54

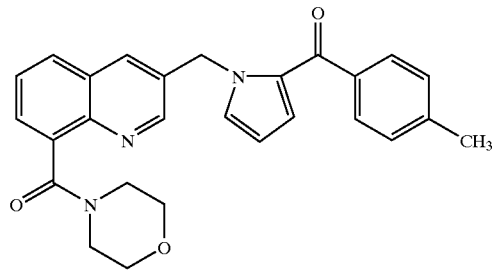

Under nitrogen atmosphere, to a suspension of the compound of Example 52 (30.0 mg) in THF (1.0 ml) was added pivaloyl chloride (10 μL), and the mixture was stirred at room temperature for 2 hours. To the mixture was added morpholine (25 μL), and the mixture was at room temperature overnight. To the reaction solution was added a saturated aqueous sodium hydrogen carbonate solution, and the mixture was extracted with ethyl acetate. The extract was washed with a saturated brine, dried over magnesium sulfate, and filtered. The solvent was evaporated under reduced pressure, and the residue was purified by silica gel column (ethyl acetate/ethanol=1/0→20/1) to give the title compound (22.5 mg, 67%).

$^1$H NMR (CDCl$_3$, 400 MHz) δ 8.82 (s, 1H), 7.94 (s, 1H), 7.80 (dd, 1H, J=1.3, 8.1 Hz), 7.67 (d, 2H, J=8.0 Hz), 7.64 (dd, 1H, J=1.3, 7.1 Hz), 7.54 (dd, 1H, J=7.1, 8.1 Hz), 7.23 (d, 2H, J=8.0 Hz), 7.10 (dd, 1H, J=1.6, 2.6 Hz), 6.84 (dd, 1H, J=1.6, 4.0 Hz), 6.29 (dd, 1H, J=2.6, 4.0 Hz), 5.85 (s, 2H), 3.85–3.96 (m, 4H), 3.55 (m, 2H), 3.13–3.16 (m, 2H), 2.41 (s, 3H).

Example 55

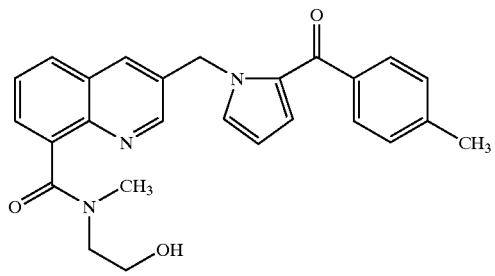

In a similar manner to the preparation of the compound of Example 54, the title compound (22.2 mg, 68%) was obtained from the compound of Example 52 (30.0 mg) and 2-methylaminoethanol, except that the purification of the product was carried out by silica gel column (chloroform/methanol=40/1→30/1).

$^1$H NMR (CDCl$_3$, 400 MHz) δ 8.79 (d, 1H, J=1.9 Hz), 8.03 (d, 1H, J=1.9 Hz), 7.82 (dd, 1H, J=1.2, 8.2 Hz), 7.75 (dd, 1H, J=1.2, 7.0 Hz), 7.67 (d, 2H, J=8.0 Hz), 7.58 (dd, 1H, J=7.0, 8.2 Hz), 7.23 (d, 2H, J=8.0 Hz), 7.11 (dd, 1H, J=1.5, 2.6 Hz), 6.84 (dd, 1H, J=1.5, 4.0 Hz), 6.29 (dd, 1H, J=2.6, 4.0 Hz), 5.83 (s, 2H), 4.00 (m, 2H), 3.80 (t, 1H, J=5.1 Hz), 3.55 (t, 1H, J=5.1 Hz), 2.78 (s, 3H), 2.41 (s, 3H).

Example 56

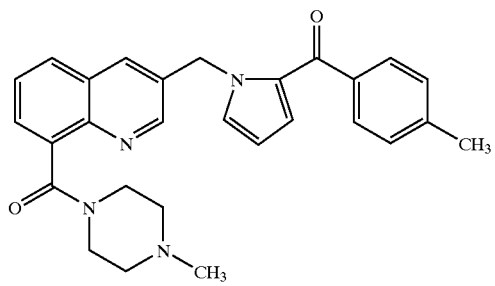

In a similar manner to the preparation of the compound of Example 54, the title compound (24.4 mg, 70%) was obtained from the compound of Example 52 (30.0 mg) and 1-methylpiperazine, provided that the purification of the product was carried out by silica gel column (chloroform/methanol=30/1→20/1).

$^1$H NMR (CDCl$_3$, 400 MHz) δ 8.81 (d, 1H, J=2.2 Hz), 7.92 (d, 1H, J=2.2 Hz), 7.78 (dd, 1H, J=1.4, 8.1 Hz), 7.67 (d, 2H, J=8.0 Hz), 7.62 (dd, 1H, J=1.4, 7.1 Hz), 7.53 (dd, 1H, J=7.1, 8.1 Hz), 7.23 (d, 2H, J=8.0 Hz), 7.10 (dd, 1H, J=1.6, 2.6 Hz), 6.83 (dd, 1H, J=1.6, 4.0 Hz), 6.28 (dd, 1H, J=2.6, 4.0 Hz), 5.89 (d, 1H, J=15.5 Hz), 5.80 (d, 1H, J=15.5 Hz), 4.00 (m, 2H), 3.68 (m, 1H), 3.18–3.20 (m, 2H), 2.67–2.72 (m, 1H), 2.51–2.54 (m, 1H), 2.41 (s, 3H), 2.34 (s, 3H), 2.23 (m, 3H).

Example 57

(57-1)

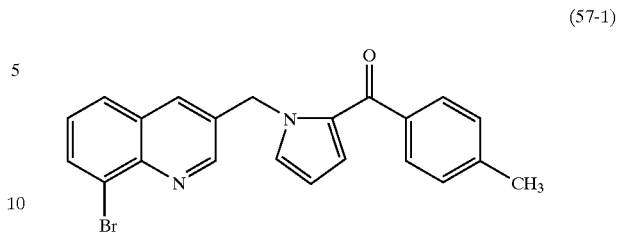

In a similar manner to the preparation of methyl 2-amino-3-formylbenzoate, 2-amino-3-bromobenzaldehyde (3.28 g, quantitatively) was obtained from (2-amino-3-bromophenyl)methanol (3.27 g).

$^1$H NMR (CDCl$_3$, 400 MHz) δ 9.83 (s, 1H), 7.62 (dd, 1H, J=1.5, 7.7 Hz), 7.48 (dd, 1H, J=1.5, 7.7 Hz), 6.67 (t, 1H, J=7.7 Hz).

(57-2)

In a similar manner to Example 51-2, 8-bromo-3-methyl-quinoline (3.23 g, 94%) was obtained from the compound of Example 57-1 (3.10 g).

$^1$H NMR (CDCl$_3$, 400 MHz) δ 8.90 (d, 1H, J=1.5 Hz), 7.99 (dd, 1H, J=1.2, 7.5 Hz), 7.94 (d, 1H, J=1.5 Hz), 7.73 (dd, 1H, J=1.2, 8.2 Hz), 7.38 (dd, 1H, J=7.5, 8.2 Hz), 2.56 (s, 3H).

(57-3)

Under nitrogen atmosphere, to a solution of the compound of Example 57-2 (1.01 g) in carbon tetrachloride (25 mL) were added N-bromosuccinimide (810 mg) and 2,2'-azobis(isobutyronitrile) (68.0 mg), and the mixture was heated under reflux for 2 hours. The reaction solution was cooled to room temperature, and the insoluble materials were removed by filtration, and the solvent in the filtrate was evaporated under reduced pressure to about 10 ml. To the resultant was added toluene, and the mixture was evaporated under reduced pressure to about 10 ml. This procedure was repeated total four times to give a solution of a crude bromo compound in toluene.

Under nitrogen atmosphere, a solution of the compound of Reference Example 1 (844 mg) in THF (13 mL) was cooled to 0° C., and thereto was added 60% NaH (191 mg). Then, the above solution of the crude bromo compound was added thereto, and the mixture was stirred at 50° C. for 6 hours. The reaction solution was cooled to room temperature, and thereto was added water. The mixture was extracted three times with ethyl acetate, and the extract was washed with water and a saturated brine, dried over magnesium sulfate, and filtered. The solvent was evaporated under reduced pressure, and the residue was purified by silica gel column (hexane/ethyl acetate=8/1→3/1→hexane/acetone=2/1→1/1) to give the title compound (950 mg, 52%).

$^1$H NMR (CDCl$_3$, 400 MHz) δ 8.91 (d, 1H, J=2.1 Hz), 8.01–8.04 (m, 2H), 7.76 (dd, 1H, J=1.0, 8.1 Hz), 7.66 (d, 2H, J=8.0 Hz), 7.39 (dd, 1H, J=7.5, 8.1 Hz), 7.23 (d, 2H, J=8.0 Hz), 7.11 (dd, 1H, J=1.6, 2.6 Hz), 6.84 (dd, 1H, J=1.6, 4.0 Hz), 6.29 (dd, 1H, J=2.6, 4.0 Hz), 5.87 (s, 2H), 2.41 (s, 3H).

Example 58

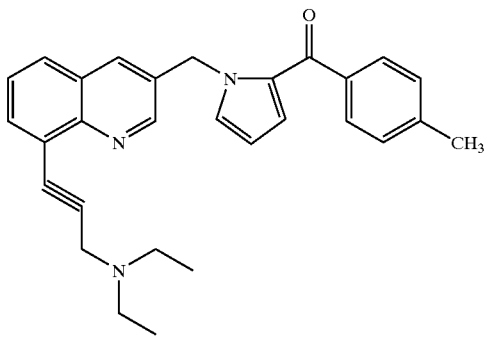

Under nitrogen atmosphere, to the compound of Example 57 (45.0 mg) and 3-diethylamino-1-propine (30 μL) were added triethyl-amine (1.0 ml) and THF (1.0 ml), and thereto were added dichloro-bistriphenylphosphine palladium (17.7 mg) and cupper iodide (3.5 mg), and the mixture was stirred at 45° C. for 4 hours, and then stirred at 50° C. for 3 hours. To the reaction solution was added a saturated aqueous sodium hydrogen carbonate solution, and the mixture was extracted with ethyl acetate. The extract was dried over magnesium sulfate, and filtered. The solvent was evaporated under reduced pressure, and the residue was purified by silica gel column (ethyl acetate→ethyl acetate/ethanol=20/1→chloroform/methanol=20/1) to give the title compound (19.1 mg, 40%).

$^1$H NMR (CDCl$_3$, 400 MHz) δ 8.88 (d, 1H, J=2.2 Hz), 7.97 (d, 1H, J=2.2 Hz), 7.86 (dd, 1H, J=1.2, 7.3 Hz), 7.73 (dd, 1H, J=1.2, 8.1 Hz), 7.67 (d, 2H, J=8.0 Hz), 7.45 (dd, 1H, J=7.3, 8.1 Hz), 7.22 (d, 2H, J=8.0 Hz), 7.10 (dd, 1H, J=1.6, 2.6 Hz), 6.82 (dd, 1H, J=1.6, 4.0 Hz), 6.27 (dd, 1H, J=2.6, 4.0 Hz), 5.85 (s, 2H), 3.89 (s, 2H), 2.80 (brs, 4H), 2.41 (s, 3H), 1.20 (t, 6H, J=7.1 Hz).

Example 59

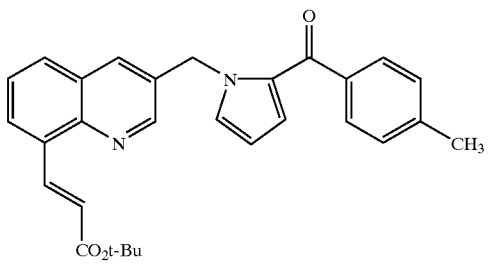

Under nitrogen atmosphere, to a mixture of the compound of Example 57 (50.0 mg), bis(dibenzylideneacetone)palladium (14.1 mg) and cesium carbonate (66.0 mg) were added dioxane (1.0 mL), t-butyl acrylate (30 μL) and a 2.47 N solution of tri-t-butylphosphine in toluene (20 μL), and the mixture was stirred at 100° C. for 3 hours. Water was added to the reaction solution, and the mixture was extracted with ethyl acetate. The extract was washed with a saturated brine, dried over magnesium sulfate, and filtered. The solvent was purified by silica gel column (ethyl acetate/hexane=5/1→3/1) to give the title compound (48.6 mg, 87%).

$^1$H NMR (CDCl$_3$, 400 MHz) δ 8.87 (d, 1H, J=2.2 Hz), 8.74 (d, 1H, J=16.2 Hz), 7.98 (d, 1H, J=2.2 Hz), 7.92 (dd, 1H, J=1.0, 7.3 Hz), 7.79 (dd, 1H, J=1.0, 8.2 Hz), 7.67 (d, 2H, J=8.0 Hz), 7.53 (dd, 1H, J=7.3, 8.2 Hz), 7.23 (d, 2H, J=8.0 Hz), 7.11 (dd, 1H, J=1.7, 2.5 Hz), 6.83 (dd, 1H, J=1.7, 4.0 Hz), 6.72 (d, 1H, J=16.2 Hz), 6.28 (dd, 1H, J=2.5, 4.0 Hz), 5.86 (s, 2H), 2.41 (s, 3H), 1.56 (s, 9H).

Example 60

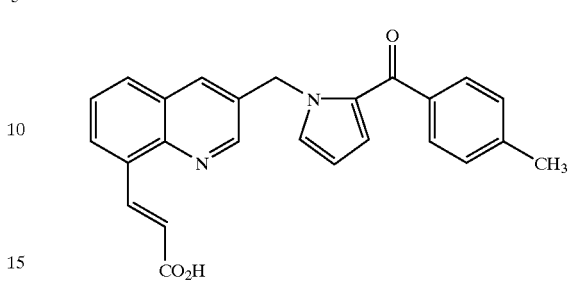

Under nitrogen atmosphere, to a solution of the compound of Example 59 (19.0 mg) in dioxane (1.0 mL) was added a 4N solution of hydrochloric acid in dioxane (0.7 mL), and the mixture was stirred at 50° C. for 5 hours. The solvent in the reaction solution was evaporated under reduced pressure, and the precipitated solid was collected by filtration, and dried to give the title compound (17.9 mg, 98%).

$^1$H NMR (DMSO-d$_6$, 400 MHz) δ 8.88 (d, 1H, J=2.2 Hz), 8.77 (d, 1H, J=16.3 Hz), 7.21 (d, 1H, J=7.3 Hz), 8.00–8.03 (m, 2H), 7.59–7.65 (m, 4H), 7.27 (d, 2H, J=7.9 Hz), 6.81 (d, 1H, J=16.3 Hz), 6.78 (dd, 1H, J=1.6, 4.0 Hz), 6.33 (dd, 1H, J=2.6, 4.0 Hz), 5.86 (s, 2H), 2.36 (s, 3H).

Example 61

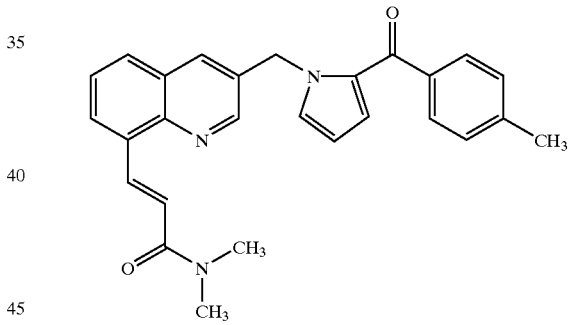

Under nitrogen atmosphere, to a mixture of the compound of Example 57 (50.0 mg), N,N-dimethylacrylamide (30 μL), bis(dibenzylideneacetone)palladium (15.0 mg) and cesium carbonate (67.6 mg) were added dioxane (1.0 mL) and a 2.47 N solution of tri-t-butylphosphine in toluene (20 μL), and the mixture was stirred at 100° C. for 3.5 hours. Water was added to the reaction solution, and the mixture was extracted with ethyl acetate. The extract was washed with a saturated brine, dried over magnesium sulfate, and filtered. The solvent was evaporated under reduced pressure, and the residue was purified by silica gel column (ethyl acetate/hexane=1/1→1/3→0/1) to give the title compound (44.6 mg, 86%).

$^1$H NMR (CDCl$_3$, 400 MHz) δ 8.87 (d, 1H, J=2.2 Hz), 8.53 (d, 1H, J=15.6 Hz), 7.96 (d, 1H, J=2.2 Hz), 7.87 (dd, 1H, J=1.2, 7.1 Hz), 7.74 (dd, 1H, J=1.2, 8.1 Hz), 7.67 (d, 2H, J=8.0 Hz), 7.51 (dd, 1H, J=7.1, 8.1 Hz), 7.49 (d, 1H, J=15.6 Hz), 7.22 (d, 2H, J=8.0 Hz), 7.12 (dd, 1H, J=1.7, 2.5 Hz), 6.83 (dd, 1H, J=1.7, 4.0 Hz), 6.28 (dd, 1H, J=2.5, 4.0 Hz), 5.85 (s, 2H), 3.21 (s, 3H), 3.09 (s, 3H), 2.40 (s, 3H).

Example 62

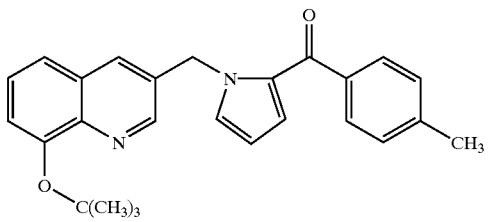

Under nitrogen atmosphere, a mixture of the compound of Example 57 (76.8 mg), sodium t-butoxide (30.8 mg) and bis(dibenzylideneacetone)palladium (18.9 mg) were added toluene (1.0 mL) and a 2.47N solution of tri-t-butylphosphine in toluene (20 μL), and the mixture was stirred at 100° C. for 9 hours. Water was added to the reaction solution, and the mixture was extracted with ethyl acetate. The extract was washed with a saturated brine, dried over magnesium sulfate, and filtered. The solvent was evaporated under reduced pressure, and the residue was purified by silica gel column (ethyl acetate/hexane=3/1→2/1) to give the title compound (12.8 mg, 17%).

$^1$H NMR (CDCl$_3$, 400 MHz) δ 8.81 (d, 1H, J=1.8 Hz), 7.93 (d, 1H, J=1.8 z), 7.68 (d, 2H, J=8.0 Hz), 7.45 (dd, 1H, J=1.5, 8.1 Hz), 7.40 (dd, 1H, J=7.4, 8.1 Hz), 7.31 (dd, 1H, J=1.5, 7.4 Hz), 7.23 (d, 2H, J=8.0 Hz), 7.08 (dd, 1H, J=1.6, 2.6 Hz), 6.81 (dd, 1H, J=1.6, 4.0 Hz), 6.25 (dd, 1H, J=2.6, 4.0 Hz), 5.84 (s, 2H), 2.41 (s, 3H), 1.49 (s, 9H).

Example 63

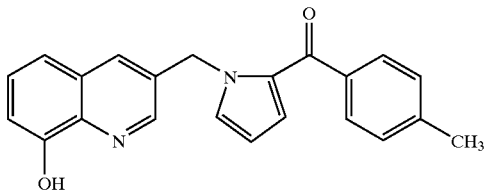

Under nitrogen atmosphere, to the compound of Example 62 (8.7 mg) were added toluene (0.5 mL) and a solution (500 μL), wherein trifluoroacetic acid (100 μL) and trifluoromethanesulfonic acid (110 μL) were dissolved in toluene (10 mL), and the mixture was stirred at room temperature for 30 minutes. The reaction solution was poured into a saturated aqueous sodium hydrogen carbonate solution, and the mixture was extracted with ethyl acetate. The extract was dried over magnesium sulfate, and filtered. The solvent was evaporated under reduced pressure, and the residue was purified by silica gel column (ethyl acetate/hexane=3/1→2/1) to give the title compound (2.4 mg, 32%).

$^1$H NMR (CDCl$_3$, 300 MHz) δ 8.68 (s, 1H), 7.99 (s, 1H), 7.67 (d, 2H, J=8.1 Hz), 7.45 (dd, 1H, J=8.0, 8.1 Hz), 7.23 (d, 2H, J=8.1 Hz), 7.17–7.30 (m, 2H), 7.11 (dd, 1H, J=1.7, 2.5 Hz), 6.84 (dd, 1H, J=1.7, 4.0 Hz), 6.29 (dd, 1H, J=2.5, 4.0 Hz), 5.85 (s, 2H), 2.41 (s, 3H).

Example 64

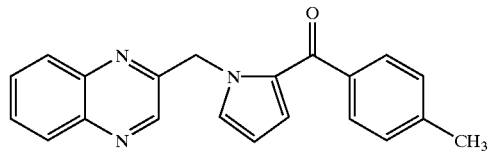

The title compound was obtained in a similar manner to Example 1 from 2-methylquinoxaline and the compound of Reference Example 1.

$^1$H NMR (300 MHz, CDCl3) δ 8.67 (s, 1H), 8.00–8.10 (m, 2H), 7.70–7.80 (m, 2H), 7.71 (d, 2H, J=8.0 Hz), 7.25 (d, 2H, J=8.0 Hz), 7.19 (dd, 1H, J=2.5, 1.7 Hz), 6.86 (dd, 1H, J=4.1, 1.7 Hz), 6.30 (dd, 1H, J=4.1, 2.5 Hz), 5.96 (s, 2H), 2.42 (s, 3H).

Example 65

(65-1)

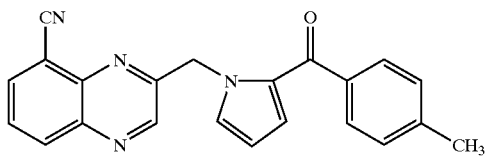

To a solution of 3-nitro-1,2-phenylenediamine (5.02 g) in ethanol (500 mL) was added at 60° C. a 40% aqueous solution of pyruvic aldehyde (17.72 g). The reaction solution was refluxed for 10 minutes, and thereto was added water (300 mL). The mixture was cooled to room temperature, and concentrated under reduced pressure. The precipitated crystals were collected by filtration, washed with cold water, and dried under reduced pressure to give 2-methyl-8-nitroquinoxaline (4.17 g, 67%) as orange crystals.

$^1$H NMR (300 MHz, CDCl$_3$) δ 8.85 (s, 1H), 8.30 (dd, 1H, J=8.4, 1.3 Hz), 8.10 (dd, 1H, J=7.5, 1.3 Hz), 7.77 (t, 1H, J=8.1 Hz), 2.84 (s, 3H).

(65-2)

To a solution of 2-methyl-8-nitroquinoxaline (3.50 g) in MeOH (350 mL) was added dropwise a 20% aqueous solution of titanium trichloride (88.64 g) at 0° C. After the addition, the reaction solution was warmed to room temperature, and the mixture was stirred for another hour, and then concentrated under reduced pressure. The resultant was neutralized by addition of an aqueous sodium carbonate solution, and the mixture was extracted five times with ethyl acetate (200 mL). The organic layers were combined, dried over magnesium sulfate, filtered, and concentrated under reduced pressure. The residue was purified by silica gel column chromatography (chloroform) to give 2-methyl-8-aminoquinoxaline (2.27 g, 77%) as red oil.

$^1$H NMR (300 MHz, CDCl$_3$) δ 8.70 (s, 1H), 7.47 (t, 1H, J=7.5 Hz), 7.39 (dd, 1H, J=8.3, 1.3 Hz), 6.92 (dd, 1H, J=7.3, 1.3 Hz), 4.95 (brs, 1H), 2.73 (s, 3H).

(65-3)

A mixture of 2-methyl-8-aminoquinoxaline (2.27 g), conc. hydrochloric acid (7.87 g) and water (10 mL) was cooled to 0° C., and vigorously stirred. To the mixture was added an aqueous solution of sodium nitrite (1.03 g) in water (10 mL) in such a manner that the temperature of the mixture was not raised over 5° C. After the addition, the mixture was further stirred for 10 minutes, and thereto was added slowly a solution of KI, which was prepared by dissolving KI (2.37 g) in water (10 mL) in such a manner that that the temperature of the reaction mixture was not raised over 5° C. After the addition, the mixture was stirred for 10 minutes, and the reaction solution was warmed to room temperature, and further stirred for one hour. The reaction solution was neutralized with a 2N NaOH, and extracted twice with chloroform. The organic layers were combined, dried over magnesium sulfate, filtered, and concentrated under reduced pressure. The residue was purified by silica gel column chromatography (hexane/ethyl acetate=10/1) to give 2-methyl-8-iodoquinoxaline (743 mg, 19%) as pale brown solid.

$^1$H NMR (300 MHz, CDCl$_3$) δ 8.70 (s, 1H), 8.34 (dd, 1H, J=7.5, 1.3 Hz), 8.07 (dd, 1H, J=8.3, 1.1 Hz), 7.44 (t, 1H, J=7.7 Hz), 2.86 (s, 3H).

(65-4)

A suspension of 2-methyl-8-iodoquinoxaline (730 mg), Zn(CN)$_2$ (423 mg) and Pd(PPh$_3$)$_4$ (313 mg) in DMF (5 mL) was stirred at 60° C. for 5 hours. The reaction solution was cooled, and thereto was added water (10 mL), and the mixture was extracted twice with a mixture of toluene and ethyl acetate (1:1) (50 mL). The organic layers were combined, dried over magnesium sulfate, filtered, and concentrated under reduced pressure. The residue was purified by silica gel column chromatography (hexane/ethyl acetate= 5/1→4/1) to give 2-methyl-8-cyano-quinoxaline (422 mg, 93%) as red brown solid.

$^1$H NMR (300 MHz, CDCl$_3$) δ 8.86 (s, 1H), 8.32 (dd, 1H, J=8.4, 1.3 Hz), 8.15 (dd, 1H, J=7.3, 1.3 Hz), 7.77 (dd, 1H, J=8.3, 7.3 Hz), 2.88 (s, 3H).

(65-5)

The title compound was obtained in a similar manner to Example 1 from the compound of Example 65-4 and the compound of Reference Example 1.

$^1$H NMR (300 MHz, CDCl$_3$) δ 8.84 (s, 1H), 8.33 (dd, 1H, J=8.4, 1.3 Hz), 8.15 (dd, 1H, J=7.3, 1.5 Hz), 7.80 (dd, 1H, J=8.6, 7.3 Hz), 7.72 (d, 2H, J=8.1 Hz), 7.25 (m, 3H), 6.89 (dd, 1H, J=4.0, 1.7 Hz), 6.33 (dd, 1H, J=4.0, 2.8 Hz), 6.01 (s, 2H), 2.42 (s, 3H).

Example 66

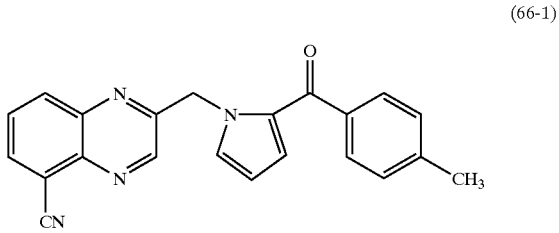

(66-1)

To a solution of 3-nitro-1,2-phenylenediamine (2.67 g) and a 2N KOH (8.7 mL) in ethanol (250 mL) was added a 40% aqueous solution of pyruvic aldehyde (17.72 g) at 60° C. The mixture was heated under reflux for 10 minutes, and thereto was added water (150 mL). The mixture was cooled to room temperature, and concentrated under reduced pressure. The precipitated crystals were collected by filtration, washed with cold water, and dried under reduced pressure to give 2-methyl-5-nitroquinoxaline (2.21 g, 67%) as pale brown solid.

$^1$H NMR (300 MHz, CDCl$_3$) δ 8.91 (s, 1H), 8.26 (dd, 1H, J=8.6, 1.2 Hz), 8.12 (d, 1H, J=7.7 Hz), 7.83 (t, 1H, J=7.7 Hz), 2.84 (s, 3H).

(66-2)

To a solution of 2-methyl-5-nitroquinoxaline (3.67 g) in MeOH (350 mL) was added dropwise a 20% aqueous titanium trichloride (92.9 g) at room temperature. After the addition, the mixture was further stirred for one hour, and concentrated under reduced pressure. The resultant was neutralized by addition of aqueous sodium carbonate solution, and the mixture was extracted four times with ethyl acetate (150 mL). The organic layers were combined, and dried over magnesium sulfate, and concentrated under reduced pressure. The residue was purified by silica gel column chromatography (chloroform) to give 2-methyl-5-aminoquinoxaline (2.44 g,79%) as orange crystals.

$^1$H NMR (300 MHz, CDCl$_3$) δ 8.55 (s, 1H), 7.51 (t, 1H, J=7.7 Hz), 7.33 (dd, 1H, J=8.4, 0.9 Hz), 6.89 (d, 1H, J=7.7 Hz), 2.75 (s, 3H).

(66-3)

2-Methyl-5-iodoquinoxaline was obtained from 2-methyl-5-aminoquinoxaline in a similar manner to Reference Example 3.

$^1$H NMR (300 MHz, CDCl$_3$) δ 8.78 (s, 1H), 8.31 (dd, 1H, J=7.3, 1.1 Hz), 8.02 (dd, 1H, J=8.4, 1.1 Hz), 7.48 (dd, 1H, J=8.3, 7.5 Hz), 2.82 (s, 3H).

(66-4)

2-Methyl-5-cyanoquinoxaline was obtained from 2-methyl 5-iodoquinoxaline in a similar manner to Example 65-4.

$^1$H NMR (300 MHz, CDCl$_3$) δ 8.91 (s, 1H), 8.27 (dd, 1H, J=8.4, 1.3 Hz), 8.12 (dd, 1H, J=7.2, 1.3 Hz), 7.82 (dd, 1H, J=8.2, 7.2 Hz), 2.77 (s, 3H).

(66-5)

The title compound was obtained from the compound of Example 66-4 and the compound of Reference Example 1 in a similar manner to Example 1.

$^1$H NMR (300 MHz, CDCl3) δ 8.73 (s, 1H), 8.29 (dd, 1H, J=8.4, 1.1 Hz), 8.14 (dd, 1H, J=7.3, 1.5 Hz), 7.82 (dd, 1H, J=8.4, 7.3 Hz), 7.69 (d, 2H, J=8.1 Hz), 7.25 (d, 2H, J=8.1 Hz), 7.18 (dd, 1H. J=2.4, 1.5 Hz), 6.90 (dd, 1H, J=4.0, 1.5 Hz), 6.34 (dd, 1H, J=4.0, 2.4 Hz), 5.97 (s, 2H), 2.42 (s, 3H).

Example 67

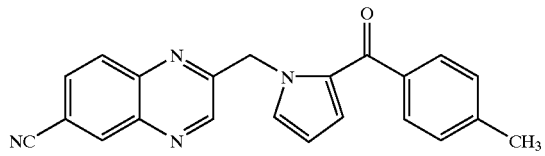

(67-1)

To a suspension of 4-nitro-1,2-phenylenediamine (10.0 g) in water (150 mL) was added dropwise a 40% aqueous solution of pyruvic aldehyde (11.76 g) at room temperature. The reaction solution was stirred at 80° C. for 4 hours, and cooled to room temperature. Water (200 mL) was added to the mixture, and the mixture was extracted with chloroform (150 mL×3). The organic layers were combined, dried over magnesium sulfate, filtered, and concentrated under reduced pressure. The residual solid was recrystallized from ethanol, collected by filtration, and dried to give 2-methyl-6-nitroquinoxaline (7.38 g, 60%) as red solid.

$^1$H NMR (300 MHz, CDCl$_3$) δ 8.99 (d, 1H, J=2.4 Hz), 8.90 (s, 1H), 8.52 (dd, 1H, J=9.2, 2.4 Hz), 8.18 (d, 1H, J=9.2 Hz), 2.84 (s, 3H).

(67-2)

To a suspension of 2-methyl-5-nitroquinoxaline (5.00 g) in MeOH (500 mL) was added dropwise a 20% aqueous solution of titanium trichloride (126.6 g) at room temperature. After the addition, the mixture was stirred for 1.5 hour, and concentrated under reduced pressure. To the mixture was added water (200 mL), and the mixture was neutralized by addition of aqueous sodium carbonate solution, and extracted with ethyl acetate (250 mL×8). The organic layers were combined, dried over magnesium sulfate, filtered, and concentrated under reduced pressure. The residue was purified by silica gel column chromatography (1% MeOH/chloroform) to give 2-methyl-6-amino-quinoxaline (2.88 g, 68%) as yellow solid.

$^1$H NMR (300 MHz, CDCl$_3$) δ 8.53 (s, 1H), 7.80 (d, 1H, J=8.8 Hz), 7.16 (m, 2H), 4.13 (brs, 2H), 2.69 (s, 3H).

(67-3)

2-Methyl-6-iodoquinoxaline was prepared from 2-methyl-6-aminoquinixaline in a similar manner to Reference Example 3.

$^1$H NMR (300 MHz, CDCl$_3$) δ 8.72 (s, 1H), 8.49 (d, 1H, J=2.0 Hz), 7.99 (dd, 1H, J=8.8, 1.8 Hz), 7.73 (d, 1H, J=8.8 Hz), 2.76 (s, 3H).

(67-4)

2-Methyl-6-cyanoquinoxaline was prepared from 2-methyl-6-iodoquinoxaline in a similar manner to Reference Example 4.

$^1$H NMR (300 MHz, CDCl$_3$) δ 8.86 (s, 1H), 8.46 (d, 1H, J=1.7 Hz), 8.11 (d, 1H, J=8.6 Hz), 7.90 (dd, 1H, J=8.2, 1.8 Hz), 2.83 (s, 3H).

(67-5)

The title compound was obtained from the compound of Example 67-4 and the compound of Reference Example 1 in a similar manner to Example 1.

$^1$H NMR (300 MHz, CDCl$_3$) δ 8.73 (s, 1H), 8.46 (d, 1H, J=1.5 Hz), 8.13 (d, 1H, J=8.4 Hz), 7.89 (dd, 1H, J=8.6, 1.6 Hz), 7.69 (d, 2H, J=8.1 Hz), 7.25 (d, 2H, J=8.1 Hz), 7.19 (dd, 1H, J=2.4, 1.5 Hz), 6.90 (dd, 1H, J=4.0, 1.5 Hz), 6.34 (dd, 1H, J=4.0, 2.4 Hz), 5.94 (s, 2H), 2.42(s, 3H).

Example 68

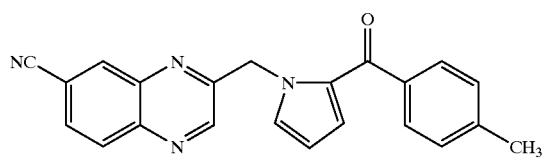

(68-1)

To a suspension of 1,2,4-triaminobenzene dihydrochloride (5.0 g) in a 10% aqueous Na$_2$CO$_3$ solution (60 mL) was added a 40% aqueous pyruvic aldehyde solution (4.59 g) at room temperature. The reaction solution was heated under reflux for 2 hours, and extracted with chloroform (60 mL×3). Teh organic layers were combined, dried over magnesium sulfate, filtered, and concentrated underreduced pressure. The residue was purified by silica gel column chromatography (2–3% methanol in chloroform to give 2-methyl-7-aminoquinozaline (3.17 g, 78%) as a yellow solid.

$^1$H NMR (300 MHz, CDCl$_3$) δ 8.46 (s, 1H), 7.83 (d, 1H, J=8.8 Hz), 7.11 (dd, 1H, J=8.8, 2.6 Hz), 7.06 (d, 1H, J=2.6 Hz), 2.69 (s, 3H). (68-2)

2-Methyl-7-idoquinozaline was prepared form 2-methyl-7-aminoquinizaline in a similar manner to Reference Example 3.

$^1$H NMR (300 MHz, CDCl$_3$) δ 8.74 (s, 1H), 8.44 (d, 1H, J=8.8 Hz), 7.95 (dd, 1H, J=8.6, 1.8 Hz), 7.78 (d, 1H, J=8.8 Hz), 2.77 (s, 3H). (68-3)

2-Methyl-7-cyanoquinozaline was prepared form 2-methyl-7-iodoquinizaline in a similar manner to Reference Example 4.

$^1$H NMR (300 MHz, CDCl$_3$) δ8.85 (s, 1H), 8.39 (d, 1H, J=1.8 Hz), 8.17 (d, 1H, J=8.6 Hz), 7.86 (dd, 1H, J=8.6, 1.8 Hz), 2.83 (s, 3H).

(68-4)

The title compound was obtained from the compound of Example 68-3 and the compound of Reference Example 1 in a similar manner to Example 1.

$^1$H NMR (300 MHz, CDCl$_3$) δ 8.80 (s, 1H), 8.41 (d, 1H, J=1.3 Hz), 8.18 (d, 1H, J=8.8 Hz), 7.87 (dd, 1H, J=8.6, 1.7 Hz), 7.69 (d, 2H, J=8.1 Hz), 7.21 (m, 3H), 6.89 (dd, 1H, J=4.0, 1.7 Hz), 6.34 (dd, 1H, J=4.0, 2.6 Hz), 5.94 (s, 2H), 2.42 (s, 3H).

Example 69

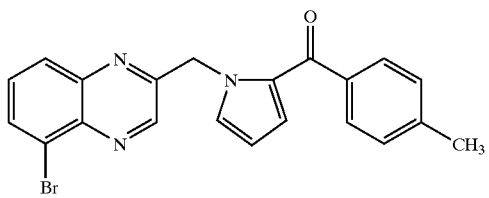

(69-1)

To a solution of 2-methyl-6-aminoquinoxaline (15.8 g) in acetic acid (150 mL) was added dropwise a solution of bromine (15.88 g) in acetic acid (11 mL) at 0° C. After the addition, the reaction solution was stirred at 0° C. for one hour, and the precipitates were collected by filtration, washed with ether, and dried to give 2-methyl-6-amino-5-bromoquinoxaline hydrobromide (29.86 g, 94%), which was neutralized to give 2-methyl-6-amino-5-bromoquinoxaline.

$^1$H NMR (400 MHz, CDCl$_3$) δ 8.70 (s, 1H), 7.79 (d, 1H, J=9.0 Hz), 7.26 (d, 1H, J=9.0 Hz), 4.67 (brs, 2H), 2.73 (s, 3H).

(69-2)

A mixture of the compound of Example 69-1 (1.0 g), conc. hydrochloric acid (3 mL) and water (15 mL) was cooled to 0° C., and stirred vigorously, and thereto was added slowly a solution of sodium nitrite (299 mg) in water (5 mL) in such a manner that the temperature of the mixture was not raised over 5° C. After the addition, the mixture was stirred for 20 minutes, and thereto was added slowly a 36% aqueous H$_3$PO$_2$ solution (10 mL) which was cooled to 0° C. After the addition, the mixture was stirred at 0° C. for 10 hours, and the reaction solution was warmed to room temperature, and allowed to stand overnight. The mixture was extracted twice with ethyl acetate, and the organic layers were combined, dried over magnesium sulfate, filtered, and concentrated under reduced pressure. The residue was purified by silica gel column chromatography (hexane/ethyl acetate=20/1→8/1) to give 2-methyl-5-bromoquinoxaline (475 mg, 51%) as pink solid.

$^1$H NMR (400 MHz, CDCl$_3$) δ 8.85 (s, 1H), 8.03 (dd, 1H, J=7.6, 1.2 Hz), 8.01 (dd, 1H, J=8.6, 1.2 Hz), 7.62 (dd, 1H, J=8.6, 7.6 Hz), 2.83 (s, 3H). (69-3)

The title compound was obtained from the compound of Reference Example 1 and the compound of Example 69-2 in a similar manner to Example 1.

$^1$H NMR (400 MHz, CDCl$_3$) δ 8.67 (s, 1H), 8.05 (dd, 1H, J=7.6, 1.2 Hz), 8.03 (dd, 1H, J=8.6, 1.2 Hz), 7.70 (d, 2H, J=8.0 Hz), 7.63 (dd, 1H, J=8.6, 7.6 Hz), 7.25 (d, 2H, J=8.0

Hz), 7.17 (dd, 1H, J=2.5, 1.7 Hz), 6.88 (dd, 1H, J=4.1, 1.7 Hz), 6.32 (dd, 1H, J=4.1, 2.5 Hz), 5.98 (s, 2H), 2.42 (s, 3H).

Example 70

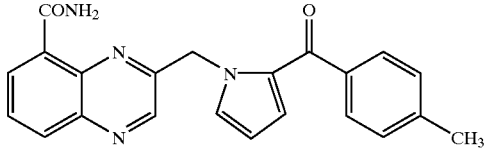

The title compound was obtained from the compound of Example 65 in a similar manner to the preparation of the compound of Example 39.

¹H NMR (300 MHz, CDCl₃) δ 9.49 (brs, 1H), 8.93 (s, 1H), 8.51 (dd, 1H, J=7.5, 1.5 Hz), 8.26 (dd, 1H, J=8.3, 1.5 Hz), 7.84 (t, 1H, J=8.3 Hz), 7.62 (d, 2H, J=8.1 Hz), 7.21 (d, 2H, J=8.1 Hz), 7.19 (m, 1H), 6.98 (dd, 1H, J=4.0, 1.5 Hz), 6.38 (dd, 1H, J=4.0, 2.7 Hz), 6.05 (s, 2H), 2.39 s, 3H).

Example 71

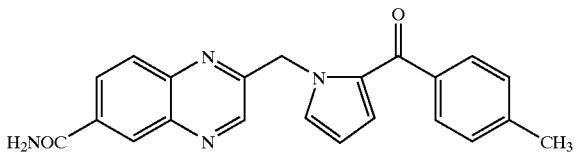

The title compound was obtained from the compound of Example 67 in a similar manner to the preparation of the compound of Example 39.

¹H NMR (300 MHz, CDCl₃) δ 8.73 (s, 1H), 8.45 (d, 1H, J=1.8 Hz), 8.23 (dd, 1H, J=8.9, 2.1 Hz), 8.11 (d, 1H, J=8.6 Hz), 7.71 (d, 2H, J=8.1 Hz), 7.25 (d, 2H, J=8.1 Hz), 7.20 (dd, 1H, J=2.6, 1.7 Hz), 6.89 (dd, 1H, J=4.0, 1.7 Hz), 6.33 (dd, 1H, J=4.0, 2.6 Hz), 6.29 (brs, 1H), 5.96 (s, 2H), 5.72 (brs, 1H), 2.42 (s, 3H).

Example 72

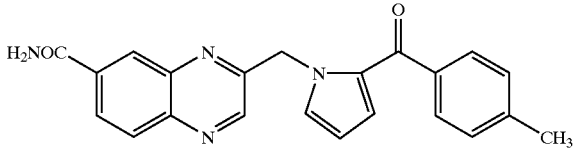

The title compound was obtained from the compound of Example 68 in a similar manner to the preparation of the compound of Example 39.

¹H NMR (400 MHz, CDCl₃) δ 8.74 (s, 1H), 8.42 (d, 1H, J=1.7 Hz), 8.18 (dd, 1H, J=8.7, 1.9 Hz), 8.12 (d, 1H, J=8.7 Hz), 7.69 (d, 2H, J=8.1 Hz), 7.24 (d, 2H, J=8.1 Hz), 7.21 (dd, 1H, J=2.6, 1.7 Hz), 6.89 (dd, 1H, J=4.0, 1.7 Hz), 6.46 (brs, 1H), 6.33 (dd, 1H, J=4.0, 2.6 Hz), 5.95 (s, 2H), 2.42 (s, 3H).

Example 73

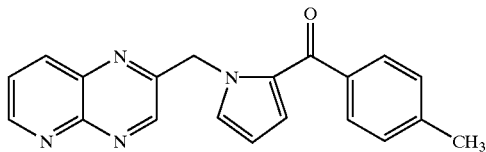

The title compound was obtained from 2-methylpyrido[2,3-b]-pyrazine and the compound of Reference Example 1 in a similar manner to the preparation of the compound of Example 1

¹H NMR (400 MHz, CDCl₃) δ 9.15 (dd, 1H, J=4.2, 1.9 Hz), 8.84 (s, 1H), 8.41 (dd, 1H, J=8.4, 1.9 Hz), 7.71 (dd, 1H, J=8.4, 4.2 Hz), 7.70 (dd, 2H, J=8.0 Hz), 7.25 (d, 2H, J=8.0 Hz), 7.19 (dd, 1H, J=2.5, 1.7 Hz), 6.89 (dd, 1H, J=4.0, 1.7 Hz), 6.33 (dd, 1H, J=4.0, 2.5 Hz), 5.98 (s, 2H), 2.42 (s, 3H).

Reference Example 4-1

Methyl 4-[(2-pyridylsulfanyl)carbonyl]benzoate

A solution of monomethyl terephthalate (1.50 g), 2,2'-dipyridyl disulfide (3.67 g) and triphenylphosphine (4.37 g) in anhydrous toluene was stirred for 24 hours under nitrogen atmosphere, and the solvent was evaporated under reduced pressure, and the residue was purified by silica gel column chromatography (chloroform) to give the title compound (3.49 g) as yellow solid.

¹H NMR (300 MHz, CDCl₃) δ 8.70 (m, 1H), 8.16 (d, 2H, J=8.6 Hz), 8.07 (d, 2H, J=8.6 Hz), 7.82 (dt, 1H, J=7.9, 2.0 Hz), 7.68 (m, 1H), 7.37 (m, 1H), 3.97 (s, 3H).

Reference Example 4-2

(1H-Pyrrol-2-yl) (4-methoxycarbonylphenyl) ketone

To a solution of pyrrole (1.68 g) in toluene (40 mL) was added dropwise methyl magnesium bromide in THF (0.93N solution, 27.8 mL) at −20 to −30° C. After the addition, the reaction solution was further stirred for 30 minutes. A solution of methyl 4-[(2-pyridylsulfanyl)-carbonyl]benzoate (8.33 mmol) in toluene (80 mL) was cooled to −78° C., and thereto was added dropwise the above toluene solution via a cannula in such a manner that the temperature of the reaction mixture was not raised over −65° C. After the addition, the reaction solution was stirred at −78° C. for 2 hours, and thereto was added a saturated aqueous ammonium chloride solution (50 mL), and the mixture was warmed to room temperature. To the reaction solution was added ethyl acetate (100 mL), and the organic layer was separated. Further, the aqueous layer was extracted with ethyl acetate (50 mL×2). The organic layers were combined, and washed successively with 9% hydrochloric acid (100 mL), 10% aqueous sodium hydrogen carbonate solution (100 mL), water (100 mL) and a saturated brine (100 mL), dried over magnesium sulfate, filterd and concentrated under reduced pressure. The residue was purified by silica gel column chromatography (hexane/ethyl acetate=5/1→4/1) to give the title compound (1.40 g) as colorless solid.

¹H NMR (CDCl₃, 400 MHz) δ 9.72 (brs, 1H), 8.15 (d, 2H, J=8.4 Hz), 7.94 (d, 2H, J=8.4 Hz), 7.19 (m, 1H), 6.87 (m, 1H), 6.37 (m, 1H), 3.97 (s, 3H).

Reference Example 4-3

[1-(3-Quinolylmethyl)-1H-pyrrol-2-yl](4-methoxycarbonylphenyl) ketone

The title compound was obtained from 3-methylquinoline and the compound of Reference Example 4-2 in a similar manner to Example 1.

$^1$H NMR (CDCl$_3$, 400 MHz) δ 8.83 (d, 1H, J=2.2 Hz), 8.09 (m, 3H), 7.95 (1H, brd, J=1.35 Hz), 7.78 (m, 3H), 7.69 (ddd, 1H, J=8.4, 6.9, 1.4 Hz), 7.53 (ddd, 1H, J=8.1, 6.9, 1.1 Hz), 7.16 (dd, 1H, J=2.4, 1.8 Hz), 6.81 (dd, 1H, J=4.1, 1.8 Hz), 6.30 (dd, 1H, J=4.1, 2.4 Hz), 5.87 (s, 2H), 3.94 (s, 3H).

Reference Example 4-4

[1-(3-Quinolylmethyl)-1H-pyrrol-2-yl](4-carboxyphenyl) ketone hydrochloride

The compound of Reference Example 4-3 (379.1 mg) was dissolved in a mixture of THF/MeOH (1:1, 30 mL), and thereto was added 2N NaOH (1.54 mL). The reaction mixture was stirred at room temperature for one day, and concentrated under reduced pressure. The residue was dissolved in a 0.5N NaOH (20 mL), and washed with ethyl acetate. The aqueous layer was acidified with a 6N hydrochloric acid, and the precipitated solid was collected by filtration, and dried to give the title compound (341.8 mg, 85%).

$^1$H NMR (DMSO-d$_6$, 400 MHz) δ 13.22 (brs, 1H), 8.82 (d, 1H, J=2.2 Hz), 8.00 (m, 4H), 7.94 (dd, 1H, J=8.1, 1.0 Hz), 7.74 (m, 3H), 7.67 (dd, 1H, J=2.3, 1.7 Hz), 7.58 (ddd, 1H, J=8.1, 6.9, 1.0 Hz), 6.81 (dd, 1H, J=4.1, 1.7 Hz), 6.35 (dd, 1H, J=4.1, 2.3 Hz), 5.87 (s, 2H).

Example 74

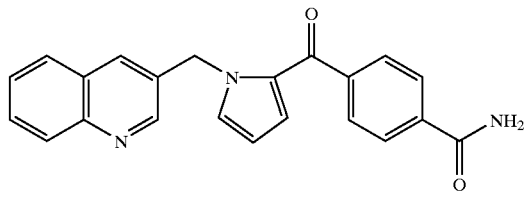

The title compound was obtained from the compound of Reference Example 4—4 and a 29% aqueous ammonia in a similar manner to Example 44.

$^1$H NMR (DMSO-d$_6$, 400 MHz) δ 8.82 (d, 1H, J=2.2 Hz), 8.10 (brs, 1H), 8.00 (m, 2H), 7.94 (m, 3H), 7.73 (m, 3H), 7.66 (dd, 1H, J=2.3, 1.8 Hz), 7.58 (ddd, 1H, J=8.1, 7.0, 1.1 Hz), 7.51 (brs, 1H), 6.80 (dd, 1H, J=4.1, 1.6 Hz), 6.35 (dd, 1H, J=4.1, 2.3 Hz), 5.86 (s, 2H).

Example 75

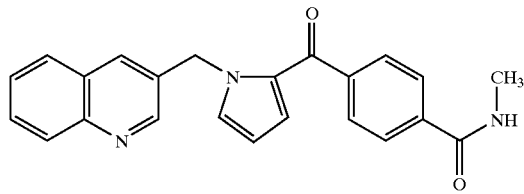

The title compound was obtained from the compound of Reference Example 4-3 and methylamine hydrochloride in a similar manner to Example 44.

$^1$H NMR (CDCl$_3$, 400 MHz) δ 8.82 (d, 1H, J=2.2 Hz), 8.08 (d, 1H, J=8.5 Hz), 7.94 (d, 1H, J=1.3 Hz), 7.79 (m, 5H), 7.69 (m, 1H), 7.53 (m, 1H), 7.16 (dd, 1H, J=2.5, 1.7 Hz), 6.80 (dd, 1H, J=4.1, 1.7 Hz), 6.30 (dd, 1H, J=4.1, 2.5 Hz), 6.21 (brs, 1H), 5.86 (s, 2H), 3.03 (s, 3H).

Example 76

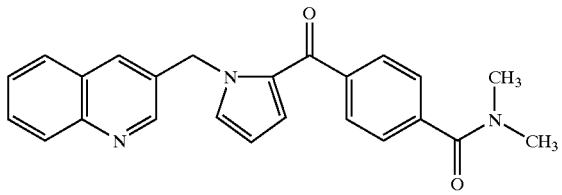

The title compound was obtained from the compound of Reference Example 4-3 and dimethylamine hydrochloride in a similar manner to Example 44.

$^1$H NMR (CDCl$_3$, 400 MHz) δ 8.82 (d, 1H, J=2.2 Hz), 8.08 (d, 1H, J=8.5 Hz), 7.94 (d, 1H, J=1.3 Hz), 7.77 (m, 3H), 7.69 (m, 1H), 7.53 (m, 1H), 7.46 (d, 2H, J=8.4 Hz), 7.16 (dd, 1H, J=2.4, 1.7 Hz), 6.83 (dd, 1H, J=4.1, 1.7 Hz), 6.30 (dd, 1H, J=4.1, 2.4 Hz), 5.86 (s, 2H), 3.13 (s, 3H), 2.96 (s, 3H).

Example 77

(77-1)

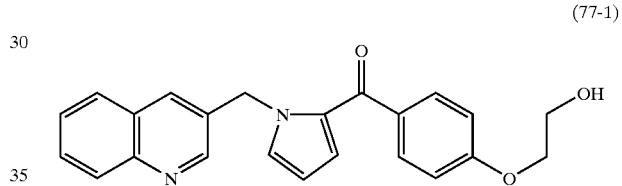

The compound of Example 15 (10.0 mg) was dissolved in THF (1.0 mL), and thereto was added a solution of diisobutyl aluminium hydride in THF (1.0 M solution, 241 mL) at 0° C. The reaction solution was treated with an aqueous hydrochloric acid solution, and extracted with ethyl acetate. The residue was purified by silica gel column chromatography to give 2-(4-{hydroxy[1-(3-quinolylmethyl)-1H-pyrrol-2-yl]methyl}phenoxy)ethanol (2.00 mg, 22%).

$^1$H NMR (CDCl$_3$, 400 MHz) δ 8.52 (d, 1H, J=2.2 Hz), 8.06 (brd, 1H, J=8.3 Hz), 7.68 (dt, 1H, J=1.3, 8.3 Hz), 7.67 (d, 1H, J=7.6 Hz), 7.52 (ddd, 1H, J=0.9, 7.6, 8.3 Hz), 7.51 (brs, 1H), 7.21 (brd, 2H, J=8.7 Hz), 6.74 (d, 2H, J=8.7 Hz), 6.73 (dd, 1H, J=1.8, 3.1 Hz), 6.17 (dd, 1H, J=3.1, 3.5 Hz), 6.04 (dd, 1H, J=1.8, 3.5 Hz), 5.81 (brs, 1H), 5.32 (d, 1H, J=16.2 Hz), 5.29 (d, 1H, J=16.2 Hz), 3.89–3.99 (m, 4H).

(77-2)

The compound of Example 77-1 (2.00 mg) was dissolved in THF (1.0 mL), and thereto was added manganese dioxide (50.0 mg), and the mixture was stirred at room temperature for 15 minutes. The reaction solution was filtered, and the filtrate was concentrated, and the residue was purified by silica gel column chromatography to give the title compound (2.00 mg, 100%).

$^1$H NMR (CDCl$_3$, 400 MHz) δ 8.81 (d, 1H, J=2.2 Hz), 8.07 (brd, 1H, J=8.6 Hz), 7.93 (brs, 1H), 7.79 (d, 2H, J=8.8 Hz), 7.76 (brd, 1H, J=7.6 Hz), 7.68 (ddd, 1H, J=1.7, 7.6, 8.6 Hz), 7.52 (dt, 1H, J=0.9, 7.6 Hz), 7.10 (dd, 1H, J=1.5, 2.5 Hz), 6.95 (d, 2H, J=8.8 Hz), 6.82 (dd, 1H, J=1.5, 4.0 Hz), 6.28 (dd, 1H, J=2.5, 4.0 Hz), 5.84 (brs, 2H), 4.15 (dt, 2H, J=5.0, 1.6 Hz), 3.97–4.02 (m, 2H).

Example 78

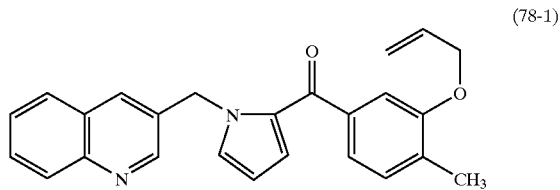

(78-1)

3-Hydroxy-4-methylbenzoic acid (7.60 g) was dissolved in methanol (400 mL), and thereto was added sulfuric acid (15.0 g), and the mixture was allowed to stand at room temperature for 10 hours. The reaction solution was concentrated to 150 mL, and diluted with water, and extracted with toluene. The extract was washed with an aqueous sodium hydrogen carbonate solution, and concentrated to give methyl 3-hydroxy-4-methylbenzoate (7.76 g, 94%). This product was dissolved in THF (140 mL), and thereto was added NaH (60% dispersion in oil, 2.22 g), and the mixture was stirred at 50° C. for one hour. To the mixture was added allyl bromide (7.00 g), and the mixture was refluxed for 5 hours. Water was added to the reaction solution, and the mixture was extracted with toluene, dried, filtered, and concentrated. The residue was purified by silica gel column chromatography to give methyl [3-(allyloxy)-4-methyl]benzoate (8.92 g, 93%).

$^1$H NMR (CDCl$_3$, 400 MHz) δ 7.56 (dd, 1H, J=1.5, 7.7 Hz), 7.47 (d, 1H, J=1.5 Hz), 7.19 (dd, 1H, J=0.5, 7.7 Hz), 6.08 (ddt, 1H, J=10.6, 17.3, 5.0 Hz), 5.45 (ddt, 1H, J=17.3, 1.6, 1.6 Hz), 5.29 (ddt, 1H, J=10.6, 1.6, 1.6 Hz), 4.60 (dt, 2H, J=5.0, 1.6 Hz), 3.90 (s, 3H), 2.30 (brs, 3H).

(78-2)

[3-(Allyloxy)-4-methylphenyl](1H-pyrrol-2-yl) ketone was obtained from the compound of Example 78-1 in a similar manner to Example 10-1.

$^1$H NMR (CDCl$_3$, 400 MHz) 9.78 (brs, 1H), 7.46 (dd, 1H, J=1.5, 7.2 Hz), 7.36 (d, 1H, J=1.5 Hz), 7.24 (dd, 1H, J=0.2, 7.2 Hz), 7.13 (dt, 1H, J=1.3, 2.7 Hz), 6.91 (ddd, 1H, J=3.8, 2.4, 1.3 Hz), 6.34 (dt, 1H, J=3.8, 2.7 Hz), 6.09 (ddt, 1H, J=10.6, 17.3, 5.0 Hz), 5.45 (ddt, 1H, J=17.3, 1.6, 1.6 Hz), 5.30 (ddt, 1H, J=10.6, 1.6, 1.6 Hz), 4.62 (dt, 2H, J=5.0, 1.6 Hz), 2.33 (brs, 3H).

(78-3)

The title compound was obtained from 3-methylquinoline and the compound of Example 78-2 in a similar manner to Example 1.

$^1$H NMR (CDCl$_3$, 400 MHz) δ 8.82 (d, 1H, J=2.2 Hz), 8.08 (d, 1H, J=8.4 Hz), 7.94 (d, 1H, J=2.0 Hz), 7.76 (brd, 1H, J=8.1 Hz), 7.69 (ddd, 1H, J=8.4, 7.0, 1.5 Hz), 7.53 (ddd, 1H, J=8.1, 7.0, 1.1 Hz), 7.30 (dd, 1H, J=1.5, 7.2 Hz), 7.23 (d, 1H, J=1.5 Hz), 7.18 (brd, 1H, J=7.2 Hz), 7.11 (dd, 1H, J=1.7, 2.5 Hz), 6.86 (dd, 1H, J=1.7, 4.0 Hz), 6.28 (dd, 1H, J=2.5, 4.0 Hz), 6.06 (ddt, 1H, J=10.6, 17.3, 5.0 Hz), 5.84 (brs, 2H), 5.42 (ddt, 1H, J=17.3, 1.6, 1.6 Hz), 5.27 (ddt, 1H, J=10.6, 1.6, 1.6 Hz), 4.57 (dt, 2H, J=5.0, 1.6 Hz), 2.30 (brs, 3H).

Example 79

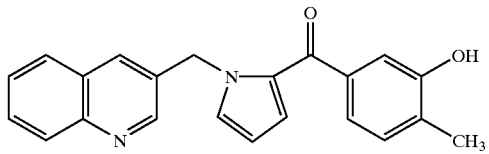

The title compound was obtained from the compound of Example 78 in a similar manner to Example 14.

$^1$H NMR (CDCl$_3$, 400 MHz) δ 8.73 (brs, 1H), 8.08 (d, 1H, J=8.4 Hz), 7.94 (brs, 1H), 7.71 (brd, 1H, J=8.1 Hz), 7.65 (ddd, 1H, J=8.4, 7.0, 1.5 Hz), 7.40–7.53 (series of m, 2H), 7.23 (d, 1H, J=1.5 Hz), 7.21 (brd, 1H, J=7.2 Hz), 7.14 (brd, 1H, J=7.2 Hz), 7.05 (dd, 1H, J=1.7, 2.5 Hz), 6.80 (dd, 1H, J=1.7, 4.0 Hz), 6.18 (dd, 1H, J=2.5, 4.0 Hz), 5.84 (brs, 2H), 2.29 (brs, 3H).

Example 80

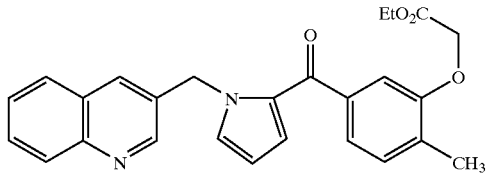

The title compound was obtained from the compound of Example 79 in a similar manner to Example 15.

$^1$H NMR (CDCl$_3$, 400 MHz) δ 8.81 (d, 1H, J=2.2 Hz), 8.07 (d, 1H, J=8.4 Hz), 7.92 (d, 1H, J=2.0 Hz), 7.76 (brd, 1H, J=8.1 Hz), 7.68 (ddd, 1H, J=8.4, 7.0, 1.5 Hz), 7.51 (ddd, 1H, J=8.1, 7.0, 1.1 Hz), 7.34 (dd, 1H, J=1.5, 7.2 Hz), 7.20 (brd, 1H, J=7.2 Hz), 7.12 (d, 1H, J=1.5 Hz), 7.10 (dd, 1H, J=1.7, 2.5 Hz), 6.83 (dd, 1H, J=1.7, 4.0 Hz), 6.27 (dd, 1H, J=2.5, 4.0 Hz), 5.83 (brs, 2H), 4.66 (s, 2H), 4.24 (q, 2H, J=7.1 Hz), 2.34 (brs, 3H), 1.27 (t, 3H, J=7.1 Hz).

Example 81

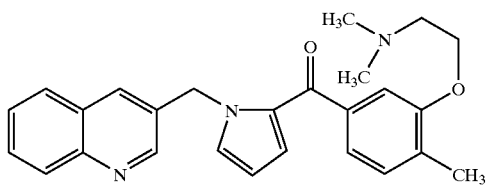

The compound of Example 79 (20.0 mg), dimethylaminoethyl chloride hydrochloride (168 mg) and potassium carbonate (400 mg) were refluxed in acetone (3.0 mL) for 3 hours. The reaction solution was poured into water, and the mixture was extracted with ethyl acetate. The extract was dried, filtered, and the solvent was evaporated under reduced pressure. The residue was purified by silica gel column chromatography to give the title compound (18.1 mg, 75%).

$^1$H NMR (CDCl$_3$, 400 MHz) δ 8.82 (d, 1H, J=2.2 Hz), 8.07 (d, 1H, J=8.4 Hz), 7.93 (d, 1H, J=2.0 Hz), 7.76 (brd, 1H, J=8.1 Hz), 7.68 (ddd, 1H, J=8.4, 7.0, 1.5 Hz), 7.52 (ddd, 1H, J=8.1, 7.0, 1.1 Hz), 7.29 (dd, 1H, J=1.5, 7.2 Hz), 7.24 (d, 1H, J=1.5 Hz), 7.17 (brd, 1H, J=7.2 Hz), 7.11 (dd, 1H, J=1.7, 2.5 Hz), 6.86 (dd, 1H, J=1.7, 4.0 Hz), 6.27 (dd, 1H, J=2.5, 4.0 Hz), 5.83 (brs, 2H), 4.11 (t, 2H, J=5.7 Hz), 2.78 (t, 2H, J=5.7 Hz), 2.36 (s, 6H), 2.27 (brs, 3H).

Example 82

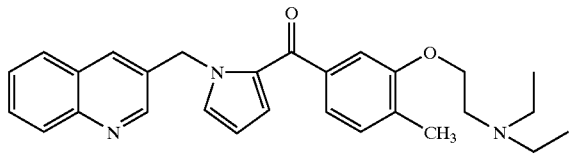

The title compound was obtained from the compound of Example 79 and diethylaminoethyl chloride hydrochloride in a similar manner to Example 81.

$^1$H NMR (CDCl3, 400 MHz) δ 8.82 (d, 1H, J=2.2 Hz), 8.07 (d, 1H, J=8.4 Hz), 7.93 (d, 1H, J=2.0 Hz), 7.76 (brd, 1H, J=8.1 Hz), 7.68 (ddd, 1H, J=8.4, 7.0, 1.5 Hz), 7.52 (ddd, 1H, J=8.1, 7.0, 1.1 Hz), 7.29 (dd, 1H, J=1.5, 7.2 Hz), 7.24 (d, 1H, J=1.5 Hz), 7.16 (brd, 1H, J=7.2 Hz), 7.11 (dd, 1H, J=1.7, 2.5 Hz), 6.86 (dd, 1H, J=1.7, 4.0 Hz), 6.27 (dd, 1H, J=2.5, 4.0 Hz), 5.84 (brs, 2H), 4.07 (t, 2H, J=5.7 Hz), 2.92 (t, 2H, J=5.7 Hz), 2.64 (q, 4H, J=7.1 Hz), 2.27 (brs, 3H), 1.07 (t, 6H, J=7.1 Hz).

Example 83

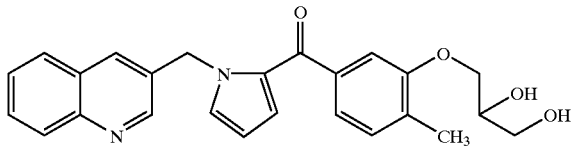

The title compound was obtained from the compound of Example 78 in a similar manner to Example 13.

$^1$H NMR (CDCl$_3$, 400 MHz) δ 8.77 (d, 1H, J=2.2 Hz), 8.07 (d, 1H, J=8.4 Hz), 7.93 (d, 1H, J=2.0 Hz), 7.75 (brd, 1H, J=8.1 Hz), 7.67 (ddd, 1H, J=8.4, 7.0, 1.5 Hz), 7.51 (ddd, 1H, J=8.1, 7.0, 1.1 Hz), 7.31 (dd, 1H, J=1.5, 7.2 Hz), 7.22 (d, 1H, J=1.5 Hz), 7.16 (brd, 1H, J=7.2 Hz), 7.12 (dd, 1H, J=1.7, 2.5 Hz), 6.84 (dd, 1H, J=1.7, 4.0 Hz), 6.28 (dd, 1H, J=2.5, 4.0 Hz), 5.82 (brs, 2H), 4.04–4.15 (series of m, 3H), 3.83 (dd, 1H, J=11.4, 3.8 Hz), 3.76 (dd, 1H, J=11.4, 5.5 Hz), 2.25 (brs, 3H).

Example 84

(84-1)

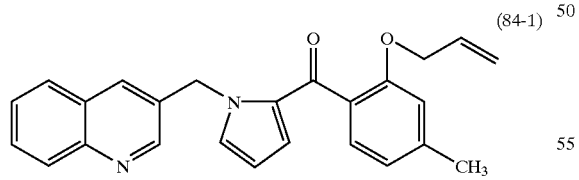

Methyl [2-(allyloxy)-4-methyl]benzoate was obtained from 2-hydroxy-4-methylbenzoic acid in a similar manner to Example 78-1.

$^1$H NMR (CDCl$_3$, 400 MHz) δ 7.73 (d, 1H, J=7.9 Hz), 6.79 (dd, 1H, J=0.6, 7.9 Hz), 6.76 (brs, 1H), 6.08 (ddt, 1H, J=10.6, 17.3, 5.0 Hz), 5.53 (ddt, 1H, J=17.3, 1.6, 1.6 Hz), 5.30 (ddt, 1H, J=10.6, 1.6, 1.6 Hz), 4.61 (dt, 2H, J=5.0, 1.6 Hz), 3.88 (s, 3H), 2.37 (brs, 3H).

(84-2)

[2-(Allyloxy)-4-methylphenyl](1H-pyrrol-2-yl) ketone was obtained from the compound of Example 81-1 in a similar manner to Example 10-1.

$^1$H NMR (CDCl$_3$, 400 MHz) δ 9.69 (brs, 1H), 7.36 (d, 1H, J=7.9 Hz), 7.08 (dt, 1H, J=1.3, 2.7 Hz), 6.82 (brd, 1H, J=7.9 Hz), 6.79 (brs, 1H), 6.67 (ddd, 1H, J=3.8, 2.4, 1.3 Hz), 6.26 (dt, 1H, J=3.8, 2.7 Hz), 5.95 (ddt, 1H, J=10.6, 17.3, 5.0 Hz), 5.30 (ddt, 1H, J=17.3, 1.6, 1.6 Hz), 5.18 (ddt, 1H, J=10.6, 1.6, 1.6 Hz), 4.56 (dt, 2H, J=5.0, 1.6 Hz), 2.39 (brs, 3H).

(84-3)

The title compound was obtained from 3-methylquinoline and the compound of Example 81-2 in a similar manner to Example 1.

$^1$H NMR (CDCl$_3$, 400 MHz) δ 8.84 (d, 1H, J=2.2 Hz), 8.08 (d, 1H, J=8.4 Hz), 7.95 (d, 1H, J=2.0 Hz), 7.76 (dd, 1H, J=1.1, 8.1 Hz), 7.68 (ddd, 1H, J=8.4, 7.0, 1.5 Hz), 7.51 (ddd, 1H, J=8.1, 7.0, 1.1 Hz), 7.20 (d, 1H, J=7.9 Hz), 7.06 (dd, 1H, J=1.7, 2.5 Hz), 6.77 (brd, 1H, J=7.9 Hz), 6.72 (brs, 1H), 6.64 (dd, 1H, J=1.7, 4.0 Hz), 6.19 (dd, 1H, J=2.5, 4.0 Hz), 5.89 (brs, 2H), 5.77 (ddt, 1H, J=10.6, 17.3, 5.0 Hz), 5.12 (ddt, 1H, J=17.3, 1.6, 1.6 Hz), 5.02 (ddt, 1H, J=10.6, 1.6, 1.6 Hz), 4.44 (dt, 2H, J=5.0, 1.6 Hz), 2.36 (brs, 3H).

Example 85

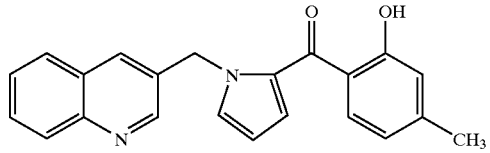

The title compound was obtained from the compound of Example 84 in a similar manner to Example 14.

$^1$H NMR (CDCl$_3$, 400 MHz) δ 8.79 (d, 1H, J=2.2 Hz), 8.07 (d, 1H, J=8.4 Hz), 7.89 (d, 1H, J=2.0 Hz), 7.75 (dd, 1H, J=1.1, 8.1 Hz), 7.74 (d, 1H, J=7.9 Hz), 7.69 (ddd, 1H, J=8.4, 7.0, 1.5 Hz), 7.52 (ddd, 1H, J=8.1, 7.0, 1.1 Hz), 7.10 (dd, 1H, J=1.7, 2.5 Hz), 6.89 (dd, 1H, J=1.7, 4.0 Hz), 6.80 (brs, 1H), 6.68 (brd, 1H, J=7.9 Hz), 6.32 (dd, 1H, J=2.5, 4.0 Hz), 5.75 (brs, 2H), 2.34 (brs, 3H).

Example 86

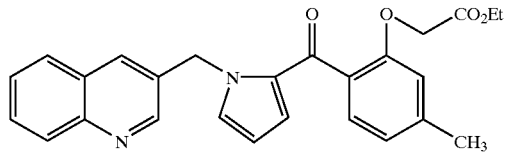

The title compound was obtained from the compound of Example 85 in a similar manner to Example 15.

$^1$H NMR (CDCl$_3$, 400 MHz) δ 8.83 (d, 1H, J=2.2 Hz), 8.08 (d, 1H, J=8.4 Hz), 7.96 (d, 1H, J=2.0 Hz), 7.77 (dd, 1H, J=1.1, 8.1 Hz), 7.68 (ddd, 1H, J=8.4, 7.0, 1.5 Hz), 7.51 (ddd, 1H, J=8.1, 7.0, 1.1 Hz), 7.21 (d, 1H, J=7.9 Hz), 7.06 (dd, 1H, J=1.7, 2.5 Hz), 6.81 (brd, 1H, J=7.9 Hz), 6.71 (brs, 1H), 6.62 (dd, 1H, J=1.7, 4.0 Hz), 6.20 (dd, 1H, J=2.5, 4.0 Hz), 5.89 (brs, 2H), 4.53 (s, 2H), 4.17 (q, 2H, J=7.1 Hz), 2.34 (brs, 3H), 1.21 (t, 3H, J=7.1 Hz).

Example 87

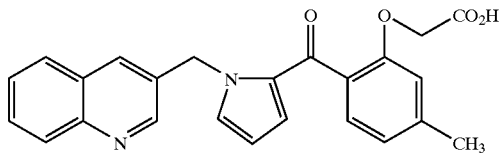

The title compound was obtained from the compound of Example 86 in a similar manner to Example 16.

$^1$H NMR (CDCl$_3$, 400 MHz) δ 8.83 (brs, 1H), 8.49 (brs, 1H), 8.43 (brd, 1H, J=8.4 Hz), 7.96 (brd, 1H, J=8.1 Hz), 7.83 (brdd, 1H, J=8.4, 7.0 Hz), 7.69 (brdd, 1H, J=8.1, 7.0 Hz), 7.34 (d, 1H, J=7.9 Hz), 7.27 (brs, 1H), 6.87 (brd, 1H, J=7.9 Hz), 6.81 (brd, 1H, J=4.0 Hz), 6.80 (brs, 1H), 6.30 (brd, 1H, J=4.0 Hz), 5.92 (brs, 2H), 4.66 (s, 2H), 2.37 (brs, 3H).

Example 88

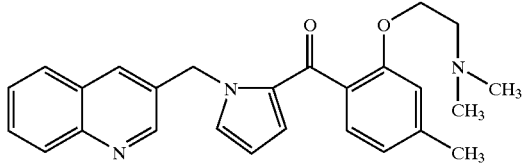

The title compound was obtained from the compound of Example 85 in a similar manner to Example 81.

$^1$H NMR (CDCl$_3$, 400 MHz) δ 8.84 (d, 1H, J=2.2 Hz), 8.08 (d, 1H, J=8.4 Hz), 7.97 (d, 1H, J=2.0 Hz), 7.78 (dd, 1H, J=1.1, 8.1 Hz), 7.69 (ddd, 1H, J=8.4, 7.0, 1.5 Hz), 7.53 (ddd, 1H, J=8.1, 7.0, 1.1 Hz), 7.19 (d, 1H, J=7.9 Hz), 7.07 (dd, 1H, J=1.7, 2.5 Hz), 6.77 (brd, 1H, J=7.9 Hz), 6.73 (brs, 1H), 6.61 (dd, 1H, J=1.7, 4.0 Hz), 6.19 (dd, 1H, J=2.5, 4.0 Hz), 5.87 (brs, 2H), 3.98 (t, 2H, J=5.7 Hz), 2.42 (t, 2H, J=5.7 Hz), 2.36 (brs, 3H), 2.08 (s, 6H).

Reference Example 5-1

(1-Benzenesulfonyl-1H-pyrrol-2-yl) [4-(methoxy)phenyl]ketone

The title compound was obtained from 4-methoxybenzoyl chloride in a similar manner to Reference Example 1–1.

$^1$H NMR (CDCl$_3$, 400 MHz) δ 8.12 (dt, 2H, J=7.2, 1.5 Hz), 7.84 (d, 2H, J=8.9 Hz), 7.73 (dd, 1H, J=1.7, 3.2 Hz), 7.65 (tt, 1H, J=1.5, 7.2 Hz), 7.58 (tt, 2H, J=1.5, 7.2 Hz), 6.93 (d, 2H, J=8.9 Hz), 6.68 (dd, 1H, J=1.7, 3.6 Hz), 6.34 (dd, 1H, J=3.2, 3.6 Hz), 3.87 (s, 3H).

Reference Example 5-2

(1H-Pyrrol-2-yl) [4-(methoxy)phenyl] ketone

The title compound was obtained from the compound of Reference Example 5-1 in a similar manner to Reference Example 1-2.

$^1$H NMR (CDCl$_3$, 400 MHz) δ 9.54 (brs, 1H), 7.94 (d, 2H, J=8.9 Hz), 7.12 (dt, 1H, J=1.3, 2.7 Hz), 6.93 (d, 2H, J=8.9 Hz), 6.89 (ddd, 1H, J=3.8, 2.4, 1.3 Hz), 6.34 (dt, 1H, J=3.8, 2.7 Hz), 3.89 (s, 3H).

Example 89

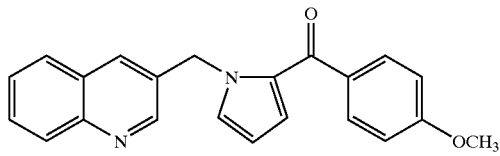

The title compound was obtained from 3-methylquinoline and the compound of Reference Example 5 in a similar manner to Example 1.

$^1$H NMR (CDCl$_3$, 400 MHz) δ 8.81 (d, 1H, J=2.2 Hz), 8.07 (brd, 1H, J=8.4 Hz), 7.92 (d, 1H, J=2.0 Hz), 7.79 (dt, 2H, J=8.4, 2.0 Hz), 7.76 (brd, 1H, J=8.1 Hz), 7.68 (ddd, 1H, J=8.4, 7.0, 1.5 Hz), 7.51 (ddd, 1H, J=8.1, 7.0, 1.1 Hz), 7.09 (dd, 1H, J=1.7, 2.5 Hz), 6.92 (dt, 2H, J=8.4, 2.0 Hz), 6.82 (dd, 1H, J=1.7, 4.0 Hz), 6.28 (dd, 1H, J=2.5, 4.0 Hz), 5.84 (brs, 2H), 3.86 (s, 3H).

Example 90

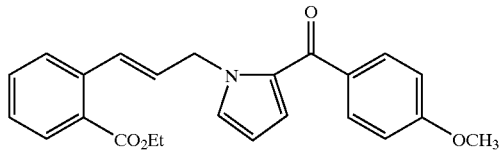

The title compound was obtained from the compound of Reference Example 5 and the compound of Example 18-2 in a similar manner to Example 18-3.

$^1$H NMR (CDCl$_3$, 400 MHz) δ 7.87 (dd, 1H, J=1.2, 7.7 Hz), 7.86 (d, 2H, J=8.8 Hz), 7.53 (brd, 1H, J=7.7 Hz), 7.43 (dt, 1H, J=1.1, 7.7 Hz), 7.30 (brd, 1H, J=15.7 Hz), 7.29 (dt, 1H, J=1.2, 7.7 Hz), 7.10 (dd, 1H, J=1.7, 2.5 Hz), 6.95 (brd, 2H, J=8.8 Hz), 6.76 (dd, 1H, J=1.7, 4.0 Hz), 6.35 (dt, 1H, J=15.7, 6.2 Hz), 6.21 (dd, 1H, J=2.5, 4.0 Hz), 5.21 (dd, 2H, J=6.2, 1.4 Hz), 4.34 (q, 2H, J=7.2 Hz), 3.88 (s, 3H), 1.37 (t, 3H, J=7.2 Hz).

Example 91

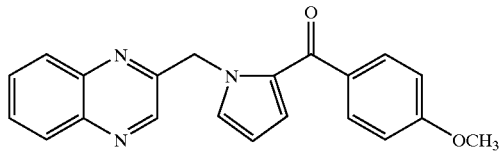

The title compound was obtained from 2-methylquinoxaline and the compound of Reference Example 5 in a similar manner to Example 1.

$^1$H NMR (CDCl$_3$, 400 MHz) δ 8.66 (s, 1H), 8.01–8.10 (m, 2H), 7.83 (d, 2H, J=8.8 Hz), 7.70–7.78 (m, 2H), 7.19 (dd, 1H, J=1.6, 2.5 Hz), 6.94 (d, 2H, J=8.8 Hz), 6.85 (dd, 1H, J=1.6, 4.0 Hz), 6.30 (dd, 1H, J=2.5, 4.0 Hz), 5.95 (brs, 2H), 3.86 (s, 3H).

Example 92

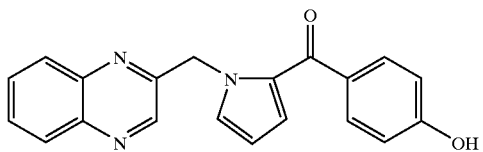

To a solution of the compound of Example 91 (530 mg) in methylene chloride (15 mL) was added dropwise at 0° C. a solution of boron tribromide in methylene chloride (6.13 mL, 1M solution). The reaction solution was warmed to room temperature, and stirred for 2 hours. The reaction solution was basified with an aqueous sodium hydrogen carbonate solution, and thereto was added ethyl acetate, and stirred for 4 hours. The aqueous layer was extracted twice with ethyl acetate, and the organic layers were combined, dried, and filtered. The solvent was evaporated under reduced pressure, and the residue was purified by silica gel chromatography to give the title compound (413 mg, 81%).

$^1$H NMR (CDCl$_3$, 400 MHz) δ 8.64 (s, 1H), 8.03–8.11 (m, 2H), 7.76 (d, 2H, J=8.8 Hz), 7.72–7.79 (m, 2H), 7.19 (dd, 1H, J=1.6, 2.5 Hz), 6.86 (d, 2H, J=8.8 Hz), 6.85 (dd, 1H, J=1.6, 4.0 Hz), 6.30 (dd, 1H, J=2.5, 4.0 Hz), 6.04 (brs, 1H), 5.95 (brs, 2H).

Example 93

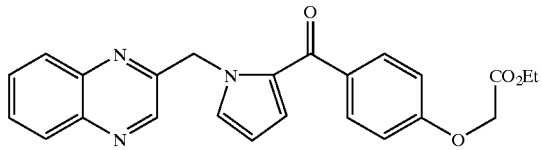

The title compound was obtained from the compound of Example 92 in a similar manner to Example 15.

$^1$H NMR (CDCl$_3$, 400 MHz) δ 8.65 (s, 1H), 8.01–8.10 (m, 2H), 7.82 (d, 2H, J=8.8 Hz), 7.70–7.78 (m, 2H), 7.19 (dd, 1H, J=1.6, 2.5 Hz), 6.94 (d, 2H, J=8.8 Hz), 6.85 (dd, 1H, J=1.6, 4.0 Hz), 6.30 (dd, 1H, J=2.5, 4.0 Hz), 5.94 (brs, 2H), 4.68 (s, 2H), 4.28 (q, 2H, J=7.1 Hz), 1.30 (t, 3H, J=7.1 Hz).

Example 94

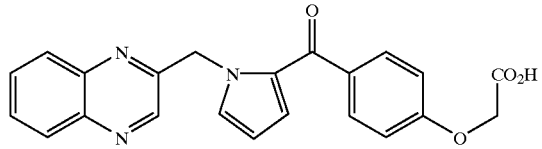

The title compound was obtained from the compound of Example 93 in a similar manner to Example 16.

$^1$H NMR (CDCl$_3$, 400 MHz) δ 8.65 (s, 1H), 8.03–8.12 (m, 2H), 7.81 (d, 2H, J=8.8 Hz), 7.72–7.79 (m, 2H), 7.19 (dd, 1H, J=1.6, 2.5 Hz), 6.94 (d, 2H, J=8.8 Hz), 6.85 (dd, 1H, J=1.6, 4.0 Hz), 6.30 (dd, 1H, J=2.5, 4.0 Hz), 5.95 (brs, 2H), 4.72 (s, 2H).

Example 95

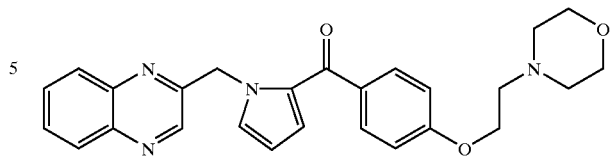

The title compound was obtained from the compound of Example 92 and N-chloroethylmorpholine hydrochloride in a similar manner to Example 81.

$^1$H NMR (CDCl$_3$, 400 MHz) δ 8.65 (s, 1H), 8.01–8.10 (m, 2H), 7.82 (d, 2H, J=8.8 Hz), 7.70–7.78 (m, 2H), 7.18 (dd, 1H, J=1.6, 2.5 Hz), 6.94 (d, 2H, J=8.8 Hz), 6.85 (dd, 1H, J=1.6, 4.0 Hz), 6.30 (dd, 1H, J=2.5, 4.0 Hz), 5.94 (brs, 2H), 4.17 (t, 2H, J=5.7 Hz), 3.74 (dd, 4H, J=4.6, 4.7 Hz), 2.83 (t, 2H, J=5.7 Hz), 2.59 (dd, 4H, J=4.6, 4.7 Hz).

Example 96

(96-1)

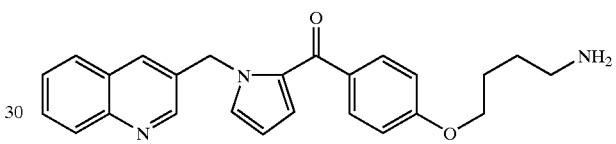

2-[4-(4-{[1-(3-Quinolylmethyl)-1H-pyrrol-2-yl]carbonyl}phenoxy)-butyl]-1H-isoindole-1,3(2H)-dione was obtained from the compound of Example 14 and N-(4-bromobutyl)phthalimide in a similar manner to Example 81.

$^1$H NMR (CDCl$_3$, 400 MHz) δ 8.81 (d, 1H, J=2.2 Hz), 8.07 (d, 1H, J=8.4 Hz), 7.92 (d, 1H, J=2.0 Hz), 7.82–7.87 (m, 2H), 7.77 (d, 2H, J=8.4 Hz), 7.76 (brd, 1H, J=8.1 Hz), 7.69–7.74 (m, 2H), 7.68 (ddd, 1H, J=8.4, 7.0, 1.5 Hz), 7.51 (ddd, 1H, J=8.1, 7.0, 1.1 Hz), 7.09 (dd, 1H, J=1.7, 2.5 Hz), 6.89 (d, 2H, J=8.4 Hz), 6.81 (dd, 1H, J=1.7, 4.0 Hz), 6.27 (dd, 1H, J=2.5, 4.0 Hz), 5.83 (brs, 2H), 4.05 (t, 2H, J=5.9 Hz), 3.78 (t, 2H, J=6.7 Hz), 1.81–1.95 (m, 4H).

(96-2)

The compound of Example 96-1 (28.0 mg) was dissolved in THF (1.0 mL) and methanol (2.0 mL), and thereto was added hydrazine hydrate (27.0 mg), and the mixture was stirred at room temperature for 1 hour. The mixture was concentrated, and thereto was added a 3N aqueous hydrochloric acid solution, and the mixture was washed with ether. The aqueous layer was basified with a 5N aqueous NaOH solution, and extracted with ethyl acetate. The organic layer was dried, filtered, and concentrated to give the title compound (18.0 mg, 85%).

$^1$H NMR (CDCl$_3$, 400 MHz) δ 8.80 (d, 1H, J=2.2 Hz), 8.07 (d, 1H, J=8.4 Hz), 7.91 (d, 1H, J=2.0 Hz), 7.77 (d, 2H, J=8.4 Hz), 7.75 (brd, 1H, J=8.1 Hz), 7.67 (ddd, 1H, J=8.4, 7.0, 1.5 Hz), 7.51 (ddd, 1H, J=8.1, 7.0, 1.1 Hz), 7.09 (dd, 1H, J=1.7, 2.5 Hz), 6.88 (d, 2H, J=8.4 Hz), 6.81 (dd, 1H, J=1.7, 4.0 Hz), 6.27 (dd, 1H, J=2.5, 4.0 Hz), 5.83 (brs, 2H), 4.05 (t, 2H, J=6.4 Hz), 2.79 (t, 2H, J=7.2 Hz), 1.84 (tt, 2H, J=6.4, 7.3 Hz), 1.64 (tt, 2H, J=7.2, 7.3 Hz).

Example 97

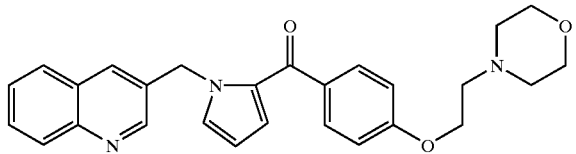

The title compound was obtained from the compound of Example 14 and N-chloroethylmorpholine hydrochloride in a similar manner to Example 81.

$^1$H NMR (CDCl$_3$, 400 MHz) δ 8.80 (d, 1H, J=2.2 Hz), 8.07 (d, 1H, J=8.4 Hz), 7.93 (d, 1H, J=2.0 Hz), 7.78 (dt, 2H, J=8.4, 2.0 Hz), 7.76 (brd, 1H, J=8.1 Hz), 7.68 (ddd, 1H, J=8.4, 7.0, 1.5 Hz), 7.51 (ddd, 1H, J=8.1, 7.0, 1.1 Hz), 7.09 (dd, 1H, J=1.7, 2.5 Hz), 6.92 (dt, 2H, J=8.4, 2.0 Hz), 6.82 (dd, 1H, J=1.7, 4.0 Hz), 6.27 (dd, 1H, J=2.5, 4.0 Hz), 5.83 (brs, 2H), 4.17 (t, 2H, J=5.7 Hz), 3.74 (dd, 4H, J=4.6, 4.7 Hz), 2.82 (t, 2H, J=5.7 Hz), 2.59 (dd, 4H, J=4.6, 4.7 Hz).

Example 98

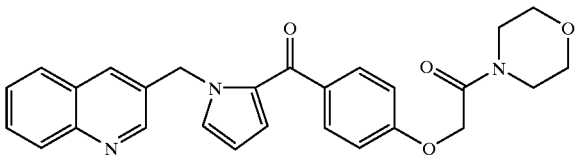

The compound of Example 16 (50.0 mg), morpholine (16.2 mg), 1-hydroxybenzotriazole (23.4 mg) and 1-(3-dimethylaminopropyl)-3-ethylcarbodiimide hydrochloride (34.4 mg) were dissolved in DMF (3.0 mL), and thereto was added triethylamine (34.6 mg). The mixture was stirred under nitrogen atmosphere at room temperature for 8 hours. To the reaction mixture was further added the same amount of the reacting reagents, and the mixture was further stirred for 2 hours. The reaction was quenched by adding a saturated aqueous sodium hydrogen carbonate solution to the mixture. The reaction mixture was extracted with ethyl acetate, dried, and filtered. The solvent was evaporated under reduced pressure, and the residue was purified by silica gel column to give the title compound (56.0 mg, 100%).

$^1$H NMR (CDCl$_3$, 400 MHz) δ 8.80 (d, 1H, J=2.2 Hz), 8.07 (d, 1H, J=8.4 Hz), 7.92 (d, 1H, J=2.0 Hz), 7.78 (dt, 2H, J=8.4, 2.0 Hz), 7.76 (brd, 1H, J=8.1 Hz), 7.68 (ddd, 1H, J=8.4, 7.0, 1.5 Hz), 7.52 (ddd, 1H, J=8.1, 7.0, 1.1 Hz), 7.11 (dd, 1H, J=1.7, 2.5 Hz), 6.97 (dt, 2H, J=8.4, 2.0 Hz), 6.82 (dd, 1H, J=1.7, 4.0 Hz), 6.28 (dd, 1H, J=2.5, 4.0 Hz), 5.84 (brs, 2H), 4.75 (s, 2H), 3.57–3.70 (series of m, 8H).

Example 99

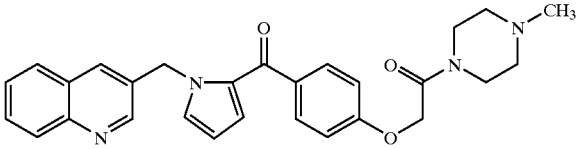

The title compound was obtained from methylpiperazine and the compound of Example 16 in a similar manner to Example 98.

$^1$H NMR (CDCl$_3$, 400 MHz) δ 8.80 (d, 1H, J=2.2 Hz), 8.07 (d, 1H, J=8.4 Hz), 7.92 (d, 1H, J=2.0 Hz), 7.78 (dt, 2H, J=8.4, 2.0 Hz), 7.76 (brd, 1H, J=8.1 Hz), 7.68 (ddd, 1H, J=8.4, 7.0, 1.5 Hz), 7.51 (ddd, 1H, J=8.1, 7.0, 1.1 Hz), 7.10 (dd, 1H, J=1.7, 2.5 Hz), 6.96 (dt, 2H, J=8.4, 2.0 Hz), 6.82 (dd, 1H, J=1.7, 4.0 Hz), 6.28 (dd, 1H, J=2.5, 4.0 Hz), 5.83 (brs, 2H), 4.74 (s, 2H), 3.64 (brt, 2H, J=4.8 Hz), 3.58 (brt, 2H, J=4.8 Hz), 2.41 (brt, 2H, J=5.1 Hz), 2.38 (brt, 2H, J=5.1 Hz), 2.29 (s, 3H).

Example 100

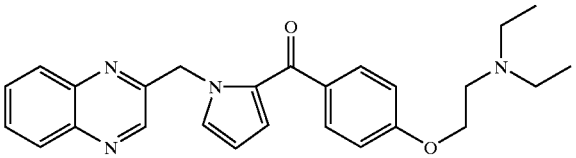

The title compound was obtained from the compound of Example 92 and diethylaminoethyl chloride hydrochloride in a similar manner to Example 81.

$^1$H NMR (CDCl$_3$, 400 MHz) δ 8.65 (s, 1H), 8.01–8.10 (m, 2H), 7.82 (d, 2H, J=8.8 Hz), 7.70–7.78 (m, 2H), 7.17 (dd, 1H, J=1.6, 2.5 Hz), 6.94 (d, 2H, J=8.8 Hz), 6.85 (dd, 1H, J=1.6, 4.0 Hz), 6.30 (dd, 1H, J=2.5, 4.0 Hz), 5.94 (brs, 2H), 4.11 (t, 2H, J=6.2 Hz), 2.90 (t, 2H, J=6.2 Hz), 2.65 (q, 4H, J=7.1 Hz), 1.08 (t, 6H, J=7.1 Hz).

Example 101

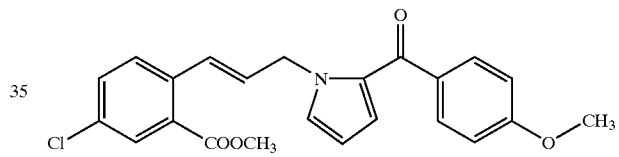

The title compound was obtained from the compound of Example 9-2 and the compound of Reference Example 5 in a similar manner to Example 9-3.

$^1$H NMR (CDCl$_3$, 400 MHz) δ 7.85 (d, 2H, J=8.8 Hz), 7.85 (d, 1H, J=2.2 Hz), 7.47 (d, 1H, J=8.5 Hz), 7.39 (dd, 1H, J=8.5, 2.2 Hz), 7.20 (dt, 1H, J=15.8, 1.4 Hz), 7.07 (dd, 1H, J=1.7, 2.5 Hz), 6.94 (d, 2H, J=8.8 Hz), 6.77 (dd, 1H, J=1.7, 4.0 Hz), 6.35 (dt, 1H, J=15.8, 6.1 Hz), 6.23 (dd, 1H, J=2.5, 4.0 Hz), 5.20 (dd, 2H, J=1.4, 6.1 Hz), 3.88 (s, 3H), 3.86 (s, 3H).

Example 102

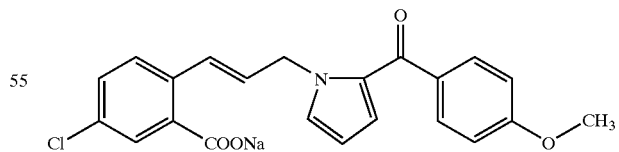

The compound of Example 101 (100 mg) was dissolved in methanol (3.0 mL) and THF (3.0 mL), and thereto was added a 1N aqueous NaOH solution (3.0 mL), and the mixture was stirred at 55° C. for 30 minutes. The reaction solution was concentrated to about 3 mL, and thereto were added a 1N aqueous NaOH solution and ether, and the mixture was stirred. The precipitated crystals were collected by filtration to give the title compound (100 mg, 98%).

¹H NMR (DMSO-d₆, 400 MHz) δ 7.78 (d, 2H, J=8.8 Hz), 7.44 (brd, 1H, J=15.8 Hz), 7.39 (d, 1H, J=8.5 Hz), 7.37 (brs, 1H), 7.31 (dd, 1H, J=1.7, 2.5 Hz), 7.11 (brd, 1H, J=8.5 Hz), 7.04 (d, 2H, J=8.8 Hz), 6.65 (dd, 1H, J=1.7, 4.0 Hz), 6.23 (dt, 1H, J=15.8, 6.1 Hz), 6.20 (dd, 1H, J=2.5, 4.0 Hz), 5.20 (dd, 2H, J=1.4, 6.1 Hz), 3.84 (s, 3H).

Examples 103 and 104

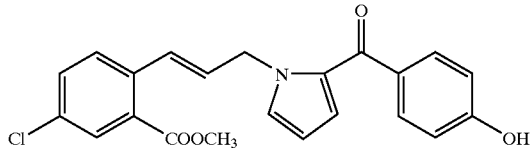

Example 103

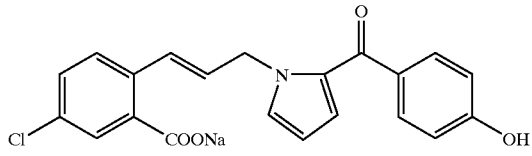

Example 104

The title compounds were obtained from the compound of Example 101 in a similar manner to Example 92.

¹H NMR (the compound of Example 103: CDCl₃, 400 MHz) δ 7.85 (d, 1H, J=2.2 Hz), 7.79 (d, 2H, J=8.7 Hz), 7.47 (d, 1H, J=8.5 Hz), 7.39 (dd, 1H, J=8.5, 2.2 Hz), 7.19 (dt, 1H, J=15.8, 1.4 Hz), 7.08 (dd, 1H, J=1.7, 2.5 Hz), 6.88 (d, 2H, J=8.7 Hz), 6.77 (dd, 1H, J=1.7, 4.0 Hz), 6.34 (dt, 1H, J=15.8, 6.0 Hz), 6.23 (dd, 1H, J=2.5, 4.0 Hz), 5.20 (dd, 2H, J=1.4, 6.0 Hz), 3.86 (s, 3H)

¹H NMR (the compound of Example 104: DMSO-d₆, 400 MHz) δ 7.68 (d, 2H, J=8.7 Hz), 7.42 (brd, 1H, J=15.8 Hz), 7.38 (d, 1H, J=8.5 Hz), 7.35 (d, 1H, J=2.2 Hz), 7.27 (dd, 1H, J=1.7, 2.5 Hz), 7.10 (dd, 1H, J=8.5, 2.2 Hz), 6.84 (d, 2H, J=8.7 Hz), 6.63 (dd, 1H, J=1.7, 4.0 Hz), 6.22 (dt, 1H, J=15.8, 6.0 Hz), 6.18 (dd, 1H, J=2.5, 4.0 Hz), 5.06 (brd, 2H, J=6.0 Hz).

Example 105

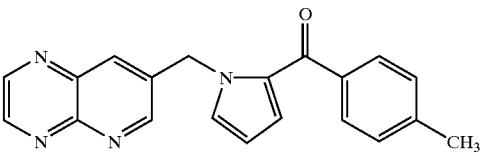

(105-1)

Under nitrogen atmosphere, to a mixture of 7-bromopyrido[2,3-b]pyrazine (300 mg), methyl boronate (100 mg) and cesium carbonate (930 mg) were added dioxane (7.0 ml), bis(dibenzilidenacetone)-palladium (80.0 mg) and triphenylphosphine (87.0 mg), and the mixture was stirred at 100° C. for 2.5 hours. To the reaction solution was added a saturated aqueous sodium hydrogen carbonate solution, and the mixture was extracted three times with ethyl acetate. The extracts were combined, washed with a saturated brine, dried over magnesium sulfate, and filtered. The solvent was evaporated under reduced pressure, and the residue was purified by silica gel column (hexane/ethyl acetate=3/1→1/1→0/1→ethyl acetate/ethanol=10/1) to give (125 mg, 60%).

¹H NMR (CDCl₃, 400 MHz) δ 9.06 (d, 1H, J=2.3 Hz), 9.02 (d, 1H, J=1.7 Hz), 8.91 (d, 1H, J=1.7 Hz), 8.24 (d, 1H, J=2.3 Hz), 2.65 (s, 3H).

(105-2)

Under nitrogen atmosphere, to a solution of the compound of Example 105-1 (107 mg) in chlorobenzene (5.0 ml) were added N-bromosuccinimide (132 mg) and 2,2'-azobis(isobutyronitrile) (10.0 mg), and the mixture was stirred at 90° C. for 2 hours. The solvent in the reaction solution was evaporated under reduced pressure to about a half volume thereof, and purified by silica gel column (ethyl acetate). The fractions containing a bromo compound were changed to a toluene solution thereof (about 3 ml) while these fractions should not be concentrated to dryness.

Under nitrogen atmosphere, a solution of the compound of Reference Example 1 (100 mg) in THF (2.0 mL) was cooled to 0° C., and thereto was added potassium t-butoxide (60.6 mg). Further, thereto was added the above toluene solution of the bromo compound, and the mixture was stirred at 50° C. for 3 hours. The reaction solution was cooled to room temperature, and thereto was added a saturated aqueous sodium hydrogen carbonate solution, and extracted with ethyl acetate. The extract was dried over magnesium sulfate, filtered, and the solvent was evaporated under reduced pressure, and the residue was purified by silica gel column to give the title compound (3.6 mg, 0.77%).

¹H NMR (CDCl₃, 400 MHz) δ 9.09 (d, 1H, J=2.4 Hz), 9.03 (d, 1H, J=1.7 Hz), 8.90 (d, 1H, J=1.7 Hz), 8.10 (d, 1H, J=2.4 Hz), 7.67 (d, 2H, J=8.0 Hz), 7.23 (d, 2H, J=8.0 Hz), 7.14 (dd, 1H, J=1.7, 2.5 Hz), 6.89 (dd, 1H, J=1.7, 4.1 Hz), 6.34 (dd, 1H, J=2.5, 4.1 Hz), 5.94 (s, 2H), 2.41 (s, 3H).

Example 106

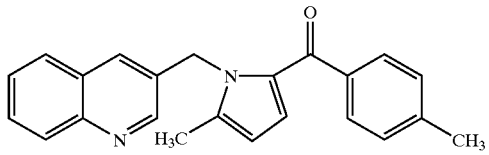

(106-1)

(4-Methylphenyl) [5-methyl-1-(phenylsulfonyl)-1H-pyrrol-2-yl] ketone was obtained from p-toluoyl chloride and 1-(phenylsulfonyl)-2-methyl-1H-pyrrole in a similar manner to Reference Example 1—1.

¹H NMR (CDCl₃, 400 MHz) δ 8.23 (d, 2H, J=7.2 Hz), 7.84 (d, 2H, J=8.1 Hz), 7.56–7.68 (m, 3H), 7.26 (d, 2H, J=8.1 Hz), 6.48 (d, 1H, J=3.5 Hz), 6.01 (d, 1H, J=3.5 Hz), 2.53 (s, 3H), 2.43 (s, 3H).

(106-2)

(4-Methylphenyl) (5-methyl-1H-pyrrol-2-yl) ketone was obtained from the compound of Example 106-1 in a similar manner to Reference Example 1-2.

¹H NMR (CDCl₃, 400 MHz) δ 9.97 (brs, 1H), 7.80 (d, 2H, J=8.0 Hz), 7.27 (d, 2H, J=8.0 Hz), 6.80 (dd, 1H, J=2.7, 3.4 Hz), 6.04 (d, 1H, J=3.0, 3.4 Hz), 2.43 (s, 3H), 2.39 (s, 3H).

(106-3)

The title compound was obtained from the compound of Example 106-2 in a similar manner to Example 1.

¹H NMR (CDCl₃, 400 MHz) δ 8.73 (d, 1H, J=2.2 Hz), 8.12 (d, 1H, J=7.8 Hz), 7.67–7.75 (m, 3H), 7.68 (d, 2H, J=8.0 Hz), 7.52 (t, 1H, J=7.8 Hz), 7.23 (d, 2H, J=8.0 Hz), 6.81 (d, 1H, J=4.0 Hz), 6.10 (d, 1H, J=4.0 Hz), 5.90 (s, 2H), 2.41 (s, 3H), 2.29 (s, 3H).

Example 107

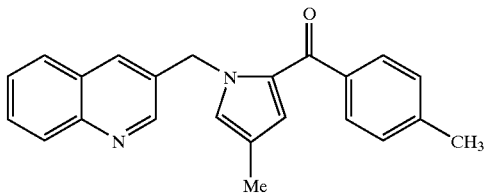
(107-1)

Ethyl 4-methyl-1-(3-quinolinylmethyl)-1H-pyrrole-2-carboxylate was obtained from ethyl 4-methyl-2-pyrrolecarboxylate in a similar manner to Example 1.

$^1$H NMR (CDCl$_3$, 400 MHz) δ 8.78 (d, 1H, J=2.2 Hz), 8.08 (d, 1H, J=7.9 Hz), 7.79 (d, 1H, J=2.2 Hz), 7.75 (d, 1H, J=7.9 Hz), 7.68 (t, 1H, J=7.9 Hz), 7.52 (t, 1H, J=7.9 Hz), 6.86 (d, 1H, J=1.3 Hz), 6.74 (d, 1H, J=1.3 Hz), 5.69 (s, 2H), 4.21 (q, 2H, J=7.1 Hz), 2.09 (s, 3H), 1.28 (t, 3H, J=7.1 Hz).
(107-2)

Under nitrogen atmosphere, to a solution of the compound of Example 107-1 (346 mg) in toluene (10 mL) that was cooled to −78° C. was added dropwise a 0.93N solution of diisobutyl aluminum hydride in toluene (1.3 mL). The mixture was stirred at −78° C. for 2.5 hours, and thereto was further added a 0.93N solution of diisobutylaluminum hydride in toluene (1.3 mL). The reaction solution was warmed gradually to room temperature over a period of 3.5 hours. To the reaction solution were added water and ethyl acetate, and the precipitated crystals were removed by filtration. The organic layer in the filtrate was collected, and washed twice with a saturated aqueous sodium hydrogen carbonate solution, and washed with a saturated brine, dried over magnesium sulfate, and filtered. The solvent was evaporated under reduced pressure, and the residue was purified by silica gel column (hexane/ethyl acetate=1/1→1/2→0/1) to give [4-methyl-1-(3-quinolinylmethyl)-1H-pyrrol-2-yl]methanol (211 mg, 71%).

$^1$H NMR (CDCl$_3$, 400 MHz) δ 8.77 (d, 1H, J=2.2 Hz), 8.09 (d, 1H, J=7.9 Hz), 7.76 (d, 1H, J=7.9 Hz), 7.75 (d, 1H, J=2.2 Hz), 7.70 (t, 1H, J=7.9 Hz), 7.54 (t, 1H, J=7.9 Hz), 6.51 (d, 1H, J=1.3 Hz), 6.04 (d, 1H, J=1.3 Hz), 5.33 (s, 2H), 4.53 (d, 2H, J=5.8 Hz), 2.08 (s, 3H), 1.38 (t, 1H, J=5.8 Hz)
(107-3)

4-Methyl-1-(3-quinolinylmethyl)-1H-pyrrole-2-carbaldehyde was obtained from the compound of Example 107-2 in a similar manner to Example 28-4.

$^1$H NMR (CDCl$_3$, 400 MHz) δ 9.48 (s, 1H), 8.79 (d, 1H, J=2.2 Hz), 8.08 (d, 1H, J=7.9 Hz), 7.89 (d, 1H, J=2.2 Hz), 7.77 (d, 1H, J=7.9 Hz), 7.69 (t, 1H, J=7.9 Hz), 7.53 (t, 1H, J=7.9 Hz), 6.86 (d, 1H, J=1.3 Hz), 6.80 (d, 1H, J=1.3 Hz), 5.70 (s, 2H), 2.11 (s, 3H).
(107-4)

(4-Methylphenyl)[4-methyl-1-(3-quinolinylmethyl)-1H-pyrrol-2-yl]methanol was obtained from the compound of Example 107-3 in a similar manner to Example 20-2.

$^1$H NMR (CDCl$_3$, 400 MHz) δ 8.65 (d, 1H, J=2.2 Hz), 8.07 (d, 1H, J=7.9 Hz), 7.69 (d, 1H, J=7.9 Hz), 7.68 (dd, 1H, J=7.9, 7.9 Hz), 7.56 (d, 1H, J=2.2 Hz), 7.52 (dd, 1H, J=7.9, 7.9 Hz), 7.21 (d, 2H, J=8.0 Hz), 7.05 (d, 2H, J=8.0 Hz), 6.46 (d, 1H, J=1.3 Hz), 5.78 (d, 1H, J=1.3 Hz), 5.76 (d, 1H, J=4.5 Hz), 5.30 (d, 1H, J=16.3 Hz), 5.21 (d, 1H, J=16.3 Hz), 2.23 (s, 3H), 2.23 (1H), 2.05 (s, 3H).
(107-5)

The title compound was obtained from the compound of Example 107-4 in a similar manner to Example 28-4.

$^1$H NMR (CDCl$_3$, 400 MHz) δ 8.81 (d, 1H, J=2.2 Hz), 8.07 (d, 1H, J=7.9 Hz), 7.95 (d, 1H, J=2.2 Hz), 7.77 (d, 1H, J=7.9 Hz), 7.67 (t, 1H, J=7.9 Hz), 7.67 (d, 2H, J=7.9 Hz), 7.51 (t, 1H, J=7.9 Hz), 7.22 (d, 2H, J=7.9 Hz), 6.88 (d, 1H, J=1.3 Hz), 6.63 (d, 1H, J=1.3 Hz), 5.79 (s, 2H), 2.41 (s, 3H), 2.09 (s, 3H).

Example 108

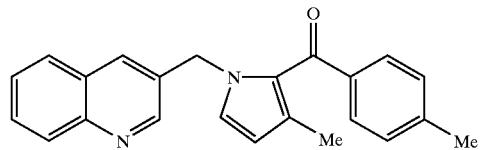
(108-1)

3-Methyl-1-(3-quinolinylmethyl)-1H-pyrrole-2-carbaldehyde was obtained from 3-methyl-1H-pyrrole-2-carbaldehyde in a similar manner to Example 20-1.

$^1$H NMR (CDCl$_3$, 400 MHz) δ 9.71 (s, 1H), 8.77 (d, 1H, J=2.2 Hz), 8.17 (d, 1H, J=7.9 Hz), 7.98 (d, 1H, J=2.2 Hz), 7.80 (d, 1H, J=7.9 Hz), 7.73 (t, 1H, J=7.9 Hz), 7.57 (t, 1H, J=7.9 Hz), 6.98 (d, 1H, J=2.4 Hz), 6.12 (d, 1H, J=2.4 Hz), 5.72 (s, 2H), 2.39 (s, 3H).
(108-2)

(4-Methylphenyl)[3-methyl-1-(3-quinolinylmethyl)-1H-pyrrol-2-yl]methanol was obtained from the compound of Example 108-1 in a similar manner to Example 20-2.

$^1$H NMR (CDCl$_3$, 400 MHz) δ 8.44 (d, 1H, J=2.2 Hz), 8.08 (d, 1H, J=7.8 Hz), 7.66 (dd, 1H, J=7.8, 7.8 Hz), 7.61 (d, 1H, J=7.8 Hz), 7.50 (dd, 1H, J=7.8, 7.8 Hz), 7.37 (d, 1H, J=2.2 Hz), 7.11 (d, 2H, J=8.0 Hz), 6.89 (d, 2H, J=8.0 Hz), 6.56 (d, 1H, J=2.7 Hz), 6.11 (s, 1H), 6.06 (d, 1H, J=2.7 Hz), 5.22 (d, 1H, J=16.3 Hz), 5.10 (d, 1H, J=16.3 Hz), 2.17 (s, 3H), 2.04 (s, 3H).
(108-3)

The title compound was obtained from the compound of Example 108-2 in a similar manner to Example 28-4.

$^1$H NMR (CDCl$_3$, 400 MHz) δ 8.72 (d, 1H, J=2.2 Hz), 8.16 (brd, 1H, J=7.7 Hz), 7.98 (brs, 1H), 7.77 (d, 1H, J=7.7 Hz), 7.71 (t, 1H, J=7.7 Hz), 7.55 (t, 1H, J=7.7 Hz), 7.52 (d, 2H, J=8.0 Hz), 7.19 (d, 2H, J=8.0 Hz), 6.97 (d, 1H, J=2.5 Hz), 6.09 (d, 1H, J=2.5 Hz), 5.64 (s, 2H), 2.38 (s, 3H), 1.82 (s, 3H).

Example 109

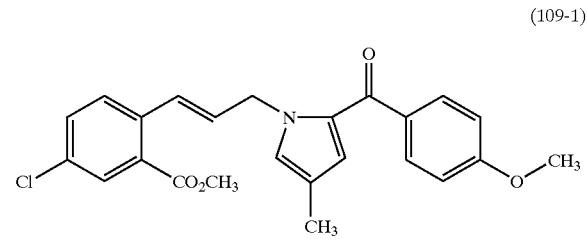
(109-1)

Ethyl 4-methyl-1-(phenylsulfonyl)-1H-pyrrole-2-carboxylate was obtained from methyl 4-methyl-1H-pyrrole-2-carboxylate in a similar manner to Example 6-1.

$^1$H NMR (CDCl$_3$, 400 MHz) δ 7.97 (d, 2H, J=7.7 Hz), 7.61 (t, 1H, J=7.7 Hz), 7.53 (dd, 2H, J=7.7, 7.7 Hz), 7.48 (d, 1H, J=2.0 Hz), 6.90 (d, 1H, J=2.0 Hz), 3.70 (s, 3H), 2.10 (s, 3H).

(109-2)

Under nitrogen atmosphere, to a solution of the compound of Example 109-1 (1.58 g) in toluene (30 mL) that was colled to −78° C. was added dropwise a 0.93N solution of diisobutylaluminum hydride in toluene (12.5 mL). The mixture was stirred at −78° C. for 1 hour, and to the reaction solution was added a 1N aqueous hydrochloric acid solution. The mixture was extracted with ethyl acetate, and the extract was washed with a saturated brine, dried over magnesium sulfate, and filtered. The solvent was evaporated under reduced pressure, and the residue was purified by silica gel column (hexane/ethyl acetate=3/1→2/1) to give [4-methyl-1-(phenylsulfonyl)-1H-pyrrol-2-yl]methanol (1.24 g, 87%).

$^1$H NMR (CDCl$_3$, 400 MHz) δ 7.81 (dd, 2H, J=1.4, 7.7 Hz), 7.61 (dt, 1H, J=7.7, 1.4 Hz), 7.52 (t, 2H, J=7.7 Hz), 7.00 (d, 1H, J=1.7 Hz), 6.11 (d, 1H, J=1.7 Hz), 4.56 (s, 2H), 2.02 (s, 3H).

(109-3)

4-Methyl-1-(phenylsulfonyl)-1H-pyrrole-2-carbaldehyde was otained from the compound of Example 109-2 in a similar manner to Example 28-4.

$^1$H NMR (CDCl$_3$, 400 MHz) δ 9.95 (s, 1H), 7.90 (dd, 2H, J=1.4, 7.7 Hz), 7.64 (dt, 1H, J=7.7, 1.4 Hz), 7.53 (t, 2H, J=7.7 Hz), 7.37 (d, 1H, J=1.8 Hz), 7.00 (d, 1H, J=1.8 Hz), 2.10 (s, 3H).

(109-4)

[4-Methyl-1-(phenylsulfonyl)-1H-pyrrol-2-yl](4-methoxyphenyl)-methanol was obtained from the compound of Example 109-3 and 4-bromoanisole in a similar manner to Example 20-2.

$^1$H NMR (CDCl$_3$, 400 MHz) δ 7.71 (dd, 2H, J=1.3, 7.8 Hz), 7.60 (dt, 1H, J=7.8, 1.3 Hz), 7.47 (t, 2H, J=7.8 Hz), 7.16 (d, 2H, J=8.6 Hz), 7.04 (d, 1H, J=2.0 Hz), 6.81 (d, 2H, J=8.6 Hz), 5.97 (s, 1H), 5.67 (d, 1H, J=2.0 Hz), 3.80 (s, 3H), 1.96 (s, 3H).

(109-5)

[4-Methyl-1-(phenylsulfonyl)-1H-pyrrol-2-yl](4-methoxyphenyl) ketone was obtained from the compound of Example 109-4 in a similar manner to Example 28-4.

$^1$H NMR (CDCl$_3$, 400 MHz) δ 8.10 (dd, 2H, J=1.6, 7.4 Hz), 7.82 (d, 2H, J=8.9 Hz), 7.64 (dt, 1H, J=7.4, 1.6 Hz), 7.57 (t, 2H, J=7.4 Hz), 7.47 (d, 1H, J=1.8 Hz), 6.92 (d, 2H, J=8.9 Hz), 6.51 (d, 1H, J=1.8 Hz), 3.87 (s, 3H), 2.10 (s, 3H).

(109-6)

(4-Methyl-1H-pyrrol-2-yl) (4-methoxyphenyl) ketone was obtained from the compound of Example 109-5 in a similar manner to Reference Example 1-2.

$^1$H NMR (CDCl$_3$, 400 MHz) δ 9.38 (brs, 1H), 7.92 (d, 2H, J=8.9 Hz), 6.97 (d, 2H, J=8.9 Hz), 6.89–6.90 (m, 1H), 6.70 (dd, 1H, J=1.2, 2.0 Hz), 3.88 (s, 3H), 2.15 (s, 3H).

(109-7)

The title compound was obtained from the compound of Example 109-6 in a similar manner to Example 18-3.

$^1$H NMR (CDCl$_3$, 400 MHz) δ 7.85 (d, 1H, J=2.3 Hz), 7.83 (d, 2H, J=8.9 Hz), 7.48 (d, 1H, J=8.5 Hz), 7.39 (dd, 1H, J=2.3, 8.5 Hz), 7.21 (dt, 1H, J=15.8, 1.4 Hz), 6.94 (d, 2H, J=8.9 Hz), 6.85 (d, 1H, J=1.1 Hz), 6.57 (d, 1H, J=1.1 Hz), 6.34 (dt, 1H, J=15.8, 6.1 Hz), 5.14 (dd, 2H, J=1.4, 6.1 Hz), 3.88 (s, 3H), 3.87 (s, 3H), 2.09 (s, 3H).

Example 109

The compound of Example 109 was also prepared as follows.

(109-8)

5-Chloroanthranilic acid (15.0 g), (CH$_3$)$_2$SO$_4$ (11.6 g) and K$_2$CO$_3$ (12.7 g) were refluxed in acetone (150 g) for 30 minutes. The mixture was concentrated to about 90 g, and thereto was added water (90 g). The mixture was extracted with toluene (75 g), and the organic layer was concentrated to give methyl 5-chloroanthranilate (15.6 g, 96%).

$^1$H NMR (CDCl$_3$, 400 MHz) δ 7.83 (d, 1H, J=2.6 Hz), 7.21 (dd, 1H, J=8.5 and 2.6 Hz), 6.61 (d, 1H, J=8.5 Hz), 5.73 (brs, 2H), 3.88 (s, 3H).

(109-9)

To conc. sulfuric acid (221 g) was added NaNO$_2$ (12.3 g), and the mixture was dissovled, during which the reaction temperature was raised to about 60° C. This solution was cooled to 10° C., and thereto was added dropwise a solution of methyl 5-chloro-2-aminobenzoate (30.0 g) in acetic acid (360 g) at a temperature of from 15 to 25° C. The mixture was warmed to 45° C., and the mixture was stirred for 40 minutes. The mixture (suspension) was added dropwise into an aqueous solution of KI (40.2 g) in water (300 mL) in such a manner that the reaction temperature was not raised over 10° C. The mixture was further stirred at 35° C. for 1.5 hour, and thereto was added water (300 mL). The mixture was extracted twice with toluene (450 g), and the organic layers were combined, washed twice with water (450 mL), and washed successively with an aqueous solution of sodium hydrogen carbonate (450 g), a 10% aqueous sodium thiosulfate solution (450 g) and water (225 mL). Then, the mixture was concentrated to give methyl 5-chloro-2-iodobenzoate (44.1 g, yield: 92%).

$^1$H NMR (CDCl$_3$, 400 MHz) δ 7.91 (d, 1H, J=8.5 Hz), 7.80 (d, 1H, J=2.6 Hz), 7.15 (dd, 1H, J=8.5 and 2.6 Hz), 3.94 (s, 3H).

(109-10)

Under nitrogen atmosphere, to a solution of the compound of Reference Example 5-2 (5 g) in THF (15 mL) was added KOtBu (3.07 g). Further, a solution of allyl bromide (4.51 g) in THF (9.0 mL) was added thereto, and the mixture was stirred at 45° C. for 2 hours. Water was added to the mixture, and the mixture was extracted twice with toluene. The organic layers were concentrated to give [1-(2-propenyl)-1H-pyrrol-2-yl][4-methoxyphenyl]ketone (6.00 g, 98%). To DMF (7.31 g) was added dropwise POCl$_3$ (11.5 g) at 10° C., and the mixture was stirred for 15 minutes. To the mixture was added THF (5.41 g), and thereto was added dropise a solution of [1-(2-propenyl)-1H-pyrrol-2-yl][4-methoxyphenyl]ketone in toluene (10 mL). The mixture was stirred at room temperature for 5 hours, and thereto was added a solution of sodium acetate (11.2 g) in water (22 g), and the mixture was stirred for 3 hours. The precipitated crystals were collected by filtration, and dried to give (4-formyl-1-(2-propenyl)-1H-pyrrol-2-yl) (4-methoxyphenyl) ketone (3.31 g). The organic layer of the filtrate was collected, concentraed, and the precipitated crystals were collected by filtration, and dried (1.48 g, total 4.79 g, 71%).

$^1$H NMR (CDCl$_3$, 400 MHz) δ 9.81 (s, 1H), 7.86 (d, 2H, J=8.6 Hz), 7.58 (d, 1H, J=1.8 Hz), 7.15 (d, 1H, J=1.8 Hz), 6.97 (d, 2H, J=8.6 Hz), 6.06 (ddt, 1H, J=10.0, 15.0 and 5.8 Hz), 5.26 (dq, 1H, J=10.0 and 1.1 Hz), 5.16 (dq, 1H, J=15.0 and 1.1 Hz), 5.05 (dt, 1H, J=5.8 and 1.1 Hz), 3.89 (s, 3H).

(109-11)

The above compound (300 mg) and TFA (4.50 g) were dissolved in CH$_2$Cl$_2$, and thereto was added Et$_3$SiH (1.30 g). The mixture was stirred at room temperature for 30 minuts, and the reaction solution was poured into a 1N aqueous NaOH solution, and extracted with toluene. The solvent was evaporated under reduced pressure to give (4-methyl-1-(2-propenyl)-1H-pyrrol-2-yl) (4-methoxyphenyl) ketone (280 mg).

$^1$H NMR (CDCl$_3$, 400 MHz) δ 7.82 (d, 2H, J=8.8 Hz), 6.94 (d, 2H, J=8.8 Hz), 6.76 (brs, 1H), 6.54 (brd, 1H, J=1.8

Hz), 6.05 (ddt, 1H, J=10.0, 15.0 and 5.8 Hz), 5.14 (dq, 1H, J=10.0 and 1.1 Hz), 5.07 (dq, 1H, J=15.0 and 1.1 Hz), 4.97 (dt, 1H, J=5.8 and 1.1 Hz), 3.87 (s, 3H), 2.08 (brs, 3H).

(109-12)

Methyl 5-chloro-2-iodobenzoate (300 mg), (4-methyl-1-(2-propenyl)-1H-pyrrol-2-yl) (4-methoxyphenyl) ketone (258 mg), NaHCO$_3$ (170 mg), and Et$_3$BnNCl (230 mg) were dissolved in DMF (3.0 g), and thereto was blown nitrogen gas for nitrogen-substitituion. To the mixture was added Pd(OAc)$_2$ (11.0 mg), and the mixture was warmed to 50° C., and stirred for 8 hours. Water was added to the reaction solution, and the mixture was extracted with toluene. The organic layer was concentrated, and the residue was purified by silica gel column chromatography to give the compound of Example 109.

Example 110

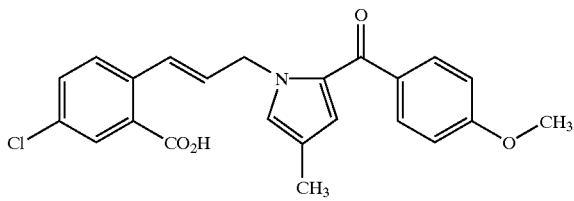

The title compound was obtained from the compound of Example 109-7 in a similar manner to Example 19.

$^1$H NMR (CDCl$_3$, 400 MHz) δ 7.97 (d, 1H, J=2.2 Hz), 7.83 (d, 2H, J=8.9 Hz), 7.50 (d, 1H, J=8.5 Hz), 7.44 (dd, 1H, J=2.2, 8.5 Hz), 7.28 (dt, 1H, J=15.5, 1.3 Hz), 6.93 (d, 2H, J=8.9 Hz), 6.86 (d, 1H, J=1.1 Hz), 6.58 (d, 1H, J=1.1 Hz), 6.35 (dt, 1H, J=15.5, 6.0 Hz), 5.15 (dd, 2H, J=1.3, 6.0 Hz), 3.85 (s, 3H), 2.09 (s, 3H).

Example 111

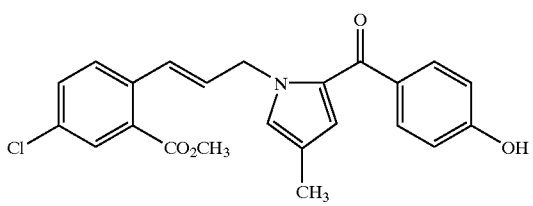

The title compound was obtained from the compound of Example 109-7 in a similar manner to Example 92.

1H NMR (CDC$_3$, 400 MHz) δ 7.85 (d, 1H, J=2.3 Hz), 7.78 (d, 2H, J=8.7 Hz), 7.47 (d, 1H, J=8.5 Hz), 7.39 (dd, 1H, J=2.3, 8.5 Hz), 7.20 (dt, 1H, J=15.8, 1.4 Hz), 6.87 (d, 2H, J=8.7 Hz), 6.86 (d, 1H, J=1.6 Hz), 6.57 (d, 1H, J=1.6 Hz), 6.33 (dt, 1H, J=15.8, 6.1 Hz), 5.13 (dd, 2H, J=1.4, 6.1 Hz), 3.87 (s, 3H), 2.09 (s, 3H).

Example 112

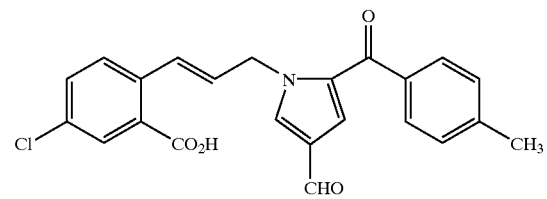

(112-1)

Under nitrogen atmosphere, to a solution of the compound of Reference Example 1-2 (2.00 g) in 1,2-dichloroethane (14 mL)-nitro-methane (14 ml) was added aluminum chloride (3.17 g), and the mixture was cooled to about −20° C. To the mixture was added a solution of dichloromethyl methyl ether (1.05 mL) in 1,2-dichloroethane (3.0 mL), and the mixture was stirred at about −20° C. for 2 hours, and then allowed to stand overnight. The reaction solution was poured into ice water, and extracted three times with chloroform. The extracts were washed with a saturated brine, dried over magnesium sulfate, and filtered. The solvent was evaporated under reduced pressure, and the residue was purified by silica gel column (hexane/ethyl acetate=3/1→1/1) to give [5-(4-methylbenzoyl)-1H-pyrrol-3-yl]carbaldehyde (1.65 g, 72%).

$^1$H NMR (CDCl$_3$, 400 MHz) δ 10.22 (brs, 1H), 9.90 (s, 1H), 7.86 (d, 2H, J=8.2 Hz), 7.73 (dd, 1H, J=1.4, 3.4 Hz), 7.31–7.34 (m, 3H), 2.46 (s, 3H).

(112-2)

The title compound was obtained from the compound of Example 111-2 and the compound of Example 9-2 in a similar manner in Example 9-3.

$^1$H NMR (CDCl$_3$, 400 MHz) δ 9.81 (s, 1H), 8.00 (d, 1H, J=1.4 Hz), 7.75 (d, 2H, J=8.2 Hz), 7.73 (d, 1H, J=1.7 Hz), 7.48 (m, 2H), 7.34 (dt, 1H, J=15.7, 1.3 Hz), 7.27 (d, 2H, J=8.2 Hz), 7.21 (d, 1H, J=1.7 Hz), 6.33 (dd, 1H, J=15.7, 6.1 Hz), 5.26 (dd, 2H, J=1.3, 6.1 Hz), 2.42 (s, 3H).

Example 113

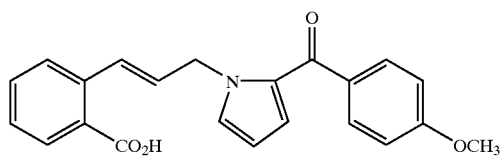

The title compound was obtained from the compound of Example 90 in a similar manner to Example 19.

$^1$H NMR (CDCl$_3$, 400 MHz) δ 8.01 (dd, 1H, J=1.2, 7.7 Hz), 7.86 (d, 2H, J=8.8 Hz), 7.57 (brd, 1H, J=7.7 Hz), 7.50 (dt, 1H, J=1.1, 7.7 Hz), 7.36 (brd, 1H, J=15.7 Hz), 7.34 (dt, 1H, J=1.2, 7.7 Hz), 7.10 (dd, 1H, J=1.7, 2.5 Hz), 6.94 (brd, 2H, J=8.8 Hz), 6.77 (dd, 1H, J=1.7, 4.0 Hz), 6.37 (dt, 1H, J=15.7, 6.2 Hz), 6.23 (dd, 1H, J=2.5, 4.0 Hz), 5.24 (dd, 2H, J=6.2, 1.4 Hz), 3.86 (s, 3H).

Example 114

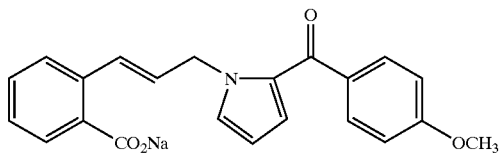

The compound of Example 113 (560 mg) was dissolved in THF (2.0 mL), and the mixture was treated with a 1N aqueous NaOH solution (1.50 mL), and the solvent was evaporated under reduced pressure. The residue was suspended in ether, and the solid was collected by filtration, and dried to give the title compound (510 mg, 89%).

$^1$H NMR (DMSO-$d_6$, 400 MHz) δ 7.78 (d, 2H, J=8.8 Hz), 7.46 (brd, 1H, J=15.7 Hz), 7.31–7.37 (m, 2H), 7.31 (dd, 1H, J=1.7, 2.5 Hz), 7.04 (d, 2H, J=8.8 Hz), 7.02–7.08 (m, 2H), 6.65 (dd, 1H, J=1.7, 4.0 Hz), 6.20 (dd, 1H, J=2.5, 4.0 Hz), 6.19 (dt, 1H, J=15.7, 6.2 Hz), 5.08 (dd, 2H, J=6.2, 1.4 Hz), 3.84 (s, 3H).

Example 115

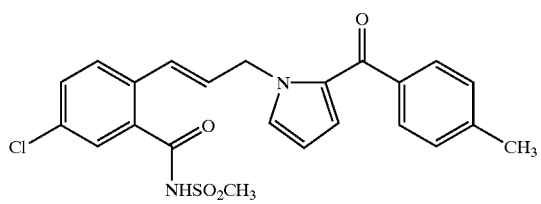

Under nitrogen atmosphere, to a solution of the compound of Example 9 (44.6 mg) in DMF (0.7 mL) was added carbonyldiimidazole (26.0 mg), and the mixture was stirred at room temperature for 2 hours. Subsequently, to the mixture were added methanesulfonamide (15.5 mg) and DBU (30 μL), and the mixture was stirred at 90° C. for 2 hours. The reaction mixture was cooled to room temperature, and thereto was added a 5% aqueous potassium hydrogen sulfate solution, and the mixture was extracted with ethyl acetate-toluene. The organic layer was washed with a 5% aqueous potassium hydrogen sulfate solution, dried over magnesium sulfate. The solvent was evaporated under reduced pressure, and the residue was purified by silica gel column (hexane/ethyl acetate=1/1→0/1) to give the title compound (30.5 mg, 57%).

$^1$H NMR (CDCl$_3$, 400 MHz) δ 8.79 (brs, 1H), 7.69 (d, 2H, J=8.0 Hz), 7.52 (d, 1H, J=2.1 Hz), 7.44 (d, 1H, J=8.4 Hz), 7.39 (dd, 1H, J=2.1, 8.4 Hz), 7.23 (d, 2H, J=8.0 Hz), 7.06 (dd, 1H, J=1.6, 2.5 Hz), 6.78 (dd, 1H, J=1.6, 4.0 Hz), 6.70 (d, 1H, J=15.6 Hz), 6.40 (dt, 1H, J=15.6, 5.4 Hz), 6.23 (dd, 1H, J=2.5, 4.0 Hz), 5.16 (d, 2H, J=5.4 Hz), 3.33 (s, 3H), 2.41 (s, 3H).

Example 116

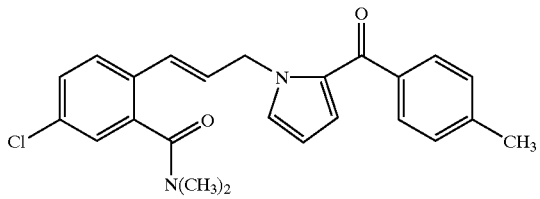

Under nitrogen atmosphere, to the compound of Example 9 (25.3 mg), dimethylamine hydrochloride (13.5 mg) and 1-hydroxy-benzotriazole (11.9 mg) were added successively DMF (0.5 ml), WSCI hydrochloride (17.5 mg), triethylamine (40 μL), and the mixture was stirred at room temperature for 11 hours. Water was added to the reaction mixture, and the mixture was extracted with ethyl acetate-toluene, washed with water and a saturated brine, and dried over magnesium sulfate. The solvent was evaporated under reduced pressure, and the residue was purified by silica gel column (hexane/ethyl acetate=2/1) to give the title compound (16.1 mg, 59%).

$^1$H NMR (CDCl$_3$, 400 MHz) δ 7.71 (d, 2H, J=8.1 Hz), 7.44 (d, 1H, J=8.4 Hz), 7.27 (dd, 1H, J=2.2, 8.4 Hz), 7.25 (d, 2H, J=8.1 Hz), 7.19 (d, 1H, J=2.2 Hz), 7.00 (dd, 1H, J=1.6, 2.5 Hz), 6.78 (dd, 1H, J=1.6, 4.0 Hz), 6.43 (dt, 1H, J=15.8, 5.7 Hz), 6.29 (d, 1H, J=15.8 Hz), 6.22 (dd, 1H, J=2.5, 4.0 Hz), 5.17 (brs, 2H), 3.02 (s, 3H), 2.66 (s, 3H), 2.43 (s, 3H).

Example 117

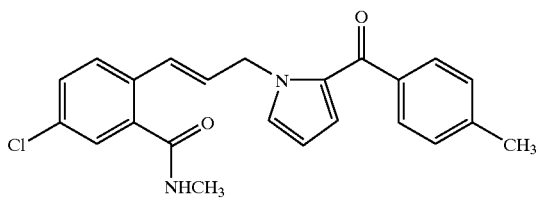

The title compound (24.6 mg, 95%) was obtained from the compound of Example 9 (25.0 mg) and methylamine hydrochloride in a similar manner to Example 116.

$^1$H NMR (CDCl$_3$, 400 MHz) δ 7.72 (d, 2H, J=8.0 Hz), 7.53 (d, 1H, J=2.2 Hz), 7.39 (d, 1H, J=8.4 Hz), 7.31 (dd, 1H, J=2.2, 8.4 Hz), 7.26(d, 2H, J=8.0 Hz), 7.04 (dd, 1H, J=1.6, 2.5 Hz), 6.79 (dd, 1H, J=1.6, 4.0 Hz), 6.72(d, 1H, J=15.7 Hz), 6.30 (dt, 1H, J=15.7, 5.7 Hz), 6.23 (dd, 1H, J=2.5, 4.0 Hz), 6.04 (brs, 1H), 5.14 (d, 2H, J=5.7 Hz), 2.94 (d, 3H, J=4.8 Hz), 2.43 (s, 3H).

Example 118

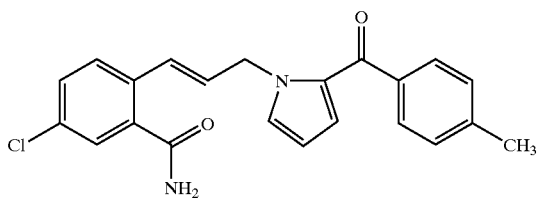

The title compound (15.4 mg, 64%) was obtained from the compound of Example 9 (24.3 mg) and ammonium chloride in a similar manner to Example 116.

$^1$H NMR (CDCl$_3$, 400 MHz) δ 7.70 (d, 2H, J=8.0 Hz), 7.60 (d, 1H, J=2.2 Hz), 7.40 (d, 1H, J=8.4 Hz), 7.34 (dd, 1H, J=2.2, 8.4 Hz), 7.26 (d, 2H, J=8.0 Hz), 7.04 (dd, 1H, J=1.7, 2.5 Hz), 6.81 (dd, 1H, J=1.7, 4.0 Hz), 6.76 (d, 1H, J=15.8 Hz), 6.32 (dt, 1H, J=15.8, 5.6 Hz), 6.23 (dd, 1H, J=2.5, 4.0 Hz), 6.09 (br, 1H), 5.78 (br, 1H), 5.16 (d, 2H, J=5.6 Hz), 2.43 (s, 3H).

The structures of the compounds of Examples 119 to 226 are shown in the following Tables. In Tables, the compounds having the indications in the columns of the starting compounds and Reference Examples were prepared by using said starting compounds in a similar manner to said Reference Examples. Following to Tables, processes for the compounds having no indication in these columns and the spectrum data of the compounds of Examples 119 to 226 are shown.

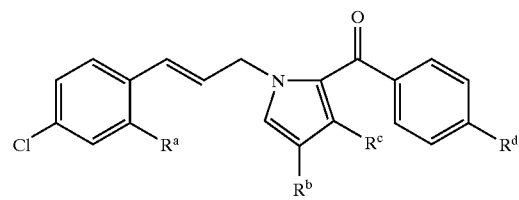

| Ex. | R$^a$ | R$^b$ | R$^c$ | R$^d$ | Starting Comp. (Ex) | Ref. Ex. |
|---|---|---|---|---|---|---|
| 119 | CO$_2$CH$_3$ | CH$_3$ | H | 2-morpholinoethoxy | | |
| 120 | CO$_2$Na | CH$_3$ | H | 2-morpholinoethoxy | 119-2 | 16 |
| 121 | CONHCH$_3$ | CH$_3$ | H | 2-morpholinoethoxy hydrochloride | 119-2 | 116 |
| 122 | CO$_2$CH$_3$ | H | H | morpholinomethyl | | |
| 123 | CO$_2$H | H | H | morpholinomethyl hydrochloride | 122 | 16 |
| 124 | CONHCH$_3$ | H | H | morpholinomethyl | 123 | 116 |
| 125 | CO$_2$H | H | H | 2-morpholinoethyl | | |
| 126 | CO$_2$H | CH$_3$ | H | morpholinomethyl | | |
| 127 | CO$_2$H | H | H | morpholino | | |
| 128 | CN | H | H | CH$_3$ | | |
| 129 | 5-tetrazolyl | H | H | CH$_3$ | | |
| 130 | CONHCH$_3$ | H | H | OCH$_3$ | 102 | 116 |
| 131 | CONHSO$_2$CH$_3$ | H | H | OCH$_3$ | 102 | 115 |
| 132 | CONHSO$_2$CH$_3$ | H | H | OH | 131 | 119-1 |
| 133 | CONHCH$_3$ | H | H | OH | 130 | 119-1 |
| 134 | 1-sodio-5-tetrazolyl | H | H | OCH$_3$ | | |
| 135 | 5-tetrazolyl | CH$_3$ | H | OCH$_3$ | 109 | 128, 129 |
| 136 | CONNaSO$_2$CH$_3$ | CH$_3$ | H | OCH$_3$ | | |
| 137 | OCH$_3$ | CH$_3$ | H | OCH$_3$ | | |
| 138 | CO$_2$CH$_3$ | CH$_3$ | H | CH$_3$ | | |
| 139 | CO$_2$Na | CH$_3$ | H | CH$_3$ | | |
| 140 | CONaSO$_2$CH$_3$ | CH$_3$ | H | CH$_3$ | 139-1 | 115 |
| 141 | OCH$_3$ | CH$_3$ | H | CH$_3$ | 137-5 138-1 | 18-3 |
| 142 | NHSO$_2$CH$_3$ | CH$_3$ | H | OCH$_3$ | | |
| 143 | OCH$_3$ | CH$_3$ | H | OH | | |
| 144 | OCH$_3$ | CH$_3$ | H | 2-morpholinoethoxy | 143 | 119-2 |
| 145 | CONHSO$_2$CH$_3$ | CH$_3$ | H | OH | 136 | 119-1 |
| 146 | CO$_2$H | CHO | H | OCH$_3$ | | |
| 147 | CONHSO$_2$Et | CH$_3$ | H | OCH$_3$ | | |
| 148 | CONHSO$_2$Ph | CH$_3$ | H | OCH$_3$ | | |
| 149 | CO$_2$CH$_3$ | H | H | H | 9-2 | 18-3 |
| 150 | CO$_2$H | H | H | H | 149 | 16 |
| 151 | CO$_2$CH$_3$ | H | Cl | CH$_3$ | | |
| 152 | CO$_2$H | H | Cl | CH$_3$ | 151 | 16 |
| 153 | CO$_2$CH$_3$ | H | H | OCH$_2$CH$_2$OH | | |
| 154 | CO$_2$H | H | H | OCH$_2$CH$_2$OH | 153 | 16 |
| 155 | CONHCH$_3$ | H | H | OCH$_2$CH$_2$OH | | |
| 156 | CONHSO$_2$CH$_3$ | H | H | OCH$_2$CH$_2$OH | | |
| 157 | CO$_2$CH$_3$ | CH$_3$ | H | OCH$_2$CH$_2$OH | | |
| 158 | CO$_2$H | CH$_3$ | H | OCH$_2$CH$_2$OH | 157 | 16 |
| 159 | CO$_2$CH$_3$ | H | H | OCH$_2$CH$_2$Cl | | |
| 160 | CO$_2$CH$_3$ | H | H | OCH$_2$CH$_2$N(CH$_2$CH$_2$OEt)$_2$ | 159-1 | 81 |
| 161 | CO$_2$H | H | H | OCH$_2$CH$_2$N(CH$_2$CH$_2$OEt)$_2$ | 160 | 16 |
| 162 | CO$_2$H | CH$_3$ | H | O(CH$_2$)$_8$N$_3$ | | |
| 163 | CO$_2$CH$_3$ | H | H | CH(OCH$_2$)$_2$CH$_2$ | | |
| 164 | CO$_2$H | H | H | CH$_2$OH | | |
| 165 | CO$_2$CH$_3$ | H | H | CH$_2$N(CH$_2$CH$_2$)$_2$CHOH | | |

-continued

| | | | | | | |
|---|---|---|---|---|---|---|
| 166 | CO$_2$CH$_3$ | H | H | pyrazolylmethyl | | |
| 167 | CO$_2$H | H | H | pyrazolylmethyl | 166 | 16 |
| 168 | CO$_2$H | H | H | 2-thiazolyl | | |
| 169 | CO$_2$CH$_3$ | H | H | CH$_2$OCH$_3$ | | |
| 170 | CO$_2$H | H | H | CH$_2$OCH$_3$ | 169 | 16 |
| 171 | CO$_2$CH$_3$ | H | H | pyrazolyl | | |
| 172 | CO$_2$H | H | H | pyrazolyl | 171 | 16 |
| 173 | CO$_2$CH$_3$ | H | H | triazolylmethyl | | |
| 220 | CO$_2$CH$_3$ | H | H | Cl | | |
| 221 | CO$_2$H | H | H | Cl | 220 | 16 |
| 222 | CO$_2$CH$_3$ | H | H | CF$_3$ | | |
| 223 | CO$_2$H | H | H | CF$_3$ | 222 | 16 |

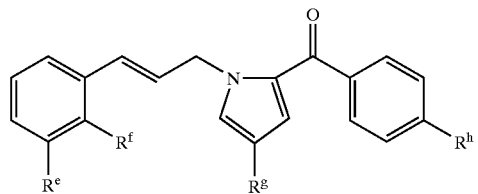

| Ex. | R$^e$ | R$^f$ | R$^g$ | R$^h$ | Starting Comp. (Ex) | Ref. Ex. |
|---|---|---|---|---|---|---|
| 174 | H | CO$_2$CH$_3$ | CH$_3$ | OCH$_3$ | 109-6, 18-2 | 18-3 |
| 175 | H | CO$_2$Na | CH$_3$ | OCH$_3$ | 174 | 16 |
| 176 | CO$_2$Et | H | H | CH$_3$ | | |
| 177 | CO$_2$Et | H | H | OCH$_3$ | 176-1, Ref. Ex. 5 | 18-3 |

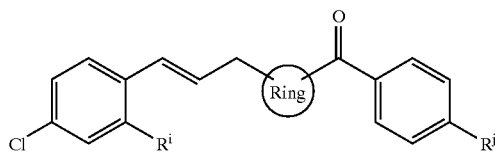

| Ex. | R$^i$ | Ring | R$^j$ | Starting Comp. (Ex) | Ref. Ex. |
|---|---|---|---|---|---|
| 178 | CO$_2$H | 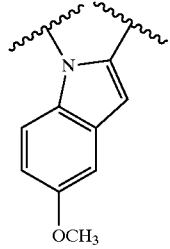 | CH$_3$ | | |
| 179 | CO$_2$CH$_3$ | 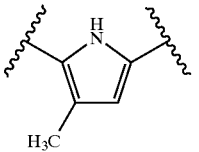 | OCH$_3$ | | |
| 180 | CO$_2$CH$_3$ | 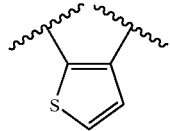 | CH$_3$ | | |
| 181 | CO$_2$CH$_3$ | 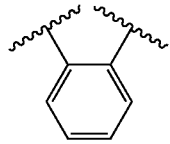 | CH$_3$ | | |

-continued
| Ex. | | Chain Ring | | | |
|---|---|---|---|---|---|
| 182 | CO₂H | 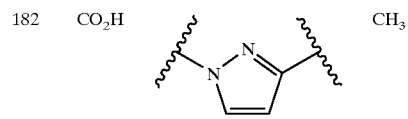 | CH₃ | | |
| 183 | CO₂CH₃ | 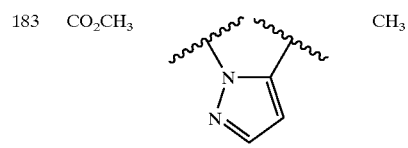 | CH₃ | | |
| 184 | CO₂H | 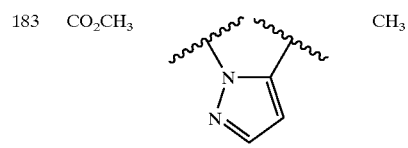 | CH₃ | 183 | 16 |
| 185 | CO₂H | 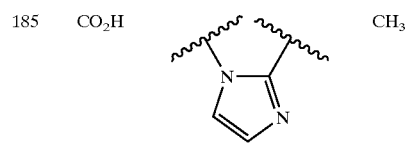 | CH₃ | | |
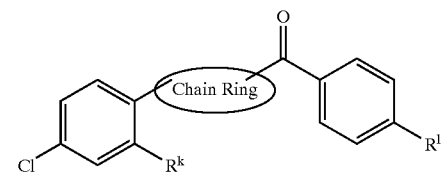
| Ex. | Rᵏ | Chain Ring | R¹ | Starting Comp. (Ex) | Ref. Ex. |
|---|---|---|---|---|---|
| 186 | CO₂H | 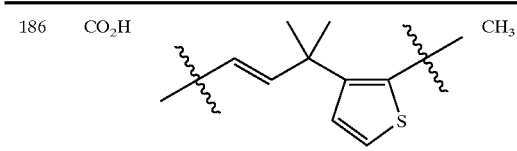 | CH₃ | | |
| 187 | CO₂CH₃ | 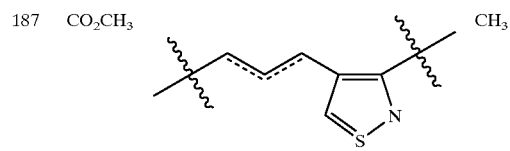 | CH₃ | | |
| 188 | CO₂CH₃ | 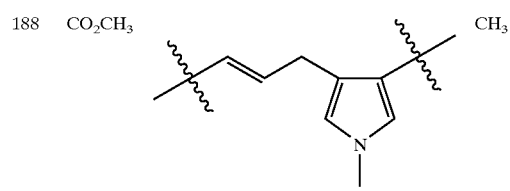 | CH₃ | | |
| 189 | CO₂CH₃ | 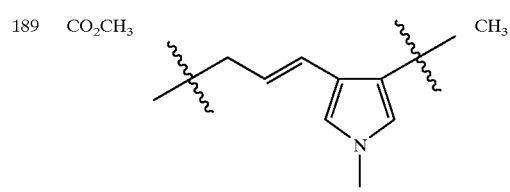 | CH₃ | | |

-continued

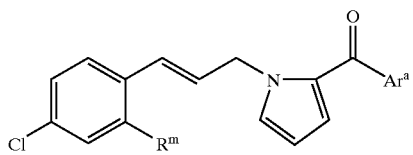

| Ex. | $R^m$ | $Ar^a$ | Starting Comp. (Ex.) | Ref. Ex. |
|---|---|---|---|---|
| 190 | $CO_2CH_3$ | 5-methylthienyl | | |
| 191 | $CO_2H$ | 5-methylthienyl | 190 | 16 |
| 192 | $CO_2CH_3$ | 1-methyl-5-indolyl | | |
| 193 | $CO_2H$ | 1-methyl-5-indolyl | 192 | 16 |
| 194 | $CO_2H$ | 2-methyl-5-thiazolyl | | |
| 195 | $CO_2H$ | 6-benzothiazolyl | | |
| 196 | $CO_2CH_3$ | 6-methyl-2-pyridyl | | |
| 197 | $CO_2H$ | 6-methyl-2-pyridyl | 196 | 16 |
| 198 | $CO_2CH_3$ | 3,4-dimethoxyphenyl | | |
| 199 | $CO_2Na$ | 3,4-dimethoxyphenyl | 198 | 16 |
| 200 | $CO_2CH_3$ | 1,3-benzodioxol-5-yl | | |
| 201 | $CO_2Na$ | 1,3-benzodioxol-5-yl | 200 | 16 |

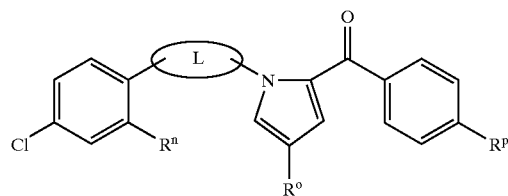

| Ex. | $R^n$ | L | $R^o$ | $R^d$ | Starting Comp. (Ex.) | Ref. Ex. |
|---|---|---|---|---|---|---|
| 202 | $CO_2H$ | (CH=CH-CH2 chain) | $CH_3$ | $OCH_3$ | | |
| 203 | $CO_2H$ | (diene chain) | $CH_3$ | $OCH_3$ | | |
| 204 | $CO_2CH_3$ | —C≡CCH₂— | H | $CH_3$ | | |
| 205 | $CO_2CH_3$ | —OCH₂CH₂— | $CH_3$ | $OCH_3$ | | |
| 206 | $CO_2H$ | —OCH₂CH₂— | $CH_3$ | $OCH_3$ | 205 | 16 |
| 207 | $CO_2CH_3$ | (methylallyl linker) | $CH_3$ | $OCH_3$ | | |
| 208 | $CO_2H$ | (methylallyl linker) | $CH_3$ | $OCH_3$ | 207 | 16 |
| 209 | $CO_2CH_3$ | (cyclopropyl linker) | $CH_3$ | $OCH_3$ | | |
| 210 | $CO_2H$ | (cyclopropyl linker) | $CH_3$ | $OCH_3$ | 209 | 16 |
| 211 | $CO_2H$ | —C≡CCH₂— | H | $CH_3$ | | |

-continued
| Ex. | | | | | | |
|---|---|---|---|---|---|---|
| 212 | CO₂CH₃ | 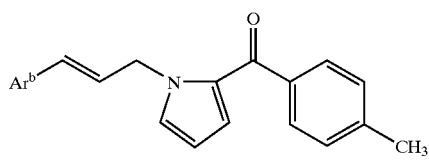 | CH₃ | OCH₃ | | |
| 213 | CO₂H | (same as above) | CH₃ | OCH₃ | 212 | 16 |
| 214 | CO₂H | —OCH₂C≡CCH₂— | H | CH₃ | | |
| 215 | CO₂CH₃ | (cis alkene linker) | CH₃ | OCH₃ | | |
| 216 | CO₂H | (cis alkene linker) | CH₃ | OCH₃ | 215 | 16 |
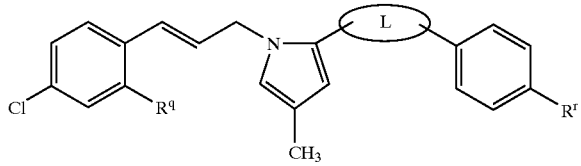
| Ex. | Arᵇ | Starting Comp. (Ex) | Ref. Ex. |
|---|---|---|---|
| 217 | isothiazole-CO₂H group | | |
| 218 | thiophene-CO₂CH₃ group | | |
| 219 | thiophene-CO₂H group | 218 | 16 |
| Ex. | Rq | L | Rr | Starting Comp. (Ex) | Ref. Ex. |
|---|---|---|---|---|---|
| 224 | CO₂H | —CONH— | OCH₃ | | |
| 225 | CO₂CH₃ | —CONCH₃— | CH₃ | | |
| 226 | CO₂H | —CONCH₃— | CH₃ | 225 | 16 |

Example 119

(119-1)

Under nitrogen atmosphere, a solution of AlCl$_3$ (180 mg) and EtSH (300 μl) in CH$_2$Cl$_2$ (1.0 mL) was cooled to 0° C., and thereto was added the compound of Example 109 (150 mg), and the mixture was stirred for 2.5 hours. The reaction solution was poured into an aqueous hydrochloric acid solution, and the mixture was extracted twice with ethyl acetate. The extract was washed with a saturated brine, and dried over MgSO$_4$. The solvent was evaporated under reduced pressure, and the residue was purified by silica gel column (hexane/ethyl acetate=3/1→2/1) to give methyl 5-chloro-2-{(1E)-3-[2-(4-hydroxybenzoyl)-4-methyl-1H-pyrrol-1-yl]-1-propenyl}benzoate (94.8 mg, 65%).

$^1$H NMR (CDCl$_3$, 400 MHz) δ 7.85 (d, 1H, J=2.3 Hz), 7.78 (d, 2H, J=8.7 Hz), 7.47 (d, 1H, J=8.5 Hz), 7.39 (dd, 1H, J=2.3, 8.5 Hz), 7.20 (dt, 1H, J=15.8, 1.4 Hz), 6.87 (d, 2H, J=8.7 Hz), 6.86 (d, 1H, J=1.6 Hz), 6.57 (d, 1H, J=1.6 Hz), 6.33 (dt, 1H, J=15.8, 6.1 Hz), 5.13 (dd, 2H, J=1.4, 6.1 Hz), 3.87 (s, 3H), 2.09 (s, 3H).

(119-2)

The title compound was obtained from the compound of Example 119-1 and N-(2-chloroethyl)morpholine hydrochloride in a similar manner to Example 81.

$^1$H NMR (CDCl$_3$, 400 MHz) δ 7.85 (d, 1H, J=2.3 Hz), 7.82 (d, 2H, J=8.8 Hz), 7.48 (d, 1H, J=8.4 Hz), 7.39 (dd, 1H, J=2.3, 8.4 Hz), 7.20 (d, 1H, J=15.8 Hz), 6.95 (d, 2H, J=8.8 Hz), 6.86 (d, 1H, J=1.1 Hz), 6.56 (d, 1H, J=1.1 Hz), 6.34 (dt, 1H, J=15.8, 6.1 Hz), 5.14 (d, 2H, J=6.1 Hz), 4.20–4.23 (m, 2H), 3.87 (s, 3H), 3.76–3.79 (m, 4H), 2.87 (m, 2H), 2.64 (m, 4H), 2.09 (s, 3H).

Example 120

$^1$H NMR (DMSO-d$_6$, 400 MHz) δ 7.74 (d, 2H, J=8.7 Hz), 7.46 (d, 1H, J=16.1 Hz), 7.40 (d, 1H, J=8.3 Hz), 7.38 (d, 1H, J=2.4 Hz), 7.11 (dd, 1H, J=2.4, 8.3 Hz), 7.08 (s, 1H), 7.03 (d, 2H, J=8.7 Hz), 6.47 (s, 1H), 6.21 (dt, 1H, J=16.1, 6.4 Hz), 5.01 (d, 2H, J=6.4 Hz), 4.16–4.19 (m, 2H), 3.57–3.59 (m, 4H), 2.71–2.73 (m, 2H), 2.48–2.51 (m, 4H), 2.03 (s, 3H).

Example 121

$^1$H NMR (DMSO-d$_6$, 400 MHz) δ 10.92 (brs, 1H), 8.31 (br, 1H), 7.77 (d, 2H, J=8.6 Hz), 7.63 (d, 1H, J=8.5 Hz), 7.41 (dd, 1H, J=2.2, 8.5 Hz), 7.34 (d, 1H, J=2.2 Hz), 7.10 (d, 2H, J=8.6 Hz), 7.09 (s, 1H), 6.46–6.52 (m, 3H), 5.09 (d, 2H, J=3.7 Hz), 4.50 (m, 2H), 3.96–3.99 (m, 2H), 3.77–3.83 (m, 2H), 3.50–3.63 (m, 4H), 3.20–3.23 (m, 2H), 2.70 (d, 3H, J=4.6 Hz), 2.04 (s, 3H).

Example 122

(122-1)

Under nitrogen atmosphere, a solution of 2,2,6,6-tetramethyl-piperidine (1.87 g) in THF (30 mL) was cooled to −78° C., and thereto was added dropwise a 1.5N solution of n-BuLi in n-hexane (8.85 mL), and the mixture was stirred at −78° C. for 5 minutes, and stirred at −30° C. for 5 minutes. Then, the mixture was cooled to −78° C., and thereto was added dropwise a solution of 1-(phenylsulfonyl)pyrrole (2.50 g) in THF (20 mL). The mixture was stirred at −78° C. for 45 minutes, and thereto was added dropwise a solution of methyl telephthalaldehyde (2.38 g) in THF (20 mL), and the mixture was further stirred at −78° C. for 1.5 hour. To the mixture was added drowpise aqueous NH$_4$Cl solution, and the mixture was warmed to room temperature. The mixture was extracted with ethyl acetate, and the organic layer was washed with a 2.5N aqueous hydrochloric acid solution and NaHCO$_3$, and dried over MgSO$_4$. The solvent was evaporated under reduced pressure, and the residue was purified by silica gel column (hexane/ethyl acetate=4/1→3/1) to give methyl 4-{hydroxy[1-(phenylsulfonyl)-1H-pyrrol-2-yl]methyl}-benzoate (3.67 g, 82%).

$^1$H NMR (CDCl$_3$, 400 MHz) δ 7.94 (d, 2H, J=8.4 Hz), 7.73 (d, 2H, J=8.4 Hz), 7.63 (m, 1H), 7.49 (m, 2H), 7.34 (dd, 1H, J=3.3, 1.8 Hz), 7.31 (d, 2H, J=8.4 Hz), 6.21 (dd, 1H, J=3.3, 3.3 Hz), 6.11 (d, 1H, J=4.6 Hz), 5.77 (m, 1H), 3.92 (s, 3H), 3.33 (d, 1H, J=4.6 Hz).

(122-2)

Under nitrogen atmosphere, a solution of the compound of Example 122-1 (3.64 g) in toluene (100 mL) was cooled to −78° C., and thereto was added dropwise a 1.01 N solution of diisobutylaluminum hydride in toluene (29.2 mL), and the mixture was stirred at −78° C. for 2 hours. To the mixture was added dropwise an aqueous NH$_4$Cl solution, and the mixture was warmed to room temperature. The mixture was extracted five times with ethyl acetate, and the extract was dried over MgSO$_4$. The solvent was evaporated under reduced pressure, and the residue was purified by silica gel column (hexane/ethyl acetate=1/1) to give 4-{hydroxy[1-(phenylsulfonyl)-1H-pyrrol-2-yl]methyl}benzoic acid (2.82 g, 84%).

$^1$H NMR (CDCl$_3$, 400 MHz) δ 7.73 (d, 2H, J=8.4 Hz), 7.61 (m, 1H), 7.49 (m, 2H), 7.33 (dd, 1H, J=3.3, 1.8 Hz), 7.28 (d, 2H, J=8.4 Hz), 7.23 (d, 2H, J=8.4 Hz), 6.20 (dd, 1H, J=3.3, 3.3 Hz), 6.07 (d, 1H, J=4.7 Hz), 5.82 (m, 1H), 4.68 (d, 2H, J=5.7 Hz), 3.21 (d, 1H, J=4.7 Hz), 1.73 (t, 1H, J=5.7 Hz).

(122-3)

The compound of Example 122-2 was treated in a similar manner to Example 28-4 to give 4-{hydroxy[1-(phenylsulfonyl)-1H-pyrrol-2-yl]methyl}benzaldehyde.

$^1$H NMR (CDCl$_3$, 400 MHz) δ 10.11 (s, 1H,), 8.13 (m, 2H), 7.96 (d, 2H, J=8.5 Hz), 7.92 (d, 2H, J=8.5 Hz), 7.85(dd, 1H, J=3.1, 1.7 Hz), 7.67 (m, 1H), 7.60 (m, 2H), 6.75 (dd, 1H, J=3.7, 1.7 Hz), 6.39 (dd, 1H, J=3.7, 3.1 Hz).

(122-4)

Under nitrogen atmosphere, to a solution of the compound of Example 122-3 (726 mg) in 1,2- dichloroethane (50 mL) were added successively morpholine (933.9 mg) and NaBH(OAc)$_3$ (908 mg), and the mixture was stirred at room temperature for 7 hours. In addition, NaBH(OAc)$_3$ (908 mg) was added to the reaction mixture, and stirred at room temperature for 2 hours. To the mixture was added NaHCO$_3$, and the mixture was extracted twice with ethyl acetate, and dried over MgSO$_4$. The solvent was evaporated under reduced pressure to give crude [4-(morpholin-4-ylmethyl)phenyl][1-(phenylsulfonyl)-1H-pyrrol-2-yl]methanol, which was dissolved in MeOH (50 mL), and thereto was added a 5N aqueous NaOH solutin (20 mL). The mixture was stirred at 65° C. for 4 hours. Water was added to the mixture, and the mixture was extracted twice with ethyl acetate, and dried over MgSO$_4$. The solvent was evaporated under reduced pressure, and the residue was purified by silica gel column (CHCl$_3$/MeOH=100/1) to give [4-(morpholin-4-yl-methyl)phenyl](1H-pyrrol-2-yl)methanol (559 mg, 97%).

$^1$H NMR (CDCl$_3$, 400 MHz) δ 9.65 (brs, 1H), 7.87 (d, 2H, J=8.2 Hz), 7.46 (d, 2H, J=8.2 Hz), 7.14 (m, 1H), 6.90 (m, 1H), 6.35 (m, 1H), 3.73 (t, 4H, J=4.7 Hz), 3.58 (s, 2H), 2.48 (t, 4H, J=4.7 Hz).

(122-5)

The title compound was obtained from the compound of Example 122-4 in a similar manner to Example 18-3.

$^1$H NMR (CDCl$_3$, 400 MHz) δ 7.85 (d, 1H, J=2.3 Hz), 7.78 (d, 2H, J=8.1 Hz), 7.48 (d, 1H, J=8.5 Hz), 7.42 (d, 2H,

J=8.1 Hz), 7.40 (dd, 1H, J=8.5, 2.3 Hz), 7.21 (d, 1H, J=15.8 Hz), 7.10 (dd, 1H, J=2.6, 1.6 Hz), 6.79 (dd, 1H, J=4.0, 1.6 Hz), 6.35 (dt, 1H, J=15.8, 6.0 Hz), 6.23 (dd, 1H, J=4.0, 2.6 Hz), 5.23 (dd, 2H, J=6.0, 1.3 Hz), 3.87 (s, 3H), 3.73 (t, 4H, J=4.6 Hz), 3.56 (s, 2H), 2.47 (t, 4H, J=4.6 Hz).

Example 123

$^1$H NMR (DMSO-d$_6$, 400 MHz) δ 7.71 (m, 3H), 7.66 (d, 1H, J=8.6 Hz), 7.52 (dd, 1H, J=8.6, 2.2 Hz), 7.43 (d, 2H, J=8.1 Hz), 7.36 (m, 1H), 7.00 (d, 1H, J=15.8 Hz), 6.70 (m, 1H), 6.48 (dt, 1H, J=15.8, 5.5 Hz), 6.23 (dd, 1H, J=3.9, 2.6 Hz), 5.20 (d, 2H, J=5.5 Hz), 3.58 (t, 4H, J=4.3 Hz), 3.54 (s, 2H), 2.37 (t, 4H, J=4.3 Hz).

Example 124

$^1$H NMR (CDCl$_3$, 400 MHz) δ 7.76 (d, 2H, J=8.1 Hz), 7.53 (d, 1H, J=2.2 Hz), 7.41 (m, 3H), 7.31 (dd, 1H, J=8.4, 2.2 Hz), 7.05 (dd, 1H, J=2.5, 1.6 Hz), 6.80 (dd, 1H, J=4.0, 1.6 Hz), 6.73 (d, 1H, J=15.8 Hz), 6.31 (dt, 1H, J=15.8, 5.8 Hz), 6.23 (dd, 1H, J=4.0, 2.5 Hz), 6.01 (brs, 1H), 5.15 (dd, 2H, J=5.8, 1.4 Hz), 3.73 (t, 4H, J=4.6 Hz), 3.56 (s, 2H), 2.95 (m, 3H), 2.47 (t, 4H, J=4.6 Hz).

Example 125

(125-1)

Under nitrogen atmosphere, a solution of methoxymethyl-triphenylphosphonium oxide (10.8 g) in Et$_2$O (60 mL) was cooled to 0° C., and thereto was added dropwise a 1.7N solution of t-BuLi in pentane (18.6 mL). After the addition, the mixture was stirred at room temperature for 30 minutes, and cooled to 0° C. To the mixture was added a solution of methyl terephthalaldehyde (5.20 g) in Et$_2$O (80 mL), and the mixture was stirred at 0° C. for 30 minutes, and stirred at room temperature for 80 minuts. To the mixture was added an aqueous NH$_4$Cl solution, and the mixture was extracted twice with Et$_2$O. The organic layer was washed twice with an aqueous NaHSO$_3$ solution, and dried over MgSO$_4$. The solvent was evaporated under reduced pressure to give crude methyl 4-[(E)-2-methoxyethenyl]benzoate (3.71 g). This product was dissolved in a mixture of THF (60 mL)-MeOH (20 mL)-water (20 mL), and thereto was added LiOH hydrate (2.04 g). The mixture was stirred at room temperature for 24 hours, and the solvent was evaporated under reduced pressure. Water was added to the resultant, and the aqueous mixture was washed with ethyl acetate, and cooled to 0° C. The pH value of the mixture was adjusted to pH=3 with a 5% aqueous KHSO$_4$ solution, and the mixture was extracted twice with ethyl acetate, and dried over MgSO$_4$. The solvent was evaporated under reduced pressure, and the residue was purified by silica gel column (CHCl$_3$/MeOH= 50/1) to give 4-[(E)-2-methoxyethenyl]benzoic acid (1.37 g, 20%).

$^1$H NMR (DMSO-d$_6$, 400 MHz) δ 12.73 (brs, 2H), 7.84 (d, 2H, J=8.4 Hz), 7.80 (d, 2H, J=8.4 Hz), 7.60 (d, 2H, J=8.4 Hz), 7.44 (d, 1H, J=13.0 Hz), 7.40 (d, 2H, J=8.4 Hz), 6.45 (d, 1H, J=7.0 Hz), 5.90 (d, 1H, J=13.0 Hz), 5.31 (d, 1H, J=7.0 Hz), 3.80 (s, 3H), 3.67 (s, 3H).

(125-2)

Under nitrogen atmosphere, to a solution of the compound of Example 125-1 (1.37 g) in toluene (150 mL) were added 2,2'-dipyridyl disulfide (2.82 g) and PPh$_3$ (3.36 g), and the mixture was stirred at room temperature for 16 hours. Then, the reaction mixture was cooled to −78° C., and thereto was added a 0.93N solution of pyrrolemagnesium bromide, which was prepared from pyrrole (1.37 g) and a 0.93N solution of methylmagnesium bromide in Et$_2$O (23.4 mL), in toluene. The mixture was stirred at −78° C. for 3 hours, and thereto was added an aqueous NH$_4$Cl solution, and the mixture was warmed to room temperature. Water was added to the mixture, and the mixture was extracted with ethyl acetate, and dried over MgSO$_4$. The solvent was evaporated under reduced pressure, and the residue was purified by silica gel column (hexane/ethyl acetate=4/1) to give {4-[(E)-2-methoxyethenyl]phenyl}(1H-pyrrol-2-yl)methanone (1.49 g, 100%).

$^1$H NMR (CDCl$_3$, 400 MHz) δ 9.76 (brs, 2H), 7.86 (d, 2H, J=8.4 Hz), 7.84 (d, 2H, J=8.4 Hz), 7.67 (d, 2H, J=8.4 Hz), 7.32 (d, 2H, J=8.4 Hz), 7.19 (d, 1H, J=13.0 Hz), 7.13 (m, 2H), 6.91 (m, 2H), 6.34 (m, 2H), 6.26 (d, 1H, J=7.0 Hz), 5.86 (d, 1H, J=13.0 Hz), 5.29 (d, 1H, J=7.0 Hz), 3.84 (s, 3H), 3.73 (s, 3H).

(125-3)

To a solution of the compound of Example 125-2 (1.02 g) in 1,4-dioxane (60 mL) were added water (15 mL) and p-toluenesulfonic acid monohydrate (220 mg), and the mixture was stirred at 101° C. for 2 hours. The solvent was evaporated under reduced pressure, and thereto was added an aqueous sodium carbonate solution, and the mixture was extracted twice with ethyl acetate-toluene. The extracts were dried over MgSO$_4$, and the solvent was evaporated under reduced pressure to give crude {4-[2-oxoethyl]phenyl}(1H-pyrrol-2-yl)methanone. Under nitrogen atmosphere, to a solution of this compound in 1,2-dichloro-ethane (50 mL) were added successively morpholine (1.61 g) and NaBH(OAc)$_3$ (1.57 g), and the mixture was stirred at room temperature for 50 hours. To the mixture was added NaBH(OAc)$_3$ (785 mg), and the mixture was stirred at room temperature for 4 hours. To the mixture was added NaHCO$_3$, and extracted twice with ethyl acetate. The solvent was evaporated under reduced pressure, and the residue was purified by silica gel column (ethyl acetate) to give [4-(2-morpholin-4-ylethyl)-phenyl](1H-pyrrol-2-yl)methanone (328 mg, 31%).

$^1$H NMR (CDCl$_3$, 400 MHz) δ 9.59 (brs, 1H), 7.85 (d, 2H, J=8.3 Hz), 7.32 (d, 2H, J=8.3 Hz), 7.13 (m, 1H), 6.89 (m, 1H), 6.34 (m, 1H), 3.75 (t, 4H, J=4.6 Hz), 2.89 (m, 2H), 2.64 (m, 2H), 2.54 (t, 4H, J=4.6 Hz).

(125-4)

Methyl 5-chloro-2-((1E)-3-{2-[4-(2-morpholin-4-ylethyl)benzoyl]-1H-pyrrol-1H-pyrrol-1yl}prop-1-enyl)benzoate was obtained from the compound of Example 125-3 in a similar manner to Example 18-3.

$^1$H NMR (CDCl$_3$, 400 MHz) δ 7.85 (d, 1H, J=2.2 Hz), 7.76 (d, 2H, J=8.2 Hz), 7.48 (d, 1H, J=8.4 Hz), 7.40 (dd, 1H, J=8.4, 2.2 Hz), 7.29 (d, 2H, J=8.2 Hz), 7.20 (d, 1H, J=15.8 Hz), 7.09 (dd, 1H, J=2.5, 1.8 Hz), 6.78 (dd, 1H, J=4.0, 1.8 Hz), 6.35 (dt, 1H, J=15.8, 6.0 Hz), 6.23 (dd, 1H, J=4.0, 2.5 Hz), 5.22 (dd, 2H, J=6.0, 1.4 Hz), 3.87 (s, 3H), 3.75 (t, 4H, J=4.6 Hz), 2.88 (m, 2H), 2.63 (m, 2H), 2.54 (t, 4H, J=4.6 Hz).

(125-5)

To a solution of the compound of Example 125-4 (117.8 g) in THF (5 mL)-MeOH (5 mL) was added a 2N aqueous NaOH solution (0.6 mL), and the mixture was stirred at room temperature for 20 hours. The solvent was evaporated under reduced pressure, and the residue was washed with ethyl acetate, and thereto was added a 5% aqueous KHSO$_4$ solution until the pH value of the mixture became pH=5–6. The precipitated solid was collected by filtration to give the title compound (45.2 mg, 39%).

$^1$H NMR (DMSO-d$_6$, 400 MHz) δ 7.71 (d, 1H, J=2.3 Hz), 7.67 (m, 3H), 7.53 (dd, 1H, J=8.5, 2.3 Hz), 7.35 (m, 3H), 7.00 (d, 1H, J=16.0 Hz), 6.69 (dd, 1H, J=4.0, 1.6 Hz), 6.48 (dt, 1H, J=16.0, 5.5 Hz), 6.23 (dd, 1H, J=4.0, 2.5 Hz), 5.20

(d, 2H, J=5.5 Hz), 3.58 (t, 4H, J=4.5 Hz), 2.82 (t, 2H, J=8.2 Hz), 2.57 (t, 2H, J=8.2 Hz), 2.45 (t, 4H, J=4.5 Hz).

Example 126

(126-1)

4-Iodophenylmethoxy-t-butyldimethylsilane (1.48 g) was dissolved in THF (50 mL), and the mixture was cooled in a dry ice-acetone bath, and thereto was added dropwise t-BuLi (2.68 mL, 1.7M hexane solution). The mixture was stirred for 40 minuts, and thereto was added a solution of the compound of Example 109-3 (709 mg) in THF (15 mL). The mixture was stirred at the same temperature for 3 hours, and then warmed to room temperature over a period of 90 minutes. To the mixture was added an aqueous $NH_4Cl$ solution, and the mixture was extracted with ethyl acetate. The organic layer was concentrated, and purified by silica gel column chromatography to give (4-t-butyldimethylsiloxymethylphenyl)(1-phenylsulfonyl-4-methyl-1H-pyrrol-2-yl)methanol (452 mg, 34%).

$^1$H NMR ($CDCl_3$, 400 MHz) δ 7.71 (m, 2H), 7.60 (m, 1H), 7.48 (m, 2H), 7.24 (d, 2H, J=8.4 Hz), 7.20 (d, 2H, J=8.4 Hz), 7.05 (m, 1H), 6.01 (d, 1H, J=4.6 Hz), 5.64 (d, 1H, J=1.8 Hz), 4.73 (s, 2H), 3.22 (d, 1H, J=4.7 Hz), 1.95 (d, 3H, J=1.0 Hz), 0.94 (s, 9H), 0.10 (s, 6H).

(126-2)

The compound of Example 126-1 was treated with acetic acid in THF-water to give (4-hydroxymethylphenyl)(1-phenylsulfonyl-4-methyl-1H-pyrrol-2-yl)methanol.

$^1$H NMR ($CDCl_3$, 400 MHz) δ 7.75 (m, 2H), 7.61 (m, 1H), 7.49 (m, 2H), 7.29 (d, 2H, J=8.1 Hz), 7.25 (d, 2H, J=8.1 Hz), 7.09 (m, 1H), 6.02 (s, 1H), 5.87 (d, 1H, J=1.7 Hz), 4.68 (s, 2H), 1.98 (d, 3H, J=0.9 Hz).

(126-3)

(4-Oxomethylphenyl)(1-phenylsulfonyl-4-methyl-1H-pyrrol-2-yl)methanone was obtained from the compound of Example 126-2 in a similar manner to Example 28-4.

$^1$H NMR ($CDCl_3$, 400 MHz) δ 10.10 (s, 1H), 8.11 (m, 2H), 7.95 (d, 2H, J=8.4 Hz), 7.91 (d, 2H, J=8.4 Hz), 7.66 (m, 1H), 7.58 (m, 3H), 6.58 (d, 1H, J=1.9 Hz), 2.12 (s, 3H).

(126-4)

[4-(Morpholin-4-ylmethyl)phenyl](1-phenylsulfonyl-4-methyl-1H-pyrrol-2-yl)methanone was obtained from the compound of Example 126-3 in a similar manner to Example 122-4.

$^1$H NMR ($CDCl_3$, 400 MHz) δ 8.11 (m, 2H), 7.76 (d, 2H, J=8.3 Hz), 7.64 (m, 1H), 7.57 (m, 2H), 7.53 (m, 1H), 7.40 (d, 2H, J=8.3 Hz), 6.56 (d, 1H, J=1.7 Hz), 3.72 (t, 4H, J=4.6 Hz), 3.55 (s, 2H), 2.45 (t, 4H, J=4.6 Hz), 2.10 (d, 3H, J=0.6 Hz).

(126-5)

[4-(Morpholin-4-ylmethyl)phenyl](4-methyl-1H-pyrrol-2-yl)-methanone was obtained from the compound of Example 126-4 in a similar manner to Reference Example 1-2.

$^1$H NMR ($CDCl_3$, 400 MHz) δ 9.34 (brs, 1H), 7.84 (d, 2H, J=8.3 Hz), 7.44 (d, 2H, J=8.3 Hz), 6.92 (m, 1H), 6.71 (m, 1H), 3.73 (t, 4H, J=4.7 Hz), 3.57 (s, 2H), 2.48 (t, 4H, J=4.7 Hz), 2.14 (s, 3H).

(126-6)

Methyl 5-chloro-2-((1E)-3-{4-methyl-2-[4-(morpholin-4-yl-methyl)benzoyl]-1H-pyrrol-1-yl}prop-1-enyl)benzoate was obtained from the compound of Example 9-2 and the compound of Example 126-5 in a similar manner to Example 18-3.

$^1$H NMR ($CDCl_3$, 400 MHz) δ 7.85 (d, 1H, J=2.2 Hz), 7.76 (d, 2H, J=8.2 Hz), 7.48 (d, 1H, J=8.5 Hz), 7.41 (d, 2H, J=8.2 Hz), 7.40 (dd, 1H, J=8.5, 2.2 Hz), 7.21 (d, 1H, J=15.7 Hz), 6.88 (m, 1H), 6.58 (m, 1H), 6.34 (dt, 1H, J=15.7, 6.1 Hz), 5.16 (dd, 2H, J=6.1, 1.4 Hz), 3.87 (s, 3H), 3.73 (t, 4H, J=4.6 Hz), 3.56 (s, 2H), 2.47 (t, 4H, J=4.6 Hz), 2.09 (s, 3H).

(126-7)

The title compound was obtained from the compound of Example 126-6 in a similar manner to Example 16.

$^1$H NMR (DMSO-$d_6$, 400 MHz) δ 7.70 (d, 2H, J=8.0 Hz), 7.43 (m, 5H), 7.12 (m, 2H), 6.48 (s, 1H), 6.23 (dt, 1H, J=15.7, 6.3 Hz), 5.04 (d, 2H, J=6.3 Hz), 3.58 (t, 4H, J=4.3 Hz), 3.53 (s, 2H), 2.38 (t, 4H, J=4.3 Hz), 2.02 (s, 3H).

Example 127

(127-1)

Under nitrogen atmosphere, to a solution of 4-fluorobenzonitrile (24.9 g) in $CH_3CN$ (500 mL) was added morpholine (53.8 g), and the mixture was stirred at 82° C. for 50 hours. The solvent was evaporated under reduced pressure, and the residue was purified by silica gel column (hexane/ethyl acetate=10/1→4/1) to give 4-morpholin-4-yl-benzonitrile (25.3 g, 65%).

$^1$H NMR ($CDCl_3$, 400 MHz) δ 7.52 (d, 2H, J=9.1 Hz), 6.87 (d, 2H, J=9.1 Hz), 3.85 (t, 4H, J=4.9 Hz), 3.28 (t, 4H, J=4.9 Hz).

(127-2)

To a solution of the compound of Example 127-1 (5.00 g) in ethylene glycol (40 mL) were added water (0.5 mL) and NaOH (4.26 g), and the mixture was stirred at 120° C. for 30 minutes. The mixture was cooled to room temperature, and thereto was added water. The mixture was washed with ethyl acetate, and the pH value thereof was adjusted to pH=6 with a 6N aqueous hydrochloric acid solution. The precipitated solid was collected by filtration to give 4-morpholin-4-ylbenzoic acid (1.69 g, 31%).

$^1$H NMR (DMSO-$d_6$, 400 MHz) δ 12.32 (brs, 1H), 7.78 (d, 2H, J=9.0 Hz), 6.97 (d, 2H, J=9.0 Hz), 3.73 (t, 4H, J=4.8 Hz), 3.24 (t, 4H, J=4.8 Hz).

(127-3)

(4-Morpholin-4-ylphenyl)(1H-pyrrol-2-yl)methanone was obtained from the compound of Example 127-2 in a similar manner to Example 125-2.

$^1$H NMR ($CDCl_3$, 400 MHz) δ 9.58 (brs, 1H), 7.93 (d, 2H, J=8.9 Hz), 7.10 (m, 1H), 6.93 (d, 2H, J=8.9 Hz), 6.90 (m, 1H), 6.34 (m, 1H), 3.88 (t, 4H, J=4.9 Hz), 3.32 (t, 4H, J=4.9 Hz).

(127-4)

Methyl 5-chloro-2-{(1E)-3-[2-(4-morpholin-4-ylbenzoyl)-1H-pyrrol-1-yl]prop-1-enyl}benzoate was obtained from the compound of Example 127-3 in a similar manner to Example 18-3.

$^1$H NMR ($CDCl_3$, 400 MHz) δ 7.85 (d, 1H, J=2.3 Hz), 7.84 (d, 2H, J=8.9 Hz), 7.47 (d, 1H, J=8.5 Hz), 7.39 (dd, 1H, J=8.5, 2.3 Hz), 7.20 (d, 1H, J=15.8 Hz), 7.06 (dd, 1H, J=2.6, 1.7 Hz), 6.90 (d, 2H, J=8.9 Hz), 6.77 (dd, 1H, J=4.0, 1.7 Hz), 6.35 (dt, 1H, J=15.8, 6.1 Hz), 6.22 (dd, 1H, J=4.0, 2.6 Hz), 5.19 (dd, 2H, J=6.1, 1.4 Hz), 3.87 (t, 4H, J=5.0 Hz), 3.87 (s, 3H), 3.30 (t, 4H, J=5.0 Hz).

(127-5)

The title compound was obtained from the compound of Example 127-4 in a similar manner to Example 16.

$^1$H NMR (DMSO-$d_6$, 400 MHz) δ 7.72 (d, 2H, J=8.9 Hz), 7.44 (d, 1H, J=16.1 Hz), 7.39 (d, 1H, J=8.4 Hz), 7.38 (d, 1H, J=2.3 Hz), 7.26 (dd, 1H, J=2.6, 1.7 Hz), 7.12 (dd, 1H, J=8.4, 2.3 Hz), 7.00 (d, 2H, J=8.9 Hz), 6.64 (dd, 1H, J=3.9, 1.7 Hz), 6.23 (dt, 1H, J=16.1, 6.4 Hz), 6.18 (dd, 1H, J=3.9, 2.6 Hz), 5.06 (d, 2H, J=6.4 Hz), 3.74 (t, 4H, J=5.1 Hz), 3.27 (t, 4H, J=5.1 Hz).

Example 128

(128-1)

5-Chloro-2-{(1E)-3-[2-(4-methylbenzoyl)-1H-pyrrol-1-yl]-1-propenyl}benzamide was obtained from the compound of Example 9 and NH$_4$Cl in a similar manner to Example 116.

$^1$H NMR (CDCl$_3$, 400 MHz) δ 7.70 (d, 2H, J=8.0 Hz), 7.60 (d, 1H, J=2.2 Hz), 7.40 (d, 1H, J=8.4 Hz), 7.34 (dd, 1H, J=2.2, 8.4 Hz), 7.26 (d, 2H, J=8.0 Hz), 7.04 (dd, 1H, J=1.7, 2.5 Hz), 6.81 (dd, 1H, J=1.7, 4.0 Hz), 6.76 (d, 1H, J=15.8 Hz), 6.32 (dt, 1H, J=15.8, 5.6 Hz), 6.23 (dd, 1H, J=2.5, 4.0 Hz), 6.09 (br, 1H), 5.78 (br, 1H), 5.16 (d, 2H, J=5.6 Hz), 2.43 (s, 3H).

(128-2)

Under nitrogen atmosphere, to a solution of 2-hydroxypyridine (2.66 g) and NEt$_3$ (4.05 mL) in THF (80 mL) was added dropwise SOCl$_2$ (1.05 mL) under ice-cooling, and the mixture was stirred for one hour. The mixture was filtered, and the solvent was evaporated under reduced pressure to give di-2-pyridyl sulfite (3.02 g, 91%).

(128-3)

Under nitrogen atmosphere, to a solution of the compound of Example 128-1 (40.0 mg) in toluene (1.5 mL) was added the compound of Example 128-2 (53.0 mg), and the mixture was refluxed for one hour. Water was added to the mixture, and the mixture was extracted with ethyl acetate. The exract was washed with a saturated brine and dried over MgSO$_4$. The solvent was evaporated under reduced pressure, and the residue was purified by silica gel column (hexane/ethyl acetate=3/1) to give the title compound (28.6 mg, 75%).

$^1$H NMR (CDCl$_3$, 400 MHz) δ 7.75 (d, 2H, J=8.0 Hz), 7.57 (d, 1H, J=8.7 Hz), 7.56 (d, 1H, J=2.1 Hz), 7.47 (dd, 1H, J=2.1, 8.7 Hz), 7.26 (d, 2H, J=8.0 Hz), 7.04 (dd, 1H, J=1.7, 2.6 Hz), 6.81 (dd, 1H, J=1.7, 4.0 Hz), 6.68–6.69 (m, 2H), 6.25 (dd, 1H, J=2.6, 4.0 Hz), 5.25 (d, 2H, J=3.8 Hz), 2.43 (s, 3H).

Example 129

Under nitrogen atmosphere, to a solution of the compound of Example 128 (25.7 mg) in DMF (0.3 mL) were added NaN$_3$ (5.8 mg) and NH$_4$Cl (4.6 mg), and the mixture was stirred at 100° C. for 6 hours. Further, thereto were added NaN$_3$ (10.6 mg) and NH$_4$Cl (9.1 mg), and the mixture was stirred at 110° C. for 9 hours. The mixture was cooled to room temperature, and thereto was added a 1N aqueous hydrochloric acid solution. The mixture was extracted with ethyl acetate-toluene, and the extract was washed twice with a 1N aqueous hydrochloric acid solution, washed with a saturated brine, and dried over MgSO$_4$. The solvent was evaporated under reduced pressure, and the residue was purified by silica gel column (hexane/ethyl acetate=3/1→acetic acid/ethyl acetate=1/100) to give the title compound (1.6 mg, 5.6%).

$^1$H NMR (CDCl$_3$, 400 MHz) δ 8.22 (d, 1H, J=2.2 Hz), 7.88 (d, 2H, J=8.1 Hz), 7.43 (dd, 1H, J=2.2, 8.3 Hz), 7.38 (d, 1H, J=8.3 Hz), 7.28 (d, 2H, J=8.1 Hz), 7.14 (dd, 1H, J=1.7, 2.5 Hz), 6.94 (dd, 1H, J=1.7, 4.1 Hz), 6.84 (d, 1H, J=15.5 Hz), 6.30 (dd, 1H, J=2.5, 4.1 Hz), 6.15 (dt, 1H, J=15.5, 5.9 Hz), 5.12 (d, 2H, J=5.9 Hz), 2.42 (s, 3H).

Example 130

$^1$H NMR (CDCl$_3$, 400 MHz) δ 7.83 (d, 2H, J=8.7 Hz), 7.54 (d, 1H, J=2.2 Hz), 7.39 (d, 1H, J=8.5 Hz), 7.31 (dd, 1H, J=8.5 and 2.2 Hz), 7.03 (dd, 1H, J=1.7 and 2.5 Hz), 6.95 (d, 2H, J=8.7 Hz), 6.78 (dd, 1H, J=1.7 and 4.0 Hz), 6.69 (brd, 1H, J=15.8 Hz), 6.30 (dt, 1H, J=15.8 and 6.0 Hz), 6.23 (dd, 1H, J=2.5 and 4.0 Hz), 6.01 (brq, 1H, J=4.9 Hz), 5.12 (dd, 2H, J=1.4 and 6.0 Hz), 3.88 (s, 3H), 2.94 (d, 3H, J=4.9 Hz).

Example 131

$^1$H NMR (CDCl$_3$, 400 MHz) δ 7.80 (d, 2H, J=8.7 Hz), 7.51 (d, 1H, J=2.2 Hz), 7.43 (d, 1H, J=8.5 Hz), 7.34 (dd, 1H, J=8.5 and 2.2 Hz), 7.0 (dd, 1H, J=1.7 and 2.5 Hz), 6.93 (d, 2H, J=8.7 Hz), 6.75 (dd, 1H, J=1.7 and 4.0 Hz), 6.73 (brd, 1H, J=15.8 Hz), 6.38 (dt, 1H, J=15.8 and 6.0 Hz), 6.22 (dd, 1H, J=2.5 and 4.0 Hz), 5.13 (dd, 2H, J=1.4 and 6.0 Hz), 3.86 (s, 31H), 3.30 (brs, 3H).

Example 132

$^1$H NMR (CDCl$_3$, 400 MHz) δ 7.73 (d, 2H, J=8.7 Hz), 7.60 (d, 1H, J=2.2 Hz), 7.53 (d, 1H, J=8.5 Hz), 7.35 (dd, 1H, J=8.5 and 2.2 Hz), 7.24 (dd, 1H, J=1.7 and 2.5 Hz), 7.04 (brd, 1H, J=15.8 Hz), 6.88 (d, 2H, J=8.7 Hz), 6.77 (dd, 1H, J=1.7 and 4.0 Hz), 6.39 (dt, 1H, J=15.8 and 6.0 Hz), 6.25 (dd, 1H, J=2.5 and 4.0 Hz), 5.17 (dd, 2H, J=1.4 and 6.0 Hz), 3.13 (brs, 3H).

Example 133

$^1$H NMR (CDCl$_3$, 400 MHz) δ 7.78 (d, 2H, J=8.7 Hz), 7.53 (d, 1H, J=2.2 Hz), 7.39 (d, 1H, J=8.5 Hz), 7.31 (dd, 1H, J=8.5 and 2.2 Hz), 7.03 (dd, 1H, J=1.7 and 2.5 Hz), 6.88 (d, 2H, J=8.7 Hz), 6.78 (dd, 1H, J=1.7 and 4.0 Hz), 6.69 (brd, 1H, J=15.8 Hz), 6.30 (dt, 1H, J=15.8 and 6.0 Hz), 6.23 (dd, 1H, J=2.5 and 4.0 Hz), 6.01 (brs, 1H), 5.12 (dd, 2H, J=1.4 and 6.0 Hz), 2.94 (d, 3H, J=4.9 Hz).

Example 134

The compound of Example 102 was treated with an acid, and further treated in a similar manner to Examples 128 and 129 to give a tetrazole compound. To this tetrazole compound (91 mg) were added MeOH (1.0 mL), THF (1.0 mL), and a 1N aqueous NaOH solution (210 μl), and the mixture was allowed to stand at room temperature for 10 minutes. The solvent was evaporated under reduced pressure, and thereto was added toluene. This procedure was repeated five times, and the precipitated solid was suspended in Et$_2$O, and collected by filtration to give the title compound (98.5 mg, 35%).

$^1$H NMR (DMSO-d$_6$, 400 MHz) δ 7.86(d, 1H, J=2.4 Hz), 7.78(d, 2H, J=8.7 Hz), 7.75(d, 1H, J=15.8 Hz), 7.60(d, 1H, J=8.5 Hz), 7.33(dd, 1H, J=1.6, 2.6 Hz), 7.25(dd, 1H, J=2.4, 8.5 Hz), 7.03(d, 2H, J=8.7 Hz), 6.65(dd, 1H, J=1.6, 3.9 Hz), 6.37(dt, 1H, J=15.8, 6.2 Hz), 6.19(dd, 1H, J=2.6, 3.9 Hz), 5.14(d, 2H, J=6.2 Hz), 3.84(s, 3H).

Example 135

$^1$H NMR (CDCl$_3$, 400 MHz) δ 8.23 (d, 1H, J=2.2 Hz), 7.99 (d, 2H, J=8.9 Hz), 7.43 (dd, 1H, J=2.2, 8.3 Hz), 7.37 (d, 1H, J=8.3 Hz), 6.97 (d, 2H, J=8.9 Hz), 6.91(d, 1H, J=1.1 Hz), 6.79 (d, 1H, J=15.5 Hz), 6.72 (d, 1H, J=1.1 Hz), 6.14 (dt, 1H, J=15.5, 5.8 Hz), 5.04 (d, 2H, J=5.8 Hz), 3.87 (s, 3H), 2.12 (s, 3H).

Example 136

A methanesulfonylamide compound was obtained from the compound of Example 110 in a similar manner to Example 115. To this methanesulfonylamide compound (74.5 mg) were added MeOH (1.0 mL), THF (1.0 mL), and a 1N aqueous NaOH solution (150 μl), and the mixture was allowed to stand at room temperature for 10 minutes. The solvent was evaporated under reduced pressure, and thereto was added toluene. This procedure was repeated three times. The precipitated solid was suspended in $Et_2O$, and collected by filtration to give the title compound (66.0 mg, 43%).

$^1$H NMR (DMSO-$d_6$, 400 MHz) δ 7.76 (d, 2H, J=8.8 Hz), 7.47 −7.49 (m, 2H), 7.25 (dd, 1H, J=2.4, 8.4 Hz), 7.11 (d, 1H, J=15.9 Hz), 7.10 (d, 1H, J=1.3 Hz), 7.02 (d, 2H, J=8.8 Hz), 6.46 (d, 1H, J=1.3 Hz), 6.29 (dt, 1H, J=15.9, 5.8 Hz), 5.05 (d, 2H, J=5.8 Hz), 3.83 (s, 3H), 2.82 (s, 3H), 2.02 (s, 3H).

Example 137

(137-1)

Methyl 4-chloro-2-methoxybenzoate was obtained from 4-chlorosalicylic acid in a similar manner to Example 109-8.

$^1$H NMR (CDCl$_3$, 400 MHz) δ 7.76 (d, 1H, J=8.8 Hz), 6.96–6.98 (m, 2H), 3.91 (s, 3H), 3.88 (s, 3H).

(137-2)

Under nitrogen atmosphere, a solution of the compound of Example 137-1 (4.50 g) in THF (75 mL) was cooled to 0° C., and thereto was added LiAlH$_4$ (984 mg) in portions. The mixture was stirred at room temperature for 2 hours, and cooled to 0° C. Water (1.0 mL), a 2N aqueous NaOH solution (2.0 mL) and water (1.0 mL) were added successively to the mixture, and the mixture was stirred at room temperature for 1 hour. The solid was collected by filtration, and washed with ethyl acetate. The filtrate and the washing were combined, washed with a saturated brine, and dried over MgSO$_4$. The solvent was evaporated under reduced pressure to give (4-chloro-2-methoxy-phenyl)methanol (3.88 g, 100%).

$^1$H NMR (CDCl$_3$, 400 MHz) δ 7.21(d, 1H, J=8.0 Hz), 6.93 (dd, 1H, J=1.9, 8.0 Hz), 6.87 (d, 1H, J=1.9 Hz), 4.64 (s, 2H), 3.86 (s, 3H).

(137-3)

4-Chloro-2-methoxybenzaldehyde was obtained from the compound of Example 137-2 in a similar manner to Example 28-4.

$^1$H NMR (CDCl$_3$, 400 MHz) δ 10.39 (s, 1H), 7.77 (d, 1H, J=8.3 Hz), 7.02 (dd, 1H, J=1.7, 8.3 Hz), 6.99 (d, 1H, J=1.7 Hz), 3.94 (s, 3H).

(137-4)

Under nitrogen atmosphere, a suspension of 60% NaH (570 mg) in THF (35 mL) was cooled to 0° C., and thereto was added dropwise triethyl 2-phosphonopropionate (2.80 mL). Then, the mixture was stirred for 10 minutes, and thereto was added the compound of Example 137-3 (2.00 g). The mixture was stirred at 60° C. for 1 hour, and thereto was added water. The mixture was extracted with ethyl acetate, washed with water and a saturated brine, and dried over MgSO$_4$. The solvent was evaporated under reduced pressure, and the residue was purified by silica gel column (toluene/ethyl acetate=10/1) to give ethyl 3-(4-chloro-2-methoxyphenyl)acrylate (2.56 g, 91%).

$^1$H NMR (CDCl$_3$, 400 MHz) δ 7.89 (d, 1H, J=16.2 Hz), 7.42 (d, 1H, J=8.3 Hz), 6.95 (dd, 1H, J=1.9, 8.3 Hz), 6.90 (d, 1H, J=1.9 Hz), 6.50 (d, 1H, J=16.2 Hz), 4.26 (q, 2H, J=7.1 Hz), 3.89 (s, 3H), 1.33 (t, 3H, J=7.1 Hz).

(137-5)

Under nitrogen atmosphere, to a solution of the compound of Example 137-4 (1.78 g) in toluene (30 mL) that was cooled to −78° C. was added dropwise a 1.0N solution of (iBu)$_2$AlH in toluene (16.5 mL). The mixture was stirred at −78° C. for 30 minutes, and thereto was added a 1N aqueous hydrochloric acid solution, and the mixture was extracted with ethyl acetate. The extract was washed with a 1N aqueous hydrochloric acid solution and a saturated brine, and dried over MgSO$_4$. The solvent was evaporated under reduced pressure, and the residue was purified by silica gel column (hexane/ethyl acetate=3/1→1/1) to give 3-(4-chloro-2-methoxyphenyl)propenol (1.36 g, 92%).

$^1$H NMR (CDCl$_3$, 400 MHz) δ 7.34 (d, 1H, J=8.2 Hz), 6.91 (dd, 1H, J=2.0, 8.2 Hz), 6.85 (d, 1H, J=2.0 Hz), 6.85 (d, 1H, J=16.0 Hz), 6.36 (dt, 1H, J=16.0, 5.8 Hz), 4.32 (d, 2H, J=5.8 Hz), 3.84 (s, 3H).

(137-6)

Under nitrogen atmosphere, the title compound was obtained from the compound of Example 137-5 and the compound of Example 109-6 in a similar manner to Example 18-3.

$^1$H NMR (CDCl$_3$, 400 MHz) δ 7.83 (d, 2H, J=8.9 Hz), 7.32 (d, 1H, J=8.2 Hz), 6.94 (d, 2H, J=8.9 Hz), 6.87 (dd, 1H, J=1.9, 8.2 Hz), 6.83 (d, 1H, J=1.3 Hz), 6.82 (d, 1H, J=1.9 Hz), 6.76 (d, 1H, J=16.0 Hz), 6.42 (dt, 1H, J=16.0, 6.4 Hz), 6.21 (d, 1H, J=1.3 Hz), 5.11 (d, 2H, J=6.4 Hz), 3.88 (s, 3H), 3.81 (s, 3H), 2.08 (s, 3H).

Example 138

(138-1)

Under nitrogen atmosphere, a solution of the compound of Example 109-3 (3.68 g) in THF (45 mL) was cooled to −78° C., and thereto was added dropwise a 0.759 N solution of 4-methylphenylmagnesium bromide in THF (20 mL), which was prepared when used, and the mixture was stirred at the same temperature for 30 minutes. To the reaction solution were added water and a 1N aqueous hydrochloric acid solution, and the mixture was extracted three times with ethyl acetate. The organic layers were washed with a 1N aqueous hydrochloric acid solution and a saturated brine, and dried over MgSO$_4$. The solvent was evaporated under reduced pressure, and the residue was purified by silica gel column (hexane/ethyl acetate=3/1) to give a crude alcohol compound. Under nitrogen atmosphere, to a solution of the crude alcohol in CHCl$_3$ (100 mL) was added MnO$_2$ (30 g), and the mixture was stirred at 50° C. for 3 hours, and stirred at room temperature overnight and filtered. The solvent was evaporated under reduced pressure, and the residue was purified by silica gel column (hexane/ethyl acetate=6/1) to give a crude ketone compound. Under nitrogen atmosphere, to a solution of the crude ketone compound in dioxane (10 mL) was added a 2N aqueous NaOH solution (20 mL), and the mixture was stirred at 80° C. for 3 hours. The mixture was acidified with a 1N aqueous hydrochloric acid solution, and the mixture was extracted twice with ethyl acetate, washed with a saturated brine, and dried over MgSO$_4$. The solvent was evaporated under reduced pressure, and the residue was purified by silica gel column (toluene/ethyl acetate=10/1) to give (4-methyl-1H-pyrrol-2-yl)(4-methylphenyl) ketone (993 mg, 34%, 3 steps).

$^1$H NMR (CDCl$_3$, 400 MHz) δ 9.38 (br, 1H), 7.80 (d, 2H, J=8.0 Hz), 7.28 (d, 2H, J=8.0 Hz), 6.91 (m, 1H), 6.70–6.71 (m, 1H), 2.43 (s, 3H), 2.14 (s, 3H).

(138-2)

The title compound was obtained from the compound of Example 9-2 and the compound of Example 138-1 in a similar manner to Example 18-3.

$^1$H NMR (CDCl$_3$, 400 MHz) δ 7.85 (d, 1H, J=2.3 Hz), 7.72 (d, 2H, J=8.0 Hz), 7.48 (d, 1H, J=8.4 Hz), 7.39 (dd, 1H, J=2.3, 8.4 Hz), 7.24 (d, 2H, J=8.0 Hz), 7.21 (d, 1H, J=15.8 Hz), 6.86 (d, 1H, J=1.3 Hz), 6.57 (d, 1H, J=1.3 Hz), 6.34 (dt, 1H, J=15.8, 6.1 Hz), 5.15 (d, 2H, J=6.1 Hz), 3.87 (s, 3H), 2.42 (s, 3H), 2.08 (s, 3H).

Example 139

(139-1)

5-Chloro-2-{(1E)-3-[2-(4-methylbenzoyl)-4-methyl-1H-pyrrol-1-yl]-1-propenyl}benzoic acid was obtained from the compound of Example 138 in a similar manner in Example 16.

$^1$H NMR (CDCl$_3$, 400 MHz) δ 7.96 (d, 1H, J=2.2 Hz), 7.71 (d, 2H, J=8.0 Hz), 7.51 (d, 1H, J=8.5 Hz), 7.45 (dd, 1H, J=2.2, 8.5 Hz), 7.27 (d, 1H, J=15.9 Hz), 7.24 (d, 2H, J=8.0 Hz), 6.86 (d, 1H, J=1.3 Hz), 6.58 (d, 1H, J=1.3 Hz), 6.36 (dt, 1H, J=15.9, 6.0 Hz), 5.17 (d, 2H, J=6.0 Hz), 2.40 (s, 3H), 2.09 (s, 3H).

(139-2)

To the compound of Example 139-1 (336 mg) were added MeOH (3.0 mL), THF (3.0 mL), and a 1N aqueous NaOH solution (850 μl), and the mixture was allowed to stand at room temperature for 10 minutes. The solvent was evaporated under reduced pressure, and Et$_2$O was added thereto. The precipitated solid was collected by filtration to give the title compound (330 mg, 93%).

$^1$H NMR (DMSO-d$_6$, 400 MHz) δ 7.65 (d, 2H, J=8.0 Hz), 7.48 (d, 1H, J=16.0 Hz), 7.41 (d, 1H, J=8.4 Hz), 7.39 (d, 1H, J=2.4 Hz), 7.30 (d, 2H, J=8.0 Hz), 7.12 (dd, 1H, J=2.4, 8.4 Hz), 7.11 (d, 1H, J=1.3 Hz), 6.47 (d, 1H, J=1.3 Hz), 6.22 (dt, 1H, J=16.0, 5.8 Hz), 5.03 (d, 2H, J=5.8 Hz), 2.39 (s, 3H), 2.02 (s, 3H).

Example 140

$^1$H NMR (DMSO-d$_6$, 400 MHz) δ 7.65 (d, 2H, J=8.1 Hz), 7.49 (d, 1H, J=8.5 Hz), 7.48 (d, 1H, J=2.5 Hz), 7.29 (d, 2H, J=8.1 Hz), 7.26 (dd, 1H, J=2.5, 8.5 Hz), 7.13 (d, 1H, J=1.4 Hz), 7.10 (d, 1H, J=15.9 Hz), 6.46 (d, 1H, J=1.4 Hz), 6.30 (dt, 1H, J=15.9, 5.8 Hz), 5.07 (d, 2H, J=5.8 Hz), 2.83 (s, 3H), 2.38 (s, 3H), 2.01 (s, 3H).

Example 141

$^1$H NMR (CDCl$_3$, 400 MHz) δ 7.72 (d, 2H, J=8.1 Hz), 7.33 (d, 1H, J=8.2 Hz), 7.25 (d, 2H, J=8.1 Hz), 6.82–6.88 (m, 3H), 6.77 (d, 1H, J=16.0 Hz), 6.55 (s, 1H), 6.42 (dt, 1H, J=16.0, 6.3 Hz), 5.13 (d, 2H, J=6.3 Hz), 3.82 (s, 3H), 2.42 (s, 3H), 2.07 (s, 3H).

Example 142

(142-1)

Under nitrogen atmosphere, a solution of 4-chloro-2-nitro-benzoic acid (4.00 g) in THF (15 mL) was cooled to 0° C., and thereto was added dropwise dimethylsulfideborane (2.51 mL), and the mixture was stirred at room temperature for 16 hours. To the reaction solution were added water and a saturated aqueous sodium hydrogen carbonate solution, and the mixture was extracted with ethyl acetate. The organic layer was washed with a saturated brine, and dried over MgSO$_4$. The solvent was evaporated under reduced pressure, and the residue was purified by silica gel column (hexane/ethyl acetate=2/1) to give (4-chloro-2-nitrophenyl)methanol (1.32 g, 36%).

$^1$H NMR (CDCl$_3$, 400 MHz) δ 8.11 (d, 1H, J=2.1 Hz), 7.74 (d, 1H, J=8.3 Hz), 7.65 (dd, 1H, J=2.1, 8.3 Hz), 4.98 (s, 1H).

(142-2)

4-Chloro-2-nitrobenzaldehyde was obtained from the compound of Example 142-1 in a similar manner to Example 28-4.

$^1$H NMR (CDCl$_3$, 400 MHz) δ 10.39 (brs, 1H), 8.11 (d, 1H, J=1.9 Hz), 7.95 (d, 1H, J=8.3 Hz), 7.77 (dd, 1H, J=1.9, 8.3 Hz).

(142-3)

Ethyl 3-(4-chloro-2-nitrophenyl)acrylate (1.08 g, 98%) was obtained from the compound of Example 142-2 (800 mg) in a similar manner to Example 137-4.

$^1$H NMR (CDCl$_3$, 400 MHz) δ 8.04 (d, 1H, J=15.8 Hz), 8.04 (d, 1H, J=2.0 Hz), 7.63 (dd, 1H, J=2.0, 8.4 Hz), 7.59 (d, 1H, J=8.4 Hz), 6.36 (d, 1H, J=15.8 Hz), 4.29 (q, 2H, J=7.1 Hz), 1.35 (t, 3H, J=7.1 Hz).

(142-4)

Under nitrogen atmosphere, to a solution of the compound of Example 142-3 (500 mg) in EtOH (12 mL) was added tin (II) chloride dihydrate (1.40 g), and the mixture was refluxed for 30 minutes. The reaction solution was poured into a saturated aqueous sodium hydrogen carbonate solution to made it basic, and extracted three times with ethyl acetate. The organic layers were washed with water and a saturated brine, and dried over MgSO$_4$. The solvent was evaporated under reduced pressure, and the residue was purified by silica gel column (hexane/ethyl acetate=5/1) to give an amino compound (201 mg). Under nitrogen atmosphere, the resulting amino compound was dissolved in THF (5.0 mL), and thereto were added NEt$_3$ (300 μl) and methanesulfonylchloride (120 μl) at 0° C., and the mixture was stirred at room temperature for 2 hours. Water was added to the mixture, and the mixture was extracted with ethyl acetate, washed with a saturated brine, and dried over MgSO$_4$. The solvent was evaporated under reduced pressure, and the residue was purified by silica gel column (hexane/ethyl acetate=3/1) to give ethyl 3-{2-[bis(methanesulfonyl)-amino]-4-chlorophenyl}acrylate (229 mg, 31%, 2 steps).

$^1$H NMR (CDCl$_3$, 400 MHz) δ 7.91 (d, 1H, J=16.0 Hz), 7.70 (d, 1H, J=8.5 Hz), 7.50 (dd, 1H, J=1.9, 8.5 Hz), 7.36 (d, 1H, J=1.9 Hz), 6.47 (d, 1H, J=16.0 Hz), 4.27 (q, 2H, J=7.1 Hz), 3.47 (s, 6H), 1.33 (t, 3H, J=7.1 Hz).

(142-5)

N-{5-Chloro-2-[(1E)-3-hydroxy-1-propenyl]phenyl}-N-(methane-sulfonyl)methanesulfonamide was obtained from the compound of Example 142-4 in a similar manner to Example 137-5.

$^1$H NMR (DMSO-d$_6$, 400 MHz) δ 7.76 (d, 1H, J=8.6 Hz), 7.67 (d, 1H, J=2.2 Hz), 7.55 (dd, 1H, J=2.2, 8.6 Hz), 7.79 (d, 1H, J=15.9 Hz), 6.54 (dt, 1H, J=15.9, 4.3 Hz), 5.04 (t, 1H, J=5.4 Hz), 4.15–4.18 (m, 2H), 3.54 (s, 6H)

(142-6)

The title compound was obtained from the compound of Example 142-5 and the compound of Example 109-6 in a similar manner to Example 18-3.

$^1$H NMR (CDCl$_3$, 400 MHz) δ 9.15 (brs, 1H), 7.87(d, 2H, J=8.8 Hz), 7.56 (d, 1H, J=2.1 Hz), 7.20 (dd, 1H, J=2.1, 8.4 Hz), 7.07(d, 1H, J=8.4 Hz), 6.97 (d, 2H, J=8.8 Hz), 6.73 (d, 1H, J=2.5 Hz), 6.40 (d, 1H, J=2.5 Hz), 6.22 (ddd, 1H, J=5.8, 10.2, 17.1 Hz), 5.44 (d, 1H, J=10.2 Hz), 5.03 (d, 1H, J=5.8 Hz), 4.99 (d, 1H, J=17.1 Hz), 3.88 (s, 3H), 2.92 (s, 3H), 2.00 (s, 3H).

Example 143

(143-1)

(4-Methyl-1H-pyrrol-2-yl) (4-hydroxyphenyl) ketone was obtained from the compound of Example 109-6 in a similar manner to Example 119-1.

$^1$H NMR (CDCl$_3$, 400 MHz) δ 9.40 (br, 1H), 7.86 (d, 2H, J=8.7 Hz), 6.90–6.93 (m, 3H), 6.72 (m, 1H), 2.15 (s, 3H).

(143-2)

Under nitrogen atmosphere, to a solution of the compound of Example 143-1 (174 mg) in DMF (4.0 mL) were added imidazole (89.7 mg) and t-butyldimethylsilyl chloride (147 mg), and the mixture was stirred at room temperature for 1.5 hours. Water was added thereto, and the mixture was extracted with ethyl acetate-toluene, washed with water and a saturated brine, and dried over MgSO$_4$. The solvent was evaporated under reduced pressure, and the residue was purified by silica gel column (hexane/ethyl acetate=5/1) to give (4-methyl-1H-pyrrol-2-yl) {4-[(t-butyldimethylsilyl)oxy]phenyl} ketone (199 mg, 73%).

$^1$H NMR (CDCl$_3$, 400 MHz) δ 9.39 (br, 1H), 7.84 (d, 2H, J=8.7 Hz), 6.89–6.92 (m, 3H), 6.71 (m, 1H), 2.15 (s, 3H), 1.00 (s, 9H), 0.25 (s, 6H).

(143-3)

A coupling compound (38.4. mg) was obtained from the compound of Example 137-5 (61.7 mg) and the compound of Example 143-2 (89.6 mg) in a similar manner to Example 18-3. Subsequently, the resuling compound was dissolvd in THF (3.0 mL), and thereto was added a 1N solution of Bu$_4$NF in THF (100 μL), and the mixture was stirred at room temperature for 1 hour. To the mixture was added a 5% aqueous KHSO$_4$ solution, and the mixture was extracted with ethyl acetate, washed with a saturated brine, and dried over MgSO$_4$. The solvent was evaporated under reduced pressure, and the residue was purified by silica gel column (hexane/ethyl acetate=3/1) to give the title compound (22.7 mg, 21%).

$^1$H NMR (CDCl$_3$, 400 MHz) δ 7.77 (d, 2H, J=8.7 Hz), 7.32 (d, 1H, J=8.2 Hz), 6.84–6.89 (m, 2H), 6.87 (d, 2H, J=8.7 Hz), 6.82 (d, 1H, J=1.9 Hz), 6.75 (d, 1H, J=16.0 Hz), 6.55 (d, 1H, J=1.9 Hz), 6.41 (dt, 1H, J=16.0, 6.3 Hz), 5.11 (d, 2H, J=6.3 Hz), 3.81 (s, 3H), 2.08 (s, 3H).

Example 144

$^1$H NMR (CDCl$_3$, 400 MHz) δ 7.82 (d, 2H, J=8.8 Hz), 7.32 (d, 1H, J=8.3 Hz), 6.95 (d, 2H, J=8.8 Hz), 6.86 (dd, 1H, J=1.9, 8.3 Hz), 6.84 (d, 1H, J=1.3 Hz), 6.82 (d, 1H, J=1.9 Hz), 6.76 (d, 1H, J=16.0 Hz), 6.54 (d, 1H, J=1.3 Hz), 6.41 (dt, 1H, J=16.0, 6.4 Hz), 5.11 (d, 2H, J=6.4 Hz), 4.22 (br, 2H), 3.81 (s, 3H), 3.78 (br, 4H), 2.88 (br, 2H), 2.64 (br, 4H), 2.08 (s, 3H).

Example 145

$^1$H NMR (DMSO-d$_6$, 400 MHz) δ 12.31 (brs, 1H), 10.14 (s, 1H), 7.64–7.67 (m, 3H), 7.54 (d, 1H, J=2.2 Hz), 7.47 (dd, 1H, J=2.2, 8.4 Hz), 7.05 (d, 1H, J=1.4 Hz), 6.83 (d, 2H, J=8.6 Hz), 6.48 (d, 1H, J=1.4 Hz), 6.48–6.51 (m, 2H), 5.08 (d, 2H, J=3.0 Hz), 3.27 (s, 3H), 2.03 (s, 3H).

Example 146

(146-1)

Methyl 5-chloro-2-{(1E)-3-[2-(4-methoxybenzoyl)-4-formyl-1H-pyrrol-1-yl]-1-propenyl}benzoate was obtained by treating the compound of Example 101 with a Vilsmeier reagent.

$^1$H NMR (CDCl$_3$, 400 MHz) δ 9.82 (s, 1H), 7.89 (d, 1H, J=2.2 Hz), 7.88 (d, 2H, J=8.9 Hz), 7.68 (d, 1H, J=1.7 Hz), 7.47 (d, 1H, J=8.4 Hz), 7.42 (dd, 1J=2.2, 8.4 Hz), 7.33 (d, 1H, J=15.8 Hz), 7.18 (d, 1H, J=1.7 Hz), 6.97 (d, 2H, J=8.9 Hz), 6.31 (dt, 1H, J=15.8, 6.3 Hz), 5.22 (d, 2H, J=6.3 Hz), 3.90 (s, 3H), 3.88 (s, 3H).

(146-2)

The title compound was obtained from the compound of Example 146-1 in a similar manner to Example 16.

$^1$H NMR (DMSO-d$_6$, 400 MHz) δ 9.78 (s, 1H), 8.13 (d, 1H, J=1.6 Hz), 7.82 (d, 2H, J=8.8 Hz), 7.70 (d, 1H, J=2.2 Hz), 7.65 (d, 1H, J=8.5 Hz), 7.50 (dd, 1H, J=2.2 8.5 Hz), 7.12 (d, 1H, J=15.8 Hz), 7.05 (d, 1H, J=1.6 Hz), 7.07 (d, 2H, J=8.8 Hz), 6.49 (dt, 1H, J=15.8, 5.4 Hz), 5.23 (d, 2H, J=5.4 Hz), 3.85 (s, 3H).

Example 147

The title compound was obtained from the compound of Example 110 and ethanesulfonamide in a similar manner to Example 136.

$^1$H NMR (CDCl$_3$, 400 MHz) δ 8.39 (brs, 1H), 7.80 (d, 2H, J=7.7 Hz), 7.55 (s, 1H), 7.36–7.44 (m, 2H), 6.93 (d, 2H, J=7.7 Hz), 6.85 (s, 1H), 6.70–6.74 (m 1H), 6.57 (s, 1H), 6.40–6.43 (m, 1H), 5.08 (br, 2H), 3.86 (s, 3H), 3.53 (br, 2H), 2.09 (s, 3H), 1.41 (t, 3H, J=7.4 Hz).

Example 148

The title compound was obtained from the compound of Example 110 and benzenesulfonamide in a similar manner to Example 136.

$^1$H NMR (DMSO-d$_6$, 400 MHz) δ 12.73 (brs, 1H), 7.95–7.97 (m, 2H), 7.75 (d, 2H, J=8.8 Hz), 7.55–7.60 (m, 5 H), 7.48 (d, 1H, J=2.3 Hz), 7.39–7.41 (m, 1H), 7.03 (d, 2H, J=8.8 Hz), 6.99 (d, 1H, J=1.3 Hz), 6.48 (d, 1H, J=1.3 Hz), 6.32–6.36 (m, 1H), 4.94 (d, 2H, J=4.7 Hz), 3.84 (s, 3H), 2.03 (s, 3H).

Example 149

The title compound was obtained from 2-benzoylpyrrole and the compound of Example 9-2 in a similar manner to Example 18-3.

$^1$H NMR (CDCl$_3$, 400 MHz) δ 7.86 (d, 1H, J=2.2 Hz), 7.81 (dd, 2H, J=1.4, 7.0 Hz), 7.43–7.56 (m, 4H), 7.40 (dd, 1H, J=2.2, 8.4 Hz), 7.21 (d, 1H, J=15.8 Hz), 7.10 (dd, 1H, J=1.7, 2.5 Hz), 6.78 (dd, 1H, J=1.7, 4.0 Hz), 6.35 (dt, 1H, J=15.8, 6.0 Hz), 6.23 (dd, 1H, J=2.5, 4.0 Hz), 5.24 (d, 2H, J=6.0 Hz), 3.87 (s, 3H).

Example 150

$^1$H NMR (CDCl$_3$, 400 MHz) δ 7.97(d, 1H, J=2.2 Hz), 7.81 (d, 2H, J=7.0 Hz), 7.42–7.55 (m, 5H), 7.27 (d, 1H, J=15.8 Hz), 7.10 (dd, 1H, J=1.7, 2.5 Hz), 6.79 (dd, 1H, J=1.7, 4.0 Hz), 6.37 (dt, 1H, J=15.8, 5.9 Hz), 6.23 (dd, 1H, J=2.5, 4.0 Hz), 5.25 (d, 2H, J=5.9 Hz).

Example 151

(151-1)

Under nitrogen atmosphere, a solutin of N-triisopropylsilyl-pyrrole (2.00 g) in acetone (40 mL) was cooled at 0° C., and thereto was added N-chlorosuccinimide (1.27 g), and the mixture was allowed to stand overnight. The solvent was evaporated under reduced pressure, and thereto was added hexane. The insoluble materials were removed by filtration. The solvent was evaporated under reduced pressure, and the residue was purified by silica gel column (hexane) to give 3-chloro-1-triisopropylsilyl-1H-pyrrole (403 mg, 18%).

$^1$H NMR (CDCl$_3$, 400 MHz) δ 6.65–6.68 (m, 2H), 6.23 (dd, 1H, J=1.4, 2.8 Hz), 1.41 (sep, 3H, J=7.5 Hz), 1.09 (d, 18H, J=7.5 Hz).

(151-2)

The compound of Example 151-1 (1.38 g) was treated with acetic acid and Bu$_4$NF in THF to give a de-silyl compound (520 mg). Under nitrogen atmosphere, to a solution of DMF (400 μL) in 1,2-dichloro-ethane (2.0 mL) was added dropwise phosphorus oxychloride (470 μL) under ice-cooling, and the mixture was stirred at room temperature for 15 minutes. The mixture was cooled again under ice-cooling, and a solution of the de-sily compound in 1,2-dichloroethane (3.0 mL) was added dropwise thereto, and the mixture was stirred at room temperature for 16 hours.

The reaction solution was poured into a saturated aqueous sodium hydrogen carbonate solution to neutralize the mixture, and the mixtuer was extracted twice with ethyl acetate. The organic layers were washed with a saturated brine, and dried over $MgSO_4$. The solvent was evaporated under reduced pressure, and the residue was purified by silica gel column (hexane/ethyl acetate=3/1) to give 3-chloro-1H-pyrrole-2-carbaldehyde (252 mg, 36%, 2 steps).

$^1$H NMR ($CDCl_3$, 400 MHz) δ 9.67 (s, 1H), 9.66 (br, 1H), 7.03–7.05 (m, 1H), 6.29–6.30 (m, 1H).

(151-3)

Under nitrogen atmosphere, to a solution of the compound of Example 151-2 (200 mg) in THF (8.0 mL) was added 60% NaH (73.4 mg), and the mixture was stirred at room temperature for 10 minutes. Subsequently, benzenesulfonylchloride (230 μL) was added to the mixture, and the mixture was stirred at room temperature for 4 hours. Water was added to the mixture, and the mixture was extracted with ethyl acetate, washed with a saturated brine, and dried over $MgSO_4$. The solvent was evaporated under reduced pressure, and the residue was purified by silica gel column (hexane/ethyl acetate=6/1→3/1) to give 1-benzenesulfonyl-3-chloro-1H-pyrrole-2-carbaldehyde (407 mg, 98%).

$^1$H NMR ($CDCl_3$, 400 MHz) δ 9.87 (s, 1H), 7.99 (dd, 2H, J=1.3, 8.3 Hz), 7.71 (d, 1H, J=3.4 Hz), 7.67 (tt, 1H, J=1.3, 7.5 Hz), 7.56 (dd, 2H, J=7.5, 8.3 Hz), 6.41 (d, 1H, J=3.4 Hz).

(151-4)

(1-Benzenesulfonyl-3-chloro-1H-pyrrol-2-yl)(4-methylphenyl)-methanone was obtained from the compound of Example 151-3 in a similar manner to Example 138-1.

$^1$H NMR ($CDCl_3$, 400 MHz) δ 9.36 (br, 1H), 7.70 (d, 2H, J=8.2 Hz), 7.27 (d, 2H, J=8.2 Hz), 6.99–7.00 (m, 1H), 6.28–6.30 (m, 1H), 2.44 (s, 3H).

(151-5)

The title compound was obtained from the compound of Example 9-2 and the compound of Example 151-4 in a similar manner to Example 18-3.

$^1$H NMR ($CDCl_3$, 400 MHz) δ 7.86 (d, 1H, J=2.4 Hz), 7.71 (d, 2H, J=8.1 Hz), 7.39 (m, 2H), 7.24 (d, 2H, J=8.1 Hz), 7.20(d, 1H, J=15.8 Hz), 6.95 (d, 1H, J=2.8 Hz), 6.22 (dt, 1H, J=15.8, 6.1 Hz), 6.19 (d, 1H, J=2.8 Hz), 4.96 (d, 2H, J=6.1 Hz), 3.87 (s, 3H), 2.42 (s, 3H).

Example 152

$^1$H NMR ($CDCl_3$, 400 MHz) δ 7.99 (d, 1H, J=1.9 Hz), 7.71 (d, 2H, J=8.0 Hz), 7.41–7.46 (m, 2H), 7.28 (d, 1H, J=15.8 Hz), 7.24 (d, 2H, J=8.0 Hz), 6.95 (d, 1H, J=2.8 Hz), 6.24 (dt, 1H, J=15.8, 6.1 Hz), 6.20 (d, 1H, J=2.8 Hz), 4.98 (d, 2H, J=6.1 Hz), 2.41 (s, 3H).

Example 153

From the compound of Example 103 and (2-bromoethoxy)tert-butyldimethylsilane, there were obtained the title compound (15%) and the siliy compound (methyl 5-chloro-N-methyl-2-[(1E)-3-{2-[4-{2-(t-butyldimethylsilyloxy)ethoxy}benzoyl]-1H-pyrrol-1-yl}-1-propenyl]-benzoate) (83%).

Silyl compound: $^1$H NMR ($CDCl_3$, 400 MHz) δ 7.85 (d, 1H, J=2.2 Hz), 7.83 (d, 2H, J=8.7 Hz), 7.47 (d, 1H, J=8.5 Hz), 7.39 (dd, 1H, J=8.5 and 2.2 Hz), 7.20 (brd, 1H, J=15.8 Hz), 7.07 (dd, 1H, J=1.7 and 2.5 Hz), 6.95 (d, 2H, J=8.7 Hz), 6.76 (dd, 1H, J=1.7 and 4.0 Hz), 6.35 (dt, 1H, J=15.8 and 6.0 Hz), 6.23 (dd, 1H, J=2.5 and 4.0 Hz), 5.20 (dd, 2H, J=1.4 and 6.0 Hz), 4.11 (brt, 2H, J=5.0 Hz), 4.00 (brt, 2H, J=5.0 Hz), 3.86 (s, 3H), 0.91 (s, 9 H), 0.11 (s, 6H).

The compound of Example 153: $^1$H NMR ($CDCl_3$, 400 MHz) δ 7.85 (d, 1H, J=2.2 Hz), 7.84 (d, 2H, J=8.7 Hz), 7.47 (d, 1H, J=8.5 Hz), 7.39 (dd, 1H, J=8.5 and 2.2 Hz), 7.19 (brd, 1H, J=15.8 Hz), 7.08 (dd, 1H, J=1.7 and 2.5 Hz), 6.96 (d, 2H, J=8.7 Hz), 6.76 (dd, 1H, J=1.7 and 4.0 Hz), 6.34 (dt, 1H, J=15.8 and 6.0 Hz), 6.23 (dd, 1H, J=2.5 and 4.0 Hz), 5.20 (dd, 2H, J=1.4 and 6.0 Hz), 4.15 (brt, 2H, J=5.0 Hz), 4.00 (brt, 2H, J=5.0 Hz), 3.86 (s, 3H).

Example 154

$^1$H NMR ($CD_3OD$, 400 MHz) δ 7.84 (d, 2H, J=8.7 Hz), 7.78–7.83 (m, 1H), 7.59 (d, 1H, J=8.5 Hz), 7.46 (brd, 1H, J=8.5 Hz), 7.27 (dd, 1H, J=1.7 and 2.5 Hz), 7.18 (brd, 1H, J=15.8 Hz), 7.08 (d, 2H, J=8.7 Hz), 6.81 (dd, 1H, J=1.7 and 4.0 Hz), 6.42 (dt, 1H, J=15.8 and 6.0 Hz), 6.29 (dd, 1H, J=2.5 and 4.0 Hz), 5.24 (dd, 2H, J=1.4 and 6.0 Hz), 4.17 (brt, 2H, J=4.9 Hz), 3.94 (brt, 2H, J=4.9 Hz).

Example 155

(155-1)

5-Chloro-N-methyl-2-[(1E)-3-{2-[4-{2-(t-butyldimethylsilyloxy)-ethoxy}benzoyl]-1H-pyrrol-1-yl}-1-propenyl]benzamide (100%) was obtained by subjecting the silyl compound of Example 153 to alkali hydrolysis, and treating the product with monomethylamine in a similar manner to Example 116.

$^1$H NMR ($CDCl_3$, 400 MHz) δ 7.81 (d, 2H, J=8.7 Hz), 7.52 (d, 1H, J=2.2 Hz), 7.38 (d, 1H, J=8.5 Hz), 7.30 (dd, 1H, J=8.5 and 2.2 Hz), 7.03 (dd, 1H, J=1.7 and 2.5 Hz), 6.95 (d, 2H, J=8.7 Hz), 6.78 (dd, 1H, J=1.7 and 4.0 Hz), 6.69 (brd, 1H, J=15.8 Hz), 6.30 (dt, 1H, J=15.8 and 6.0 Hz), 6.23 (dd, 1H, J=2.5 and 4.0 Hz), 6.10 (brq, 1H, J=4.9 Hz), 5.12 (dd, 2H, J=1.4 and 6.0 Hz), 4.11 (brt, 2H, J=5.0 Hz), 4.00 (brt, 2H, J=5.0 Hz), 2.93 (d, 3H, J=4.9 Hz), 0.91 (s, 9H), 0.11 (s, 6H).

(155-2)

The title compound was obtained by treating the compound of Example 155-1 with p-toluenesulfonic acid monohydrate in MeOH-THF to remove the silyl group.

$^1$H NMR ($CDCl_3$, 400 MHz) δ 7.83 (d, 2H, J=8.7 Hz), 7.53 (d, 1H, J=2.2 Hz), 7.39 (d, 1H, J=8.5 Hz), 7.31 (dd, 1H, J=8.5 and 2.2 Hz), 7.03 (dd, 1H, J=1.7 and 2.5 Hz), 6.97(d, 2H, J=8.7 Hz), 6.78(dd, 1H, J=1.7 and 4.0 Hz), 6.70 (brdt, 1H, J=15.8 and 1.4 Hz), 6.31 (dt, 1H, J=15.8 and 6.0 Hz), 6.23 (dd, 1H, J=2.5 and 4.0 Hz), 6.20 (brq, 1H, J=4.9 Hz), 5.13 (dd, 2H, J=1.4 and 6.0 Hz), 4.16 (brt, 2H, J=5.0 Hz), 4.01 (brt, 2H, J=5.0 Hz), 2.94 (d, 3H, J=4.9 Hz).

Example 156

(156-1)

The silyl compound of Example 153 was subjected to alkali hydrolysis, and treated in a similar manner to Example 115 to give N-5-chloro-2-[(1E)-3-{2-[4-{2-(t-butyldimethylsilyloxy)ethoxy}benzoyl]-1H-pyrrol-1-yl}-1-propenyl]benzoyl)methanesulfonamide.

$^1$H NMR ($CDCl_3$, 400 MHz) δ 7.88 (d, 2H, J=8.7 Hz), 7.49 (d, 1H, J=2.2 Hz), 7.42 (d, 1H, J=8.5 Hz), 7.36 (dd, 1H, J=8.5 and 2.2 Hz), 7.04 (dd, 1H, J=1.7 and 2.5 Hz), 6.93 (d, 2H, J=8.7 Hz), 6.76 (dd, 1H, J=1.7 and 4.0 Hz), 6.67 (brd, 1H, J=15.8 Hz), 6.39 (dt, 1H, J=15.8 and 6.0 Hz), 6.23 (dd, 1H, J=2.5 and 4.0 Hz), 5.12 (dd, 2H, J=1.4 and 6.0 Hz), 4.10 (brt, 2H, J=5.0 Hz), 3.99 (brt, 2H, J=5.0 Hz), 3.31 (brs, 3H), 0.91 (s, 9H), 0.11 (s, 6H).

(156-2)

The title compound was obtained from the compound of Example 156-1 in a similar manner to Example 155-2.

$^1$H NMR ($CDCl_3$, 400 MHz) δ 7.78 (d, 2H, J=8.7 Hz), 7.48 (brs, 1H), 7.42 (d, 1H, J=8.5 Hz), 7.35 (brd, 1H, J=8.5

Hz), 7.05 (dd, 1H, J=1.7 and 2.5 Hz), 6.92 (d, 2H, J=8.7 Hz), 6.76 (dd, 1H, J=1.7 and 4.0 Hz), 6.64 (brd, 1H, J=15.8 Hz), 6.39 (dt, 1H, J=15.8 and 6.0 Hz), 6.23 (dd, 1H, J=2.5 and 4.0 Hz), 5.13 (brd, 2H, J=6.0 Hz), 4.10 (brt, 2H, J=5.0 Hz), 3.96 (brt, 2H, J=5.0 Hz), 3.30 (brs, 3H).

Example 157

(157-1)

Methyl 5-chloro-2-[(1E)-3-{2-[4-{2-(t-butyldimethylsilyloxy)-ethoxy}benzoyl]-4-methyl-1H-pyrrol-1-yl}-1-propenyl]benzoate was obtained from the compound of Example 119-1 in a similar manner to Example 153.

$^1$H NMR (CDCl$_3$, 400 MHz) δ 7.85 (d, 1H, J=2.3 Hz), 7.81 (d, 2H, J=8.8 Hz), 7.48 (d, 1H, J=8.4 Hz), 7.39 (dd, 1H, J=2.3, 8.4 Hz), 7.20 (d, 1H, J=15.7 Hz), 6.95 (d, 2H, J=8.8 Hz), 6.85 (d, 1H, J=1.2 Hz), 6.56 (d, 1H, J=1.2 Hz), 6.34 (dt, 1H, J=15.7, 6.1 Hz), 5.13 (d, 2H, J=6.1 Hz), 4.11 (t, 2H, J=5.0 Hz), 4.00 (t, 2H, J=5.0 Hz), 3.87 (s, 3H), 2.09 (s, 3H), 0.92 (s, 9H), 0.11 (s, 6H).

(157-2)

Under nitrogen atmosphere, the title compound was obtained from the compound of Example 157-1 in a similar manner to Example 155-2.

$^1$H NMR (CDCl$_3$, 400 MHz) δ 7.85 (d, 1H, J=2.3 Hz), 7.83 (d, 2H, J=8.8 Hz), 7.48 (d, 1H, J=8.5 Hz), 7.39 (dd, 1H, J=2.3, 8.5 Hz), 7.20 (d, 1H, J=15.8 Hz), 6.96 (d, 2H, J=8.8 Hz), 6.86 (d, 1H, J=1.3 Hz), 6.56 (d, 1H, J=1.3 Hz), 6.33 (dt, 1H, J=15.8, 6.1 Hz), 5.14 (d, 2H, J=6.1 Hz), 4.16 (t, 2H, J=4.5 Hz), 4.00 (t, 2H, J=4.5 Hz), 3.87 (s, 3H), 2.09 (s, 3H).

Example 158

$^1$H NMR (DMSO-d$_6$, 400 MHz) δ 13.35 (brs, 1H), 7.73 (d, 2H, J=8.7 Hz), 7.72 (d, 1H, J=2.3 Hz), 7.66 (d, 1H, J=8.5 Hz), 7.53 (dd, 1H, J=2.3, 8.5 Hz), 7.10 (d, 1H, J=1.6 Hz), 7.04 (d, 1H, J=16.0 Hz), 7.02 (d, 2H, J=8.7 Hz), 6.50 (d, 1H, J=1.6 Hz), 6.45 (dt, 1H, J=16.0, 5.4 Hz), 5.11 (d, 2H, J=5.4 Hz), 4.91 (t, 1H, J=5.0 Hz), 4.07 (t, 2H, J=5.0 Hz), 3.74 (dt, 2H, J=5.0, 5.0 Hz), 2.04 (s, 3H).

Example 159

(159-1)

Under nitrogen atmosphere, to a solution of the compound of Example 153 (290 mg) and NEt$_3$ (467 mg) in CH$_2$Cl$_2$ (7.0 mL) was added a solultion of methanesulfonylchloride (227 mg) in CH$_2$Cl$_2$ (1.0 mL) at 0° C. The mixture was stirred at the same temperature for 20 minutes, and the mixture was partially concentrated. The resultant was diluted with ethyl acetate, washed with water, and concentrated. The residue was purified by silica gel column chromatography to give methyl 5-chloro-N-methyl-2-[(1E)-3-{2-[4-{2-(methanesulfonyloxy)ethoxy}-benzoyl]-1H-pyrrol-1-yl}-1-propenyl]benzoate (355 mg, 100%).

$^1$H NMR (CDCl$_3$, 400 MHz) δ 7.84 (d, 1H, J=2.2 Hz), 7.84 (d, 2H, J=8.7 Hz), 7.47 (d, 1H, J=8.5 Hz), 7.39 (dd, 1H, J=8.5 and 2.2 Hz), 7.19 (brd, 1H, J=15.8 Hz), 7.09 (dd, 1H, J=1.7 and 2.5 Hz), 6.95 (d, 2H, J=8.7 Hz), 6.76 (dd, 1H, J=1.7 and 4.0 Hz), 6.34 (dt, 1H, J=15.8 and 6.0 Hz), 6.23 (dd, 1H, J=2.5 and 4.0 Hz), 5.20 (dd, 2H, J=1.4 and 6.0 Hz), 4.61 (brt, 2H, J=4.5 Hz), 4.32 (brt, 2H, J=4.5 Hz), 3.87 (s, 3H), 3.11 (s, 3H).

(159-2)

The title compound was obtained by treating the compound of Example 159-1 with LiCl.

$^1$H NMR (CDCl$_3$, 400 MHz) δ 7.84 (d, 1H, J=2.2 Hz), 7.83 (d, 2H, J=8.7 Hz), 7.47 (d, 1H, J=8.5 Hz), 7.39 (dd, 1H, J=8.5 and 2.2 Hz), 7.19 (brd, 1H, J=15.8 Hz), 7.08 (dd, 1H, J=1.7 and 2.5 Hz), 6.96 (d, 2H, J=8.7 Hz), 6.76 (dd, 1H, J=1.7 and 4.0 Hz), 6.34 (dt, 1H, J=15.8 and 6.0 Hz), 6.23 (dd, 1H, J=2.5 and 4.0 Hz), 5.20 (dd, 2H, J=1.4 and 6.0 Hz), 4.30 (t, 2H, J=5.8 Hz), 3.87 (s, 3H), 3.85 (t, 2H, J=5.8 Hz).

Example 160

$^1$H NMR (CDCl$_3$, 400 MHz) δ 7.85 (d, 1H, J=2.2 Hz), 7.83 (d, 2H, J=8.7 Hz), 7.47 (d, 1H, J=8.5 Hz), 7.40 (dd, 1H, J=8.5 and 2.2 Hz), 7.20 (brd, 1H, J=15.8 Hz), 7.07 (dd, 1H, J=1.7 and 2.5 Hz), 6.94 (d, 2H, J=8.7 Hz), 6.76 (dd, 1H, J=1.7 and 4.0 Hz), 6.34 (dt, 1H, J=15.8 and 6.0 Hz), 6.22 (dd, 1H, J=2.5 and 4.0 Hz), 5.20 (dd, 2H, J=1.4 and 6.0 Hz), 4.13 (t, 2H, J=6.1 Hz), 3.87 (s, 3H), 3.16–3.21 (m, 4H), 3.54 (t, 4H, J=6.2 Hz), 3.48 (q, 4H, J=7.0 Hz), 3.36 (t, 2H, J=6.1 Hz), 2.87 (t, 4H, J=6.2 Hz), 1.19 (t, 6H, J=7.0 Hz).

Example 161

$^1$H NMR (CD$_3$OD, 400 MHz) δ 7.85 (d, 2H, J=8.7 Hz), 7.62 (d, 1H, J=2.2 Hz), 7.54 (d, 1H, J=8.5 Hz), 7.34 (dd, 1H, J=8.5 and 2.2 Hz), 7.28 (dd, 1H, J=1.7 and 2.5 Hz), 7.14 (brd, 1H, J=15.8 Hz), 7.11 (d, 2H, J=8.7 Hz), 6.76 (dd, 1H, J=1.7 and 4.0 Hz), 6.42 (dt, 1H, J=15.8 and 6.0 Hz), 6.27 (dd, 1H, J=2.5 and 4.0 Hz), 5.22 (dd, 2H, J=1.4 and 6.0 Hz), 4.47 (t, 2H, J=6.1 Hz), 3.82 (t, 4H, J=6.2 Hz), 3.74 (t, 2H, J=6.1 Hz), 3.50–3.62 (m, 8H), 1.20 (t, 6H, J=7.0 Hz).

Example 162

The compound of Example 111 and 8-bromoctan-1-ol were reacted in a similar manner to Example 81, and the resulting alcohol compound was converted into a iodo compound, and reacted with NaN$_3$ to give an azide compound. This azide compound was converted into the title compound by the method of Example 16.

$^1$H NMR (CDCl$_3$, 400 MHz) δ 7.96 (brs, 1H), 7.75 (d, 1H, J=2.3 Hz), 7.68 (d, 2H, J=8.8 Hz), 7.33 (d, 1H, J=8.5 Hz), 7.24 (dd, 1H, J=2.3, 8.5 Hz), 7.20 (d, 1H, J=15.8 Hz), 6.77 (d, 2H, J=8.8 Hz), 6.73 (d, 1H, J=1.3 Hz), 6.46 (d, 1H, J=1.3 Hz), 6.17 (dt, 1H, J=15.8, 6.1 Hz), 3.86 (d, 2H, J=6.4 Hz), 3.19 (t, 2H, J=6.9 Hz), 1.97 (brs, 3H), 1.69 (brquintet, 2H, J=6.4 Hz), 1.53 (brquintet, 2H, J=6.9 Hz), 1.01–1.42 (series of m, 8H).

Example 163

(163-1)

Under nitrogen atmosphere, to a solution of methyl terephthalaldehydate (10.0 g) in toluene (200 mL) were added p-toluenesulfonic acid monohydrate (130 mg) and 1,3-propanediol (5.56 g), and the mixture was stirred at 111° C. for 3.5 hours. The mixture was cooled to room temperature, washed twice with a NaHCO$_3$ solution, and dried over MgSO$_4$. The solvent was evaporated under reduced pressure to give crude methyl 4-(1,3-dioxan-2-yl)benzoate (14.2 g). To a solution of this compound (14.2 g) in THF (150 mL)-MeOH (150 mL) was added a 6N NaOH solution (50.8 mL), and the mixture was stirred at room temperature for 78 hours. The solvent was evaporated under reduced pressure, and the residue was washed with ethyl acetate, and thereto was added a 6N aqueous hydrochloric acid to adjust the pH value thereof to pH=2. The precipitated solid was collected by filtration to give 4-(1,3-dioxan-2-yl)benzoic acid (11.725 g, 93%).

$^1$H NMR (DMSO-d$_6$, 400 MHz) δ 7.93 (d, 2H, J=8.2 Hz), 7.51 (d, 2H, J=8.2 Hz), 5.58 (s, 1H), 4.15 (m, 2H), 3.95 (m, 2H), 2.00 (m, 1H), 1.45 (m, 1H).

(163-2)

[4-(1,3-Dioxan-2-yl)phenyl](1H-pyrrol-2-yl)methanone was obtained from the compound of Example 163-1 in a similar manner to Example 125-2.

¹H NMR (CDCl₃, 400 MHz) δ 9.68 (s, 1H), 7.90 (d, 2H, J=8.4 Hz), 7.61 (d, 2H, J=8.4 Hz), 7.13 (m, 1H), 6.85 (m, 1H), 6.33 (m, 1H), 5.58 (s, 1H), 4.31 (m, 2H), 4.03 (m, 2H), 2.26 (m, 1H), 1.48 (m, 1H).

(163-3)

The title compound was obtained from the compound of Example 163-2 in a similar manner to Example 18-3.

¹H NMR (CDCl₃, 400 MHz) δ 7.85 (d, 1H, J=2.3 Hz), 7.81 (d, 2H, J=8.3 Hz), 7.57 (d, 2H, J=8.3 Hz), 7.47 (d, 1H, J=8.5 Hz), 7.40 (dd, 1H, J=8.5, 2.3 Hz), 7.20 (d, 1H, J=15.8 Hz), 7.09 (dd, 1H, J=2.3, 1.8 Hz), 6.74 (dd, 1H, J=4.0, 1.8 Hz), 6.34 (dt, 1H, J=15.8, 6.0 Hz), 6.22 (dd, 1H, J=4.0, 2.3 Hz), 5.57 (s, 1H), 5.22 (dd, 2H, J=6.0, 1.4 Hz), 4.30 (m, 2H), 4.03 (m, 2H), 3.86 (s, 3H), 2.26 (m, 1H), 1.48 (m, 1H).

Example 164

(164-1)

To a solution of the compound of Example 163 (63.6 mg) in acetone (15 mL) were added water (1.5 mL) and pyridinium p-toluenesulfonate (10.3 mg), and the mixture was stirred at 56° C. for 12 hours. The solvent was evaporated under reduced pressure, and to the resultant was added a NaHCO₃ solution. The mixture was extracted twice with ethyl acetate-toluene, and dried over MgSO₄. The solvent was evaporated under reduced pressure, and the residue was purified by silica gel column (hexane/ethyl acetate=4/1) to give methyl 5-chloro-2-{(1E)-3-[2-(4-formylbenzoyl)-1H-pyrrol-1-yl]prop-1-enyl}benzoate (36.8 mg).

¹H NMR (CDCl₃, 400 MHz) δ 10.11 (s, 1H), 7.97 (d, 2H, J=8.4 Hz), 7.94 (d, 2H, J=8.4 Hz), 7.87 (d, 1H, J=2.2 Hz), 7.48 (d, 1H, J=8.4 Hz), 7.41 (dd, 1H, J=8.4, 2.2 Hz), 7.21 (d, 1H, J=15.8 Hz), 7.15 (dd, 1H, J=2.5, 1.6 Hz), 6.76 (dd, 1H, J=4.1, 1.6 Hz), 6.34 (dt, 1H, J=15.8, 6.0 Hz), 6.26 (dd, 1H, J=4.1, 2.5 Hz), 5.25 (dd, 2H, J=6.0, 1.5 Hz), 3.87 (s, 3H).

(164-2)

Under nitrogen atmosphere, a solution of the compound of Example 164-1 (34.4 mg) in THF (5.0 mL)-MeOH (5.0 mL) was cooled to 0° C., and thereto was added NaBH₄ (3.20 mg), and the mixture was stirred at 0° C. for 1 hour. The solvent was evaporated under reduced pressure, and the residue was purified by silica gel column (CHCl₃/MeOH= 10/1) to give methyl 5-chloro-2-((1E)-3-{2-[4-(hydroxymethyl)benzoyl]-1H-pyrrol-1-yl}prop-1-enyl)benzoate (32.5 mg, 94%).

¹H NMR (CDCl₃, 400 MHz) δ 7.86 (d, 1H, J=2.3 Hz), 7.82 (d, 2H, J=8.2 Hz), 7.48 (d, 1H, J=8.5 Hz), 7.45 (d, 2H, J=8.2 Hz), 7.40 (dd, 1H, J=8.5, 2.3 Hz), 7.21 (d, 1H, J=15.8 Hz), 7.10 (dd, 1H, J=2.6, 1.7 Hz), 6.77 (dd, 1H, J=4.0, 1.7 Hz), 6.35 (dt, 1H, J=15.8, 6.0 Hz), 6.23 (dd, 1H, J=4.0, 2.6 Hz), 5.23 (dd, 2H, J=6.0, 1.4 Hz), 4.79 (d, 2H, J=4.8 Hz), 3.87 (s, 3H), 1.76 (t, 1H, J=4.8 Hz).

(164-3)

The title compound was obtained from the compound of Example 164-2 in a similar manner to Example 16.

¹H NMR (CDCl₃, 400 MHz) δ 7.96 (d, 1H, J=2.2 Hz), 7.77 (d, 2H, J=8.2 Hz), 7.50 (d, 1H, J=8.5 Hz), 7.45 (dd, 1H, J=8.5, 2.2 Hz), 7.38 (d, 2H, J=8.2 Hz), 7.22 (d, 1H, J=15.8 Hz), 7.09 (dd, 1H, J=2.5, 1.6 Hz), 6.77 (dd, 1H, J=4.0, 1.6 Hz), 6.36 (dt, 1H, J=15.8, 5.7 Hz), 6.23 (dd, 1H, J=4.0, 2.5 Hz), 5.24 (dd, 2H, J=5.7, 1.4 Hz), 4.73 (s, 2H).

Example 165

(165-1)

To a solution of the compound of Example 163-2 (300 mg) in acetone (30 mL) were added water (3 mL) and p-toluenesulfonic acid monohydrate (66 mg), and the mixture was stirred at 56° C. for 1.5 hour. The solvent was evaporated under reduced pressure, and thereto was added a NaHCO₃ solution, and the mixture was extracted twice with ethyl acetate-toluene, and dried over MgSO₄. The solvent was evaporated under reduced pressure to give crude (4-formylphenyl)(1H-pyrrol-2-yl)methanone (258 mg). To a solution of this compound (170 mg) in 1,2-dichloroethane (20 mL) were added successively 4-piperidone monohydrate hydrochloride (263 mg), triethylamine (261 mg) and NaBH(OAc)₃ (546 mg), and the mixture was stirred at room temperature for 71 hours. To the mixture was added NaHCO₃, and the mixture was extracted twice with ethyl acetate, and dried over MgSO₄. The solvent was evaporated under reduced pressure, and the residue was purified by silica gel column (hexane/ethyl acetate=2/1→1/1) to give 1-[4-(1H-pyrrol-2-ylcarbonyl)benzyl]piperidin-4-one (80.1 mg, 33%).

¹H NMR (CDCl₃, 400 MHz) δ 9.73 (brs, 1H), 7.89 (d, 2H, J=8.2 Hz), 7.49 (d, 2H, J=8.2 Hz), 7.16 (m, 1H), 6.91 (m, 1H), 6.35 (m, 1H), 3.70 (s, 2H), 2.79 (t, 4H, J=6.1 Hz), 2.49 (t, 4H, J=6.1 Hz).

(165-2)

Methyl 5-chloro-2-[(1E)-3-(2-{4-[(4-oxopiperidin-1-yl)methyl]-benzoyl}-1H-pyrrol-1-yl)prop-1-enyl]benzoate was obtained from the compound of Example 165-1 in a similar manner to Example 18-3.

¹H NMR (CDCl₃, 400 MHz) δ 7.86 (d, 1H, J=2.3 Hz), 7.80 (d, 2H, J=8.2 Hz), 7.48 (d, 1H, J=8.5 Hz), 7.45 (d, 2H, J=8.2 Hz), 7.40 (dd, 1H, J=8.5, 2.3 Hz), 7.21(d, 1H, J=15.8 Hz), 7.11 (dd, 1H, J=2.4, 1.8 Hz), 6.80 (dd, 1H, J=4.0, 1.8 Hz), 6.35 (dt, 1H, J=15.8, 6.0 Hz), 6.24 (dd, 1H, J=4.0, 2.4 Hz), 5.23 (dd, 2H, J=6.0, 1.4 Hz), 3.87 (s, 3H), 3.69 (s, 2H), 2.78 (t, 4H, J=6.1 Hz), 2.48 (t, 4H, J=6.1 Hz).

(165-3)

Under nitrogen atmosphere, a solution of the compound of Example 165-2 (76.4 mg) in THF (10 mL)-MeOH (10 mL) was cooled to 0° C., and thereto was added NaBH₄ (5.90 mg), and the mixture was stirred at 0° C. for 1 hour. The solvent was evaporated under reduced pressure, and the residue was purified by silica gel column (CHCl₃/MeOH= 10/1) to give the title compound (67.5 mg, 88%).

¹H NMR (CDCl₃, 400 MHz) δ 7.86 (d, 1H, J=2.3 Hz), 7.78 (d, 2H, J=8.1 Hz), 7.48 (d, 1H, J=8.4 Hz), 7.40 (m, 3H), 7.21 (d, 1H, J=15.8 Hz), 7.09 (dd, 1H, J=2.6, 1.6 Hz), 6.79 (dd, 1H, J=4.0, 1.6 Hz), 6.35 (dt, 1H, J=15.8, 6.0 Hz), 6.23 (dd, 1H, J=4.0, 2.6 Hz), 5.23 (dd, 2H, J=6.0, 1.3 Hz), 3.87 (s, 3H), 3.72 (m, 1H), 3.56 (s, 2H), 2.77 (m, 2H), 2.18 (m, 2H), 1.90 (m, 2H), 1.62 (m, 2H).

Example 166

(166-1)

Under nitrogen atmosphere, a solution of pyrazole (743 mg) in DMF (10 mL) was cooled to 0° C., and thereto was added NaH (480 mg, 60%). The mixture was stirred at 0° C. for 10 minutes, and stirred at room temperature for one hour. Methyl 4-(bromomethyl)benzoate (2.50 g) was added to the mixture, and the mixture was stirred at room temperature for 2 hours. To the mixture was added ice water (50 mL), and extracted three times with ethyl acetate-toluene, and dried over MgSO₄. The solvent was evaporated under reduced pressure, and the residue was purified by silica gel column (hexane/ethyl acetate=10/1→3/1) to give methyl 4-(1H-pyrazol-1-ylmethyl)benzoate (2.17 g, 92%).

¹H NMR (CDCl₃, 400 MHz) δ 8.00 (d, 2H, J=8.3 Hz), 7.57 (d, 1H, J=2.2 Hz), 7.42 (d, 1H, J=2.2 Hz), 7.23 (d, 2H, J=8.3 Hz), 6.31 (dd, 1H, J=2.2, 2.2 Hz), 5.38 (s, 2H), 3.90 (s, 3H).

(166-2)

4-(1H-Pyrazol-1-ylmethyl)benzoic acid was obtained from the compound of Example 166-1 in a similar manner to Example 16.

¹H NMR (DMSO-d₆, 400 MHz) δ 12.98 (brs, 1H), 7.90 (d, 2H, J=8.2 Hz), 7.86 (d, 1H, J=2.2 Hz), 7.49 (d, 1H, J=2.2 Hz), 7.26 (d, 2H, J=8.2 Hz), 6.29 (dd, 1H, J=2.2, 2.2 Hz), 5.42 (s, 2H).
(166-3)
[4-(1H-Pyrazol-1-ylmethyl)phenyl](1H-pyrrol-2-yl)methanone was obtained from the compound of Example 166-2 in a similar manner to Example 125-2.
¹H NMR (CDCl₃, 400 MHz) δ 10.00 (brs, 1H), 7.87 (d, 2H, J=8.3 Hz), 7.59 (d, 1H, J=2.2 Hz), 7.45 (d, 1H, J=2.2 Hz), 7.28 (d, 2H, J=8.3 Hz), 7.14 (m, 1H), 6.86 (m, 1H), 6.33 (m, 2H), 5.42 (s, 2H).
(166-4)
The title compound was obtained from the compound of Example 166-3 in a similar manner to Example 18-3.
¹H NMR (CDCl₃, 400 MHz) δ 7.85 (d, 1H, J=2.3 Hz), 7.79 (d, 2H, J=8.2 Hz), 7.58 (d, 1H, J=2.2 Hz), 7.47 (d, 1H, J=8.4 Hz), 7.44 (d, 1H, J=2.2 Hz), 7.40 (dd, 1H, J=8.4, 2.3 Hz), 7.25 (d, 2H, J=8.2 Hz), 7.19 (d, 1H, J=15.7 Hz), 7.09 (dd, 1H, J=2.6, 1.7 Hz), 6.75 (dd, 1H, J=4.0, 1.7 Hz), 6.33 (dt, 1H, J=15.7, 6.0 Hz), 6.32 (dd, 1H, J=2.2, 2.2 Hz), 6.22 (dd, 1H, J=4.0, 2.6 Hz), 5.40 (s, 2H), 5.22 (dd, 2H, J=6.0, 1.4 Hz), 3.86 (s, 3H).

Example 167

¹H NMR (CDCl₃, 400 MHz) δ 7.93 (d, 1H, J=1.8 Hz), 7.77 (d, 2H, J=8.1 Hz), 7.59 (d, 1H, J=1.2 Hz), 7.44 (m, 3H), 7.23 (m, 3H), 7.07 (s, 1H), 6.73 (dd, 1H, J=4.0, 1.4 Hz), 6.31 (m, 2H), 6.19 (dd, 1H, J=4.0, 2.6 Hz), 5.39 (s, 2H), 5.20 (d, 2H, J=5.7 Hz).

Example 168
(168-1)
Under nitrogen atmosphere, a solution of 2-bromothiazole (2.00 g) in Et₂O (38 mL) was cooled to −78° C., and thereto was added a 1.5N solution of n-BuLi in hexane (8.5 mL), and the mixture was stirred at −78° C. for 30 minutes. To the mixture was added a 1.0N solution of ZnCl₂ in Et₂O (12.2 mL), and the mixture was stirred at −78° C. for 10 minutes, and stirred at room temperature for 30 minutes. To the mixture were added successively Pd(PPh₃)₄ (704 mg) and ethyl 4-iodobenzoate (2.26 g), and the mixture was stirred at 66° C. for 1 hour. To the mixture was added a 1.0N solution of ZnCl₂ in Et₂O (12.2 mL), and the mixture was stirred at 66° C. for 2 hours. To the mixture was added THF (60 mL), and the mixture was stirred at 66° C. for 2.5 hours. To the mixture were added a 0.18N aqueous solution of ethylenediaminetetraacetic acid disodium salt dihydrate (300 mL), and sodium hydrogen carbonate until the pH value of the mixture became pH=8. The mixture was extracted with ethyl acetate, washed with an aqueous NaHSO₃ solution, and dried over MgSO₄. The solvent was evaporated under reduced pressure, and the residue was purified by silica gel column (hexane/ethyl acetate=12.5/1) to give ethyl 4-(1,3-thiazol-2-yl)benzoate (1.35 g, 71%).
¹H NMR (CDCl₃, 400 MHz) δ 8.12 (d, 2H, J=8.5 Hz), 8.04 (d, 2H, J=8.5 Hz), 7.93 (d, 1H, J=3.2 Hz), 7.42 (d, 1H, J=3.2 Hz), 4.41 (q, 2H, J=7.1 Hz), 1.42 (3H, t, J 7.1 Hz).
(168-2)
4-(1,3-Thiazol-2-yl)benzoic acid was obtained from the compound of Example 168-1 in a similar manner to Example 16.
¹H NMR (DMSO-d₆, 400 MHz) δ 13.16 (brs, 1H), 8.08 (d, 2H, J=8.7 Hz), 8.05 (d, 2H, J=8.7 Hz), 8.01 (d, 1H, J=3.2 Hz), 7.90 (d, 1H, J=3.2 Hz).
(168-3)
1H-Pyrrol-2-yl[4-(1,3-thiazol-2-yl)phenyl]methanone was obtained from the compound of Example 168-2 in a similar manner to Example 125-2.

¹H NMR (CDCl₃, 400 MHz) δ 9.67 (brs, 1H), 8.10 (d, 2H, J=8.5 Hz), 7.99 (d, 2H, J=8.5 Hz), 7.94 (d, 1H, J=3.2 Hz), 7.42 (d, 1H, J=3.2 Hz), 7.17 (m, 1H), 6.93 (m, 1H), 6.37 (m, 1H).
(168-4)
Methyl 5-chloro-2-((1E)-3-{2-[4-(1,3-thiazol-2-yl)benzoyl]-1H-pyrrol-1-yl}prop-1-enyl)benzoate was obtained from the compound of Example 168-3 in a similar manner to Example 18-3.
¹H NMR (CDCl₃, 400 MHz) δ 8.06 (d, 2H, J=8.4 Hz), 7.93 (d, 1H, J=3.3 Hz), 7.91 (d, 2H, J=8.4 Hz), 7.86 (d, 1H, J=3.3 Hz), 7.49 (d, 1H, J=8.3 Hz), 7.41 (dd, 1H, J=8.3, 2.4 Hz), 7.41 (d, 1H, J=2.4 Hz), 7.22 (d, 1H, J=15.8 Hz), 7.13 (dd, 1H, J=2.3, 1.8 Hz), 6.82 (dd, 1H, J=4.0, 1.8 Hz), 6.36 (dt, 1H, J=15.8, 6.0 Hz), 6.26 (dd, 1H, J=4.0, 2.3 Hz), 5.25 (dd, 2H, J=6.0, 1.4 Hz), 3.87 (s, 3H).
(168-5)
The title compound was obtained from the compound of Example 168-4 in a similar manner to Example 16.
¹H NMR (DMSO-d₆, 400 MHz) δ 13.32 (brs, 1H), 8.08 (d, 2H, J=8.4 Hz), 8.01 (d, 1H, J=3.2 Hz), 7.89 (d, 1H, J=3.2 Hz), 7.87 (d, 2H, J=8.4 Hz), 7.72 (d, 1H, J=2.3 Hz), 7.68 (d, 1H, J=8.5 Hz), 7.54 (dd, 1H, J=8.5, 2.3 Hz), 7.41 (dd, 1H, J=2.5, 1.6 Hz), 7.01 (d, 1H, J=15.9 Hz), 6.78 (dd, 1H, J=4.0, 1.6 Hz), 6.50 (dt, 1H, J=15.9, 5.4 Hz), 6.27 (dd, 1H, J=4.0, 2.5 Hz), 5.23 (d, 2H, J=5.4 Hz).

Example 169
(169-1)
Under nitrogen atmosphere, a solution of 4-(hydroxymethyl)-benzoic acid (5.00 g) in DMF (200 mL) was cooled to 0° C., and thereto was added NaH (2.76 g, 60%). The mixture was stirred at the same temperature for 10 minutes, and stirred at room temperature for 20 minutes. The mixture was cooled to 0° C., and thereto were added DMF (100 mL) and iodomethane (18.7 g), and the mixuture was stirred at room temperature for 48 hours. The solvent was evaporated under reduced pressure, and the residue was purified by silica gel column (hexane/ethyl acetate=15/1) to give methyl 4-(methoxymethyl)benzoate (4.27 g, 72%).
¹H NMR (CDCl₃, 400 MHz) δ 8.02 (d, 2H, J=8.3 Hz), 7.40 (d, 2H, J=8.3 Hz), 4.51 (s, 2H), 3.91 (s, 3H), 3.42 (s, 3H).
(169-2)
4-(Methoxymethyl)benzoic acid was obtained from the compound of Example 169-1 in a similar manner to Example 16.
¹H NMR (DMSO-d₆, 400 MHz) δ 12.91 (brs, 1H), 7.92 (d, 2H, J=8.2 Hz), 7.42 (d, 2H, J=8.2 Hz), 4.48 (s, 2H), 3.31 (s, 3H).
(169-3)
[4-(Methoxymethyl)phenyl](1H-pyrrol-2-yl)methanone was obtained from the compound of Example 169-2 in a similar manner to Example 125-2.
¹H NMR (CDCl₃, 400 MHz) δ 9.78 (brs, 1H), 7.90 (d, 2H, J=8.3 Hz), 7.46 (d, 2H, J=8.3 Hz), 7.15 (m, 1H), 6.89 (m, 1H), 6.34 (m, 1H), 4.55 (s, 2H), 3.44 (s, 3H).
(169-4)
The title compound was obtained from the compound of Example 169-3 in a similar manner to Example 18-3.
¹H NMR (CDCl₃, 400 MHz) δ 7.86 (d, 1H, J=2.3 Hz), 7.81 (d, 2H, J=8.2 Hz), 7.48 (d, 1H, J=8.5 Hz), 7.42 (d, 2H, J=8.2 Hz), 7.40 (dd, 1H, J=8.5, 2.3 Hz), 7.21 (d, 1H, J=15.8 Hz), 7.10 (dd, 1H, J=2.6, 1.7 Hz), 6.78 (dd, 1H, J=4.0, 1.7 Hz), 6.35 (dt, 1H, J=15.8, 6.0 Hz), 6.23 (dd, 1H, J=4.0, 2.6 Hz), 5.23 (dd, 2H, J=6.0, 1.4 Hz), 4.53 (s, 2H), 3.87 (s, 3H), 3.43 (s, 3H).

Example 170

$^1$H NMR (CDCl$_3$, 400 MHz) δ 7.83 (brs, 1H), 7.71 (d, 2H, J=7.9 Hz), 7.37 (m, 3H), 7.28 (d, 2H, J=7.9 Hz), 6.97 (brs, 1H), 6.68 (m, 1H), 6.17 (m, 1H), 6.09 (brs, 1H), 5.03 (brs, 2H), 4.42 (s, 2H), 3.38 (s, 3H).

Example 171

(171-1)

Under nitrogen atmosphere, a solution of pyrazole (2.43 g) in DMSO (90 mL) was cooled to 0° C., and thereto was added successively NaH (1.57 g, 60%), and the mixture was stirred at room temperature for 30 minutes. To the mixture was added ethyl 4-fluorobenzoate (6.00 g) and the mixture was stirred at 110–120° C. for 20 hours. The mixture was cooled to room temperature, and thereto was added ice water (150 mL). The mixture was extracted twice with ethyl acetate, and dried over MgSO$_4$. The solvent was evaporated under reduced pressure, and the residue was purified by silica gel column (hexane/ethyl acetate=50/3→50/4) to give ethyl 4-(1H-pyrazol-1-yl)benzoate (6.12 g, 79%).

$^1$H NMR (CDCl$_3$, 400 MHz) δ 8.14 (d, 2H, J=8.9 Hz), 8.01 (d, 1H, J=2.5 Hz), 7.79 (d, 2H, J=8.9 Hz), 7.76 (d, 1H, J=2.5 Hz), 6.51 (dd, 1H, J=2.5, 2.5 Hz), 4.40 (q, 2H, J=7.1 Hz), 1.41 (t, 3H, J=7.1 Hz).

(171-2)

4-(1H-Pyrazol-1-yl)benzoic acid was obtained from the compound of Example 171-1 in a similar manner to Example 16.

$^1$H NMR (DMSO-d$_6$, 400 MHz) δ 13.03 (brs, 1H), 8.63 (d, 1H, J=2.5 Hz), 8.05 (d, 2H, J=8.9 Hz), 7.98 (d, 2H, J=8.9 Hz), 7.82 (d, 1H, J=2.5 Hz), 6.60 (dd, 1H, J=2.5, 2.5 Hz).

(171-3)

[4-(1H-Pyrazol-1-yl)phenyl](1H-pyrrol-2-yl)methanone was obtained from the compound of Example 171-2 in a similar manner to Example 125-2.

$^1$H NMR (CDCl$_3$, 400 MHz) δ 9.65 (brs, 1H), 8.04 (d, 2H, J=8.8 Hz), 8.03 (d, 1H, J=2.4 Hz), 7.84 (d, 2H, J=8.8 Hz), 7.78 (d, 1H, J=2.4 Hz), 7.17 (m, 1H), 6.92 (m, 1H), 6.53 (dd, 1H, J=2.4, 2.4 Hz), 6.37 (m, 1H).

(171-4)

The title compound was obtained from the compound of Example 171-3 in a similar manner to Example 18-3.

$^1$H NMR (CDCl$_3$, 400 MHz) δ 8.02 (dd, 1H, J=2.5, 0.4 Hz), 7.95 (d, 2H, J=8.8 Hz), 7.86 (d, 1H, J=2.5 Hz), 7.80 (d, 2H, J=8.8 Hz), 7.77 (d, 1H, J=2.5 Hz), 7.49 (d, 1H, J=8.5 Hz), 7.41 (ddd, 1H, J=8.5, 2.5, 0.4 Hz), 7.21 (d, 1H, J=15.8 Hz), 7.12 (dd, 1H, J=2.5, 1.8 Hz), 6.81 (dd, 1H, J=4.0, 1.8 Hz), 6.52 (dd, 1H, J=2.5, 2.5 Hz), 6.35 (dt, 1H, J=15.8, 6.0 Hz), 6.26 (dd, 1H, J=4.0, 2.5 Hz), 5.24 (dd, 2H, J=6.0, 1.5 Hz), 3.87 (s, 3H).

Example 172

$^1$H NMR (DMSO-d$_6$, 400 MHz) δ 13.32 (brs, 1H), 8.63 (d, 1H, J=2.4 Hz), 7.98 (d, 2H, J=8.7 Hz), 7.88 (d, 2H, J=8.7 Hz), 7.82 (d, 1H, J=2.4 Hz), 7.72 (d, 1H, J=2.5 Hz), 7.67 (d, 1H, J=8.6 Hz), 7.53 (dd, 1H, J=8.6, 2.5 Hz), 7.39 (dd, 1H, J=2.5, 1.6 Hz), 7.01 (d, 1H, J=15.9 Hz), 6.77 (dd, 1H, J=4.0, 1.6 Hz), 6.61 (dd, 1H, J=2.4, 2.4 Hz), 6.50 (dt, 1H, J=15.9, 5.5 Hz), 6.26 (dd, 1H, J=4.0, 2.5 Hz), 5.22 (d, 2H, J=5.5 Hz).

Example 173

(173-1)

Methyl 4-(1H-1,2,4-triazol-1-ylmethyl)benzoate was obtained from 1,2,4-triazole in a similar manner to Example 166-1.

$^1$H NMR (CDCl$_3$, 400 MHz) δ 8.12 (s, 1H), 8.05 (d, 2H, J=8.4 Hz), 8.00 (s, 1H), 7.31 (d, 2H, J=8.4 Hz), 5.42 (s, 2H), 3.92 (s, 3H).

(173-2)

4-(1H-1,2,4-Triazol-1-ylmethyl)benzoic acid was obtained from the compound of Example 173-1 in a similar manner to Example 16.

$^1$H NMR (DMSO-d$_6$, 400 MHz) δ 12.95 (brs, 1H), 8.69 (s, 1H), 8.01 (s, 1H), 7.92 (d, 2H, J=8.3 Hz), 7.34 (d, 2H, J=8.3 Hz), 5.51 (s, 2H).

(173-3)

1H-Pyrrol-2-yl[4-(1H-1,2,4-triazol-1-ylmethyl)phenyl]methanone was obtained from the compound of Example 173-2 in a similar manner to Example 125-2.

$^1$H NMR (CDCl$_3$, 400 MHz) δ 9.59 (bs, 1H), 8.15 (s, 1H), 8.02 (s, 1H), 7.90 (d, 2H, J=8.3 Hz), 7.36 (d, 2H, J=8.3 Hz), 7.15 (m, 1H), 6.86 (m, 1H), 6.35 (m, 1H), 5.44 (s, 2H).

(173-4)

The title compound was obtained from the compound of Example 173-3 in a similar manner to Example 18-3.

$^1$H NMR (CDCl$_3$, 400 MHz) δ 8.13 (s, 1H), 8.01 (s, 1H), 7.86 (d, 1H, J=2.2 Hz), 7.82 (d, 2H, J=8.3 Hz), 7.47 (d, 1H, J=8.3 Hz), 7.40 (dd, 1H, J=8.3, 2.2 Hz), 7.32 (d, 2H, J=8.3 Hz), 7.20 (d, 1H, J=15.8 Hz), 7.11 (dd, 1H, J=2.4, 1.7 Hz), 6.75 (dd, 1H, J=4.1, 1.7 Hz), 6.33 (dt, 1H, J=15.8, 6.0 Hz), 6.23 (dd, 1H, J=4.1, 2.4 Hz), 5.43 (s, 2H), 5.22 (dd, 2H, J=6.0, 1.5 Hz), 3.86 (s, 3H).

Example 174

$^1$H NMR (CDCl$_3$, 400 MHz) δ 7.86 (dd, 1H, J=1.3 and 7.8 Hz), 7.83 (d, 2H, J=8.8 Hz), 7.54 (brd, 1H, J=7.6 Hz), 7.43 (dt, 1H, J=1.1 and 7.8 Hz), 7.29 (dt, 1H, J=1.3 and 7.6 Hz), 7.27 (brd, 1H, J=15.7 Hz), 6.94 (d, 2H, J=8.8 Hz), 6.88 (brd, 1H, J=0.9 Hz), 6.56 (brd, 1H, J=1.4 Hz), 6.34 (dt, 1H, J=15.7 and 6.5 Hz), 5.15 (dd, 2H, J=1.4 and 6.5 Hz), 3.88 (s, 3H), 3.87 (s, 3H), 2.09 (brs, 3H).

Example 175

$^1$H NMR (CD$_3$OD, 400 MHz) δ 7.82 (d, 2H, J=8.8 Hz), 7.53 (brd, 1H, J=7.6 Hz), 7.47 (dd, 1H, J=1.3 and 7.8 Hz), 7.26 (dt, 1H, J=1.3 and 7.6 Hz), 7.22 (dt, 1H, J=1.1 and 7.8 Hz), 7.15 (brd, 1H, J=15.7 Hz), 7.10 (brs, 1H), 7.05 (d, 2H, J=8.8 Hz), 6.58 (brd, 1H, J=1.4 Hz), 6.41 (dt, 1H, J=15.7 and 6.5 Hz), 5.13 (dd, 2H, J=1.4 and 6.5 Hz), 3.92 (s, 3H), 2.11 (brs, 3H).

Example 176

(176-1)

Ethyl 3-(3-bromo-1-propen-1-yl)benzoate was obtained from ethyl 3-iodobenzoate in a similar manner to Example 9-1, 9-2.

$^1$H NMR (CDCl$_3$, 400 MHz) δ 8.06 (t, 1H, J=1.4 Hz), 7.95 (dt, 1H, J=7.8 and 1.4 Hz), 7.56 (dt, 1H, J=7.8 and 1.4 Hz), 7.41 (t, 1H, J=7.8 Hz), 6.68 (brd, 1H, J=15.6 Hz), 6.49 (dt, 1H, J=15.6 and 7.7 Hz), 4.39 (q, 2H, J=7.1 Hz), 4.16 (dd, 2H, J=7.7 and 0.8 Hz), 1.41 (t, 3H, J=7.1 Hz).

(176-2)

The title compound was obtained from the compound of Example 176-1 and the compound of Reference Example 1.

$^1$H NMR (CDCl$_3$, 400 MHz) δ 8.02 (t, 1H, J=1.4 Hz), 7.90 (dt, 1H, J=7.8 and 1.4 Hz), 7.74 (brd, 2H, J=8.1 Hz), 7.54 (dt, 1H, J=7.8 and 1.4 Hz), 7.36 (t, 1H, J=7.8 Hz), 7.25 (brd, 2H, J=8.1 Hz), 7.05 (dd, 1H, J=2.6 and 1.6 Hz), 6.78 (dd, 1H, J=4.0 and 1.6 Hz), 6.46–6.57 (m, 2H), 6.23 (dd, 1H, J=4.0 and 2.6 Hz), 5.21–5.25 (m, 2H), 4.37 (q, 2H, J=7.1 Hz), 2.43 (brs, 3H), 1.39 (t, 3H, J=7.1 Hz).

Example 177

¹H NMR (CDCl₃, 400 MHz) δ 8.02 (t, 1H, J=1.4 Hz), 7.89 (dt, 1H, J=7.8 and 1.4 Hz), 7.85 (brd, 2H, J=8.1 Hz), 7.54 (dt, 1H, J=7.8 and 1.4 Hz), 7.36 (t, 1H, J=7.8 Hz), 7.04 (dd, 1H, J=2.6 and 1.6 Hz), 6.95 (brd, 2H, J=8.1 Hz), 6.77 (dd, 1H, J=4.0 and 1.6 Hz), 6.46–6.57 (m, 2H), 6.23 (dd, 1H, J=4.0 and 2.6 Hz), 5.19–5.24 (m, 2H), 4.37 (q, 2H, J=7.1 Hz), 3.88 (s, 3H), 1.39 (t, 3H, J=7.1 Hz).

Example 178

(178-1)

Under nitrogen atmosphere, to a solution of 5-methoxyindole-2-carboxylic acid (1.00 g) in Et₂O (40 mL) was added LiAlH₄ (280 mg) at 0° C., and the mixture was stirred under reflux for 3 hours. The mixture was treated with ethyl acetate, diluted with an aqueous hydrochloric acid solution, and extracted with ethyl acetate. The mixture was concentrated to give a crude alcohol compound (840 mg, 91%), which was dissolved in THF (10 mL), and stirred with MnO₂ (4.20 g) at room temperature for 5 hours. The mixture was filtered on celite, and the filtrate was concentrated, and the residue was purified by silica gel column chromatography to give 5-methoxyindole-2-carbaldehyde (300 mg, 36%).

¹H NMR (CDCl₃, 400 MHz) δ 9.80 (s, 1H), 8.90 (brs, 1H), 7.34 (brd, 1H, J=8.9 Hz), 7.19 (dd, 1H, J=2.1 and 0.8 Hz), 7.11 (brs, 1H), 7.08 (dd, 1H, J=8.9 and 2.1 Hz), 3.86 (s, 3H).

(178-2)

1-Benzenesulfonyl-5-methoxy-1H-indole-2-carbaldehyde was obtained from the compound of Example 178-1 and benzenesulfonyl chloride in a similar manner to Example 6-1.

¹H NMR (CDCl₃, 400 MHz) δ 10.51 (s, 1H), 8.13 (brd, 1H, J=8.9 Hz), 7.74 (dq, 2H, J=8.3 and 1.0 Hz), 7.54 (tt, 1H, J=8.3 and 1.0 Hz), 7.41 (tt, 2H, J=8.3 and 1.0 Hz), 7.40 (brs, 1H), 7.15 (dd, 1H, J=8.9 and 2.1 Hz), 6.99 (brd, 1H, J=2.1 Hz), 3.82 (s, 3H).

(178-3)

To Mg (72.0 mg) was added THF (0.50 mL), and the mixture was warmed at 40° C. under nitrogen atmosphere. A drop of bromotoluene was added thereto, and the mixture was stirred for 10 minutes. To the mixture was added dropwise a solution of bromotoluene (513 mg) in THF (5.5 mL), and the mixture was further stirred for 2 hours to give a 0.5M Grignard solution. To a solution of the compound of Example 178-2 (50.0 mg) in THF (1.0 mL) was added the above 0.5 M Grignard solution (0.320 mL) at −75° C. under nitrogen atmosphere, and the mixture was stirred for 10 minutes, and further added thereto the Grignard solution (0.160 mL). The mixture was stirred for 10 minutes, and thereto was added a 5% aqueous KHSO₄ solution, and the mixture was warmed to room temperature. The mixture was extracted with ethyl acetate, and concentrated to give a crude alcohol (70 mg). This compound was dissolved in CHCl₃ (4.0 mL), and the mixture was stirred with MnO₂ (350 mg) at room temperature for 8 hours. The mixture was filtered on celite, and the filtrate was concentrated, and the residue was purified by silica gel column chromatography to give (1-benzenesulfonyl-5-methoxy-1H-indol-2-yl)(4-methylphenyl)methanone (17.0 mg, 24%). The starting alcohol (22.0 mg, 31%) and the unreacted reagent in the Grignard reaction (10 mg) were recovered.

¹H NMR (CDCl₃, 400 MHz) δ 8.02 (brd, 1H, J=8.9 Hz), 7.98 (dq, 2H, J=8.3 and 1.0 Hz), 7.87 (brd, 2H, J=8.2 Hz), 7.55 (tt, 1H, J=8.3 and 1.0 Hz), 7.46 (tt, 2H, J=8.3 and 1.0 Hz), 7.29 (brd, 2H, J=8.2 Hz), 7.06 (dd, 1H, J=8.9 and 2.1 Hz), 6.97 (brd, 1H, J=2.1 Hz), 6.86 (d, 1H, J=0.8 Hz), 3.82 (s, 3H), 2.44 (brs, 3H).

(178-4)

To a solution of the compound of Example 178-3 (17.0 mg) in dioxane (3.0 mL) was added a 5N NaOH (3.0 mL) under nitrogen atmosphere and the mixture was stirred at 90° C. for 6 hours. The mixture was concentrated, and the resultant was diluted with water, and extracted with ethyl acetate. The extract was concentrated, and the residue was purified by silica gel column chromatography to give (5-methoxy-1H-indol-2-yl)(4-methylphenyl)methanone (12.0 mg, 100 %).

¹H NMR (CDCl₃, 400 MHz) δ 9.19 (brs, 1H), 7.90 (brd, 2H, J=8.2 Hz), 7.37 (brd, 1H, J=8.9 Hz), 7.33 (brd, 2H, J=8.2 Hz), 7.09 (brs, 1H), 7.08 (brd, 1H, J=2.1 Hz), 7.06 (dd, 1H, J=8.9 and 2.1 Hz), 3.86 (s, 3H), 2.47 (brs, 3H).

(178-5)

Methyl 5-chloro-2-{(1E)-3-[5-methoxy-2-(4-methylbenzoyl)-1H-indol-1-yl]prop-1-enyl}benzoate was obtained from the compound of Example 178-4 and the compound of Example 9-2 in a similar manner to Example 18-3.

¹H NMR (CDCl₃, 400 MHz) δ 7.84 (brd, 2H, J=8.2 Hz), 7.82 (d, 1H, J=2.2 Hz), 7.45 (brd, 1H, J=8.9 Hz), 7.43 (d, 1H, J=8.5 Hz), 7.36 (dd, 1H, J=8.5 and 2.2 Hz), 7.30 (brd, 2H, J=8.2 Hz), 7.21 (dt, 1H, J=15.8 and 1.7 Hz), 7.08 (dd, 1H, J=8.9 and 2.1 Hz), 7.07 (brs, 1iH, J=2.1 Hz), 6.96 (d, 1H, J=0.6 Hz), 6.32 (dt, 1H, J=15.8 and 5.8 Hz), 5.36 (dd, 2H, J=1.7 and 5.8 Hz), 3.84 (s, 3H), 3.77 (s, 3H), 2.46 (brs, 3H).

(178-6)

The title compound was obtained from the compound of Example 178-5 in a similar manner to Example 16.

¹H NMR (CD₃OD, 400 MHz) δ 7.85 (brd, 2H, J=8.2 Hz), 7.70 (d, 1H, J=2.2 Hz), 7.55 (brd, 1H, J=9.1 Hz), 7.53 (d, 1H, J=8.6 Hz), 7.39 (brd, 2H, J=8.2 Hz), 7.36 (dd, 1H, J=8.6 and 2.2 Hz), 7.26 (dt, 1H, J=15.8 and 1.7 Hz), 7.17 (brs, 1H, J=2.4 Hz), 7.08 (dd, 1H, J=9.1 and 2.4 Hz), 7.00 (d, 1H, J=0.6 Hz), 6.40 (dt, 1H, J=15.8 and 5.8 Hz), 5.39 (dd, 2H, J=1.7 and 5.8 Hz), 3.85 (s, 3H), 2.49 (brs, 3H).

Example 179

The title compound was obtained as a by-product when preparing the compound of Example 109.

¹H NMR (CDCl₃, 400 MHz) δ 9.43 (brs, 1H), 7.89 (d, 1H, J=2.2 Hz), 7.88 (d, 2H, J=8.9 Hz), 7.44 (d, 1H, J=8.3 Hz), 7.41 (dd, 1H, J=2.2 and 8.3 Hz), 7.24 (brd, 1H, J=15.7 Hz), 6.96 (d, 2H, J=8.9 Hz), 6.67 (brd, 1H, J=2.4 Hz), 6.11 (dt, 1H, J=15.7 and 6.7 Hz), 3.92 (s, 3H), 3.88 (s, 3H), 3.58 (dd, 2H, J=1.4 and 6.7 Hz), 2.10 (brs, 3H).

Example 180

(180-1)

Under nitrogen atmosphere, to a solution of 3-thiophene-carboxyaldehyde (9.81 g) in toluene (200 mL) were added p-toluene-sulfonic acid monohydrate (190 mg) and ethylene glycol (6.52 g), and the mixture was stirred at 111° C. for 5 hours. The mixture was cooled to room temperature, washed twice with an aqueous NaHCO₃ solution, dried over MgSO₄. The solvent was evaporated under reduced pressure to give 3-(1,3-dioxolan-2-yl)thiophene (10.4 g).

¹H NMR (CDCl₃, 400 MHz) δ 7.42 (m, 1H), 7.32 (dd, 1H, J=5.0, 3.0 Hz), 7.16 (dd, 1H, J=5.0, 1.2 Hz), 5.91 (s, 1H), 4.11 (m, 2H), 4.03 (m, 2H).

(180-2)

Under nitrogen atmosphere, a solution of the compound of Example 180-1 (12.0 g) in Et₂O (100 mL) was cooled to 0° C., and thereto was added a 2.46N solution of n-BuLi in hexane (30.1 mL), and the mixture was stirred at 0° C. for 5 minutes, and further stirred at 35° C. for 1 hour. The mixture was cooled to −78° C., and thereto was added dropwise a solution of $I_2$ (18.8 g) in $Et_2O$ (150 mL), and the mixture was stirred at −78° C. for 20 minutes. The mixture was warmed to room temperature, and thereto was added an aqueous $NH_4Cl$ solution, and the mixture was extracted twice with ethyl acetate. The organic layer was washed with $NaHSO_3$, dried over $MgSO_4$, and the solvent was evaporated under reduced pressure to give 3-(1,3-dioxolan-2-yl)-2-iodothiophene (20.11 g, 100%).

$^1$H NMR (CDCl$_3$, 400 MHz) δ 7.44 (d, 1H, J=5.6 Hz), 6.98 (d, 1H, J=5.6 Hz), 5.75 (s, 1H), 4.13 (m, 2H).

(180-3)

(2E)-3-[3-(1,3-Dioxolan-2-yl)thien-2-yl]prop-2-enal was obtained from the compound of Example 180-2 in a similar manner to Example 109-12.

$^1$H NMR (CDCl$_3$, 400 MHz) δ 10.19 (s, 1H), 9.75 (d, 1H, J=7.6 Hz), 8.39 (dd, 1H, J=15.8, 0.5 Hz), 7.54 (d, 1H, J=5.3 Hz), 7.48 (d, 1H, J=5.3 Hz), 6.67 (dd, 1H, J=15.8, 7.6).

(180-4)

Under hydrogen atmosphere, to a solution of the compound of Example 180-3 (1.00 g) in ethyl acetate (150 mL) was added a 5% Pd/BaSO$_4$ (4.00 g), and the mixture was stirred for 13.5 hours. The solvent was evaporated under reduced pressure to give 3-[3-(1,3-dioxolan-2-yl)thien-2-yl] propanal (1.00 g, 99%).

$^1$H NMR (CDCl$_3$, 400 MHz) δ 9.82 (t, 1H, J=1.0 Hz), 7.09 (d, 1H, J=5.3 Hz), 7.05 (d, 1H, J=5.3 Hz), 5.87 (s, 1H), 4.12 (m, 2H), 4.01 (m, 2H), 3.22 (t, 2H, J=7.3 Hz), 2.86 (dt, 2H, J=7.3, 1.0).

(180-5)

Under nitrogen atmosphere, a 2.46N solution of LiN(iPr)$_2$ in THF (1.91 mL) was cooled to 0° C., and thereto was added dropwise nBu$_3$SnH (1.37 g), and the mixture was stirred at 0° C. for 20 minutes. The mixture was cooled to −78° C., and thereto was added dropwise a solution of the compound of Example 180-4 (996 mg) in THF (4.0 mL), and the mixture was stirred at −78° C. for 20 minutes. To the mixture was added dropwise an aqueous NH$_4$Cl solution, and the mixture was warmed to room temperature. The mixture was extracted twice with ethyl acetate, and the organic layer was washed with water, and dried over MgSO$_4$. The solvent was evaporated under reduced pressure to give a crude tin-addition compound. Under nitrogen atmosphere, to a solution of PPh$_3$ (1.85 g) in CH$_2$Cl$_2$ (7 mL) were added successively imidazole (480.0 mg) and I$_2$ (1.79 g), and the mixture was stirred at room temperature for 10 minutes. The mixture was cooled to 0° C., and thereto was added dropwise a solution of the above tin-addition compound in CH$_2$Cl$_2$ (6 mL). The mixture was stirred at 0° C. for 5 minutes, and stirred at room temperature for 30 minutes. To the mixture were added hexane (150 mL) and CH$_3$CN (20 mL), and the hexane layer was evaporated under reduced pressure to give a crude iodo compound. Under nitrogen atmosphere, to a solution of this iodo compound in THF (47 mL) was added 1,8-diazabicyclo[5.4.0]undec-7-ene (2.15 g), and the mixture was stirred at room temperature for 93 hours. To the mixture was added hexane, and the mixture was washed with an aqueous 5% KHSO$_4$ solution and water, and dried over MgSO$_4$. The solvent was evaporated under reduced pressure, and the residue was purified by silica gel column (hexane/ethyl acetate=100/1) to give tributyl{(1E)-3-[3-(1,3-dioxolan-2-yl) thien-2-yl]prop-1-enyl}tin (365 mg, 16%).

$^1$H NMR (CDCl$_3$, 400 MHz) δ 7.09 (d, 1H, J=5.3 Hz), 7.07 (d, 1H, J=5.3 Hz), 6.06 (m, 2H), 5.86 (s, 1H), 4.08 (m, 2H), 3.99 (m, 2H), 3.72 (d, 2H, J=4.2 Hz), 1.51 (m, 6H), 1.30 (m, 6H), 0.90 (m, 15H).

(180-6)

To the compound of Example 180-5 (365 mg) were added methyl 5-chloro-2-iodobenzoate (223 mg), Pd$_2$(dba)$_3$·CHCl$_3$ (39.0 mg), PPh$_3$ (35.0 mg) and THF (5.0 mL), and the mixture was stirred for 10 hours under nitrogen atmosphere. The mixture was cooled to room temperature, and the solvent was evaporated under reduced pressure, and the residue was purified by silica gel column chromatography (hexane/ethyl acetate=8/1→6/1) to give methyl 5-chloro-2-{(1Z)-3-[3-(1, 3-dioxolan-2-yl)thien-2-yl]prop-1-enyl}benzoate (168 mg, 61%).

$^1$H NMR (CDCl$_3$, 400 MHz) δ 7.86 (d, 1H, J=2.3 Hz), 7.48 (d, 1H, J=8.5 Hz), 7.40 (dd, 1H, J=8.5, 2.3 Hz), 7.21 (d, 1H, J=15.6 Hz), 7.12 (d, 1H, J=5.3 Hz), 7.09 (d, 1H, J=5.3 Hz), 6.22 (dt, 1H, J=15.6, 6.8 Hz), 5.92 (s, 1H), 4.14 (m, 2H), 4.03 (m, 2H), 3.89 (s, 3H), 3.84 (dd, 2H, J=6.8, 1.5).

(180-7)

Methyl 5-chloro-2-[(1Z)-3-(3-formylthien-2-yl)prop-1-enyl]-benzoate was obtained from the compound of Example 180-6 in a similar manner to Example 155-2.

$^1$H NMR (CDCl$_3$, 400 MHz) δ 10.10 (s, 1H), 7.88 (d, 1H, J=2.2 Hz), 7.47 (d, 1H, J=8.4 Hz), 7.44 (d, 1H, J=5.4 Hz), 7.42 (dd, 1H, J=8.4, 2.2 Hz), 7.27 (d, 1H, J=15.7 Hz), 7.16 (d, 1H, J=5.4 Hz), 6.24 (dt, 1H, J=15.7, 6.7 Hz), 4.15 (dd, 2H, J=6.7, 1.5 Hz), 3.90 (s, 3H).

(180-8)

Methyl 5-chloro-2-((1Z)-3-{3-[hydroxy-(4-methylphenyl)methyl]-thien-2-yl}prop-1-enyl)benzoate was obtained from the compound of Example 180-7 in a similar manner to Example 138-1, which was further treated in a similar manner to Example 28-4 to give the title compound.

$^1$H NMR (CDCl$_3$, 400 MHz) δ 7.85 (d, 1H, J=2.2 Hz), 7.72 (d, 2H, J=8.1 Hz), 7.47 (d, 1H, J=8.4 Hz), 7.39 (dd, 1H, J=8.4, 2.2 Hz), 7.27 (d, 2H, J=8.1 Hz), 7.22 (d, 1H, J=15.7 Hz), 7.17 (d, 1H, J=5.3 Hz), 7.14 (d, 1H, J=5.3 Hz), 6.29 (dt, 1H, J=15.7, 7.0 Hz), 3.82 (d, 2H, J=7.0 Hz), 3.89 (s, 3H), 2.43 (s, 3H).

Example 181

(181-1)

2-Bromobenzaldehyde (11.4 g) was dissolved in toluene (150 mL), and thereto were added ethyleneglycol (4.58 g) and p-toluenesulfonic acid monohydrate (135 mg), and the mixture was refluxed for 6 hours with azeotropic distillation. The reaction solution was washed with an aqueous sodium hydrogen carbonate solution, and the solvent was evaporated under reduced pressure to give 2-(2-bromophenyl)-1, 3-dioxolane (13.4 g, 95%).

$^1$H NMR (CDCl$_3$, 400 MHz) δ 7.60 (dd, 1H, J=7.6, 1.8 Hz), 7.57 (dd, 1H, J=7.6, 1.8 Hz), 7.34 (ddd, 1H, J=7.6, 7.6, 1.8 Hz), 7.22 (ddd, 1H, J=7.6, 7.6, 1.8 Hz), 6.10 (s, 1H), 4.15 (m, 2H), 4.09 (m, 2H).

(181-2)

A solution of the compound of Example 181-1 (6.00 g) in THF (60 mL) was cooled to −78° C., and thereto was added dropwise nBuLi (11.7 mL, 2.46 M hexane solution). The mixture was stirred for 20 minutes, and thereto was added ZnCl$_2$ (28.8 mL, 1.0 M Et$_2$O solution), and the mixture was further stirred for 30 minutes. To the mixture were added a solution of propargyl bromide (3.12 g) in THF (40 mL) and CuI (499 mg). The reaction solution was gradually warmed to room temperature, and thereto was added an aqueous NH$_4$Cl solution, and the mixture was extracted twice with ethyl acetate. The organic layers were combined, dried, filtered, and concentrated. The residue was purified by silica gel column chromatography to give a crude acetylene compound (810 mg). To a solution of this compound in $CH_2Cl_2$ (60 mL) was added $Pd(PPh_3)_2Cl_2$ (60.5 mg). Under ice-cooling, $n$-$Bu_3SnH$ (1.88 g) was added dropwise to the mixture, and the mixture was stirred at the same temperature for 30 minutes. The solvent was evaporated under reduced pressure, and the residue was purified by silica gel column chromatography to give tributyl{(1E)-3-[2-(1,3-dioxolan-2-yl)phenyl]prop-1-enyl}tin (944 mg, 46%).
$^1$H NMR (CDCl$_3$, 400 MHz) δ 7.57 (m, 2H), 7.25 (m, 2H), 6.10 (td, 1H, J=18.9, 5.8 Hz), 5.93 (ddd, 1H, J=18.8, 1.4, 1.4 Hz), 4.14 (m, 2H), 4.02 (m, 2H), 3.63 (dd, 2H, J=5.8, 1.4 Hz), 1.46 (m, 6H), 1.31 (m, 6H), 0.83 (m, 15H).

(181-3)

Methyl 5-chloro-2-{(1E)-3-[2-(1,3-dioxolan-2-yl)phenyl]prop-1-enyl}benzoate was obtained from the compound of Example 181-2 in a similar manner to Example 180-3.
$^1$H NMR (CDCl$_3$, 400 MHz) δ 7.82 (d, 1H, J=2.3 Hz), 7.60 (dd, 1H, J=8.5, 2.3 Hz), 7.46 (d, 1H, J=8.5 Hz), 7.38 (dd, 1H, J=8.5, 2.3 Hz), 7.32 (dd, 1H, J=8.5, 2.3 Hz), 7.27 (m, 2H), 7.12 (d, 1H, J=15.7 Hz), 6.25 (dt, 1H, J=15.7, 6.7 Hz), 6.05 (s, 1H), 4.14 (m, 2H), 4.06 (m, 2H), 3.87 (s, 3H), 3.74 (dd, 2H, J=6.7, 1.4).

(181-4)

Methyl 5-chloro-2-[(1E)-3-(2-formylphenyl)prop-1-enyl]benzoate was obtained from the compound of Example 181-3 in a similar manner to Example 155-2, which was further treated in a similar manner to Example 138-1 to give methyl 5-chloro-2-((1E)-3-{2-[hydroxy(4-methyl-phenyl)methyl]phenyl}prop-1-enyl)benzoate. This compound was treated in a similar manner to Example 28-4 to give the title compound.
$^1$H NMR (CDCl$_3$, 400 MHz) δ 7.80 (d, 1H, J=1.6 Hz), 7.70 (d, 2H, J=8.2 Hz), 7.44 (dd, 1H, J=7.3, 1.6 Hz), 7.40 (d, 1H, J=7.3 Hz), 7.30 (m, 4H), 7.22 (d, 2H, J=8.2 Hz), 7.05 (d, 1H, J=15.7 Hz), 6.15 (dt, 1H, J=15.7, 6.9 Hz), 3.87 (s, 3H), 3.60 (dd, 2H, J=6.9, 1.3 Hz), 2.41 (s, 3H).

Example 182

(182-1)

Under nitrogen atmosphere, to a solution of 3-pyrazolcarboxy-aldehyde (500 mg) in THF (50 mL) were added KOtBu (643 mg) and 18-crown-6 (138 mg), and the mixture was stirred at room temperature for 15 minutes. To the mixture was added allyl bromide (630 mg), and the mixture was stirred at room temperature for 1 hour. To the reaction mixture was added an aqueous $NH_4Cl$ solution, and the mixture was extracted twice with ethyl acetate, and dried over $MgSO_4$. The solvent was evaporated under reduced pressure, and the residue was purified by silica gel column (hexane/ethyl acetate=8/1) to give 1-allyl-1H-pyrazole-5-carbaldehyde (23.1 mg, 3%) and 1-allyl-1H-pyrazole-3-carbaldehyde (413.1 mg, 58%).

1-Allyl-1H-pyrazole-5-carbaldehyde: $^1$H NMR (CDCl$_3$, 400 MHz) δ 9.87 (s, 1H), 7.60 (d, 1H, J=2.0 Hz), 6.93 (d, 1H, J=2.0 Hz), 6.00 (dddd, 1H, J=17.1, 10.3, 5.7, 5.7 Hz), 5.20 (dd, 1H, J=10.3, 1.2 Hz), 5.17 (ddd, 2H, J=5.7, 1.5, 1.5 Hz), 5.10 (dd, 1H, J=17.1, 1.2).

1-allyl-1H-pyrazole-3-carbaldehyde: $^1$H NMR (CDCl$_3$, 400 MHz) δ 9.98 (s, 1H), 7.47 (d, 1H, J=2.4 Hz), 6.84 (d, 1H, J=2.4 Hz), 6.05 (dddd, 1H, J=16.3, 10.2, 6.0, 6.0 Hz), 5.35 (dd, 1H, J=10.2, 1.1 Hz), 5.28 (dd, 1H, J=16.3, 1.1 Hz), 4.85 (ddd, 2H, J=6.0, 1.4 and 1.4).

(182-2)

In a similar manner to Example 138-1, (1-allyl-1H-pyrazol-3-yl)(4-methylphenyl)methanol was obtained from 1-allyl-1H-pyrazol-3-carbaldehyde, and (1-allyl-1H-pyrazol-3-yl)(4-methylphenyl)methanone was obtained in a similar manner to Example 28-4.
$^1$H NMR (CDCl$_3$, 400 MHz) δ 8.15 (d, 2H, J=8.2 Hz), 7.47 (d, 1H, J=2.4 Hz), 7.28 (d, 2H, J=8.2 Hz), 6.95 (d, 1H, J=2.4 Hz), 6.07 (dddd, 1H, J=16.3, 10.2, 6.0, 6.0 Hz), 5.33 (dd, 1H, J=10.2, 1.1 Hz), 5.27 (dd, 1H, J=16.3, 1.1 Hz), 4.85 (ddd, 1H, J=6.0, 1.3, 1.3 Hz), 2.42 (s, 3H).

(182-3)

Methyl 5-chloro-2-{(1E)-3-[3-(4-methylbenzoyl)-1H-pyrazol-1-yl]prop-1-enyl}benzoate was obtained from the compound of Example 182-2 in a similar manner to Example 109-12.
$^1$H NMR (CDCl$_3$, 400 MHz) δ 8.17 (d, 2H, J=8.2 Hz), 7.91 (d, 1H, J=2.0 Hz), 7.57 (d, 1H, J=2.4 Hz), 7.48 (d, 1H, J=8.4 Hz), 7.45 (dd, 1H, J=8.4, 2.0 Hz), 7.39 (d, 1H, J=15.7 Hz), 7.28 (d, 2H, J=8.2 Hz), 6.98 (d, 1H, J=2.4 Hz), 6.27 (dt, 1H, J=15.7, 6.4 Hz), 5.04 (dd, 2H, J=6.4, 1.4 Hz), 3.90 (s, 3H), 2.43 (s, 3H).

(182-4)

The title compound was obtained from the compound of Example 182-3 in a similar manner to Example 16.
$^1$H NMR (DMSO-d$_6$, 400 MHz) δ 8.10 (d, 2H, J=8.1 Hz), 7.94 (brs, 1H), 7.62 (brs, 1H), 7.57 (m, 2H), 7.31 (m, 3H), 6.87 (d, 1H, J=1.7 Hz), 6.35 (dt, 1H, J=15.9, 6.6 Hz), 5.01 (d, 2H, J=6.6 Hz), 2.38 (s, 3H).

Example 183

(183-1)

(1-Allyl-1H-pyrazol-5-yl)(4-methylphenyl)methanol was obtained from 1-allyl-1H-pyrazole-5-carbaldehyde (Example 182-1) in a similar manner to Example 138-1, and (1-allyl-1H-pyrazol-5-yl)(4-methyl-phenyl)methanone was obtained in a similar manner to Example 28-4.
$^1$H NMR (CDCl$_3$, 400 MHz) δ 7.80 (d, 2H, J=8.2 Hz), 7.56 (d, 1H, J=2.0 Hz), 7.30 (d, 2H, J=8.2 Hz), 6.66 (d, 1H, J=2.0 Hz), 6.07 (m, 1H), 5.15 (m, 3H), 2.45 (s, 3H).

(183-2)

The title compound was obtained from the compound of Example 183-1 in a similar manner to Example 109-12.
$^1$H NMR (CDCl$_3$, 400 MHz) δ 7.83 (d, 1H, J=2.3 Hz), 7.82 (d, 2H, J=8.5 Hz), 7.59 (d, 1H, J=2.0 Hz), 7.45 (d, 1H, J=8.5 Hz), 7.38 (dd, 1H, J=8.5, 2.3 Hz), 7.30 (d, 2H, J=8.5 Hz), 7.26 (d, 1H, J=15.8 Hz), 6.69 (d, 1H, J=2.0 Hz), 6.34 (dt, 1H, J=15.8, 6.1 Hz), 5.37 (dd, 2H, J=6.1, 1.3 Hz), 3.85 (s, 3H), 2.45 (s, 3H).

Example 184

$^1$H NMR (DMSO-d$_6$, 400 MHz) δ 7.79 (d, 2H, J=8.1 Hz), 7.64 (d, 1H, J=2.0 Hz), 7.57 (brs, 1H), 7.49 (d, 1H, J=8.5 Hz), 7.43 (d, 1H, J=16.0 Hz), 7.37 (d, 2H, J=8.1 Hz), 7.25 (d, 1H, J=8.5 Hz), 6.75 (d, 1H, J=2.0 Hz), 6.32 (dt, 1H, J=16.0, 5.7 Hz), 5.22 (d, 2H, J=5.7 Hz), 2.40 (s, 3H).

Example 185

(185-1)

A suspension of N,N-dimethyl-1H-imidazole-1-sulfonamide (2.02 g) in THF (50 mL) was cooled to −78° C., and thereto was added dropwise n-BuLi (4.77 mL, 2.66 M hexane solution), and the mixture was stirred for 30 minutes. To the mixture was added p-tolyl benzaldehyde (2.08 g), and the mixture was warmed to room temperature over a period of 1 hour, and then stirred for 16 hours. The mixture was extracted with aqueous hydrochloric acid solution, washed with Et$_2$O, and basified with an aqueous NaOH solution. This solution was extracted with Et$_2$O, and the organic layer was dried and filtered. The solvent was evaporated under reduced pressure to give 2-[hydroxy(4-methylphenyl)methyl]-N,N-dimethyl-1H-imidazole-1-sulfonamide.
$^1$H NMR (CDCl$_3$, 400 MHz) δ 7.26 (d, 2H, J=8.1 Hz), 7.24 (d, 1H, J=1.6 Hz), 7.14 (d, 2H, J=8.1 Hz), 7.07 (d, 1H, J=1.6 Hz), 6.15 (s, 1H), 2.70 (s, 6H), 2.32 (s, 3H).

(185-2)

N,N-Dimethyl-2-(4-methylbenzoyl)-1H-imidazole-1-sulfonamide was obtained from the compound of Example 185-1 in a similar manner to Example 28-4.

$^1$H NMR (CDCl$_3$, 400 MHz) δ 7.95 (d, 2H, J=8.3 Hz), 7.52 (d, 1H, J=1.4 Hz), 7.29 (d, 2H, J=8.3 Hz), 7.16 (d, 1H, J=1.4 Hz), 3.10 (s, 6H), 2.43 (s, 3H).

(185-3)

The compound of Example 185-2 was treated with hydrochloric acid in THF to give 1H-imidazol-2-yl(4-methylphenyl)methanone.

$^1$H NMR (CDCl$_3$, 400 MHz) δ 10.72 (brs, 1H), 8.52 (d, 2H, J=8.3 Hz), 7.39 (s, 0.5 H), 7.32 (d, 2H, J=8.3 Hz), 7.32 (s, 0.5 H), 2.44 (s, 3H).

(185-4)

(1-Allyl-1H-imidazol-2-yl)(4-methylphenyl)methanone was obtained from the compound of Example 185-3 in a similar manner to Example 109-10.

$^1$H NMR (CDCl$_3$, 400 MHz) δ 8.17 (d, 2H, J=8.2 Hz), 7.28 (d, 2H, J=8.2 Hz), 7.25 (m, 1H), 7.16 (m, 1H), 6.07 (dddd, 1H, J=17.0, 10.2, 5.7, 5.7 Hz), 5.24 (dd, 1H, J=10.2, 1.2 Hz), 5.14 (dd, 1H, J=17.0, 1.2 Hz), 5.09 (ddd, 2H, J=5.7, 1.4, 1.4 Hz), 2.42 (s, 3H).

(185-5)

Methyl 5-chloro-2-{(1E)-3-[2-(4-methylbenzoyl)-1H-imidazol-1-yl]prop-1-enyl}benzoate was obtained from the compound of Example 185-4 in a similar manner to Example 109-12.

$^1$H NMR (CDCl$_3$, 400 MHz) δ 8.19 (d, 2H, J=8.3 Hz), 7.88 (d, 1H, J=2.2 Hz), 7.47 (d, 1H, J=8.4 Hz), 7.42 (dd, 1H, J=8.4, 2.2 Hz), 7.31 (d, 1H, J=15.8 Hz), 7.29 (m, 2H), 7.27 (d, 2H, J=8.3 Hz), 6.31 (dt, 1H, J=15.8, 6.3 Hz), 5.26 (dd, 2H, J=6.3, 1.4 Hz), 3.88 (s, 3H), 2.42 (s, 3H).

(185-6)

The title compound was obtained from the compound of Example 185-5 in a similar manner to Example 16.

$^1$H NMR (DMSO-d$_6$, 400 MHz) δ 8.16 (d, 2H, J=8.2 Hz), 7.66 (d, 1H, J=0.8 Hz), 7.56 (d, 1H, J=16.1 Hz), 7.44 (d, 1H, J=2.4 Hz), 7.44 (d, 1H, J=8.4 Hz), 7.33 (d, 2H, J=8.2 Hz), 7.22 (d, 1H, J=0.8 Hz), 7.15 (dd, 1H, J=8.4, 2.4 Hz), 6.27 (dt, 1H, J=16.1, 6.5 Hz), 5.16 (dd, 2H, J=6.5, 0.8 Hz), 2.39 (s, 3H).

Example 186

(186-1)

To a suspension of NaH (6.12 g, 60% dispersion in oil) in DMF (70 mL) was added dropwise a mixture of MeI (21.7 g) and methyl thien-3-ylacetate (11.0 g) under ice-cooling. The reaction solution was stirred at room temperature for 5 hours, and cooled again with ice. To the mixture was added dropwise an aquoues hydrochloric acid solution, and the mixture was diluted with water. The mixture was extracted with ethyl acetate-toluene, and the organic layer was dried, filtered and concentrated. The residue was purified by silica gel chromatography (hexane/ethyl acetate=100:3) to give methyl 2-methyl-2-thien-3-yl-propionate (11.2 g, 91%).

$^1$H NMR (CDCl$_3$, 400 MHz) δ 7.26 (dd, 1H, J=5.0 and 3.0 Hz), 7.10 (dd, 1H, J=1.4 and 3.0 Hz), 7.08 (dd, 1H, J=5.0 and 1.4 Hz), 3.65 (s, 3H), 1.58 (s, 6H).

(186-2)

The compound of Example 186-1 was formylated using Cl$_2$CHOCH$_3$ and SnCl$_4$, and protected with ethyleneglycol, and the ester group was converted into a formyl group to give 2-[2-(1,3-dioxolan-2-yl)thien-3-yl]-2-methylpropanal.

$^1$H NMR (CDCl$_3$, 400 MHz) δ 9.59(s, 1H), 7.31 (d, 1H, J=5.3 Hz), 7.00 (d, 1H, J=5.3 Hz), 5.98 (s, 1H), 4.11 (m, 2H), 4.01 (m, 2H), 1.44 (s, 6H).

(186-3)

The compound of Example 186-2 was treated with CBr$_4$ and PPh$_3$, and the resulting dibromoolefin was treated with n-BuLi to give 2-[3-(1,1-dimethylprop-2-ynyl) thien-2-yl]-1,3-dioxolane.

$^1$H NMR (CDCl$_3$, 400 MHz) δ 7.16 (d, 1H, J=5.3 Hz), 7.03 (d, 1H, J=5.3 Hz), 6.06 (s, 1H), 4.14 (m, 2H), 4.03 (m, 2H), 2.31 (s, 1H), 1.56 (s, 6H).

(186-4)

The compound of Example 186-3 was treated with n-Bu$_3$SnH and Pd(PPh$_3$)$_2$Cl$_2$ to give tributyl{3-[2-(1,3-dioxolan-2-yl)thien-3-yl]-3-methylbut-1-enyl}tin.

$^1$H NMR (CDCl$_3$, 400 MHz) δ 7.21 (d, 1H, J=5.3 Hz), 6.97 (d, 1H, J=5.3 Hz), 6.33 (s, 1H), 6.22 (d, 1H, J=19.3 Hz), 5.98 (d, 1H, J=19.3 Hz), 4.12 (m, 2H), 3.95 (m, 2H), 1.48 (m, 6H), 1.43 (s, 6H), 1.29 (m, 6H), 0.88 (m, 15H).

(186-5)

Methyl 5-chloro-2-{(1E)-3-[2-(1,3-dioxolan-2-yl)thien-3-yl]-3-methylbut-1-enyl}benzoate was obtained from the compound of Example 186-4 in a similar manner to Example 180-3.

$^1$H NMR (CDCl$_3$, 400 MHz) δ 7.87 (d, 1H, J=2.3 Hz), 7.54 (d, 1H, J=8.5 Hz), 7.41 (dd, 1H, J=8.5 and 2.3 Hz), 7.24 (d, 1H, J=5.3 Hz), 7.18 (d, 1H, J=16.1 Hz), 7.03 (d, 1H, J=5.3 Hz), 6.36 (d, 1H, J=16.1 Hz), 6.33 (s, 1H), 4.12 (m, 2H), 3.90 (s, 3H), 3.89 (s, 3H), 1.57 (s, 6H).

(186-6)

Methyl 5-chloro-2-[(1E)-3-(2-formylthien-3-yl)-3-methylbut-1-enyl]benzoate was obtained from the compound of Example 186-5 in a similar manner to Example 155-2.

$^1$H NMR (CDCl$_3$, 400 MHz) δ 10.33 (d, 1H, J=1.2 Hz), 7.90 (d, 1H, J=2.3 Hz), 7.42 (m, 4H), 7.22 (d, 1H, J=16.1 Hz), 7.19 (d, 1H, J=5.1 Hz), 6.37 (d, 1H, J=16.1 Hz), 3.89 (s, 3H), 1.67 (s, 6H).

(186-7)

Methyl 5-chloro-2-((1E)-3-{2-[hydroxy-(4-methylphenyl)methyl]-thien-3-yl}-3-methylbut-1-enyl)benzoate was obtained from the compound of Example 186-6 in a similar manner Example 138-1.

$^1$H NMR (CDCl$_3$, 400 MHz) δ 7.86 (d, 1H, J=1.8 Hz), 7.40 (m, 2H), 7.24 (d, 2H, J=8.1 Hz), 7.23 (d, 1H, J=5.0 Hz), 7.07 (d, 2H, J=8.1 Hz), 7.04 (d, 1H, J=5.0 Hz), 7.03 (d, 1H, J=15.9 Hz), 6.38 (d, 1H, J=3.6 Hz), 6.36 (d, 1H, J=15.9 Hz), 3.85 (s, 3H), 3.45 (d, 1H, J=3.6 Hz), 2.31 (s, 3H), 1.57 (s, 6H).

(186-8)

Methyl 5-chloro-2-{(1E)-3-methyl-3-[2-(4-methylbenzoyl)thien-3-yl]but-1-enyl}benzoate was obtained from the compound of Example 186-7 in a similar manner to Example 28-4.

$^1$H NMR (CDCl$_3$, 400 MHz) δ 7.79 (d, 1H, J=2.2 Hz), 7.66 (d, 2H, J=8.2 Hz), 7.37 (d, 1H, J=5.1 Hz), 7.25 (dd, 1H, J=8.5 and 2.2 Hz), 7.20 (d, 1H, J=8.5 Hz), 7.17 (d, 1H, J=5.1 Hz), 7.14 (d, 2H, J=8.2 Hz), 7.02 (d, 1H, J=16.2 Hz), 6.34 (d, 1H, J=16.2 Hz), 3.87 (s, 3H), 2.38 (s, 3H), 1.57 (s, 6H).

(186-9)

The title compound was obtained from the compound of Example 186-8 in a similar manner to Example 16.

$^1$H NMR (CDCl$_3$, 400 MHz) δ 7.85 (d, 1H, J=2.3 Hz), 7.62 (d, 2H, J=8.2 Hz), 7.34 (d, 1H, J=5.1 Hz), 7.24 (dd, 1H, J=8.5 and 2.3 Hz), 7.17 (d, 1H, J=8.5 Hz), 7.14 (d, 1H, J=5.1 Hz), 7.09 (d, 2H, J=8.2 Hz), 7.08 (d, 1H, J=16.2 Hz), 6.25 (d, 1H, J=16.2 Hz), 2.35 (s, 3H), 1.53 (s, 6H).

Example 187

(187-1)

Methyl 4-allylisothiazole-3-carboxylate was obtained from methyl 4-iodoisothiazole-3-carboxylate in a similar manner to Example 180-3.

$^1$H NMR (CDCl$_3$, 400 MHz) δ 8.40 (s, 1H), 6.01 (dddd, 1H, J=16.8, 10.2, 6.6, 6.6 Hz), 5.12 (m, 2H), 3.98 (s, 3H), 3.76 (dd, 2H, J=6.6, 1.0).

(187-2)

4-Allylisothiazole-3-carbaldehyde was obtained from the compound of Example 187-1 in a similar manner to Example 137-5.

$^1$H NMR (CDCl$_3$, 400 MHz) δ 10.14 (s, 1H), 8.37 (s, 1H), 5.99 (dddd, 1H, J=16.9, 10.2, 6.6, 6.6 Hz), 5.11 (m, 2H), 3.76 (dd, 2H, J=6.6, 1.1).

(187-3)

(4-Allylisothiazol-3-yl)(4-methylphenyl)methanol was obtained from the compound of Example 187-2 in a similar manner to Example 138-1, and (4-allylisothiazol-3-yl)(4-methylphenyl)methanone was obtained in a similar manner to Example 28-4.

$^1$H NMR (CDCl$_3$, 400 MHz) δ 8.40 (s, 1H), 7.98 (d, 2H, J=8.3 Hz), 7.29 (d, 2H, J=8.3 Hz), 6.00 (dddd, 1H, J=16.3, 9.7, 6.6, 6.6 Hz), 5.11 (m, 2H), 3.69 (dd, 2H, J=6.6, 1.0 Hz), 2.44 (s, 3H).

(187-4)

The title compound was obtained from the compound of Example 187-3 in a similar manner to Example 109-12.

$^1$H NMR (CDCl$_3$, 400 MHz) δ 8.62 (s, 1H), 8.51 (s, 1H), 7.99 (d, 2H, J=8.2 Hz), 7.94 (d, 2H, J=8.2 Hz), 7.88 (d, 1H, J=2.3 Hz), 7.84 (d, 1H, J=2.3 Hz), 7.40 (m, 3H), 7.27 (m, 5H), 7.19 (d, 1H, J=15.7 Hz), 6.82 (d, 1H, J=15.9 Hz), 6.28 (m, 2H), 3.90 (s, 3H), 3.88 (s, 3H), 3.84 (m, 2H), 2.43 (s, 6H).

Example 188 and Example 189

(188-1)

Under nitrogen atmosphere, to a solution of 60% NaH (285 mg) in DMF (10 mL) was added the compound of Reference Example 3 (1.20 g) under ice-cooling, and the mixture was stirred for 20 minutes. Subsequently, triisopropylsilyl chloride (1.40 g) was added dropwise thereto, and the mixture was stirred at 0° C. for 4 hours. The reaction solution was poured into water, and the mixture was etxtracted with ethyl acetate-toluene. The organic layer was washed with water and dried over MgSO$_4$. The solvent was evaporated under reduced pressure, and the residue was purified by silica gel column (ethyl acetate) to give (1H-pyrrole-1-triisopropylsilyl-3-yl) (4-methylphenyl) ketone (2.08 g, 94%).

$^1$H NMR (CDCl$_3$, 400 MHz) δ 7.77 (d, 2H, J=8.0 Hz), 7.33 (dd, 1H, J=1.7, 1.7 Hz), 7.26 (d, 2H, J=8.0 Hz), 6.78-6.80 (m, 2H), 2.43 (s, 3H), 1.47 (sep, 3H, J=7.5 Hz), 1.11 (d, 18H, J=7.5 Hz).

(188-2)

Under nitrogen atmosphere, to a solution of the compound of Example 188-1 (1.00 g) in CH$_3$CN (20 mL) were added I$_2$ (185 mg) and ammonium cerium (IV) nitrate (963 mg), and the mixture was stirred at room temperature for 3 hours. The solvent was evaporated under reduced pressure, and thereto was added an aqueous sodium sulfite solution, and the mixture was extracted with ethyl acetate. The organic layer was washed with water and a saturated brine, and dried over MgSO$_4$. The solvent was evaporated under reduced pressure, and the residue was purified by silica gel column (hexane/ethyl acetate=15/1→8/1) to give (4-iodo-1H-pyrrole-1-triisopropylsilyl-3-yl) (4-methyl-phenyl) ketone (870 mg).

$^1$H NMR (CDCl$_3$, 400 MHz) δ 7.73 (d, 2H, J=8.1 Hz), 7.25 (d, 2H, J=8.1 Hz), 7.06 (d, 1H, J=2.2 Hz), 6.91 (d, 1H, J=2.2 Hz), 2.43 (s, 3H), 1.43 (sep, 3H, J=7.5 Hz), 1.10 (d, 18H, J=7.5 Hz).

(188-3)

Under nitrogen atmosphere, to a solution of the compound of Example 188-2 (750 mg) in THF (7.0 mL) was added a solution of Bu$_4$NF (420 mg) in THF (3.0 mL), and the mixture was stirred at room temperature for 1 hour. To the mixture was added a 5% aqueous KHSO$_4$ solution, and the mixture was extracted with ethyl acetate, washed with a saturated brine, and dried over MgSO$_4$. The solvent was evaporated under reduced pressure, and the residue was purified by silica gel column (hexane/ethyl acetate=3/1→1/1) to give (4-iodo-1H-pyrrol-3-yl) (4-methylphenyl) ketone (364 mg).

$^1$H NMR (CDCl$_3$, 400 MHz) δ 8.87 (br, 1H), 7.73 (d, 2H, J=8.1 Hz), 7.25 (d, 2H, J=8.1 Hz), 7.15 (dd, 1H, J=2.2, 3.1 Hz), 7.00 (dd, 1H, J=2.2, 2.2 Hz), 2.42 (s, 3H).

(188-4)

Under nitrogen atmosphere, to a solution of the compound of Example 188-3 (250 mg) in THF (5.0 mL) were added successively KOt-Bu (108 mg) and MeI (100 μl), and the mixture was stirred at room temperature for 30 minutes. Water was added to the mixture, and the mixture was extracted with ethyl acetate, washed with a saturated brine, and dried over MgSO$_4$. The solvent was evaporated under reduced pressure, and the residue was purified by silica gel column (hexane/ethyl acetate=3/1) to give (4-iodo-1-methyl-1H-pyrrol-3-yl) (4-methyl-phenyl) ketone (219 mg, 39%, 3 steps).

$^1$H NMR (CDCl$_3$, 400 MHz) δ 7.70 (d, 2H, J=8.0 Hz), 7.24 (d, 2H, J=8.0 Hz), 6.97 (d, 1H, J=2.3 Hz), 6.81 (d, 1H, J=2.3 Hz), 3.69 (s, 3H), 2.42 (s, 3H).

(188-5)

Under nitrogen atmosphere, to a solution of the compound of Example 188-4 (200 mg) and allyltributyltin (314 mg) in THF (5.0 mL) were added successivly Pd(PPh$_3$)$_4$ (101 mg) and LiCl (41.2 mg), and the mixture was refluxed for 10 hours. The solvent was evaporated under reduced pressure, and the residue was purified by silica gel column (hexane/ethyl acetate=5/1) to give (4-allyl-1-methyl-1H-pyrrol-3-yl) (4-methylphenyl) ketone (52.0 mg, 35%).

$^1$H NMR (CDCl$_3$, 400 MHz) δ 7.67 (d, 2H, J=8.0 Hz), 7.23 (d, 2H, J=8.0 Hz), 6.93 (d, 1H, J=2.2 Hz), 6.45 (d, 1H, J=2.2 Hz), 6.06 (ddt, 1H, J=10.1, 17.0, 6.8 Hz), 5.11 (dd, 1H, J=17.0, 2.0 Hz), 5.02 (dd, 1H, J=10.1, 2.0 Hz), 3.62 (s, 3H), 3.59(d, 2H, J=6.8 Hz), 2.41(s, 3H).

(188-6)

Under nitrogen atmosphere, to a suspension of methyl 5-chloro-2-iodobenzoate (Example 109-9) (63.6 mg), the compound of Example 188-5 (45.0 mg), sodium hydrogen carbonate (33.3 mg), and BnEt$_3$NCl (47.5 mg) in DMF (3.0 mL) was added Pd(OAc)$_2$ (10.5 mg), and the mixture was stirred at 80° C. for 6 hours. Water was added to the mixture, and the mixture was extracted with ethyl acetate-toluene, and the organic layer was washed with water and a saturated brine, and dried over MgSO$_4$. The solvent was evaporated under reduced pressure, and the residue was purified by silica gel column (hexane/ethyl acetate=5/1→3/1) to give the compound of Example 188 (10.2 mg, 13%) and the compound of Example 189 (9.5 mg, 12%).

The compound of Example 188: $^1$H NMR (CDCl$_3$, 400 MHz) δ 7.81 (d, 1H, J=2.2 Hz), 7.69 (d, 2H, J=7.9 Hz), 7.52 (d, 1H, J=8.5 Hz), 7.37 (d, 1H, J=2.2, 8.5 Hz), 7.24 (d, 2H, J=7.9 Hz), 7.17 (d, 1H, J=15.7 Hz), 6.94 (d, 1H, J=2.2 Hz), 6.52 (d, 1H, J=2.2 Hz), 6.41 (dt, 1H, J=15.7, 7.0 Hz), 3.88 (s, 3H), 3.76 (d, 2H, J=7.0 Hz), 3.63 (s, 3H), 2.42 (s, 3H).

The compound of Example 189: ¹H NMR (CDCl₃, 400 MHz) δ 7.84 (d, 1H, J=2.3 Hz), 7.67 (d, 2H, J=8.0 Hz), 7.38 (dd, 1H, J=2.3, 8.3 Hz), 7.29 (d, 1H, J=8.3 Hz), 7.22 (d, 2H, J=8.0 Hz), 6.95 (d, 1H, J=16.0 Hz), 6.87 (d, 1H, J=2.2 Hz), 6.76 (d, 1H, J=2.2 Hz), 6.07 (dt, 1H, J=16.0, 7.2 Hz), 3.91 (s, 3H), 3.80 (d, 2H, J=7.2 Hz), 3.62 (s, 3H), 2.42 (s, 3H).

Example 190

(190-1)

(5-Methylthien-2-yl)(1H-pyrrol-2-yl)methanone was obtained from 5-methyl-2-thiophenecarboxylic acid in a similar manner to Example 125-2.
¹H NMR (CDCl₃, 400 MHz) δ 9.60 (brs, 1H), 7.75 (d, 1H, J=3.7 Hz), 7.13 (m, 1H), 7.11 (m, 1H), 6.84 (m, 1H), 6.35 (m, 1H), 2.57 (d, 3H, J=0.4 Hz).

(190-2)

The title compound was obtained from the compound of Example 190-1 in a similar manner to Example 18-3.
¹H NMR (CDCl₃, 400 MHz) δ 7.85 (d, 1H, J=2.3 Hz), 7.59 (d, 1H, J=3.7 Hz), 7.46 (d, 1H, J=8.5 Hz), 7.39 (dd, 1H, J=8.5, 2.3 Hz), 7.18 (d, 1H, J=15.8 Hz), 7.07 (dd, 1H, J=2.6, 1.6 Hz), 7.04 (dd, 1H, J=4.0, 1.6 Hz), 6.81 (m, 1H), 6.33 (dt, 1H, J=15.8, 6.1 Hz), 6.24 (dd, 1H, J=4.0, 2.6 Hz), 5.14 (dd, 2H, J=6.1, 1.4 Hz), 3.87 (s, 3H), 2.56 (d, 3H, J=0.6 Hz).

Example 191

¹H NMR (DMSO-d₆, 400 MHz) δ 7.88 (d, 1H, J=1.5 Hz), 7.55 (d, 1H, J=3.7 Hz), 7.38 (d, 1H, J=8.3 Hz), 7.32 (m, 2H), 7.00 (m, 2H), 6.73 (d, 1H, J=3.7 Hz), 6.22 (dt, 1H, J=15.7, 5.8 Hz), 6.14 (m, 1H), 5.01 (d, 2H, J=5.8 Hz), 2.48 (s, 3H).

Example 192

(192-1)

Under nitrogen atmosphere, a solution of indole-5-carboxylic acid (1.05 g) in DMF (40 mL) was cooled to 0° C., and thereto was added NaH (544 mg, 60%), and the mixture was stirred at the same temperature for 10 minutes, and stirred at room temperature for 30 minutes. The mixture was cooled to 0° C., and thereto was added iodomethane (3.68 g), and the mixture was stirred at room temperature for 48 hours. Water was added to the mixture, and the mixture was extracted three times with ethyl acetate-toluene, and dried over MgSO₄. The solvent was evaporated under reduced pressure to give a crude methyl 1-methylindole-5-carboxylate. To a solution of the crude methyl 1-methylindole-5-carboxylate in THF (50 mL)-MeOH (50 mL) was added a 6N NaOH solution (5.4 mL), and the mixture was stirred at room temperature for 144 hours. The solvent was evaporated under reduced pressure. The residue was washed with ethyl acetate, and thereto was added a 6N aqueous hydrochloric acid solution to adjust the pH value thereof to pH=5-6. The mixture was extracted twice with ethyl acetate, and dried over MgSO₄. The solvent was evaporated under reduced pressure to give 1-methyl-1H-indol-5-carboxylic acid (1.08 g, 96%).
¹H NMR (DMSO-d₆, 400 MHz) δ 12.42 (brs, 1H,), 8.23 (d, 1H, J=1.2 Hz), 7.76 (dd, 1H, J=8.6, 1.2 Hz), 7.50 (d, 1H, J=8.6 Hz), 7.43 (d, 1H, J=3.1 Hz), 6.57 (dd, 1H, J=3.1, 0.7 Hz), 3.82 (s, 3H).

(192-2)

(1-Methyl-1H-indol-5-yl)(1H-pyrrol-2-yl)methanone was obtained from the compound of Example 125-2 in a similar manner to Example 192-1.
¹H NMR (CDCl₃, 400 MHz) δ 9.62 (brs, 1H), 8.30 (d, 1H, J=1.6 Hz), 7.86 (dd, 1H, J=8.6, 1.6 Hz), 7.40 (d, 1H, J=8.6 Hz), 7.14 (d, 1H, J=3.1 Hz), 7.12 (m, 1H), 6.96 (m, 1H), 6.62 (dd, 1H, J=3.1, 0.9Hz), 6.36 (m, 1H), 3.85 (s, 3H).

(192-3)

The title compound was obtained from the compound of the compound of Example 192-2 in a similar manner to Example 18-3.
¹H NMR (CDCl₃, 400 MHz) δ 8.21 (d, 1H, J=1.6 Hz), 7.85 (d, 1H, J=2.3 Hz), 7.80 (dd, 1H, J=8.6, 1.6 Hz), 7.48 (d, 1H, J=8.5 Hz), 7.39 (dd, 1H, J=8.5, 2.3 Hz), 7.37 (d, 1H, J=8.6 Hz), 7.22 (d, 1H, J=15.8 Hz), 7.13 (d, 1H, J=3.1 Hz), 7.08 (dd, 1H, J=2.4, 1.8 Hz), 6.81 (dd, 1H, J=4.0, 1.8 Hz), 6.59 (dd, 1H, J=3.1, 0.6 Hz), 6.38 (dt, 1H, J=15.8, 6.1 Hz), 6.24 (dd, 1H, J=4.0, 2.4 Hz), 5.23 (dd, 2H, J=6.1, 1.4 Hz), 3.87 (s, 3H).

Example 193

¹H NMR (DMSO-d₆, 400 MHz) δ 8.06 (d, 1H, J=1.6 Hz), 7.65 (d, 1H, J=2.3 Hz), 7.63 (dd, 1H, J=8.6, 1.6 Hz), 7.60 (d, 1H, J=8.5 Hz), 7.52 (d, 1H, J=8.6 Hz), 7.44 (d, 1H, J=3.1 Hz), 7.42 (dd, 1H, J=8.5, 2.3 Hz), 7.31 (dd, 1H, J=2.6, 1.6 Hz), 7.20 (d, 1H, J=16.2 Hz), 6.67 (dd, 1H, J=3.9, 1.6 Hz), 6.58 (dd, 1H, J=3.1, 0.5 Hz), 6.43 (dt, 1H, J=16.2, 5.9 Hz), 6.22 (dd, 1H, J=3.9, 2.6 Hz), 5.18 (d, 2H, J=5.9 Hz), 3.84 (s, 3H).

Example 194

(194-1)

Under nitrogen atmosphere, a solution of KOtBu (11.5 g) in THF (203 mL) was cooled to 0° C., and thereto were added dropwise ethyl chloroacetate (12.5 g) and ethyl formate (7.60 g) in THF (40 mL). After the addition, the mixture was stirred at 0° C. for 3 hours, and further stirred at room temperature for 16 hours. Water and a 6N aqueous hydrochloric acid solution were added to the mixture, and the mixture was extracted with Et₂O, and dried over MgSO₄. The solvent was evaporated under reduced pressure to give ethyl 2-chloroformyl-propionate. Under nitrogen atmosphere, to a solution of ethyl 2-chloroformylpropionate in acetone (250 mL) was added thioacetamide (7.74 g), and the mixture was stirred at 56° C. for 6 hours, and stirred at room temperature for 16 hours. The solvent was evaporated under reduced pressure, and the residue was purified by silica gel column (hexane/ethyl acetate=12.5/1→10/1) to give ethyl 2-methyl-1,3-thiazole-5-carboxylate (5.74 g, 32%).
¹H NMR (CDCl₃, 400 MHz) δ 8.24 (s, 1H), 4.35 (q, 2H, J=7.1 Hz), 2.75 (s, 3H), 1.37 (t, 3H, J=7.1 Hz).

(194-2)

To a solution of the compound of Example 194-1 (5.74 g) in THF (100 mL)-MeOH (100 mL) was added a 6N NaOH solution (27 mL), and the mixture was stirred at room temperature for 16 hours. The solvent was evaporated under reduced pressure, and thereto was added a 6N aqueous hydrochloric acid solution, and the mixture was extracted with ethyl acetate, and dried over MgSO₄. The solvent was evaporated under reduced pressure to give 2-methyl-1,3-thiazole-5-carboxylic acid (4.02 g, 86%).
¹H NMR (DMSO-d₆, 400 MHz) δ 13.31 (brs, 1H), 8.17 (s, 1H), 2.70 (s, 3H).

(194-3)

Under nitrogen atmosphere, to a solution of the compound of Example 194-2 (1.35 g) in toluene (150 mL) were added 2,2'-dipyridyl-disulfide (4.15 g) and PPh₃ (4.94 g), and the mixture was stirred at room temperature for 16 hours. Then, the mixture was cooled to −78° C., and thereto was added a 1N pyrrolemagnesium bromide, which was prepared from pyrrole (2.02 g) and a 0.93N solution of methyl-magnesium bromide in Et₂O (34.4 mL), in toluene, and the mixture was stirred at −78° C. for 3 hours. To the mixture was added an aqueous NH₄Cl solution, and the mixture was warmed to room temperature. To the mixture was added water, and the mixure was extracted with ethyl acetate, and dried over MgSO₄. The solvent was evaporated under reduced pressure, and the residue was purified by silica gel column (hexane/ethyl acetate=4/1) to give (2-methyl-1,3-thiazol-5-yl)(1H-pyrrol-2-yl)methanone (1.12 g, 62%).
¹H NMR (CDCl₃, 400 MHz) δ 9.67 (brs, 1H), 8.36 (s, 1H), 7.16 (m, 1H), 7.13 (m, 1H), 6.38 (m, 1H), 2.79 (s, 3H).
(194-4)
Under nitrogen atmosphere, to a solution of the compound of Example 9-2 (443 mg) in CH₂Cl₂ (20 mL) were added N-bromosuccinimide (348 mg) and PPh₃ (513 mg), and the mixture was stirred at room temperature for 2 hours. The solvent was evaporated under reduced pressure, and the residue was purified by silica gel column (hexane/ethyl acetate=20/1) to give a bromo compound (462 mg, 82%). Under nitrogen atmosphere, to a solution of the compound of Example 194-3 (195 mg) in THF (10 mL) was added KOtBu (125 mg). Further, a solution of the bromo compound (294 mg) in THF (10 mL) was added thereto, and the mixture was stirred at room temperature for 1 hour. To the mixture was added an aqueous NH₄Cl solution, and the mixture was extracted with ethyl acetate, and dried over MgSO₄. The solvent was evaporated under reduced pressure, and the residue was purified by silica gel column (hexane/ethyl acetate=8/1→6/1) to give methyl 5-chloro-2-((1E)-3-{2-[(2-methyl-1,3-thiazol-5-yl)carbonyl]-1H-pyrrol-1-yl}prop-1-enyl)benzoate (248 mg, 61%).
¹H NMR (CDCl₃, 400 MHz) δ 8.20 (s, 1H), 7.86 (d, 1H, J=2.2 Hz), 7.46 (d, 1H, J=8.4 Hz), 7.40 (dd, 1H, J=8.4, 2.2 Hz), 7.18 (d, 1H, J=15.7 Hz), 7.12 (m, 1H), 7.08 (m, 1H), 6.30 (m, 2H), 5.15 (dd, 2H, J=6.0, 1.3 Hz), 3.87 (s, 3H), 2.77 (s, 3H).
(194-5)
To a solution of the compound of Example 194-4 (248 mg) in THF (7.5 mL)-MeOH (7.5 mL) was added a 2N NaOH solution (1.6 mL), and the mixture was stirred at room temperature for 48 hours. The solvent was evaporated under reduced pressure, and thereto was added a 2N aqueous hydrochloric acid solution, and the mixture was extracted with ethyl acetate, and dried over MgSO₄. The solvent was evaporated under reduced pressure, and the residue was purified by silica gel column (CHCl₃/MeOH=34/1→10/1) to give the title compound (181 mg, 76%).
¹H NMR (DMSO-d₆, 400 MHz) δ 8.26 (s, 1H), 7.67 (d, 1H, J=2.3 Hz), 7.61 (d, 1H, J=8.5 Hz), 7.46 (dd, 1H, J=8.5, 2.3 Hz), 7.40 (dd, 1H, J=2.5, 1.6 Hz), 7.15 (dd, 1H, J=4.1, 1.6 Hz), 7.09 (d, 1H, J=15.7 Hz), 6.40 (dt, 1H, J=15.7, 5.7 Hz), 6.28 (dd, 1H, J=4.1, 2.5 Hz), 5.12 (dd, 2H, J=5.7, 1.1 Hz), 2.71 (s, 3H).

Example 195
(195-1)
A solution of ethyl p-aminobenzoate (23.2 g) and potassium thiocyanate (40.9 g) in acetic acid (280 mL) was cooled to 0° C., and thereto was added dropwise bromine (22.4 g), and the mixture was stirred at 0° C. for 20 minuts, and stirred at room temperature for 135 minutes, and stirred for 5 hours. The precipitated solid was collected by filtration to give ethyl 2-amino-1,3-benzothiazole-6-carboxylate (9.62 g, 31%)
¹H NMR (DMSO-d₆, 400 MHz) δ 8.65 (brs, 2H), 8.38 (d, 1H, J=1.7 Hz), 7.89 (dd, 1H, J=8.5, 1.7 Hz), 7.44 (d, 1H, J=8.5 Hz), 4.30 (q, 2H, J=7.1 Hz), 1.32 (t, 3H, J=7.1 Hz).
(195-2)
Under nitrogen atmosphere, a solution of the compound of Example 195-1 (3.09 g) and copper (II) bromide (10.8 g) in CH₃CN (200 mL) was cooled to 0° C., and thereto was added dropwise isobutyl nitrite (6.27 g), and the mixture was stirred at 0° C. for 10 minutes, and stirred at room temperature for 2 hours. Water was added to the mixture, and the mixture was extracted twice with Et₂O. The organic layer was washed with water, and dried over MgSO₄. The solvent was evaporated under reduced pressure to give a crude ethyl 2-bromo-1,3-benzo-thiazole-6-carboxylate (8.16 g). Under nitrogen atmosphere, to a solution of this compound (4.00 g) in DMSO (100 mL)-CH₃CN (100 mL) were added successively Pd(PPh₃)₄(485 mg) and sodium formate (4.76 g), and the mixture was stirred at 100° C. for 75 minutes. The solvent was evaporated under reduced pressure, and thereto was added water, and the mixture was extracted four times with Et₂O, and dried over MgSO₄. The solvent was evaporated under reduced pressure, and the residue was purified by silica gel column (hexane/ethyl acetate=10/1) to give ethyl 1,3-benzothiazole-6-carboxylate (1.21 g, 42%).
¹H NMR (CDCl₃, 400 MHz) δ 9.15 (s, 1H), 8.71 (dd, 1H, J=1.6, 0.5 Hz), 8.21 (dd, 1H, J=8.6, 1.6 Hz), 8.17 (dd, 1H, J=8.6, 0.5 Hz), 4.44 (q, 2H, J=7.1 Hz), 1.44 (t, 3H, J=7.1 Hz).
(195-3)
To a solution of the compound of Example 195-2 (1.21 g) in THF (50 mL)-EtOH (50 mL) was added a 2N NaOH solution (14.6 mL), and the mixture was stirred at room temperature for 64 hours. The solvent was evaporated under reduced pressure, and thereto was added water, and washed with ethyl acetate. The mixture was cooled to 0° C., and thereto was added a 2.5N aqueous hydrochloric acid to adjust the pH value thereof to pH=3. The mixtuer was extracted five times with ethyl acetate, and dried over MgSO₄. The solvent was evaporated under reduced pressure to give 1,3-benzothiazole-6-carboxylic acid (983.1 mg, 94%).
¹H NMR (DMSO-d₆, 400 MHz) δ 13.10 (brs, 1H), 9.58 (s, 1H), 8.81 (d, 1H, J=1.3 Hz), 8.17 (d, 1H, J=8.5 Hz), 8.08 (dd, 1H, J=8.5, 1.3 Hz).
(195-4)
Ethyl 2-bromo-1,3-benzothiazole-6-carboxylate was obtained from the compound of Example 195-3 in a similar manner to Example 125-2.
¹H NMR (CDCl₃, 400 MHz) δ 9.71 (brs, 1H), 9.16 (s, 1H), 8.56 (d, 1H, J=1.2 Hz), 8.24 (d, 1H, J=8.5 Hz), 8.09 (dd, 1H, J=8.5, 1.2 Hz), 7.19 (m, 1H), 6.95 (m, 1H), 6.39 (m, 1H).
(195-5)
Methyl 2-{(1E)-3-[2-(1,3-benzothiazol-6-ylcarbonyl)-1H-pyrrol-1-yl]prop-1-enyl}-5-chlorobenzoate was obtained from the compound of Example 195-4 in a similar manner to Example 18-3.
¹H NMR (CDCl₃, 400 MHz) δ 9.14 (s, 1H), 8.48 (d, 1H, J=1.3 Hz), 8.20 (d, 1H, J=8.5 Hz), 8.01 (dd, 1H, J=8.5, 1.3 Hz), 7.86 (d, 1H, J=2.2 Hz), 7.49 (d, 1H, J=8.5 Hz), 7.41 (dd, 1H, J=8.5, 2.2 Hz), 7.22 (d, 1H, J=15.8 Hz), 7.14 (dd, 1H, J=2.4, 1.8 Hz), 6.81 (dd, 1H, J=4.0, 1.8 Hz), 6.36 (dt, 1H, J=15.8, 5.9 Hz), 6.27 (dd, 1H, J=4.0, 2.4 Hz), 5.26 (dd, 2H, J=5.9, 1.5 Hz), 3.87 (s, 3H).
(195-6)
The title compound was obtained from the compound of Example 195-5 in a similar manner to Example 16.
¹H NMR (DMSO-d₆, 400 MHz) δ 9.56 (s, 1H), 8.62 (d, 1H, J=1.5 Hz), 8.17 (d, 1H, J=8.5 Hz), 7.90 (dd, 1H, J=8.5, 1.5 Hz), 7.64 (d, 1H, J=2.2 Hz), 7.59 (d, 1H, J=8.5 Hz), 7.39 (m, 2H), 7.26 (d, 1H, J=15.3 Hz), 6.76 (dd, 1H, J=4.0, 1.6 Hz), 6.42 (dt, 1H, J=15.3, 5.9 Hz), 6.25 (dd, 1H, J=4.0, 2.5 Hz), 5.20 (d, 2H, J=5.9 Hz).

Example 196

(196-1)

Under nitrogen atmosphere, a solution of 2,2,6,6-tetramethyl-piperidine (5.00 mL) in THF (120 mL) was cooled to −78° C., and thereto was added dropwise a 1.6N solution of BuLi in hexane (18.5 mL), and the mixture was stirred at room temperature for 30 minutes. The mixture was cooled again to −78° C., and thereto was added a solution of N-benzenesulfonylpyrrole (5.58 g) in THF (25 mL). The mixture was stirred for 30 minutes, and thereto was added a solution of 6-methyl-pyridine-2-aldehyde (3.94 g) in THF (20 mL), and the mixture was stirred at −78° C. for 2 hours. Water was added to the mixture, and the mixture was extracted twice with ethyl acetate. The organic layer was washed with a saturated brine and dried over $MgSO_4$. The solvent was evaporated under reduced pressure, and the precipitated solid was suspended in a mixed solvent of hexane/ethyl acetate=5/1, and collected by filtration to give [1-(phenylsulfonyl)-1H-pyrrol-2-yl](6-methylpyridin-2-yl)methanol (6.78 g, 77%).

$^1$H NMR (CDCl$_3$, 400 MHz) δ 7.99 (dd, 2H, J=1.3, 8.4 Hz), 7.61 (tt, 1H, J=1.3, 7.4 Hz), 7.49-7.56 (m, 3H), 7.30 (dd, 1H, J=1.7, 3.3 Hz), 7.08 (d, 1H, J=7.6 Hz), 7.04 (d, 1H, J=7.7 Hz), 6.25 (d, 1H, J=5.3 Hz), 6.16 (dd, 1H, J=3.3, 3.3 Hz), 5.76 (dd, 1H, J=1.7, 3.3 Hz), 5.14 (d, 1H, J=5.3 Hz), 2.55 (s, 3H).

(196-2)

Under nitrogen atmosphere, to a solution of the compound of Example 196-1 (5.83 g) in CHCl$_3$ (90 mL) was added MnO$_2$ (31.2 g), and the mixture was stirred at room temperature for 1 hour, and filtered. The solvent was evaporated under reduced pressure to give a crude ketone compound (5.94 g). Under nitrogen atmosphere, to a solution of the crude ketone compound (4.62 g) in dioxane (30 mL) was added a 2N aqueous NaOH solution (27 mL), and the mixture was stirred at 80° C. for 1 hour. The reaction solution was cooled to room temperature, and the pH value of the mixture was adjusted to pH=8 with conc. hydrochloric acid and a saturated aqueous sodium hydrogen carbonate solution, and the mixture was extracted twice with ethyl acetate. The extract was washed with a saturated brine, and dried over MgSO$_4$. The solvent was evaporated under reduced pressure, and the residue was purified by silica gel column (toluene/ethyl acetate=3/2) to give (1H-pyrrol-2-yl)(6-methylpyridin-2-yl) ketone (2.68 g, 100%).

$^1$H NMR (CDCl$_3$, 400 MHz) δ 11.7 (br, 1H), 8.08 (d, 1H, J=7.7 Hz), 7.78 (dd, 1H, J=7.7, 7.7 Hz), 7.48 (br, 1H), 7.33 (d, 1H, J=7.7 Hz), 7.11-7.12 (m, 1H), 6.36-6.38 (m, 1H), 2.70 (s, 3H).

(196-3)

The title compound was obtained from the compound of Example 196-2 and the compound of Example 9-2 in a similar manner to Example 18-3.

$^1$H NMR (CDCl$_3$, 400 MHz) δ 7.85 (d, 1H, J=2.3 Hz), 7.71-7.72 (m, 2H), 7.49 (d, 1H, J=8.4 Hz), 7.40 (dd, 1H, J=2.3, 8.4 Hz), 7.36 (dd, 1H, J=1.7, 4.1 Hz), 7.28-7.30 (m, 1H), 7.23 (d, 1H, J=15.8 Hz), 7.10 (dd, 1H, J=1.7, 2.5 Hz), 6.38 (dt, 1H, J=15.8, 6.1 Hz), 6.25 (dd, 1H, J=2.5, 4.1 Hz), 5.25 (d, 2H, J=6.1 Hz), 3.87 (s, 3H), 2.65 (s, 3H).

Example 197

$^1$H NMR (CDCl$_3$, 400 MHz) δ 7.78-7.82 (m, 2H), 7.49 (d, 1H, J=7.6 Hz), 7.35-7.38 (m, 2H), 7.26 (d, 1H, J=8.3 Hz), 7.07 (dd, 1H, J=1.6, 2.5 Hz), 6.77 (dd, 1H, J=1.6, 4.1 Hz), 6.42 (d, 1H, J=15.8 Hz), 6.23 (dd, 1H, J=2.5, 4.1 Hz), 6.05 (dt, 1H, J=15.8, 4.2 Hz), 5.27 (d, 2H, J=4.2 Hz), 2.79 (s, 3H).

Example 198

(198-1)

(1-Phenylsulfonyl-1H-pyrrol-2-yl) (3,4-dimethoxyphenyl) ketone was obtained from veratroyl chloride and pyrrolesulfonamide.

$^1$H NMR (CDCl$_3$, 400 MHz) δ 9.55 (brs, 1H), 7.62 (dd, 1H, J=8.3 and 2.0 Hz), 7.48 (d, 1H, J=2.0 Hz), 7.13 (dt, 1H, J=1.3 and 2.6 Hz), 6.94 (d, 1H, J=8.3 Hz), 6.92 (ddd, 1H, J=3.8, 2.4 and 1.3 Hz), 6.35 (dt, 1H, J=3.8 and 2.6 Hz), 3.97 (s, 3H), 3.96 (s, 3H).

(198-2)

The title compound was obtained from the compound of Example 198-1 and the compound of Example 9-2 in a similar manner to Example 18-3.

$^1$H NMR (CDCl$_3$, 400 MHz) δ 7.85 (d, 1H, J=2.2 Hz), 7.52 (dd, 1H, J=8.3 and 2.0 Hz), 7.48 (d, 1H, J=8.5 Hz), 7.44 (d, 1H, J=2.0 Hz), 7.40 (dd, 1H, J=8.5 and 2.2 Hz), 7.21 (dt, 1H, J=15.8 and 1.4 Hz), 7.09 (dd, 1H, J=1.7 and 2.5 Hz), 6.91 (d, 1H, J=8.3 Hz), 6.80 (dd, 1H, J=1.7 and 4.0 Hz), 6.36 (dt, 1H, J=15.8 and 6.1 Hz), 6.23 (dd, 1H, J=2.5 and 4.0 Hz), 5.20 (dd, 2H, J=1.4 and 6.1 Hz), 3.96 (s, 3H), 3.94 (s, 3H), 3.87 (s, 3H).

Example 199

$^1$H NMR (DMSO-d$_6$, 400 MHz) δ 7.43 (dd, 1H, J=8.3 and 2.0 Hz), 7.42 (brd, 1H, J=15.8 Hz), 7.38 (d, 1H, J=8.5 Hz), 7.37 (brs, 1 Hz), 7.34 (brs, 1H), 7.31 (dd, 1H, J=1.7 and 2.5 Hz), 7.09 (dd, 1H, J=8.5 and 2.2 Hz), 7.05 (d, 1H, J=8.3 Hz), 6.70 (dd, 1H, J=1.7 and 4.0 Hz), 6.23 (dt, 1H, J=15.8 and 6.1 Hz), 6.20 (dd, 1H, J=2.5 and 4.0 Hz), 5.08 (brd, 2H, J=6.1 Hz), 3.84 (s, 3H), 3.82 (s, 3H).

Example 200

(200-1)

1,3-Benzodioxol-5-yl(1H-pyrrol-2-yl)methanone was obtained from piperonyl chloride and pyrrolesulfonamide.

$^1$H NMR (CDCl$_3$, 400 MHz) δ 9.50 (brs, 1H), 7.55 (dd, 1H, J=8.1 and 1.7 Hz), 7.48 (d, 1H, J=1.7 Hz), 7.12 (dt, 1H, J=1.3 and 2.7 Hz), 6.89 (d, 1H, J=8.1 Hz), 6.88 (ddd, 1H, J=3.8, 2.4 and 1.3 Hz), 6.34 (dt, 1H, J=3.8 and 2.7 Hz), 6.06 (s, 2H).

(200-2)

The title compound was obtained from the compound of Example 200-1 and the compound of Example 9-2 in a similar manner to Example 18-3.

$^1$H NMR (CDCl$_3$, 400 MHz) δ 7.85 (d, 1H, J=2.2 Hz), 7.48 (d, 1H, J=8.5 Hz), 7.44 (dd, 1H, J=8.1 and 1.7 Hz), 7.40 (dd, 1H, J=8.5 and 2.2 Hz), 7.35 (d, 1H, J=1.7 Hz), 7.18 (dt, 1H, J=15.8 and 1.4 Hz), 7.08 (dd, 1H, J=1.7 and 2.5 Hz), 6.86 (d, 1H, J=8.1 Hz), 6.78 (dd, 1H, J=1.7 and 4.0 Hz), 6.33 (dt, 1H, J=15.8 and 6.1 Hz), 6.23 (dd, 1H, J=2.5 and 4.0 Hz), 6.04 (s, 2H), 5.19 (dd, 2H, J=1.4 and 6.1 Hz), 3.87 (s, 3H).

Example 201

$^1$H NMR (DMSO-d$_6$, 400 MHz) δ 7.40 (brd, 1H, J=15.8 Hz), 7.38 (dd, 1H, J=8.1 and 1.7 Hz), 7.38-7.32 (m, 2H), 7.31 (dd, 1H, J=1.7 and 2.5 Hz), 7.28 (d, 1H, J=1.7 Hz), 7.10 (m, 1H), 7.01 (d, 1H, J=8.1 Hz), 6.67 (dd, 1H, J=1.7 and 4.0 Hz), 6.22 (brdt, 1H, J=15.8 and 6.1 Hz), 6.19 (dd, 1H, J=2.5 and 4.0 Hz), 6.13 (s, 2H), 5.07 (brd, 2H, J=6.1 Hz).

Example 202

(202-1)

Under nitrogen atmosphere, to a solution of the compound of Example 109-6 (300 mg) in DMF (4.0 mL) were added successively 60% NaH (69.8 mg) and 4-bromo-1-butene (170 μL), and the mixture was stirred at 80° C., during which 60% NaH (45.0 mg) and 4-bromo-1-butene (200 μL) were added thereto, and the mixture was stirred for total 9 hours. Water was added to the reaction solution, and the mixture was extracted with ethyl acetate-toluene. The organic layer was washed twice with water, and washed with a saturated brine, and dried over MgSO$_4$. The solvent was evaporated under reduced pressure, and the residue was purified by silica gel column (hexane/ethyl acetate=6/1→2/1) to give [1-(4-buten-1-yl)-4-methyl-1H-pyrrol-2-yl](4-methoxyphenyl)methanone (242 mg, 65%).
$^1$H NMR (CDCl$_3$, 400 MHz) δ 7.80 (d, 2H, J=8.8 Hz), 6.94 (d, 2H, J=8.8 Hz), 6.74 (d, 1H, J=1.3 Hz), 6.52 (d, 1H, J=1.3 Hz), 5.79 (ddt, 1H, J=10.4, 17.1, 7.1 Hz), 5.06 (dd, 1H, J=17.1, 1.7 Hz), 5.02 (dd, 1H, J=10.4, 1.7 Hz), 4.38 (t, 2H, J=7.1 Hz), 3.88 (s, 3H), 2.54 (dt, 2H, J=7.1, 7.1 Hz), 2.07 (s, 3H).

(202-2)
Under nitrogen atmosphere, a suspension of methyl 5-chloro-2-iodobenzoate (Example 109-9) (220 mg), the compound of Example 202-1 (200 mg), Pd(OAc)$_2$ (22.9 mg), BnEt3NCl (171 mg), sodium hydrogen carbonate (130 mg), tri-o-tolylphosphine (68.4 mg) in DMF (4.0 mL) was stirred at 80° C. for 4 hours, and stirred at 100° C. for 11 hours, during which silver (I) carbonate (207 mg) was added thereto. The mixture was cooled to room temperature, and the mixture was filtered. Water was added to the filtrate, and the mixture was extracted with ethyl acetate/toluene. The organic layer was washed with water and a saturated brine, and dried over MgSO$_4$. The solvent was evaporated under reduced pressure, and the residue was purified by silica gel column (hexane/ethyl acetate=7/1→5/1) to give methyl 5-chloro-2-{(1E)-4-[2-(4-methoxybenzoyl)-4-methyl-1H-pyrrol-1-yl]-1-butenyl}benzoate (55.0 mg, 17%).
$^1$H NMR (CDCl$_3$, 400 MHz) δ 7.81 (d, 1H, J=2.2 Hz), 7.77 (d, 2H, J=8.8 Hz), 7.36 (d, 1H, J=8.5 Hz), 7.32 (dd, 1H, J=2.2, 8.5 Hz), 7.10 (d, 1H, J=15.7 Hz), 6.90 (d, 2H, J=8.8 Hz), 6.77 (d, 1H, J=1.4 Hz), 6.51 (d, 1H, J=1.4 Hz), 6.08 (dt, 1H, J=15.7, 7.1 Hz), 4.49 (t, 2H, J=7.1 Hz), 3.89 (s, 3H), 3.87 (s, 3H), 2.72 (dt, 2H, J=7.1, 7.1 Hz), 2.07 (s, 3H).

(202-3)
The title compound was obtained from the compound of Example 202-2 in a similar manner to Example 16.
$^1$H NMR (CDCl$_3$, 400 MHz) δ 7.93 (d, 1H, J=1.7 Hz), 7.76 (d, 2H, J=8.8 Hz), 7.37 (m, 2H), 7.16 (d, 1H, J=15.6 Hz), 6.90 (d, 2H, J=8.8 Hz), 6.78 (d, 1H, J=1.3 Hz), 6.52 (d, 1H, J=1.3 Hz), 6.09 (dt, 1H, J=15.6, 6.9 Hz), 4.50 (t, 2H, J=6.9 Hz), 3.86 (s, 3H), 2.72 (dt, 2H, J=6.9, 6.9 Hz), 2.07 (s, 3H).

Example 203

(203-1)
(2E,4E)-5-(4-Chloro-2-methoxycarbonylphenyl)-2,4-pentadienoic acid was obtained from methyl 5-chloro-2-iodobenzoate (Example 109-9) (600 mg) and 1,3-butadiene-1-carboxylic acid (240 mg) in a similar manner to Example 202-2.
$^1$H NMR (DMSO-d$_6$, 400 MHz) δ 12.38 (brs, 1H), 7.85 (d, 1H, J=8.6 Hz), 7.82 (d, 1H, J=2.3 Hz), 7.68 (dd, 1H, J=2.3, 8.6 Hz), 7.53 (d, 1H, J=15.5 Hz), 7.34 (dd, 1H, J=11.0, 15.1 Hz), 7.10 (dd, 1H, J=11.0, 15.5 Hz), 6.07 (d, 1H, J=15.1 Hz), 3.87 (s, 3H).

(203-2)
Methyl 5-chloro-2-[(1E,3E)-5-hydroxy-1,3-pentadienyl] benzoate was obtained from the compound of Example 203-1 (173 mg) in a similar manner to Example 9-2.
$^1$H NMR (CDCl$_3$, 400 MHz) δ 7.86 (d, 1H, J=2.3 Hz), 7.55 (d, 1H, J=8.5 Hz), 7.43 (dd, 1H, J=2.3, 8.5 Hz), 7.34 (d, 1H, J=15.5 Hz), 6.70 (dd, 1H, J=10.6, 15.5 Hz), 6.49 (dd, 1H, J=10.6, 15.1 Hz), 6.01 (dd, 1H, J=15.1, 5.7 Hz), 4.27 (d, 2H, J=5.7 Hz), 3.91 (s, 3H).

(203-3)
Methyl 5-chloro-2-{(1E,3E)-5-[2-(4-methoxybenzoyl)-4-methyl-1H-pyrrol-1-yl]-1,3-pentadienyl}benzoate was obtained from the compound of Example 203-2 and Example 109-6 in a similar manner to Example 18-3.
$^1$H NMR (CDCl$_3$, 400 MHz) δ 7.84 (d, 1H, J=2.2 Hz), 7.82 (d, 2H, J=8.8 Hz), 7.51 (d, 1H, J=8.5 Hz), 7.40 (dd, 1H, J=2.2, 8.5 Hz), 7.30 (d, 1H, J=15.6 Hz), 6.95 (d, 2H, J=8.8 Hz), 6.79 (d, 1H, J=1.3 Hz), 6.67 (dd, 1H, J=10.5, 15.6 Hz), 6.56 (d, 1H, J=1.3 Hz), 6.30 (dd, 1H, J=10.5, 15.0 Hz), 6.09 (dt, 1H, J=15.0, 6.0 Hz), 5.05 (d, 2H, J=6.0 Hz), 3.90 (s, 3H), 3.88 (s, 3H), 2.10 (s, 3H).

(203-4)
The title compound was obtained from the compound of Example 203-3 in a similar manner to Example 16.
$^1$H NMR (CDCl$_3$, 400 MHz) δ 7.97 (d, 1H, J=2.3 Hz), 7.82 (d, 2H, J=8.8 Hz), 7.53 (d, 1H, J=8.5 Hz), 7.45 (dd, 1H, J=2.3, 8.5 Hz), 7.37 (d, 1H, J=15.6 Hz), 6.95 (d, 2H, J=8.8 Hz), 6.80 (d, 1H, J=1.5 Hz), 6.68 (dd, 1H, J=10.4, 15.6 Hz), 6.57 (d, 1H, J=1.5 Hz), 6.33 (dd, 1H, J=10.4, 15.0 Hz), 6.10 (dt, 1H, J=15.0, 6.0 Hz), 5.06 (d, 2H, J=6.0 Hz), 3.87 (s, 3H), 2.10 (s, 3H).

Example 204

(204-1)
[1-(2-propin-1-yl)-1H-pyrrol-2-yl](4-methylphenyl)methanone was obtained from the compound of Reference Example 1 and propargyl chloride in a similar manner to Example 202-1.
$^1$H NMR (CDCl$_3$, 400 MHz) δ 7.73 (d, 2H, J=8.1 Hz), 7.29 (dd, 1H, J=1.6, 2.6 Hz), 7.26 (d, 2H, J=8.1 Hz), 6.78 (dd, 1H, J=1.6, 4.0 Hz), 6.22 (dd, 1H, J=2.6, 4.0 Hz), 5.30 (d, 2H, J=2.6 Hz), 2.45 (t, 1H, J=2.6 Hz), 2.43 (s, 3H).

(204-2)
The title compound was obtained from methyl 5-chloro-2-iodo-benzoate (Example 109-9) and the compound of Example 204-1 in a similar manner to Example 48.
$^1$H NMR (CDCl$_3$, 400 MHz) δ 7.93 (d, 1H, J=2.2 Hz), 7.74 (d, 2H, J=8.0 Hz), 7.56 (dd, 1H, J=1.7, 2.7 Hz), 7.49 (d, 1H, J=8.3 Hz), 7.43 (dd, 1H, J=2.2, 8.3 Hz), 7.26 (d, 2H, J=8.0 Hz), 6.80 (dd, 1H, J=1.7, 4.0 Hz), 6.26 (dd, 1H, J=2.7, 4.0 Hz), 5.58 (s, 2H), 3.89 (s, 3H), 2.43 (s, 3H).

Example 205

(205-1)
Under nitrogen atmosphere, a solution of 5-chlorosalicylic acid (5.00 g) in MeOH (100 mL) was cooled to 0° C., and thereto was added dropwise SOCl$_2$ (3.20 mL). After the addition, the mixture was stirred at 60° C. for 10 hours. The solvent was evaporated under reduced pressure, and the residue was dissolved in ethyl acetate, washed twice with water, washed with a saturated brine, and dried over MgSO$_4$. The solvent was evaporated under reduced pressure, and the residue was purified by silica gel column (hexane/ethyl acetate=5/1) to give methyl 5-chloro-2-hydroxybenzoate (4.03 g, 74%).
$^1$H NMR (CDCl$_3$, 400 MHz) δ 10.68 (s, 1H), 7.81 (d, 1H, J=2.7 Hz), 7.40 (dd, 1H, J=2.7, 8.9 Hz), 6.94 (d, 1H, J=8.9 Hz), 3.96 (s, 3H).

(205-2)
Under nitrogen atmosphere, a solution of the compound of Example 205-1 (500 mg) in DMF (10 mL) was cooled to 0° C., and thereto were added successively 60% NaH (122 mg) and (2-bromoethoxy)tert-butyldimethylsilane (960 mg), and the mixture was stirred at 50° C. for 2 hours, and stirred at 80° C. for 4 hours. The reaction solution was poured into a 5% aqueous KHSO$_4$ solution, and the mixture was extracted with ethyl acetate-toluene. The organic layer was washed with water and a saturated brine, and dried over MgSO₄. The solvent was evaporated under reduced pressure, and the residue was purified by silica gel column (hexane/ethyl acetate=12/1→8/1) to give methyl 2-[2-(t-butyldimethylsilyl)oxy]ethoxy-5-chlorobenzoate (553 mg, 60%).
¹H NMR (CDCl₃, 400 MHz) δ 7.72 (d, 1H, J=2.7 Hz), 7.38 (dd, 1H, J=2.7, 8.9 Hz), 6.97 (d, 1H, J=8.9 Hz), 4.11 (t, 2H, J=5.4 Hz), 3.98 (t, 2H, J=5.4 Hz), 3.88 (s, 3H), 0.89 (s, 9H), 0.08 (s, 6H).
(205-3)
Under nitrogen atmosphere, to a solution of the compound of Example 205-2 (350 mg) in THF (6.0 mL) were added successively acetic acid (200 μL) and Bu₄NF (400 mg), and the mixture was stirred at room temperature for 2 hours. To the mixture was added a 5% aqueous KHSO₄ solution, and the mixture was extracted with ethyl acetate. The extract was washed with water and a saturated brine, and dried over MgSO₄. The solvent was evaporated under reduced pressure, and the residue was purified by silica gel column (hexane/ethyl acetate=3/1→1/3) to give methyl 5-chloro-2-(2-hydroxyethoxy)benzoate (187 mg, 80%).
¹H NMR (CDCl₃, 400 MHz) δ 7.80 (d, 1H, J=2.7 Hz), 7.44 (dd, 1H, J=2.7, 8.8 Hz), 6.96 (d, 1H, J=8.8 Hz), 4.21 (t, 2H, J=4.5 Hz), 3.90-3.92 (m, 2H), 3.90 (s, 3H), 3.59 (brs, 1H).
(205-4)
The title compound was obtained from the compound of Example 205-3 and the compound of Example 109-6 in a similar manner to Example 18-3.
¹H NMR (CDCl₃, 400 MHz) δ 7.79 (d, 2H, J=8.8 Hz), 7.75 (d, 1H, J=2.7 Hz), 7.36 (dd, 1H, J=2.7, 8.9 Hz), 7.05 (d, 1H, J=1.4 Hz), 6.95 (d, 2H, J=8.8 Hz), 6.88 (d, 1H, J=8.9 Hz), 6.57 (d, 1H, J=1.4 Hz), 4.72 (t, 2H, J=4.8 Hz), 4.40 (t, 2H, J=4.8 Hz), 3.91 (s, 3H), 3.88 (s, 3H), 2.08 (s, 3H).

Example 206
¹H NMR (DMSO-d₆, 400 MHz) δ 13.0 (brs, 1H), 7.72 (d, 2H, J=8.5 Hz), 7.62 (d, 1H, J=2.6 Hz), 7.50 (dd, 1H, J=2.6, 8.9 Hz), 7.14-7.17 (m, 2H), 7.03 (d, 2H, J=8.5 Hz), 6.48 (s, 1H), 4.64 (t, 2H, J=4.8 Hz), 4.33 (t, 2H, J=4.8 Hz), 3.84 (s, 3H), 2.01 (s, 3H).

Example 207
(207-1)
Under nitrogen atmosphere, to a solution of methyl 5-chloro-2-iodobenzoate (Example 109-9) (202 mg) and (2E)-2-methyl-3-tributyl-stannylprop-2-en-1-ol (230 mg) in THF (5.0 mL) were added successively bis(dibenzylideneacetone)palladium (26.8 mg) and tri-(2-furyl)-phosphine (31.4 mg), and the mixture was refluxed for 22 hours. The solvent was evaporated under reduced pressure, and the residue was purified by silica gel column (hexane/ethyl acetate=8/1→3/1→1/1) to give (2E)-3-(4-chloro-2-methoxycarbonylphenyl)-2-methylpropenol (72.0 mg, 47%).
¹H NMR (CDCl₃, 400 MHz) δ 7.94 (d, 1H, J=2.3 Hz), 7.45 (dd, 1H, J=2.3, 8.3 Hz), 7.23 (d, 1H, J=8.3 Hz), 6.88 (q, 1H, J=1.3 Hz), 4.22 (d, 2H, J=6.0 Hz), 3.87 (s, 3H), 1.72 (d, 3H, J=1.3 Hz), 1.64 (t, 1H, J=6.0 Hz).
(207-2)
The title compound was obtained from the compound of Example 207-1 and the compound of Example 109-6 in a similar manner to Example 18-3.
¹H NMR (CDCl₃, 400 MHz) δ 7.89 (d, 1H, J=2.3 Hz), 7.82 (d, 2H, J=8.8 Hz), 7.40 (dd, 1H, J=2.3, 8.3 Hz), 7.15 (d, 1H, J=8.3 Hz), 6.93 (d, 2H, J=8.8 Hz), 6.90 (d, 1H, J=1.4 Hz), 6.55 (d, 1H, J=1.4 Hz), 6.47 (s, 1H), 5.10 (s, 2H), 3.87 (s, 3H), 3.81 (s, 3H), 2.11 (s, 3H), 1.65 (s, 3H).

Example 208
¹H NMR (CDCl₃, 400 MHz) δ 7.99 (d, 1H, J=2.3 Hz), 7.80 (d, 2H, J=8.8 Hz), 7.45 (dd, 1H, J=2.3, 8.3 Hz), 7.18 (d, 1H, J=8.3 Hz), 6.91 (d, 2H, J=8.8 Hz), 6.89 (d, 1H, J=1.3 Hz), 6.55 (d, 1H, J=1.3 Hz), 6.49 (s, 1H), 5.08 (s, 2H), 3.84 (s, 3H), 2.09 (s, 3H), 1.66 (s, 3H).

Example 209
(209-1)
Under nitrogen atmosphere, a solution of the compound of Example 9-2 (250 mg) in CH₂Cl₂ (5.0 mL) was cooled to 0° C., and thereto was added dropwise a 1.02N solution of Et₂Zn in hexane (3.50 mL), and the mixture was stirred at the same temperature for 30 minutes. To the mixture was added dropwise CH₂I₂ (500 μL), and the mixture was stirred at 0° C. for 1 hour, and stirred at room temperature for 3 hours. To the mixture was added a 1N aqueous hydrochloric acid solution, and the mixture was extracted with ethyl acetate. The extract was washed with a saturated brine, and dried over MgSO₄. The solvent was evaporated under reduced pressure, and the residue was purified by silica gel column (hexane/ethyl acetate=3/2) to give methyl 5-chloro-2-[2-(hydroxymethyl)cyclopropyl]benzoate (189 mg, 71%).
¹H NMR (CDCl₃, 400 MHz) δ 7.92 (d, 1H, J=2.3 Hz), 7.40 (dd, 1H, J=2.3, 8.4 Hz), 7.08 (d, 1H, J=8.4 Hz), 3.94 (s, 3H), 3.95-4.01 (m, 1H), 3.16-3.21 (m, 2H), 2.31-2.35 (m, 1H), 1.13-1.23 (m, 2H), 0.83-0.87 (m, 1H).
(209-2)
The title compound was obtained from the compound of Example 209-1 and the compound of Example 109-6 in a similar manner to Example 18-3.
¹H NMR (CDCl₃, 400 MHz) δ 7.80 (d, 2H, J=8.8 Hz), 7.80 (d, 1H, J=2.3 Hz), 7.31 (dd, 1H, J=2.3, 8.4 Hz), 6.94 (d, 2H, J=8.8 Hz), 6.90 (d, 1H, J=8.4 Hz), 6.85 (d, 1H, J=1.4 Hz), 6.53 (d, 1H, J=1.4 Hz), 4.53 (dd, 1H, J=6.3, 14.0 Hz), 4.29 (dd, 1H, J=7.2, 14.0 Hz), 3.92 (s, 3H), 3.88 (s, 3H), 2.69-2.73 (m, 1H), 2.08 (s, 3H), 1.63-1.70 (m, 1H), 1.05-1.10 (m, 1H), 0.93-0.98 (m, 1H).
Example 210
¹H NMR (CDCl₃, 400 MHz) δ 7.91 (d, 1H, J=2.4 Hz), 7.80 (d, 2H, J=8.8 Hz), 7.36 (dd; 1H, J=2.4, 8.4 Hz), 6.96 (d, 1H, J=8.4 Hz), 6.93 (d, 2H, J=8.8 Hz), 6.85 (d, 1H, J=1.3 Hz), 6.54 (d, 1H, J=1.3 Hz), 4.63 (dd, 1H, J=6.1, 14.0 Hz), 4.23 (dd, 1H, J=7.4, 14.0 Hz), 3.87 (s, 3H), 2.72-2.77 (m, 1H), 2.07 (s, 3H), 1.65-1.70 (m, 1H), 1.08-1.13 (m, 1H), 0.96-1.01 (m, 1H).

Example 211
(211-1)
A carboxylic acid (969 mg) was obtained from methyl 5-chloro-2-iodobenzoate (Example 109-9) (1.00 g) in a similar manner to Example 16. Under nitrogen atmosphere, to the carboxylic acid (969 mg) were added successively toluene (3.0 mL), SOCl₂ (500 μl) and a drop of DMF, and the mixture was stirred 70° C. for 1 hour. The solvent was subjected three times to azeotropic distillation with toluene, and thereto were added successively toluene (3.0 mL), t-butanol (3.0 mL) and N,N'-dimethylaminopyridine (500 mg). The mixture was stirred at 50° C. for 8 hours, and water was added thereto. The mixture was extracted with ethyl acetate, and the extract was washed with a saturated brine, and dried over MgSO₄. The solvent was evaporated under reduced pressure, and the residue was purified by silica gel column (hexane/ethyl acetate=10/1) to give t-butyl 5-chloro-2-iodobenzoate (536 mg, 47%).
¹H NMR (CDCl₃, 400 MHz) δ 7.85 (d, 1H, J=8.4 Hz), 7.65 (d, 1H, J=2.6 Hz), 7.10 (dd, 1H, J=2.6, 8.4 Hz), 1.62 (s, 9H).
(211-2)

The title compound was obtained from the compound of Example 204-1 and the compound of Example 211-1 in a similar manner to Example 48.
$^1$H NMR (CDCl$_3$, 400 MHz) δ 7.83 (d, 1H, J=2.2 Hz), 7.73 (d, 2H, J=8.1 Hz), 7.57 (dd, 1H, J=1.6, 2.6 Hz), 7.46 (d, 1H, J=8.3 Hz), 7.39 (dd, 1H, J=2.2, 8.3 Hz), 7.26 (d, 2H, J=8.1 Hz), 6.79 (dd, 1H, J=1.6, 4.0 Hz), 6.23 (dd, 1H, J=2.6, 4.0 Hz), 5.57 (s, 2H), 2.43 (s, 3H), 1.58 (s, 9H).
(211-3)
Under nitrogen atmosphere, to a solution of the compound of Example 211-2 (21.0 mg) in dioxane (1.0 mL) were added water (1.0 mL) and a 4N solution of hydrochloric acid in dioxane (1.0 mL), and the mixture was stirred at room temperature for 6 hours. A 4N hydrochloric acid in dioxane (1.0 ml) was added thereto, and the nixiture was stirred at room temperature for 30 minutes, and then thereto was added acetic acid (2.0 mL), and the mixture was stirred at 50° C. for 1 hour. The solvent was evaporated under reduced pressure, and thereto was added a 1N aqueous hydrochloric acid solution. The mixture was extracted with ethyl acetate, and dried over MgSO$_4$. The solvent was purified by silica gel column (hexane/ethyl acetate=1/1→ethyl acetate/acetic acid=100/1) to give the title compound (6.8 mg, 37%).
$^1$H NMR (DMSO-d$_6$, 400 MHz) δ 13.54 (brs, 1H), 7.86 (d, 1H, J=2.3 Hz), 7.68 (d, 2H, J=8.0 Hz), 7.67 (dd, 1H, J=1.6, 2.6 Hz), 7.63 (dd, 1H, J=2.3, 8.3 Hz), 7.55 (d, 1H, J=8.3 Hz), 7.33 (d, 2H, J=8.0 Hz), 6.72 (dd, 1H, J=1.6, 3.9 Hz), 6.26 (dd, 1H, J=2.6, 3.9 Hz), 5.55 (s, 2H), 2.40 (s, 3H).

Example 212

(212-1)
(2E)-3-(4-Chloro-2-methoxycarbonylphenyl)-3-methylpropenol was obtained from (2E)-3-methyl-3-tributylstannylprop-2-en-1-ol and methyl 5-chloro-2-iodobenzoate (Example 109-9) in a similar manner to Example 207-1.
$^1$H NMR (CDCl$_3$, 400 MHz) δ 7.81 (d, 1H, J=2.3 Hz), 7.42 (dd, 1H, J=2.3, 8.2 Hz), 7.16 (d, 1H, J=8.2 Hz), 5.11 (tq, 1H, J=6.3, 1.3 Hz), 4.30 (d, 2H, J=6.3 Hz), 3.86 (s, 3H), 1.98 (d, 3H, J=1.3 Hz).
(212-2)
The title compound was obtained from the compound of Example 212-1 and the compound of Example 109-6 in a similar manner to Example 18-3.
$^1$H NMR (CDCl$_3$, 400 MHz) δ 7.81 (d, 2H, J=8.8 Hz), 7.78 (d, 1H, J=2.3 Hz), 7.38 (dd, 1H, J=2.3, 8.2 Hz), 7.13 (d, 1H, J=8.2 Hz), 6.94 (d, 2H, J=8.8 Hz), 6.89 (d, 1H, J=1.3 Hz), 6.53 (d, 1H, J=1.3 Hz), 5.50 (t, 1H, J=6.9 Hz), 5.13 (d, 2H, J=6.9 Hz), 3.88 (s, 3H), 3.81 (s, 3H), 2.08 (s, 3H), 2.08 (s, 3H).

Example 213

$^1$H NMR (CDCl$_3$, 400 MHz) δ 7.90 (d, 1H, J=2.3 Hz), 7.80 (d, 2H, J=8.8 Hz), 7.43 (dd, 1H, J=2.3, 8.2 Hz), 7.15 (d, 1H, J=8.2 Hz), 6.93 (d, 2H, J=8.8 Hz), 6.90 (d, 1H, J=1.2 Hz), 6.53 (d, 1H, J=1.2 Hz), 5.52 (t, 1H, J=6.7 Hz), 5.12 (d, 2H, J=6.7 Hz), 3.87 (s, 3H), 2.10 (s, 3H), 2.06 (s, 3H).

Example 214

(214-1)
[1-(4-Chloro-2-butynyl)-1H-pyrrol-2-yl](4-methylphenyl) ketone was obtained from the compound of Reference Example 1 and 1,4-dichloro-2-butyne in a similar manner to Example 202-1.
$^1$H NMR (CDCl$_3$, 400 MHz) δ 7.72 (d, 2H, J=7.9 Hz), 7.26 (d, 2H, J=7.9 Hz), 7.25-7.26 (m, 1H), 6.77 (dd, 1H, J=1.7, 4.0 Hz), 6.22 (dd, 1H, J=2.6, 4.0 Hz), 5.35 (t, 2H, J=2.1 Hz), 4.18 (t, 2H, J=2.1 Hz), 2.43 (s, 3H).

(214-2)
Under nitrogen atmosphere, to a solution of the compound of Example 205-1 (52.0 mg) in DMF (1.5 mL) was added 60% NaH (11.2 mg), and the mixture was stirred at room temperature for 20 minutes. Then, thereto was added a solution of the compound of Example 214-1 (77.0 mg) in DMF (1.5 mL), and the mixture was stirred at room temperature for 4 hours, and stirred at 60° C. for 6 hours. To the mixture was added a 1N aqueous hydrochloric acid solution, and the mixture was extracted with ethyl acetate-toluene. The organic layer was washed with water and a saturated brine, and dried over MgSO$_4$. The solvent was evaporated under reduced pressure, and the residue was purified by silica gel column (hexane/ethyl acetate=5/1→3/1) to give methyl 5-chloro-2-{[4-{2-(4-methylbenzoyl)-1H-pyrrol-1-yl}-2-butynyl]oxy}benzoate (57.3 mg, 49%).
$^1$H NMR (CDCl$_3$, 400 MHz) δ 7.77 (d, 1H, J=2.7 Hz), 7.70 (d, 2H, J=8.1 Hz), 7.30 (dd, 1H, J=2.7, 8.9 Hz), 7.25 (d, 2H, J=8.1 Hz), 7.13 (dd, 1H, J=1.7, 2.6 Hz), 7.02 (d, 1H, J=8.9 Hz), 6.75 (dd, 1H, J=1.7, 4.0 Hz), 6.19 (dd, 1H, J=2.6, 4.0 Hz), 5.30 (t, 2H, J=1.9 Hz), 4.81 (t, 2H, J=1.9 Hz), 3.88 (s, 3H), 2.43 (s, 3H).
(214-3)
The title compound was obtained from the compound of Example 214-2 in a similar manner to Example 16.
$^1$H NMR (CDCl$_3$, 400 MHz) δ 8.08 (d, 1H, J=2.7 Hz), 7.69 (d, 2H, J=8.0 Hz), 7.37 (dd, 1H, J=2.7, 8.9 Hz), 7.26 (d, 2H, J=8.0 Hz), 7.06 (dd, 1H, J=1.7, 2.6 Hz), 7.05 (d, 1H, J=8.9 Hz), 6.77 (dd, 1H, J=1.7, 4.0 Hz), 6.21 (dd, 1H, J=2.6, 4.0 Hz), 5.31 (t, 2H, J=1.8 Hz), 4.94 (t, 2H, J=1.8 Hz), 2.44 (s, 3H).

Example 215

(215-1)
Methyl 5-chloro-2-(3-hydroxy-1-propyn-1-yl)benzoate was obtained from methyl 5-chloro-2-iodobenzoate (Example 109-9) and propargyl alcohol in a similar manner to Example 48.
$^1$H NMR (CDCl$_3$, 400 MHz) δ 7.93 (d, 1H, J=2.1 Hz), 7.49 (d, 1H, J=8.3 Hz), 7.44 (dd, 1H, J=2.1, 8.3 Hz), 4.54 (d, 2H, J=4.9 Hz), 3.93 (s, 3H), 2.01 (br, 1H).
(215-2)
Under nitrogen atmosphere, to a solution of the compound of Example 215-1 (100 mg) in MeOH (2.5 mL) was added a Lindler catalyst (35.2 mg), and the mixture was subjected to hydrogenolysis at room temperature for 5 hours. The mixture was filtered on cerite, and the solvent was evaporated under reduced pressure, and the residue was purified by silica gel column (hexane/ethyl acetate=2/1) to give methyl 5-chloro-2-[(1Z)-3-hydroxy-1-propen-1-yl]benzoate (43.7 mg, 43%).
$^1$H NMR (CDCl$_3$, 400 MHz) δ 7.95 (d, 1H, J=2.3 Hz), 7.46 (dd, 1H, J=2.3, 8.3 Hz), 7.18 (d, 1H, J=8.3 Hz), 6.98 (d, 1H, J=11.6 Hz), 5.97 (dt, 1H, J=11.6, 5.8 Hz), 4.54 (d, 1H, J=5.7 Hz), 4.19 (dd, 2H, J=5.7, 5.8 Hz), 3.89 (s, 3H).
(215-3)
The title compound was obtained from the compound of Example 215-2 and the compound of Example 109-6 in a similar manner to Example 18-3.
$^1$H NMR (CDCl$_3$, 400 MHz) δ 7.98 (d, 1H, J=2.3 Hz), 7.79 (d, 2H, J=8.8 Hz), 7.47 (dd, 1H, J=2.3, 8.2 Hz), 7.26 (d, 1H, J=8.2 Hz), 7.01 (d, 1H, J=11.5 Hz), 6.94 (d, 2H, J=8.8 Hz), 6.69 (d, 1H, J=1.3 Hz), 6.51 (d, 1H, J=1.3 Hz), 5.95 (dt, 1H, J=11.5, 6.6 Hz), 5.03 (d, 2H, J=6.6 Hz), 3.88 (s, 3H), 3.86 (s, 3H), 2.04 (s, 3H).

Example 216
¹H NMR (CDCl₃, 400 MHz) δ 8.00 (d, 1H, J=2.2 Hz), 7.77 (d, 2H, J=8.8 Hz), 7.50 (dd, 1H, J=2.2, 8.2 Hz), 7.23 (d, 1H, J=8.2 Hz), 6.91-6.95 (m, 3H), 6.74 (s, 1H), 6.55 (s, 1H), 5.90 (dt, 1H, J=11.4, 5.9 Hz), 5.01 (d, 2H, J=5.9 Hz), 3.85 (s, 3H), 2.05 (s, 3H).

Example 217
(217-1)
4-Aminoisothiazole-3-carboxylic acid hydrochloride was treated with MeOH and hydrochloric acid, and further treated in a similar manner to Example 109-9 to give methyl 4-iodoisothiazole-3-carboxylate. This compound and acrolein are treated in a similar manner to Example 109-12 to give methyl 4-[(1E)-3-oxoprop-1-enyl]isothiazole-3-carboxylate.
¹H NMR (CDCl₃, 400 MHz) δ 9.76 (d, 1H,-J=7.7 Hz), 9.00 (d, 1H, J=0.3 Hz), 8.27 (dd, 1H, J=16.1, 0.3 Hz), 6.62 (dd, 1H, J=16.1, 7.7 Hz), 4.04 (s, 3H).
(217-2)
Methyl 4-[(1E)-3-hydroxyprop-1-enyl]isothiazole-3-carboxylate was obtained from the compound of Example 217-1 in a similar manner to Example 164-2.
¹H NMR (CDCl₃, 400 MHz) δ 8.70 (s, 1H), 7.27 (d, 1H, J=16.0 Hz), 6.31 (dt, 1H, J=16.0, 5.6 Hz), 4.36 (dd, 2H, J=5.6, 1.6 Hz), 1.59 (brs, 1H). (217-3)
Methyl 4-{(1E)-3-[2-(4-methylbenzoyl)-1H-pyrrol-1-yl]prop-1-enyl}isothiazole-3-carboxylate was obtained from the compound of Example 217-2 in a similar manner to Example 18-3.
¹H NMR (CDCl₃, 400 MHz) δ 8.69 (s, 1H), 7.74 (d, 2H, J=8.1 Hz), 7.26 (d, 2H, J=8.1 Hz), 7.14 (d, 1H, J=16.0 Hz), 7.06 (dd, 1H, J=2.6, 1.6 Hz), 6.79 (dd, 1H, J=4.0, 1.6 Hz), 6.43 (dt, 1H, J=16.0, 6.0 Hz), 6.23 (dd, 1H, J=4.0, 2.6 Hz), 5.20 (dd, 2H, J=6.0, 1.4 Hz), 3.96 (s, 3H), 2.43 (s, 3H).
(217-4)
The title compound was obtained from the compound of Example 217-3 in a similar manner to Example 16.
¹H NMR (DMSO-d₆, 400 MHz) δ 8.90 (s, 1H), 7.67 (d, 2H, J=8.0 Hz), 7.33 (dd, 1H, J=2.5, 1.6 Hz), 7.31 (d, 2H, J=8.0 Hz), 6.99 (d, 1H, J=15.6 Hz), 6.66 (dd, 1H, J=4.0, 1.6 Hz), 6.34 (dt, 1H, J=15.6, 5.9 Hz), 6.21 (dd, 1H, J=4.0, 2.5 Hz), 5.12 (d, 2H, J=5.9 Hz), 2.38 (s, 3H).

Example 218
(218-1)
Thiophene-3-caboxylic acid was treated with lithium diisopropylamide and iodine, and the resultant was reacted with (CH₃)₂SO₄ in the presence of K₂CO₃ to give methyl 4-iodothiophene-3-carboxylate.
¹H NMR (CDCl₃, 400 MHz) δ 7.41 (d, 1H, J=5.6 Hz), 7.33 (d, 1H, J=5.6 Hz), 3.89 (s, 3H).
(218-2)
Methyl 4-[(1E)-3-oxoprop-1-enyl]thiophene-3-carboxylate was obtained from the compound of Example 218-1 in a similar manner to Example 109-12.
¹H NMR (CDCl₃, 400 MHz) δ 9.73 (d, 1H, J=7.7 Hz), 8.58 (d, 1H, J=15.9 Hz), 7.53 (d, 1H, J=5.3 Hz), 7.39 (d, 1H, J=5.3 Hz), 6.60 (dd, 1H, J=15.9, 7.7 Hz), 3.93 (s, 3H).
(218-3)
Methyl 4-[(1E)-3-hydroxyprop-1-enyl]thiophene-3-carboxylate was obtained from the compound of Example 218-2 in a similar manner to Example 164-2.
¹H NMR (CDCl₃, 400 MHz) δ 7.63 (d, 1H, J=15.9 Hz), 7.38 (d, 1H, J=5.4 Hz), 7.06 (d, 1H, J=5.4 Hz), 6.38 (dt, 1H, J=15.9, 5.6 Hz), 4.34 (d, 2H, J=5.6 Hz), 3.86 (s, 3H), 1.67 (brs, 1H).
(218-4)
The title compound was obtained from the compound of Example 218-3 in a similar manner to Example 18-3.
¹H NMR (CDCl₃, 400 MHz) δ 7.75 (d, 2H, J=8.1 Hz), 7.48 (d, 1H, J=15.9 Hz), 7.36 (d, 1H, J=5.4 Hz), 7.25 (d, 2H, J=8.1 Hz), 7.05 (dd, 1H, J=2.4, 1.7 Hz), 7.03 (d, 1H, J=5.4 Hz), 6.78 (dd, 1H, J=4.0, 1.7 Hz), 6.47 (dt, 1H, J=15.9, 6.0 Hz), 6.23 (dd, 1H, J=4.0, 2.4 Hz), 5.22 (dd, 2H, J=6.0, 1.5 Hz), 3.83 (s, 3H), 2.43 (s, 3H).

Example 219
¹H NMR (CDCl₃, 400 MHz) δ 7.74 (d, 2H, J=8.1 Hz), 7.53 (d, 1H, J=16.0 Hz), 7.43 (d, 1H, J=5.4 Hz), 7.25 (d, 2H, J=8.1 Hz), 7.07 (d, 1H, J=5.4 Hz), 7.05 (dd, 1H, J=2.6, 1.7 Hz), 6.79 (dd, 1H, J=4.0, 1.7 Hz), 6.50 (dt, 1H, J=16.0, 6.1 Hz), 6.23 (dd, 1H, J=4.0, 2.6 Hz), 5.23 (dd, 2H, J=6.1, 1.4 Hz), 2.41 (s, 3H).

Example 220
The title compound was obtained from the compound of Example 9-2 and (1H-pyrrol-2-yl)(4-chlorophenyl)methanone in a similar manner to Example 18-3.
¹H NMR (CDCl₃, 400 MHz) δ 7.86 (d, 1H, J=2.2 Hz), 7.77 (d, 2H, J=8.5 Hz), 7.47 (d, 1H, J=8.4 Hz), 7.43 (d, 2H, J=8.5 Hz), 7.40 (dd, 1H, J=2.2, 8.4 Hz), 7.20 (d, 1H, J=15.8 Hz), 7.11 (dd, 1H, J=1.6, 2.6 Hz), 6.75 (dd, 1H, J=1.6, 4.0 Hz), 6.33(dt, 1H, J=15.8, 6.0 Hz), 6.24(dd, 1H, J=2.6, 4.0 Hz), 5.22(d, 2H, J=6.0 Hz), 3.86 (s, 3H).

Example 221
¹H NMR (DMSO-d₆, 400 MHz) δ 7.76 (d, 2H, J=8.5 Hz), 7.72 (d, 1H, J=2.3 Hz), 7.67 (d, 1H, J=8.6 Hz), 7.56 (d, 2H, J=8.5 Hz), 7.54 (dd, 1H, J=2.3, 8.6 Hz), 7.39 (dd, 1H, J=1.6, 2.5 Hz), 6.98 (d, 1H, J=16.0 Hz), 6.72 (dd, 1H, J=1.6, 4.0 Hz), 6.48 (dt, 1H, J=16.0, 5.4 Hz), 6.25 (dd, 1H, J=2.5, 4.0 Hz), 5.21 (d, 2H, J=5.4 Hz).

Example 222
The title compound was obtained from the compound of Example 9-2 and (1H-pyrrol-2-yl)(4-trifluoromethylphenyl)methanone in a similar manner to Example 18-3.
¹H NMR (CDCl₃, 400 MHz) δ 7.90 (d, 2H, J=8.1 Hz), 7.86 (d, 1H, J=2.2 Hz), 7.71 (d, 2H, J=8.1 Hz), 7.48 (d, 1H, J=8.4 Hz), 7.41 (dd, 1H, J=2.2, 8.4 Hz), 7.21 (d, 1H, J=15.8 Hz), 7.14 (dd, 1H, J=1.6, 2.5 Hz), 6.75 (dd, 1H, J=1.6, 4.1 Hz), 6.33 (dt, 1H, J=15.8, 5.9 Hz), 6.25 (dd, 1H, J=2.5, 4.1 Hz), 5.24 (d, 2H, J=5.9 Hz), 3.86 (s, 3H).

Example 223
¹H NMR (CDCl₃, 400 MHz) 7.98 (d, 1H, J=2.1 Hz), 7.89 (d, 2H, J=8.1 Hz), 7.70 (d, 2H, J=8.1 Hz), 7.51 (d, 1H, J=8.5 Hz), 7.47 (dd, 1H, J=2.1, 8.5 Hz), 7.26 (d, 1H, J=15.3 Hz), 7.13 (dd, 1H, J=1.6, 2.5 Hz), 6.76 (dd, 1H, J=1.6, 4.1 Hz), 6.36 (dt, 1H, J=15.3, 5.9 Hz), 6.25 (dd, 1H, J=2.5, 4.1 Hz), 5.26 (d, 2H, J=5.9 Hz).

Example 224
(224-1)
Methyl 1-allyl-4-methyl-1H-pyrrole-2-carboxylate was obtained from methyl 4-methyl-1H-pyrrole-2-carboxylate in a similar manner to Example 109-10.
¹H NMR (CDCl₃, 400 MHz) δ 6.77 (d, 1H, J=1.3 Hz), 6.63 (d, 1H, J=1.3 Hz), 5.99 (ddt, 1H, J=10.2, 17.1, 5.4 Hz), 5.13 (d, 1H, J=10.2 Hz), 4.98 (d, 1H, J=17.1 Hz), 4.89 (d, 2H, J=5.4 Hz), 3.78 (s, 3H), 2.07 (s, 3H).
(224-2)
1-Allyl-4-methyl-1H-pyrrole-2-carboxylic acid was obtained from the compound of Example 224-1 in a similar manner to Example 16.

¹H NMR (CDCl₃, 400 MHz) δ 6.91 (d, 1H, J=1.4 Hz), 6.69 (d, 1H, J=1.4 Hz), 5.99 (ddt, 1H, J=10.2, 17.0, 5.5 Hz), 5.14 (d, 1H, J=10.2 Hz), 5.00 (d, 1H, J=17.0 Hz), 4.88 (d, 2H, J=5.5 Hz), 2.08 (s, 3H).
(224-3)
Under nitrogen atmosphere, to a solution of the compound of Example 224-2 (152 mg) and p-anisidine (123 mg) in CH₂Cl₂ (5.0 mL) was added NEt₃ (400 μL). The mixture was cooled to 0° C., and thereto was added N,N-bis(2-oxo-3-oxazolidinyl)phosphinic chloride (332 mg), and the mixture was stirred at room temperature for 13 hours. Water was added to the mixture, and the mixture was extracted with ethyl acetate. The extract was washed with a saturated brine and dried over MgSO₄. The solvent was evaporated under reduced pressure, and the residue was purified by silica gel column (hexane/ethyl acetate=10/1→5/1→3/1) to give 1-allyl-N-(4-methoxyphenyl)-4-methyl-1H-pyrrole-2-carboxamide (181 mg, 73%).
¹H NMR (CDCl₃, 400 MHz) δ 7.43 (br, 1H), 7.43 (d, 2H, J=9.0 Hz), 6.87 (d, 2H, J=9.0 Hz), 6.62 (d, 1H, J=1.2 Hz), 6.50 (d, 1H, J=1.2 Hz), 6.03 (ddt, 1H, J=10.2, 17.0, 5.5 Hz), 5.13 (d, 1H, J=10.2 Hz), 5.02 (d, 1H, J=17.0 Hz), 4.95 (d, 2H, J=5.5 Hz), 3.80 (s, 3H), 2.10 (s, 3H).
(224-4)
Methyl 5-chloro-2-[(1E)-3-(2-{[(4-methoxyphenyl)amino]-carbonyl}-4-methyl-1H-pyrrol-1-yl)prop-1-enyl]benzoate was obtained from the compound of Example 224-3 in a similar manner to Example 109-12.
¹H NMR (CDCl₃, 400 MHz) δ 7.84 (d, 1H, J=2.3 Hz), 7.51 (brs, 1H), 7.47 (d, 1H, J=8.4 Hz), 7.44 (d, 2H, J=9.0 Hz), 7.38 (dd, 1H, J=2.3, 8.4 Hz), 7.10 (d, 1H, J=15.8 Hz), 6.88 (d, 2H, J=9.0 Hz), 6.70 (d, 1H, J=1.2 Hz), 6.53 (d, 1H, J=1.2 Hz), 6.31 (dt, 1H, J=15.8, 5.9 Hz), 5.12 (d, 2H, J=5.9 Hz), 3.86 (s, 3H), 3.80 (s, 3H), 2.11 (s, 3H).
(224-5)
The title compound was obtained from the compound of Example 224-4 in a similar manner to Example 16.
¹H NMR (CDCl₃, 400 MHz) δ 7.93 (d, 1H, J=2.4 Hz), 7.56 (brs, 1H), 7.48 (d, 1H, J=8.5 Hz), 7.42 (dd, 1H, J=2.4, 8.5 Hz), 7.42 (d, 2H, J=9.0 Hz), 7.13 (d, 1H, J=15.8 Hz), 6.85 (d, 2H, J=9.0 Hz), 6.70 (d, 1H, J=1.5 Hz), 6.54 (d, 1H, J=1.5 Hz), 6.31 (dt, 1H, J=15.8, 5.7 Hz), 5.13 (d, 2H, J=5.7 Hz), 3.78 (s, 3H), 2.10 (s, 3H).

Example 225

An amide comound 1-allyl-N,4-dimethyl-N-(4-methylphenyl)-1H-pyrrole-2-carboxamide was obtained from the compound of Example 224-2 and N-methyl-p-toluidine in a similar manner to Example 224-3. Subsequently, this compound was converted into the title compound in a similar manner to Example 109-12.
¹H NMR (CDCl₃, 400 MHz) δ 7.85 (d, 1H, J=2.3 Hz), 7.51 (d, 1H, J=8.5 Hz), 7.41 (dd, 1H, J=2.3, 8.5 Hz), 7.12 (d, 1H, J=15.7 Hz), 7.09 (d, 2H, J=8.1 Hz), 6.99 (d, 2H, J=8.1 Hz), 6.50 (d, 1H, J=1.2 Hz), 6.31 (dt, 1H, J=15.7, 6.0 Hz), 5.45 (d, 1H, J=1.2 Hz), 5.00 (d, 2H, J=6.0 Hz), 3.85 (s, 3H), 3.38 (s, 3H), 2.34 (s, 3H), 1.85 (s, 3H).

Example 226

¹H NMR (CDCl₃, 400 MHz) δ 7.94 (d, 1H, J=2.2 Hz), 7.52 (d, 1H, J=8.5 Hz), 7.44 (dd, 1H, J=2.2, 8.5 Hz), 7.26 (d, 1H, J=15.8 Hz), 7.09 (d, 2H, J=8.2 Hz), 7.00 (d, 2H, J=8.2 Hz), 6.50 (d, 1H, J=1.4 Hz), 6.29 (dt, 1H, J=15.8, 6.1 Hz), 5.47 (d, 1H, J=1.4 Hz), 5.00 (d, 2H, J=6.1 Hz), 3.38 (s, 3H), 2.33 (s, 3H), 1.85 (s, 3H).

Example 227

Compound G (the free compound of the compound of Example 136) was obtained by the following reaction scheme.

Preparation of Compound A

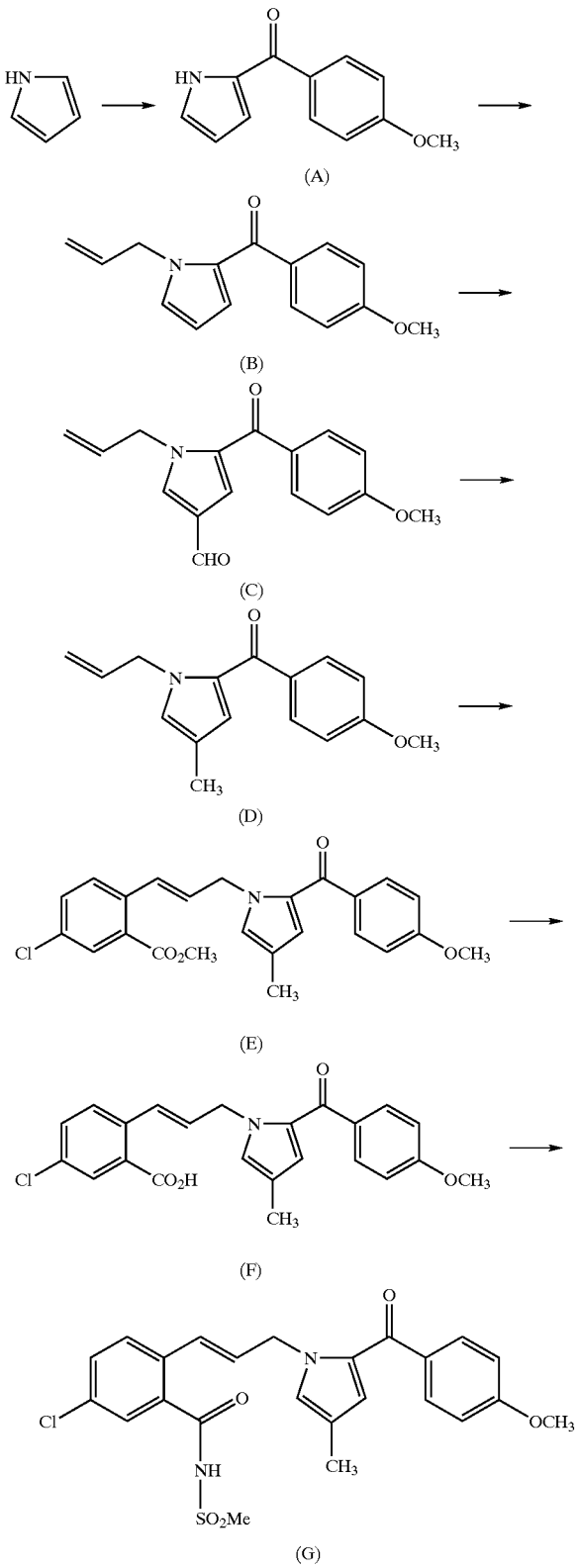

A mixture of magnesium (4.12 g, 170 mmol) and THF (20 ml) was cooled to 10° C., and thereto was added dropwise a solution of ethyl bromide (20.1 g, 185 mmol) in THF (60 ml) at an inner temperature of from 20 to 25° C. The mixture was warmed to 30° C., and stirred for 1 hour, and thereto was added dropwise a solution of pyrrole (10.3 g, 154 mmol) in toluene (80 ml) at 30-35° C. The solution was stirred for 0.5 hour, and warmed to 40° C. To the mixture was added dropwise a solution of p-anisoyl choride (13.2 g, 77.1 mmol) in toluene (20 ml) at 40-45° C., and the mixture was further stirred for 0.5 hour. To the mixture were added an aqueous ammonium chloride solution and toluene, and the mixture was stirred. The organic layer was separated and concentrated. The residue was recrystallized from 2-propanol/water (1:2) to give Compound A (13.7 g, 88%).

$^1$H NMR (CDCl$_3$, 400 MHz) δ 9.54 (brs, 1H), 7.94 (d, 2H, J=8.9 Hz), 7.12 (dt, 1H, J=1.3, 2.7 Hz), 6.93 (d, 2H, J=8.9 Hz), 6.89 (ddd, 1H, J=3.8, 2.4, 1.3 Hz), 6.34 (dt, 1H, J=3.8, 2.7 Hz), 3.89 (s, 3H).

Preparation of Compound C

Under nitrogen atmosphere, to a solution of potassium t-butoxide (61.3 g, 546 mmol) in THF (400 g) was added dropwise a solution of Compound A (100 g, 497 mmol) in THF (200 g), and the mixture was warmed to 45° C. The mixture was stirred for 15 minutes, and thereto was added dropwise a solution of allyl bromide (90.2 g, 746 mmol) in THF (200 g). The mixture was stirred at the same temperature for 2 hours, diluted with toluene (800 g), and washed with water (800 g). The toluene layer was concentrated to give a solution of Compound B in toluene.

Separately, DMF (84.8 g, 1.16 mol) was cooled to 15° C., and thereto was added dropwise phosphorus oxychloride (133.6 g, 871 mmol) in such a manner that the inner temperature was not raised to over 20° C. The mixture was stirred for 20 minutes, and thereto was added THF (62.7 g, 871 mmol), and thereto was added a solution of Compound B (70 g, 260 mmol) in toluene (140 g) in such a manner that the inner temperature was not raised to over 20° C. The mixture was stirred at room temperature for 5 hours, and thereto was added an aqueous solution of sodium acetate (357 g, 4.35 mol) in water (714 g) during which the inner temperature was raised. After the addition, the mixture was stirred at room temperature overnight. Seed crystals of Compound C (100 mg, 371 μmol) were added to the mixture, and the mixture was stirred for 3 hours. The precipitated crystals were collected by filtration, washed with water and toluene, and dried. The organic layer of the filtrate was washed with water, and concentrated. The precipitated crystals were collected by filtration, washed with cold toluene, and dried. The resulting crystals were combined with the above crystals to give Compound C (50.6 g, 67%).

$^1$H NMR (Compound B: CDCl$_3$, 400 MHz) δ 7.84 (d, 2H, J=8.9 Hz), 6.98 (dd, 1H, J=2.5 and 1.7 Hz), 6.94 (d, 2H, J=8.9 Hz), 6.73 (dd, 1H, J=4.0 and 1.7 Hz), 6.19 (dd, 1H, J=4.0 and 2.5 Hz), 6.07 (ddt, 1H, J=17.1, 10.2 and 5.7 Hz), 5.16 (dq, 1H, J=10.2 and 1.1 Hz), 5.06 (dq, 1H, J=17.1 and 1.1 Hz), 5.03 (dt, 2H, J=5.7 and 1.1 Hz), 3.88 (s, 3H).

$^1$H NMR (Compound C: CDCl$_3$, 400 MHz) δ 9.81 (s, 1H), 7.85 (d, 2H, J=8.9 Hz), 7.58 (d, 1H, J=2.3 Hz), 7.16 (d, 1H, J=2.3 Hz), 6.97 (d, 2H, J=8.9 Hz), 6.06 (ddt, 1H, J=17.1, 10.2 and 5.7 Hz), 5.26 (dq, 1H, J=10.2 and 1.1 Hz), 5.16 (dq, 1H, J=17.1 and 1.1 Hz), 5.05 (dt, 2H, J=5.7 and 1.1 Hz), 3.89 (s, 3H).

Preparation of Compound D

Compound C (10.0 g, 37.1 mmol) was dissolved in methylene chloride (212 g) and trifluoroacetic acid (212 g, 1.86 mol), and the mixture was cooled to 0° C. To the mixture was added t-butyl-dimethylsilane (21.6 g, 186 mmol), and the mixture was stirred at the same temperature for 6 hours. The reaction solution was diluted with toluene (470 g), and the mixture was poured into a 3N aqueous sodium hydroxide solution. The organic layer was separated and treated with an activated carbon, and filtered. The filtrate was concentrated to give Compound D (8.42 g, 89%).

$^1$H NMR (CDCl$_3$, 400 MHz) δ 7.81 (d, 2H, J=8.9 Hz), 6.94 (d, 2H, J=8.9 Hz), 6.77 (br, 1H), 6.54 (brd, 1H, J=1.4 Hz), 6.05 (ddt, 1H, J=10.0, 15.0 and 5.8 Hz), 5.14 (dq, 1H, J=10.0 and 1.1 Hz), 5.07 (dq, 1H, J=15.0 and 1.1 Hz), 4.97 (dt, 2H, J=5.8 and 1.1 Hz), 3.87 (s, 3H), 2.08 (brs, 3H).

Preparation of Compound E

Under nitrogen atmosphere, to a mixture of methyl 5-chloro-2-iodobenzoate (146 mg, 0.492 mmol), Compound D (128 mg, 0.501 mmol), sodium hydrogen carbonate (86.0 mg, 1.01 mmol) and benzyltriethyl-ammonium chloride (120 mg, 0.527 mmol) were added acetonitrile (1.0 ml) and palladium acetate (5.7 mg, 0.0254 mmol), and the mixture was warmed to 50° C., and stirred for 16 hours. Water was added to the reaction solution, and the mixture was extracted with toluene. The extract was washed with a 10% aqueous sodium thiosulfate solution, and dried over magnesium sulfate. The resultant was filtered and the solvent was evaporated under reduced pressure to give Compound E (207 mg).

$^1$H NMR (CDCl$_3$, 400 MHz) δ 7.85 (d, 1H, J=2.3 Hz), 7.83 (d, 2H, J=8.9 Hz), 7.48 (d, 1H, J=8.5 Hz), 7.39 (dd, 1H, J=2.3, 8.5 Hz), 7.21 (d, 1H, J=15.8 Hz), 6.94 (d, 2H, J=8.9 Hz), 6.85 (d, 1H, J=1.1 Hz), 6.57 (d, 1H, J=1.1 Hz), 6.34 (dt, 1H, J=15.8, 6.1 Hz), 5.14 (d, 2H, J=6.1 Hz), 3.88 (s, 3H), 3.87 (s, 3H), 2.09 (s, 3H).

Preparation of Compound F

Under nitrogen atmosphere, to a mixture of Compound E (400 mg, 0.944 mmol) in a mixed solvent of THF (2.0 ml) and methanol (2.0 ml) was added a 1N aqueous sodium hydroxide solution (1.0 ml, 1.0 mmol), and the mixture was stirred at 50° C. for 1 hour. The solvent was evaporated under reduced pressure, and thereto were added toluene (3.5 ml) and water (2.5 ml). The mixture was stirred at 0° C. for 4 hours to give a sodium salt of Compoun F (258 mg).

$^1$H NMR (DMSO-d$_6$, 400 MHz) δ 7.76 (d, 2H, J=8.8 Hz), 7.47 (d, 1H, J=16.0 Hz), 7.40 (d, 1H, J=8.3 Hz), 7.39 (d, 1H, J=2.4 Hz), 7.12 (dd, 1H, J=2.4, 8.3 Hz), 7.08 (d, 1H, J=1.2 Hz), 7.03 (d, 2H, J=8.8 Hz), 6.47 (d, 1H, J=1.2 Hz), 6.22 (dt, 1H, J=16.0, 6.4 Hz), 5.01 (d, 2H, J=6.4 Hz), 3.84 (s, 3H), 2.03 (s, 3H).

To a sodium salt of Compound F was added 1N hydrochloric acid, and the mixture was extrated with ethyl acetate. The solvent was evaporated under reduced pressure to give the residue (226 mg), which was further recrystallized from acetonitrile (5.0 ml) to give Compound F (122 mg).

$^1$H NMR (CDCl$_3$, 400 MHz) δ 7.97 (d, 1H, J=2.2 Hz), 7.83 (d, 2H, J=8.9 Hz), 7.50 (d, 1H, J=8.5 Hz), 7.44 (dd, 1H, J=2.2, 8.5 Hz), 7.28 (d, 1H, J=15.5 Hz), 6.93 (d, 2H, J=8.9 Hz), 6.86 (d, 1H, J=1.1 Hz), 6.58 (d, 1H, J=1.1 Hz), 6.35 (dt, 1H, J=15.5, 6.0 Hz), 5.15 (d, 2H, J=6.0 Hz), 3.85 (s, 3H), 2.09 (s, 3H).

Preparation of Compound G

Under nitrogen atmosphere, to a solution of isopropyl chloroformate (920 μl 8.08 mmol) in THF (3.0 ml), which was cooled at 0° C., was added dropwise a solution of Compound F (3.00 g, 7.32 mmol) and N-methylmorpholine (845 μl, 7.69 mmol) in THF (8.0 ml), and the mixture was stirred at 0° C. for 30 minutes. The insoluble materials were removed by filtration, and washed with THF (5.0 ml) to give a solution of a mixed acid anhydride of Compound F in THF.

$^1$H NMR (CDCl$_3$, 400 MHz) δ 7.93 (d, 1H, J=2.2 Hz), 7.83 (d, 2H, J=8.8 Hz), 7.53 (d, 1H, J=8.5 Hz), 7.47 (dd, 1H,

J=2.2, 8.5 Hz), 7.27 (d, 1H, J=15.8 Hz), 6.94 (d, 2H, J=8.8 Hz), 6.85 (d, 1H, J=1.2 Hz), 6.56 (d, 1H, J=1.2 Hz), 6.40 (dt, 1H, J=15.8, 6.2 Hz), 5.12 (d, 2H, J=6.2 Hz), 5.08 (sep, 1H, J=6.3 Hz), 3.87 (s, 3H), 2.08 (s, 3H), 1.41 (d, 6H, J=6.3 Hz).

Under nitrogen atmosphere, to a solution of potassium t-butoxide (1.07 g, 9.54 mmol) in THF (11 ml) was added methanesulfonamide (910 mg, 9.57 mmol), and the mixture was stirred at room temperature for 1 hour. Then, the mixture was cooled to −10° C., and thereto was slowly added dropwise the above solution of the mixed acid anhydride of Compound F in THF, and the mixture was stirred at −10° C. for 8 hours. To the mixture was added 1N hydrochloric acid (32.9 g), and the mixture was extracted with ethyl acetate (30 ml), and dried over magnesium suflate. The solvent was evaporated under reduced pressure, and the precipitated solid (3.65 g) was recrystallized from isopropyl alcohol (70 ml) to give Compound G (3.00 g, 84%).

$^1$H NMR (CDCl$_3$, 400 MHz) δ 8.67 (brs, 1H), 7.80 (d, 2H, J=8.8 Hz), 7.54 (d, 1H, J=2.1 Hz), 7.46 (d, 1H, J=8.4 Hz), 7.41 (dd, 1H, J=2.1, 8.4 Hz), 6.94 (d, 2H, J=8.8 Hz), 6.85 (d, 1H, J=1.5 Hz), 6.67 (d, 1H, J=15.8 Hz), 6.58 (d, 1H, J=1.5 Hz), 6.41 (dt, 1H, J=15.8, 5.5 Hz), 5.09 (d, 2H, J=5.5 Hz), 3.87 (s, 3H), 3.35 (s, 3H), 2.09 (s, 3H).

The compounds of other Examples can also be prepared in a similar manner to the process shown in the above reaction scheme.

Experiment 1

Effects on the Extracellular Matrix Production by TGF-β

The effect of the compounds of Examples on the production of proteoglycan when TGF-β was added to fibroblast was evaluated.

NRK-49F cells (rat fibroblast) were cultured in Dulbecco's Modified Eagle Medium (DMEM: manufactured by GIBCO) containing 10% bovine serum, and used in this experiment. The cells were put into a 96-well plate in an amount of 2.5×10$^4$ cells/100 μl/well. On the next day, the medium in the plate was exchanged to the DMEM medium containing 3 ng/ml of TGF-β (manufactured by Nacalai Tesque, Inc.), 0.5 μCi/well of [$^{35}$S]-Na$_2$SO$_4$, and a test compound. Twenty-four hours thereafter, the supernatant was collected, and subjected to SDS-polyacrylamide gel electrophoresis (SDS-PAGE) in a conventional manner. The gel after electrophoresis was dried with a gel drier, and exposed to an imaging plate, which was analyzed with BSA2000 (manufactured by Fuji Photo Film). The radioactivity of proteoglycan to be electrophoresed was measured, and the TGF-β inhibitory rate was calculated by the following equation.

TGF-β Inhibitory rate (%)=(A−B)×100/(A−C)

A: Radioactivity in the presence of TGF-β without a test compound

B: Radioactivity in the presence of TGF-β and a test compound

C: Radioactivity in the absence of TGF-β and a test compound

The TGF-β inhibitory rates (%) of the test compound at concentrations of 3 μM and 10 μM are shown in Table 1. From the results, the pyrrole derivatives of the present invention inhibit the activity of TGF-β and inhibit the production of proteoglycan in fibroblast.

TABLE 1

| Compound | 3 μM | 10 μM |
| --- | --- | --- |
| Comp. of Ex. 2 | 33 | 61 |
| Comp. of Ex. 3 | 25 | 38 |
| Comp. of Ex. 5 | 6 | 51 |
| Comp. of Ex. 6 | 66 | 88 |
| Comp. of Ex. 7 | 44 | 78 |
| Comp. of Ex. 8 | 16 | 46 |
| Comp. of Ex. 9 | 88 | 91 |
| Comp. of Ex. 10 | 63 | 86 |
| Comp. of Ex. 14 | 40 | 56 |
| Comp. of Ex. 19 | 51 | 72 |
| Comp. of Ex. 20 | 61 | 90 |
| Comp. of Ex. 25 | 6 | 74 |
| Comp. of Ex. 31 | 34 | 38 |
| Comp. of Ex. 33 | 74 | 91 |
| Comp. of Ex. 38 | 51 | 40 |
| Comp. of Ex. 43 | 31 | 66 |
| Comp. of Ex. 61 | 15 | 86 |
| Comp. of Ex. 64 | 43 | 75 |
| Comp. of Ex. 66 | 88 | 94 |
| Comp. of Ex. 67 | 55 | 75 |
| Comp. of Ex. 73 | 70 | 85 |
| Comp. of Ex. 76 | 56 | 58 |
| Comp. of Ex. 83 | 42 | 47 |
| Comp. of Ex. 85 | 29 | 75 |
| Comp. of Ex. 91 | 66 | 73 |
| Comp. of Ex. 97 | 58 | 75 |
| Comp. of Ex. 103 | 55 | 90 |
| Comp. of Ex. 105 | 14 | 48 |
| Comp. of Ex. 107 | 90 | 95 |
| Comp. of Ex. 108 | 42 | 56 |
| Comp. of Ex. 111 | 90 | 118 |
| Comp. of Ex. 112 | 23 | 73 |
| Comp. of Ex. 115 | 46 | 56 |
| Comp. of Ex. 117 | 71 | 83 |
| Comp. of Ex. 120 | 99 | 117 |
| Comp. of Ex. 128 | 14 | 80 |
| Comp. of Ex. 134 | 59 | 80 |
| Comp. of Ex. 136 | 87 | 88 |
| Comp. of Ex. 137 | 74 | 85 |
| Comp. of Ex. 167 | 67 | 96 |
| Comp. of Ex. 178 | 83 | 97 |
| Comp. of Ex. 180 | 80 | 83 |
| Comp. of Ex. 188 | | 84 |
| Comp. of Ex. 190 | 65 | 85 |
| Comp. of Ex. 193 | 86 | 98 |
| Comp. of Ex. 195 | 52 | 103 |

Experiment 2

Evaluation Using Rat Thy-1 Nephritis Model

The anti-fibrosis activity was evaluated on the compounds of Examples 9, 14, 110, 120 and 136 by using a rat Thy-1 nephritis model, which is an animal model for kidney fibrosis (cf., "Kidney and Dialysis", vol. 31, p.343-347 (1991)). Thy-1 is one of the surface antigens of thymocyte.

Male Wister rats were purchased from Charles River Japan, Inc. at an age of 3-weeks old. After pre-feeding, the animals were used in 10 this experiment when their body weights became about 100 g. The animals were kept in a room being controlled at a temperature of 24±2° C. under a humidity of 55±10%, with an illumination cycle of light on (8:00 to 20:00). The animals were given food (CRF-1, Oriental Yeast Co. Ltd.) and sterilized tap water ad libitum.

Anti-Thy-1 monoclonal antibody (OX-7, Biosource International Inc.) was administered to the rats at a dose of 50 μg/100 g of body weight at the tail vein. Then, the animals were grouped into the vehicle-treated group (n=8) and the test compound-treated group (n=8) with respect to the body-weight. From the day of administration of anti-Thy-1 monoclonal antibody, a test compound, which was suspended in a 0.5% carboxymethylcellulose (vehicle), was orally administered to the animals once a day at a dose of 15 or 150 mg/kg/day by using an oral sonde. To the vehicle-treated group, a vehicle was administered likewise.

After the administration for 7 days, the right kidney of the rats was taken out, and the content of hydroxyproline therein, which was an index for organ fibrosis, was measured according to the method of J. F. Woessner, et al. (Arch. Biochem. Biophys. Vol.93 p440 (1961)). That is, the kidney was homogenized, and 500 μL of the suspension was dried, and thereto was added a 4N aqueous sodium hydroxide solution (225 μL). The mixture was heated on a heat block at 100° C. for 15 minutes to hydrolyze proteins, and the mixture was neutralized with a 1.4 M aqueous citric acid solution (275 μL). The mixture was centrifuged at 3000 rpm for 10 minutes at room temperature, and the supernatant was collected as a kidney extract. To the extract were added Chloramine T solution and an Ehrlich solution (which was prepared by adding n-propanol (31 ml) to p-dimethylaminobenzaldehyde (7.5 g), and further slowly adding thereto a 60% perchloric acid (13 mL), and followed by adjusting the volume to 50 ml by distilled water), and the mixture was reacted at 65° C. for 15 minutes. The OD 550 (absorbance at 550 nm) was measured, and the concentration of hydroxyproline was calcurated from the analytical curve of hydroxyproline. The content of hydroxyproline thus obtained was adjusted with respect to the protein amount in the kidney extract.

The results are shown in Tables 2 to 5. Each value was expressed in average value±standard deviation of 8 animals in each group. As compared with the values of normal rats, the hydroxyproline content in the kideny of rats treated with anti-Thy-1 antibody was increased, and it was found that the extracellular matrix was accumulated in the kidney. In the group treated with the pyrrole derivative of the present invention, the hydroxyproline content was decreased as compared to the vehicle-treated group, and it was found that the pyrrole derivatives of the present invention inhibit the accumulation of extracellular matrix in the kidney.

TABLE 2

| Groups | Hydroxyproline content (μg/mg protein) |
|---|---|
| Normal Rat | 6.7 ± 1.6 |
| Anti-Thy-1 antibody + the vehicle | 8.7 ± 2.0# |
| Anti-Thy-1 antibody + the compound of Example 9 (15 mg/kg) | 7.2 ± 2.1 |
| Anti-Thy-1 antibody + the compound of Example 14 (150 mg/kg) | 6.3 ± 1.3* |

P < 0.05 in Student's t-test as compared with the normal rat group
*P <0.05 in Student's t-test as compared with the group treated with the anti-Thy-1 antibody and the vehicle

TABLE 3

| Groups | Hydroxyproline content (μg/mg protein) |
|---|---|
| Normal Rat | 8.2 ± 0.8 |
| Anti-Thy-1 antibody + the vehicle | 11.8 ± 0.6## |
| Anti-Thy-1 antibody + the compound of Example 110 (1.5 mg/kg) | 10.1 ± 0.8** |
| Anti-Thy-1 antibody + the compound of Example 110 (5 mg/kg) | 9.5 ± 0.8** |
| Anti-Thy-1 antibody + the compound of Example 110 (15 mg/kg) | 9.7 ± 0.7** |
| Anti-Thy-1 antibody + the compound of Example 110 (50 mg/kg) | 9.5 ± 0.6** |

P < 0.01 in Student's t-test as compared with the normal rat group.
**P < 0.01 in Williams test as compared with the group treated with the anti-Thy-1 antibody and the vehicle.

TABLE 4

| Groups | Hydroxyproline content (μg/mg protein) |
|---|---|
| Normal Rat | 8.0 ± 0.5 |
| Anti-Thy-1 antibody + the vehicle | 10.8 ± 1.8## |
| Anti-Thy-1 antibody + the compound of Example 120 (1.5 mg/kg) | 9.7 ± 1.0* |
| Anti-Thy-1 antibody + the compound of Example 120 (5 mg/kg) | 9.3 ± 0.9** |
| Anti-Thy-1 antibody + the compound of Example 120 (15 mg/kg) | 7.9 ± 1.0** |
| Anti-Thy-1 antibody + the compound of Example 120 (50 mg/kg) | 8.1 ± 1.5** |

P < 0.01 in Student's t-test as compared with the normal rat group.
*, **P < 0.05, P < 0.01, respectively, in Williams test as compared with the group treated with the anti-Thy-1 antibody and the vehicle.

TABLE 5

| Groups | Hydroxyproline content (μg/mg protein) |
|---|---|
| Normal Rat | 11.3 ± 0.7 |
| Anti-Thy-1 antibody + the vehicle | 16.1 ± 1.6## |
| Anti-Thy-1 antibody + the compound of Example 136 (1.5 mg/kg) | 17.2 ± 2.2 |
| Anti-Thy-1 antibody + the compound of Example 136 (5 mg/kg) | 13.4 ± 1.0** |
| Anti-Thy-1 antibody + the compound of Example 136 (15 mg/kg) | 12.2 ± 1.6** |
| Anti-Thy-1 antibody + the compound of Example 136 (50 mg/kg) | 11.2 ± 1.4** |

P < 0.01 in Student's t-test as compared with the normal rat group.
**P < 0.01 in Williams test as compared with the group treated with the anti-Thy-1 antibody and the vehicle.

Industrial Applicability

According to the present invention, the pyrrole derivatives being useful as medicaments such as fibrosis inhibitors for organs and tissues are provided.

What is claimed is:

1. A pyrrole derivative of the formula:

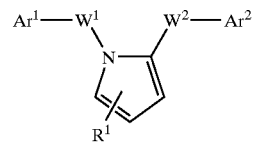

wherein $W^2$ is —CO—;

$Ar^2$ is an optionally substituted aryl;

$W^1$ is an optionally substituted $C_2$–$C_5$ alkylene, an optionally substituted $C_2$–$C_5$ alkenylene, an optionally substituted $C_2$–$C_5$ alkynylene, an optionally substituted —O—$C_1$–$C_5$ alkylene, an optionally substituted —O—$C_2$–$C_5$ alkenylene, or an optionally substituted —O—$C_2$–$C_5$ alkynylene;

$Ar^1$ is an aryl which is substituted at the ortho- or meta-position thereof with respect to the binding position of $W^1$ by a group selected from carboxyl, an alkoxycarbonyl, a carbamoyl having optionally alkyl-substituent(s), a cyclic aminocarbonyl, an alkylsulfonylcarbamoyl, an arylsulfonylcarbamoyl, an alkylsulfonyl, a sulfamoyl having optionally alkyl-substituent(s), a cyclic aminosulfonyl, tetrazolyl, cyano, an alkoxy and an alkylsulfonylamino, and said aryl being optionally further substituted; and the number of $R^1$ is one or more, and each is independently hydrogen, a halogen or an optionally substituted alkyl;

or a prodrug thereof, or a pharmaceutically acceptable salt thereof.

2. The pyrrole derivative according to claim 1, wherein $W^1$ is an optionally substituted $C_2$–$C_5$ alkylene, an optionally substituted $C_2$–$C_5$ alkenylene, an optionally substituted $C_2$–$C_5$ alkynylene, or a prodrug thereof, or a pharmaceutically acceptable salt thereof.

3. The pyrrole derivative according to claim 1, wherein $W^1$ is an optionally substituted trans-$C_3$–$C_4$ alkenylene; and $Ar^1$ is an aryl, which is substituted at the ortho-position thereof with respect to the binding position of $W^1$ by a group selected from carboxyl, an alkoxycarbonyl, a carbarnoyl having optionally alkyl-substituent (s), a cyclic aminocarbonyl, an alkylsulfonylcarbamoyl an arylsulfonylcarbamoyl, tetrazolyl, cyano, an alkoxy and an alkylsulfonylamino, and said aryl being optionally further substituted by a halogen, cyano, an optionally substituted alkoxy or an optionally substituted alkyl, or a prodrug thereof, or a pharmaceutically acceptable salt thereof.

4. The pyrrole derivative according to claim 1, which is a compound of the formula:

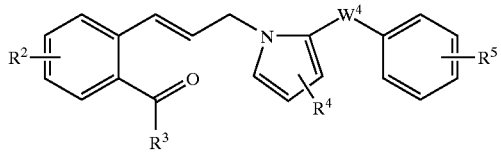

wherein $W^4$ is —CO—;

$R^2$ is a halogen, cyano, an optionally substituted alkoxy or an optionally substituted alkyl;

$R^3$ is a hydroxyl, an alkoxy, an amino having optionally alkyl-substituent(s), a cyclic amino or an alkylsulfonylamino; $R^4$ is a hydrogen, a halogen or an alkyl; $R^5$ is an optionally substituted alkoxy or an optionally substituted alkyl, or a prodrug thereof, or a pharmaceutically acceptable salt thereof.

5. The pyrrole derivative according to claim 4, wherein $W^4$ is —CO—; $R^2$ is a halogen, cyano, an alkoxy being optionally substituted by a halogen or an alkoxy, or an alkyl being optionally substituted by a halogen or an alkoxy; $R^4$ is hydrogen or an alkyl; $R^5$ is an alkoxy being optionally substituted by a halogen, an alkoxy or morpholino, or an alkyl being optionally substituted by a halogen, an alkoxy or morpholino, or a prodrug thereof, or a pharmaceutically acceptable salt thereof.

6. The pyrrole derivative according to claim 4 or 5, which is a compound of the formula:

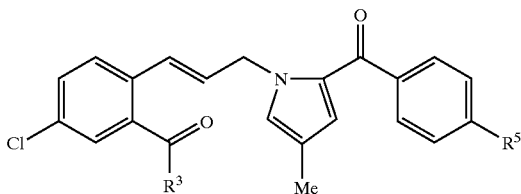

wherein $R^3$ and $R^5$ are as defined in claim 4, or a prodrug thereof, or a pharmaceutically acceptable salt thereof.

7. A pharmaceutical composition containing the pyrrole derivative according to claim 1, or a prodrug thereof, or a pharmaceutically acceptable salt thereof; and a pharmaceutically acceptable carrier.

8. The pharmaceutical composition according to claim 7, which is a TGF-δ inhibitor.

9. The pharmaceutical composition according to claim 7, which is a fibrosis inhibitor.

* * * * *

UNITED STATES PATENT AND TRADEMARK OFFICE
CERTIFICATE OF CORRECTION

| | |
|---|---|
| PATENT NO. | : 6,759,429 B2 |
| APPLICATION NO. | : 10/352067 |
| DATED | : July 6, 2004 |
| INVENTOR(S) | : Tokunaga et al. |

Page 1 of 1

It is certified that error appears in the above-identified patent and that said Letters Patent is hereby corrected as shown below:

<u>Column 91</u>

Please change the table heading in the second table in column 91, which appears after the second formula, as follows: "$R^d$" to --$R^p$--.

<u>Column 152</u>

Lines 33-34: please amend as follows: "The pharmaceutical composition according to claim 7, which is a TGF-δ inhibitor" to --The pharmaceutical composition according to claim 7, which is a TGF-β inhibitor.--

Signed and Sealed this

Fourth Day of March, 2008

JON W. DUDAS
*Director of the United States Patent and Trademark Office*